US009273141B2

(12) United States Patent
Algate et al.

(10) Patent No.: US 9,273,141 B2
(45) **Date of Patent: *Mar. 1, 2016**

(54) B CELL MATURATION ANTIGEN (BCMA) BINDING PROTEINS

(71) Applicant: Glaxo Group Limited, Brentford (GB)

(72) Inventors: Paul Algate, Issaquah, WA (US); Stephanie Jane Clegg, Stevenage (GB); Jennifer L. Craigen, Stevenage (GB); Paul Andrew Hamblin, Stevenage (GB); Alan Peter Lewis, Stevenage (GB); Patrick Mayes, Collegeville, PA (US); Radha Shah Parmar, Stevenage (GB); Trevor Anthony Kenneth Wattam, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 23 days.

This patent is subject to a terminal disclaimer.

(21) Appl. No.: 13/795,314

(22) Filed: Mar. 12, 2013

(65) Prior Publication Data

US 2013/0280280 A1 Oct. 24, 2013

Related U.S. Application Data

(63) Continuation of application No. PCT/EP2012/059762, filed on May 24, 2012.

(60) Provisional application No. 61/490,732, filed on May 27, 2011.

(51) Int. Cl.

| | |
|---|---|
| ***C07K 16/00*** | (2006.01) |
| ***C07K 16/28*** | (2006.01) |
| ***C07K 16/30*** | (2006.01) |
| ***A61K 39/00*** | (2006.01) |

(52) U.S. Cl.

CPC ......... *C07K 16/3061* (2013.01); *C07K 16/2878* (2013.01); *A61K 2039/505* (2013.01); *C07K 2317/24* (2013.01); *C07K 2317/33* (2013.01); *C07K 2317/41* (2013.01); *C07K 2317/73* (2013.01); *C07K 2317/732* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 5,635,483 | A | 6/1997 | Pettit et al. | |
| 5,968,753 | A | 10/1999 | Tseng-Law et al. | |
| 6,214,345 | B1 | 4/2001 | Firestone et al. | |
| 6,884,869 | B2 | 4/2005 | Senter et al. | |
| 6,962,702 | B2 | 11/2005 | Hansen et al. | |
| 7,091,186 | B2 | 8/2006 | Senter et al. | |
| 7,498,298 | B2 | 3/2009 | Doronina et al. | |
| 7,553,816 | B2 | 6/2009 | Senter et al. | |
| 7,659,241 | B2 | 2/2010 | Senter et al. | |
| 7,745,394 | B2 | 6/2010 | Doronina et al. | |
| 7,750,116 | B1 | 7/2010 | Doronina et al. | |
| 7,829,531 | B2 | 11/2010 | Senter et al. | |
| 7,837,980 | B2 | 11/2010 | Alley et al. | |
| 7,851,437 | B2 | 12/2010 | Senter et al. | |
| 7,964,566 | B2 | 6/2011 | Doronina et al. | |
| 7,964,567 | B2 | 6/2011 | Doronina et al. | |
| 7,994,135 | B2 | 8/2011 | Doronina et al. | |
| 8,039,273 | B2 | 10/2011 | Jeffrey | |
| 8,163,551 | B2 | 4/2012 | Alley et al. | |
| 8,288,352 | B2 | 10/2012 | Doronina et al. | |
| 8,343,928 | B2 | 1/2013 | Doronina et al. | |
| 8,455,622 | B2 | 6/2013 | McDonagh et al. | |
| 8,512,707 | B2 | 8/2013 | Doronina et al. | |
| 8,557,780 | B2 | 10/2013 | Doronina et al. | |
| 8,568,728 | B2 | 10/2013 | Jeffrey | |
| 8,574,907 | B2 | 11/2013 | Alley et al. | |
| 2002/0028178 | A1 | 3/2002 | Hanna et al. | |
| 2014/0105915 | A1 * | 4/2014 | Algate et al. | 424/173.1 |

FOREIGN PATENT DOCUMENTS

| | | | |
|---|---|---|---|
| WO | WO 00/40716 | A2 | 7/2000 |
| WO | WO 01/12812 | A2 | 2/2001 |
| WO | WO 01/24811 | A1 | 4/2001 |
| WO | WO 01/60397 | A1 | 8/2001 |
| WO | WO 2010/104949 | A2 | 9/2010 |
| WO | WO 2011/108008 | A2 | 9/2011 |
| WO | WO 2012/066058 | A1 | 5/2012 |
| WO | WO 2012/163805 | A1 | 12/2012 |

OTHER PUBLICATIONS

Abcam (KD value: A quantitative measurement of antibody affinity http://www.abcam.com/index.html?pageconfig=resource&rid=15749&source=pagetrap&viapagetrap=kd, Nov. 19, 2014).*

Claudio, et al., "A molecular compendium of genes expressed in multiple myeloma," *Blood*, vol. 100, No. 6, pp. 2175-2186, (2002).

Ryan, et al., "Antibody targeting of B-cell maturation antigen on malignant plasma cells", *Mol. Cancer Ther.*, vol. 6, No. 11, pp. 3009-3018 (2007).

Shadidi, et al., "An Anti-leukemic Single Chain Fv Antibody Selected from a Synthetic Human Phage Antibody Library", *BBRC*, vol. 280, pp. 548-552 (2001).

Shu, et al., "B cell maturation protein is a receptor for the tumor necrosis factor family member TALL-1," *PNAS*, vol. 97, No. 16, pp. 9156-9161 (2000).

Yamane-Ohnuki, et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity", *Biotechnology and Bioengineering*, vol. 87, No. 5, pp. 614-622 (2004).

* cited by examiner

*Primary Examiner* — Peter J Reddig

(74) *Attorney, Agent, or Firm* — Elizabeth J. Hecht; Edward J. Gimmi

(57) ABSTRACT

The present invention concerns antigen binding proteins and fragments thereof which specifically bind B Cell Maturation Antigen (BCMA), particularly human BCMA (hBCMA) and which inhibit the binding of BAFF and APRIL to the BCMA receptor. Further disclosed are pharmaceutical compositions, screening and medical treatment methods.

15 Claims, 27 Drawing Sheets

ARH77-10B5

H929

Normal: n=18
Myeloma: Progressive: n=23
Myeloma: Stable:n=6
Myeloma: Remission: n=12
Myeloma: Other: n=5
MGUS: n=3
Other PCD: n=2
*note: data above or below standards not graphed

SEQUENCE LISTING

```
<160> NUMBER OF SEQ ID NOS: 199

<210> SEQ ID NO 1
<211> LENGTH: 5
<212> TYPE: PRT
<213> ORGANISM: mus musculus

<400> SEQUENCE: 1

Asn Tyr Trp Met His
 1               5


<210> SEQ ID NO 2
<211> LENGTH: 17
<212> TYPE: PRT
<213> ORGANISM: mus musculus

<400> SEQUENCE: 2

Ala Thr Tyr Arg Gly His Ser Asp Thr Tyr Tyr Asn Gln Lys Phe Lys
 1               5                   10                  15

Gly


<210> SEQ ID NO 3
<211> LENGTH: 12
<212> TYPE: PRT
<213> ORGANISM: mus musculus

<400> SEQUENCE: 3

Gly Ala Ile Tyr Asn Gly Tyr Asp Val Leu Asp Asn
 1               5                   10


<210> SEQ ID NO 4
<211> LENGTH: 11
<212> TYPE: PRT
<213> ORGANISM: mus musculus

<400> SEQUENCE: 4

Ser Ala Ser Gln Asp Ile Ser Asn Tyr Leu Asn
 1               5                   10


<210> SEQ ID NO 5
<211> LENGTH: 7
<212> TYPE: PRT
<213> ORGANISM: mus musculus

<400> SEQUENCE: 5

Tyr Thr Ser Asn Leu His Ser
 1               5


<210> SEQ ID NO 6
<211> LENGTH: 9
<212> TYPE: PRT
```

<213> ORGANISM: mus musculus

<400> SEQUENCE: 6

Gln Gln Tyr Arg Lys Leu Pro Trp Thr
 1               5

<210> SEQ ID NO 7
<211> LENGTH: 121
<212> TYPE: PRT
<213> ORGANISM: mus musculus

<400> SEQUENCE: 7

Glu Val Gln Leu Gln Gln Ser Gly Ala Val Leu Ala Arg Pro Gly Ala
 1               5                   10                  15

Ser Val Lys Met Ser Cys Lys Gly Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Ala Thr Tyr Arg Gly His Ser Asp Thr Tyr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Ala Ile Tyr Asn Gly Tyr Asp Val Leu Asp Asn Trp Gly
            100                 105                 110

Gln Gly Thr Leu Val Thr Val Ser Ser
        115                 120

<210> SEQ ID NO 8
<211> LENGTH: 363
<212> TYPE: DNA
<213> ORGANISM: mus musculus

<400> SEQUENCE: 8
gaggtgcagc tgcagcagag cggcgccgtg ctggccaggc ccggagctag cgtgaagatg      60
agctgcaagg gcagcggcta caccttcacc aactactgga tgcactgggt gaaacagagg     120
cccggccagg gactggagtg gatcggcgcc acctacaggg gccacagcga cacctactac     180
aaccagaagt tcaagggcaa ggccaagctg accgccgtga cctcaaccag caccgcctac     240
atggaactga gcagcctgac caacgaggac agcgccgtct attactgcac caggggcgcc     300
atctacaacg gctacgacgt gctggacaat tggggccagg gaacactagt gaccgtgtcc     360
agc                                                                   363

<210> SEQ ID NO 9
<211> LENGTH: 108
<212> TYPE: PRT
<213> ORGANISM: mus musculus

<400> SEQUENCE: 9

Asp Ile Gln Leu Thr Gln Thr Thr Ser Ser Leu Ser Ala Ser Leu Gly
 1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Asp Gly Thr Val Glu Leu Val Ile
        35                  40                  45

Tyr Tyr Thr Ser Asn Leu His Ser Gly Val Pro Ser Arg Phe Ser Gly

```
    50                  55                  60

Ser Gly Ser Gly Thr Asp Tyr Ser Leu Thr Ile Gly Tyr Leu Glu Pro
65                  70                  75                  80

Glu Asp Val Ala Thr Tyr Tyr Cys Gln Gln Tyr Arg Lys Leu Pro Trp
                85                  90                  95

Thr Phe Gly Gly Gly Ser Lys Leu Glu Ile Lys Arg
            100                 105


<210> SEQ ID NO 10
<211> LENGTH: 324
<212> TYPE: DNA
<213> ORGANISM: mus musculus

<400> SEQUENCE: 10

gatatccagc tgacccagac cacaagcagc ctgagcgcct ccctgggcga cagggtgacc      60

attagctgca gcgccagcca ggacatcagc aactacctga actggtacca gcagaagccc     120

gacggcaccg tggagctcgt gatctactac acctccaacc tgcacagcgg cgtgcccagc     180

aggttctctg gcagcggcag cggcaccgac tacagcctga ccatcggcta tctggagccc     240

gaggacgtcg ccacctacta ctgccagcag tacaggaagc tgccctggac cttcggcgga     300

ggctctaagc tggagattaa gcgt                                            324


<210> SEQ ID NO 11
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 11

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser
        115                 120


<210> SEQ ID NO 12
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 12

caggtgcagc tggtccagag cggcgccgaa gtgaagaagc ccggcagctc cgtgaaagtg      60

agctgcaagg ccagcggcgg caccttcagc aactactgga tgcactgggt gaggcaggcc     120
```

-continued

```
cccggacagg gcctggagtg gatgggcgcc acctacaggg gccacagcga cacctactac    180

aaccagaagt tcaagggccg ggtgaccatc accgccgaca agagcaccag caccgcctac    240

atggaactga gcagcctcag gagcgaggac accgctgtgt attactgcgc caggggcgcc    300

atctacaacg gctacgacgt gctggacaac tggggccagg gcacactagt gaccgtgtcc    360

agc                                                                  363


<210> SEQ ID NO 13
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 13

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser
        115                 120


<210> SEQ ID NO 14
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 14

caggtgcagc tggtccagag cggcgccgaa gtgaagaagc ccggcagctc cgtgaaagtg     60

agctgcaagg ccagcggcta caccttcacc aactactgga tgcactgggt gaggcaggcc    120

cccggacagg gcctggagtg gatgggcgcc acctacaggg gccacagcga cacctactac    180

aaccagaagt tcaagggccg ggtgaccatc accgccgaca agagcaccag caccgcctac    240

atggaactga gcagcctcag gagcgaggac accgctgtgt attactgcgc caggggcgcc    300

atctacaacg gctacgacgt gctggacaac tggggccagg gcacactagt gaccgtgtcc    360

agc                                                                  363


<210> SEQ ID NO 15
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 15

Gln Val Gln Leu Val Gln Ser Gly Ala Glu Val Lys Lys Pro Gly Ser
```

```
 1               5                  10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asn Gly Tyr Asp Val Leu Asp Asn Trp Gly
            100                 105                 110

Gln Gly Thr Leu Val Thr Val Ser Ser
        115                 120


<210> SEQ ID NO 16
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 16

caggtgcagc tggtccagag cggcgccgaa gtgaagaagc ccggcagctc cgtgaaagtg      60

agctgcaagg ccagcggcta caccttcacc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcac caggggcgcc     300

atctacaacg gctacgacgt gctggacaac tggggccagg gcacactagt gaccgtgtcc     360

agc                                                                   363


<210> SEQ ID NO 17
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asn Gly Tyr Asp Val Leu Asp Asn Trp Gly
            100                 105                 110

Gln Gly Thr Leu Val Thr Val Ser Ser
```

115 120

<210> SEQ ID NO 18
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 18
caggtgcagc tggtccagag cggcgccgaa gtgaagaagc ccggcagctc cgtgaaagtg 60
agctgcaagg gcagcggcta caccttcacc aactactgga tgcactgggt gaggcaggcc 120
cccggacagg gcctggagtg gatgggcgcc acctacaggg gccacagcga cacctactac 180
aaccagaagt tcaagggccg ggtgaccatc accgccgaca cgagcaccag caccgcctac 240
atggaactga gcagcctcag gagcgaggac accgctgtgt attactgcac caggggcgcc 300
atctacaacg gctacgacgt gctggacaac tggggccagg gcacactagt gaccgtgtcc 360
agc 363

<210> SEQ ID NO 19
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 19

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asn Tyr
20 25 30

Trp Met His Trp Val Arg Gln Ala Pro Gly Gln Gly Leu Glu Trp Ile
35 40 45

Gly Ala Thr Tyr Arg Gly His Ser Asp Thr Tyr Tyr Asn Gln Lys Phe
50 55 60

Lys Gly Arg Ala Thr Leu Thr Ala Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Gly Ala Ile Tyr Asn Gly Tyr Asp Val Leu Asp Asn Trp Gly
100 105 110

Gln Gly Thr Leu Val Thr Val Ser Ser
115 120

<210> SEQ ID NO 20
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 20
caggtgcagc tggtccagag cggcgccgaa gtgaagaagc ccggcagctc cgtgaaagtg 60
agctgcaagg gcagcggcta caccttcacc aactactgga tgcactgggt gaggcaggcc 120
cccggacagg gcctggagtg gatcggcgcc acctacaggg gccacagcga cacctactac 180
aaccagaagt tcaagggccg ggcgaccctc accgccgaca cgagcaccag caccgcctac 240
atggaactga gcagcctcag gagcgaggac accgctgtgt attactgcac caggggcgcc 300
atctacaacg gctacgacgt gctggacaac tggggccagg gcacactagt gaccgtgtcc 360
agc 363

<210> SEQ ID NO 21
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 21

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asn Tyr
20 25 30

Trp Met His Trp Val Arg Gln Ala Pro Gly Gln Gly Leu Glu Trp Met
35 40 45

Gly Ala Thr Tyr Arg Gly His Ser Asp Thr Tyr Tyr Asn Gln Lys Phe
50 55 60

Lys Gly Arg Val Thr Ile Thr Ala Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Gly Ala Ile Tyr Asp Gly Tyr Asp Val Leu Asp Asn Trp Gly
100 105 110

Gln Gly Thr Leu Val Thr Val Ser Ser
115 120

<210> SEQ ID NO 22
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 22
caggtgcagc tggtccagag cggcgccgaa gtgaagaagc ccggcagctc cgtgaaagtg 60
agctgcaagg gcagcggcta caccttcacc aactactgga tgcactgggt gaggcaggcc 120
cccggacagg gcctggagtg gatgggcgcc acctacaggg gccacagcga cacctactac 180
aaccagaagt tcaagggccg ggtgaccatc accgccgaca cgagcaccag caccgcctac 240
atggaactga gcagcctcag gagcgaggac accgctgtgt attactgcac caggggcgcc 300
atctacgacg gctacgacgt gctggacaac tggggccagg gcacactagt gaccgtgtcc 360
agc 363

<210> SEQ ID NO 23
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 23

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asn Tyr
20 25 30

-continued

```
Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120
```

```
<210> SEQ ID NO 24
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 24

caggtgcagc tggtccagag cggcgccgaa gtgaagaagc ccggcagctc cgtgaaagtg      60

agctgcaagg ccagcggcgg caccttcagc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcgc caggggcgcc     300

atctacgacg gctacgacgt gctggacaac tggggccagg gcacactagt gaccgtgtcc     360

agc                                                                   363
```

```
<210> SEQ ID NO 25
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 25

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120
```

```
<210> SEQ ID NO 26
<211> LENGTH: 363
```

<212> TYPE: DNA
<213> ORGANISM: Artificial Sequence
<220> FEATURE:
<223> OTHER INFORMATION: Humansed antibody sequence

<400> SEQUENCE: 26
caggtgcagc tggtccagag cggcgccgaa gtgaagaagc ccggcagctc cgtgaaagtg 60
agctgcaagg ccagcggcta caccttcacc aactactgga tgcactgggt gaggcaggcc 120
cccggacagg gcctggagtg gatgggcgcc acctacaggg gccacagcga cacctactac 180
aaccagaagt tcaagggccg ggtgaccatc accgccgaca agagcaccag caccgcctac 240
atggaactga gcagcctcag gagcgaggac accgctgtgt attactgcgc caggggcgcc 300
atctacgacg gctacgacgt gctggacaac tggggccagg gcacactagt gaccgtgtcc 360
agc 363

<210> SEQ ID NO 27
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 27

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Trp Met His Trp Val Arg Gln Ala Pro Gly Gln Gly Leu Glu Trp Met
35 40 45

Gly Ala Thr Tyr Arg Gly His Ser Asp Thr Tyr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Gly Ala Ile Tyr Asp Gly Tyr Asp Val Leu Asp Asn Trp Gly
100 105 110

Gln Gly Thr Leu Val Thr Val Ser Ser
115 120

<210> SEQ ID NO 28
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 28
caggtgcagc tggtccagag cggcgccgaa gtgaagaagc ccggcagctc cgtgaaagtg 60
agctgcaagg ccagcggcta caccttcacc aactactgga tgcactgggt gaggcaggcc 120
cccggacagg gcctggagtg gatgggcgcc acctacaggg gccacagcga cacctactac 180
aaccagaagt tcaagggccg ggtgaccatc accgccgaca agagcaccag caccgcctac 240
atggaactga gcagcctcag gagcgaggac accgctgtgt attactgcac caggggcgcc 300
atctacgacg gctacgacgt gctggacaac tggggccagg gcacactagt gaccgtgtcc 360
agc 363

<210> SEQ ID NO 29
<211> LENGTH: 121
<212> TYPE: PRT
<213> ORGANISM: Artificial Sequence
<220> FEATURE:
<223> OTHER INFORMATION: Humansed antibody sequence

<400> SEQUENCE: 29

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asn Tyr
20 25 30

Trp Met His Trp Val Arg Gln Ala Pro Gly Gln Gly Leu Glu Trp Ile
35 40 45

Gly Ala Thr Tyr Arg Gly His Ser Asp Thr Tyr Tyr Asn Gln Lys Phe
50 55 60

Lys Gly Arg Ala Thr Leu Thr Ala Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Gly Ala Ile Tyr Asp Gly Tyr Asp Val Leu Asp Asn Trp Gly
100 105 110

Gln Gly Thr Leu Val Thr Val Ser Ser
115 120

<210> SEQ ID NO 30
<211> LENGTH: 363
<212> TYPE: DNA
<213> ORGANISM: Artificial Sequence
<220> FEATURE:
<223> OTHER INFORMATION: Humansed antibody sequence

<400> SEQUENCE: 30
caggtgcagc tggtccagag cggcgccgaa gtgaagaagc ccggcagctc cgtgaaagtg 60
agctgcaagg gcagcggcta caccttcacc aactactgga tgcactgggt gaggcaggcc 120
cccggacagg gcctggagtg gatcggcgcc acctacaggg gccacagcga cacctactac 180
aaccagaagt tcaagggccg ggcgaccctc accgccgaca cgagcaccag caccgcctac 240
atggaactga gcagcctcag gagcgaggac accgctgtgt attactgcac caggggcgcc 300
atctacgacg gctacgacgt gctggacaac tggggccagg gcacactagt gaccgtgtcc 360
agc 363

<210> SEQ ID NO 31
<211> LENGTH: 108
<212> TYPE: PRT
<213> ORGANISM: Artificial Sequence
<220> FEATURE:
<223> OTHER INFORMATION: Humansed antibody sequence

<400> SEQUENCE: 31

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Asn Leu His Ser Gly Val Pro Ser Arg Phe Ser Gly
50 55 60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105


<210> SEQ ID NO 32
<211> LENGTH: 324
<212> TYPE: DNA
<213> ORGANISM: Artificial Sequence
<220> FEATURE:
<223> OTHER INFORMATION: Humansed antibody sequence

<400> SEQUENCE: 32

gacatccaga tgacccagag ccctagctca ctgagcgcca gcgtgggcga cagggtgacc      60

attacctgct ccgccagcca ggacatcagc aactacctga actggtacca gcagaagccc     120

ggcaaggccc ccaagctgct gatctactac acctccaacc tgcactccgg cgtgcccagc     180

aggttcagcg gaagcggcag cggcaccgat ttcaccctga ccatctccag cctgcagccc     240

gaggacttcg ccacctacta ctgccagcag tacaggaagc tcccctggac tttcggccag     300

ggcaccaaac tggagatcaa gcgt                                            324


<210> SEQ ID NO 33
<211> LENGTH: 108
<212> TYPE: PRT
<213> ORGANISM: Artificial Sequence
<220> FEATURE:
<223> OTHER INFORMATION: Humansed antibody sequence

<400> SEQUENCE: 33

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105


<210> SEQ ID NO 34
<211> LENGTH: 324
<212> TYPE: DNA
<213> ORGANISM: Artificial Sequence
<220> FEATURE:
<223> OTHER INFORMATION: Humansed antibody sequence

<400> SEQUENCE: 34

gacatccaga tgacccagag ccctagctca ctgagcgcca gcgtgggcga cagggtgacc      60

attacctgct ccgccagcca ggacatcagc aactacctga actggtacca gcagaagccc     120

ggcaaggccc ccaagctgct gatctactac acctccaacc tgcactccgg cgtgcccagc     180
```

aggttcagcg gaagcggcag cggcaccgat tacaccctga ccatctccag cctgcagccc 240
gaggacttcg ccacctacta ctgccagcag tacaggaagc tcccctggac tttcggccag 300
ggcaccaaac tggagatcaa gcgt 324

<210> SEQ ID NO 35
<211> LENGTH: 108
<212> TYPE: PRT
<213> ORGANISM: Artificial Sequence
<220> FEATURE:
<223> OTHER INFORMATION: Humansed antibody sequence

<400> SEQUENCE: 35

Asp Ile Gln Leu Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Glu Leu Val Ile
35 40 45

Tyr Tyr Thr Ser Asn Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Tyr Arg Lys Leu Pro Trp
85 90 95

Thr Phe Gly Gln Gly Thr Lys Leu Glu Ile Lys Arg
100 105

<210> SEQ ID NO 36
<211> LENGTH: 324
<212> TYPE: DNA
<213> ORGANISM: Artificial Sequence
<220> FEATURE:
<223> OTHER INFORMATION: Humansed antibody sequence

<400> SEQUENCE: 36
gacatccagc tgacccagag ccctagctca ctgagcgcca gcgtgggcga cagggtgacc 60
attacctgct ccgccagcca ggacatcagc aactacctga actggtacca gcagaagccc 120
ggcaaggccc ccgagctggt gatctactac acctccaacc tgcactccgg cgtgcccagc 180
aggttcagcg gaagcggcag cggcaccgat tacaccctga ccatctccag cctgcagccc 240
gaggacttcg ccacctacta ctgccagcag tacaggaagc tcccctggac tttcggccag 300
ggcaccaaac tggagatcaa gcgt 324

<210> SEQ ID NO 37
<211> LENGTH: 310
<212> TYPE: PRT
<213> ORGANISM: homo sapiens

<400> SEQUENCE: 37

Met Pro Leu Leu Leu Leu Leu Pro Leu Leu Trp Ala Gly Ala Leu Ala
1 5 10 15

Met Leu Gln Met Ala Gly Gln Cys Ser Gln Asn Glu Tyr Phe Asp Ser
20 25 30

Leu Leu His Ala Cys Ile Pro Cys Gln Leu Arg Cys Ser Ser Asn Thr
35 40 45

Pro Pro Leu Thr Cys Gln Arg Tyr Cys Asn Ala Ser Val Thr Asn Ser
50 55 60

Val Lys Gly Thr Asn Ser Gly Glu Asn Leu Tyr Phe Gln Gly Asp Pro
65 70 75 80

Lys Ser Cys Asp Lys Thr His Thr Cys Pro Pro Cys Pro Ala Pro Glu
85 90 95

Leu Leu Gly Gly Pro Ser Val Phe Leu Phe Pro Pro Lys Pro Lys Asp
100 105 110

Thr Leu Met Ile Ser Arg Thr Pro Glu Val Thr Cys Val Val Val Asp
115 120 125

Val Ser His Glu Asp Pro Glu Val Lys Phe Asn Trp Tyr Val Asp Gly
130 135 140

Val Glu Val His Asn Ala Lys Thr Lys Pro Arg Glu Glu Gln Tyr Asn
145 150 155 160

Ser Thr Tyr Arg Val Val Ser Val Leu Thr Val Leu His Gln Asp Trp
165 170 175

Leu Asn Gly Lys Glu Tyr Lys Cys Lys Val Ser Asn Lys Ala Leu Pro
180 185 190

Ala Pro Ile Glu Lys Thr Ile Ser Lys Ala Lys Gly Gln Pro Arg Glu
195 200 205

Pro Gln Val Tyr Thr Leu Pro Pro Ser Arg Asp Glu Leu Thr Lys Asn
210 215 220

Gln Val Ser Leu Thr Cys Leu Val Lys Gly Phe Tyr Pro Ser Asp Ile
225 230 235 240

Ala Val Glu Trp Glu Ser Asn Gly Gln Pro Glu Asn Asn Tyr Lys Thr
245 250 255

Thr Pro Pro Val Leu Asp Ser Asp Gly Ser Phe Phe Leu Tyr Ser Lys
260 265 270

Leu Thr Val Asp Lys Ser Arg Trp Gln Gln Gly Asn Val Phe Ser Cys
275 280 285

Ser Val Met His Glu Ala Leu His Asn His Tyr Thr Gln Lys Ser Leu
290 295 300

Ser Leu Ser Pro Gly Lys
305 310

<210> SEQ ID NO 38
<211> LENGTH: 930
<212> TYPE: DNA
<213> ORGANISM: homo sapiens

<400> SEQUENCE: 38
atgccgctgc tgctactgct gcccctgctg tgggcagggg cgctagctat gctgcagatg 60
gccggccagt gcagccagaa cgagtacttc gacagcctgc tgcacgcctg catcccctgc 120
cagctgagat gcagcagcaa cacacctcct ctgacctgcc agagatactg caacgccagc 180
gtgaccaaca gcgtgaaggg caccaactcc ggagagaacc tgtacttcca aggggatccc 240
aaatcttgtg acaaaactca cacatgccca ccgtgcccag cacctgaact cctgggggga 300
ccgtcagtct tcctcttccc cccaaaaccc aaggacaccc tcatgatctc ccggacccct 360
gaggtcacat gcgtggtggt ggacgtgagc cacgaagacc ctgaggtcaa gttcaactgg 420
tacgtggacg gcgtggaggt gcataatgcc aagacaaagc cgcgggagga gcagtacaac 480
agcacgtacc gtgtggtcag cgtcctcacc gtcctgcacc aggactggct gaatggcaag 540
gagtacaagt gcaaggtctc caacaaagcc ctcccagccc ccatcgagaa aaccatctcc 600
aaagccaaag ggcagccccg agagccacag gtgtacaccc tgcccccatc ccgggatgag 660
ctgaccaaga accaggtcag cctgacctgc ctggtcaaag gcttctatcc cagcgacatc 720

-continued gccgtggagt gggagagcaa tgggcagccg gagaacaact acaagaccac gcctcccgtg 780
ctggactccg acggctcctt cttcctctac agcaagctca ccgtggacaa gagcaggtgg 840
cagcagggga acgtcttctc atgctccgtg atgcatgagg ctctgcacaa ccactacacg 900
cagaagagcc tctccctgtc tccgggtaaa 930

<210> SEQ ID NO 39
<211> LENGTH: 307
<212> TYPE: PRT
<213> ORGANISM: homo sapiens

<400> SEQUENCE: 39

Met Pro Leu Leu Leu Leu Leu Pro Leu Leu Trp Ala Gly Ala Leu Ala
1 5 10 15

Met Ala Gly Gln Cys Ser Gln Asn Glu Tyr Phe Asp Ser Leu Leu His
20 25 30

Ala Cys Ile Pro Cys Gln Leu Arg Cys Ser Ser Asn Thr Pro Pro Leu
35 40 45

Thr Cys Gln Arg Tyr Cys Asn Ala Ser Val Thr Asn Ser Val Lys Gly
50 55 60

Thr Asn Ser Gly Glu Asn Leu Tyr Phe Gln Gly Asp Pro Lys Ser Cys
65 70 75 80

Asp Lys Thr His Thr Cys Pro Pro Cys Pro Ala Pro Glu Leu Leu Gly
85 90 95

Gly Pro Ser Val Phe Leu Phe Pro Pro Lys Pro Lys Asp Thr Leu Met
100 105 110

Ile Ser Arg Thr Pro Glu Val Thr Cys Val Val Val Asp Val Ser His
115 120 125

Glu Asp Pro Glu Val Lys Phe Asn Trp Tyr Val Asp Gly Val Glu Val
130 135 140

His Asn Ala Lys Thr Lys Pro Arg Glu Glu Gln Tyr Asn Ser Thr Tyr
145 150 155 160

Arg Val Val Ser Val Leu Thr Val Leu His Gln Asp Trp Leu Asn Gly
165 170 175

Lys Glu Tyr Lys Cys Lys Val Ser Asn Lys Ala Leu Pro Ala Pro Ile
180 185 190

Glu Lys Thr Ile Ser Lys Ala Lys Gly Gln Pro Arg Glu Pro Gln Val
195 200 205

Tyr Thr Leu Pro Pro Ser Arg Asp Glu Leu Thr Lys Asn Gln Val Ser
210 215 220

Leu Thr Cys Leu Val Lys Gly Phe Tyr Pro Ser Asp Ile Ala Val Glu
225 230 235 240

Trp Glu Ser Asn Gly Gln Pro Glu Asn Asn Tyr Lys Thr Thr Pro Pro
245 250 255

Val Leu Asp Ser Asp Gly Ser Phe Phe Leu Tyr Ser Lys Leu Thr Val
260 265 270

Asp Lys Ser Arg Trp Gln Gln Gly Asn Val Phe Ser Cys Ser Val Met
275 280 285

His Glu Ala Leu His Asn His Tyr Thr Gln Lys Ser Leu Ser Leu Ser
290 295 300

Pro Gly Lys
305

<210> SEQ ID NO 40

<211> LENGTH: 921
<212> TYPE: DNA
<213> ORGANISM: homo sapiens

<400> SEQUENCE: 40

```
atgccgctgc tgctactgct gcccctgctg tgggcagggg cgctagctat ggccggccag      60

tgcagccaga acgagtactt cgacagcctg ctgcacgcct gcatcccctg ccagctgaga     120

tgcagcagca acacacctcc tctgacctgc cagagatact gcaacgccag cgtgaccaac     180

agcgtgaagg gcaccaactc cggagagaac ctgtacttcc aaggggatcc caaatcttgt     240

gacaaaactc acacatgccc accgtgccca gcacctgaac tcctgggggg accgtcagtc     300

ttcctcttcc ccccaaaacc caaggacacc ctcatgatct cccggacccc tgaggtcaca     360

tgcgtggtgg tggacgtgag ccacgaagac cctgaggtca agttcaactg gtacgtggac     420

ggcgtggagg tgcataatgc caagacaaag ccgcgggagg agcagtacaa cagcacgtac     480

cgtgtggtca gcgtcctcac cgtcctgcac caggactggc tgaatggcaa ggagtacaag     540

tgcaaggtct ccaacaaagc cctcccagcc cccatcgaga aaaccatctc caaagccaaa     600

gggcagcccc gagagccaca ggtgtacacc ctgcccccat cccgggatga gctgaccaag     660

aaccaggtca gcctgacctg cctggtcaaa ggcttctatc ccagcgacat cgccgtggag     720

tgggagagca atgggcagcc ggagaacaac tacaagacca cgcctcccgt gctggactcc     780

gacggctcct tcttcctcta cagcaagctc accgtggaca agagcaggtg gcagcagggg     840

aacgtcttct catgctccgt gatgcatgag gctctgcaca accactacac gcagaagagc     900

ctctccctgt ctccgggtaa a                                               921
```

<210> SEQ ID NO 41
<211> LENGTH: 306
<212> TYPE: PRT
<213> ORGANISM: cynomolgous macaque

<400> SEQUENCE: 41

```
Met Pro Leu Leu Leu Leu Leu Pro Leu Leu Trp Ala Gly Ala Leu Ala
1               5                   10                  15

Met Ala Arg Gln Cys Ser Gln Asn Glu Tyr Phe Asp Ser Leu Leu His
            20                  25                  30

Asp Cys Lys Pro Cys Gln Leu Arg Cys Ser Ser Thr Pro Pro Leu Thr
        35                  40                  45

Cys Gln Arg Tyr Cys Asn Ala Ser Met Thr Asn Ser Val Lys Gly Met
    50                  55                  60

Asn Ser Gly Glu Asn Leu Tyr Phe Gln Gly Asp Pro Lys Ser Cys Asp
65                  70                  75                  80

Lys Thr His Thr Cys Pro Pro Cys Pro Ala Pro Glu Leu Leu Gly Gly
                85                  90                  95

Pro Ser Val Phe Leu Phe Pro Pro Lys Pro Lys Asp Thr Leu Met Ile
            100                 105                 110

Ser Arg Thr Pro Glu Val Thr Cys Val Val Val Asp Val Ser His Glu
        115                 120                 125

Asp Pro Glu Val Lys Phe Asn Trp Tyr Val Asp Gly Val Glu Val His
    130                 135                 140

Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175
```

```
Glu Tyr Lys Cys Lys Val Ser Asn Lys Ala Leu Pro Ala Pro Ile Glu
            180                 185                 190

Lys Thr Ile Ser Lys Ala Lys Gly Gln Pro Arg Glu Pro Gln Val Tyr
        195                 200                 205

Thr Leu Pro Pro Ser Arg Asp Glu Leu Thr Lys Asn Gln Val Ser Leu
    210                 215                 220

Thr Cys Leu Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Lys Leu Thr Val Asp
            260                 265                 270

Lys Ser Arg Trp Gln Gln Gly Asn Val Phe Ser Cys Ser Val Met His
        275                 280                 285

Glu Ala Leu His Asn His Tyr Thr Gln Lys Ser Leu Ser Leu Ser Pro
    290                 295                 300

Gly Lys
305


<210> SEQ ID NO 42
<211> LENGTH: 918
<212> TYPE: DNA
<213> ORGANISM: cynomolgous macaque

<400> SEQUENCE: 42

atgccgctgc tgctactgct gcccctgctg tgggcagggg cgctagctat ggccagacag     60

tgcagccaga acgagtactt cgacagcctg ctgcacgact gcaagccctg ccagctgaga    120

tgcagcagca cacctcctct gacctgccag agatactgca acgccagcat gaccaacagc    180

gtgaagggca tgaactccgg agagaacctg tacttccaag gggatcccaa atcttgtgac    240

aaaactcaca catgcccacc gtgcccagca cctgaactcc tggggggacc gtcagtcttc    300

ctcttccccc caaaacccaa ggacaccctc atgatctccc ggacccctga ggtcacatgc    360

gtggtggtgg acgtgagcca cgaagaccct gaggtcaagt tcaactggta cgtggacggc    420

gtggaggtgc ataatgccaa gacaaagccg cgggaggagc agtacaacag cacgtaccgt    480

gtggtcagcg tcctcaccgt cctgcaccag gactggctga atggcaagga gtacaagtgc    540

aaggtctcca acaaagccct cccagccccc atcgagaaaa ccatctccaa agccaaaggg    600

cagccccgag agccacaggt gtacaccctg cccccatccc gggatgagct gaccaagaac    660

caggtcagcc tgacctgcct ggtcaaaggc ttctatccca gcgacatcgc cgtggagtgg    720

gagagcaatg ggcagccgga gaacaactac aagaccacgc ctcccgtgct ggactccgac    780

ggctccttct tcctctacag caagctcacc gtggacaaga gcaggtggca gcaggggaac    840

gtcttctcat gctccgtgat gcatgaggct ctgcacaacc actacacgca gaagagcctc    900

tccctgtctc cgggtaaa                                                  918


<210> SEQ ID NO 43
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 43

Gln Val Gln Leu Val Gln Ser Gly Ala Glu Val Lys Lys Pro Gly Ser
 1               5                  10                  15
```

```
Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
        435                 440                 445

Pro Gly Lys
    450


<210> SEQ ID NO 44
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 44

caggtgcagc tggtccagag cggcgccgaa gtgaagaagc ccggcagctc cgtgaaagtg      60

agctgcaagg ccagcggcgg caccttcagc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcgc caggggcgcc     300

atctacaacg gctacgacgt gctggacaac tggggccagg gcacactagt gaccgtgtcc     360

agcgccagca ccaagggccc cagcgtgttc cccctggccc ccagcagcaa gagcaccagc     420

ggcggcacag ccgccctggg ctgcctggtg aaggactact tccccgaacc ggtgaccgtg     480

tcctggaaca gcggagccct gaccagcggc gtgcacacct tccccgccgt gctgcagagc     540

agcggcctgt acagcctgag cagcgtggtg accgtgccca gcagcagcct gggcacccag     600

acctacatct gtaacgtgaa ccacaagccc agcaacacca aggtggacaa gaaggtggag     660

cccaagagct gtgacaagac ccacacctgc ccccccctgcc ctgcccccga gctgctggga     720

ggccccagcg tgttcctgtt ccccccccaag cctaaggaca ccctgatgat cagcagaacc     780

cccgaggtga cctgtgtggt ggtggatgtg agccacgagg accctgaggt gaagttcaac     840

tggtacgtgg acggcgtgga ggtgcacaat gccaagacca agcccaggga ggagcagtac     900

aacagcacct accgggtggt gtccgtgctg accgtgctgc accaggattg gctgaacggc     960

aaggagtaca agtgtaaggt gtccaacaag gccctgcctg cccctatcga gaaaaccatc    1020

agcaaggcca agggccagcc cagagagccc caggtgtaca ccctgccccc tagcagagat    1080

gagctgacca agaaccaggt gtccctgacc tgcctggtga agggcttcta ccccagcgac    1140

atcgccgtgg agtgggagag caacggccag cccgagaaca actacaagac cacccccccct    1200

gtgctggaca gcgatggcag cttcttcctg tacagcaagc tgaccgtgga caagagcaga    1260

tggcagcagg gcaacgtgtt cagctgctcc gtgatgcacg aggccctgca caatcactac    1320

acccagaaga gcctgagcct gtcccctggc aag                                 1353


<210> SEQ ID NO 45
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 45

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
```

```
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 46
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 46
caggtgcagc tggtccagag cggcgccgaa gtgaagaagc ccggcagctc cgtgaaagtg 60
agctgcaagg ccagcggcta caccttcacc aactactgga tgcactgggt gaggcaggcc 120
cccggacagg gcctggagtg gatgggcgcc acctacaggg gccacagcga cacctactac 180
aaccagaagt tcaagggccg ggtgaccatc accgccgaca agagcaccag caccgcctac 240
atggaactga gcagcctcag gagcgaggac accgctgtgt attactgcgc caggggcgcc 300
atctacaacg gctacgacgt gctggacaac tggggccagg gcacactagt gaccgtgtcc 360
agcgccagca ccaagggccc cagcgtgttc cccctggccc ccagcagcaa gagcaccagc 420
ggcggcacag ccgccctggg ctgcctggtg aaggactact tccccgaacc ggtgaccgtg 480
tcctggaaca gcggagccct gaccagcggc gtgcacacct tccccgccgt gctgcagagc 540
agcggcctgt acagcctgag cagcgtggtg accgtgccca gcagcagcct gggcacccag 600
acctacatct gtaacgtgaa ccacaagccc agcaacacca aggtggacaa gaaggtggag 660
cccaagagct gtgacaagac ccacacctgc ccccctgcc ctgcccccga gctgctggga 720
ggccccagcg tgttcctgtt cccccccaag cctaaggaca ccctgatgat cagcagaacc 780
cccgaggtga cctgtgtggt ggtggatgtg agccacgagg accctgaggt gaagttcaac 840
tggtacgtgg acggcgtgga ggtgcacaat gccaagacca agcccaggga ggagcagtac 900
aacagcacct accgggtggt gtccgtgctg accgtgctgc accaggattg gctgaacggc 960
aaggagtaca agtgtaaggt gtccaacaag gccctgcctg cccctatcga gaaaaccatc 1020
agcaaggcca agggccagcc cagagagccc caggtgtaca ccctgccccc tagcagagat 1080
gagctgacca agaaccaggt gtccctgacc tgcctggtga agggcttcta ccccagcgac 1140
atcgccgtgg agtgggagag caacggccag cccgagaaca actacaagac cacccccct 1200 gtgctggaca gcgatggcag cttcttcctg tacagcaagc tgaccgtgga caagagcaga 1260
tggcagcagg gcaacgtgtt cagctgctcc gtgatgcacg aggccctgca caatcactac 1320
acccagaaga gcctgagcct gtcccctggc aag 1353

<210> SEQ ID NO 47
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 47

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Trp Met His Trp Val Arg Gln Ala Pro Gly Gln Gly Leu Glu Trp Met
35 40 45

Gly Ala Thr Tyr Arg Gly His Ser Asp Thr Tyr Tyr Asn Gln Lys Phe
50 55 60

```
Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asn Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 48
<211> LENGTH: 1353
<212> TYPE: DNA
```

<213> ORGANISM: Artificial Sequence
<220> FEATURE:
<223> OTHER INFORMATION: Humansed antibody sequence

<400> SEQUENCE: 48

```
caggtgcagc tggtccagag cggcgccgaa gtgaagaagc ccggcagctc cgtgaaagtg      60
agctgcaagg ccagcggcta caccttcacc aactactgga tgcactgggt gaggcaggcc     120
cccggacagg gcctggagtg gatgggcgcc acctacaggg gccacagcga cacctactac     180
aaccagaagt tcaagggccg ggtgaccatc accgccgaca agagcaccag caccgcctac     240
atggaactga gcagcctcag gagcgaggac accgctgtgt attactgcac caggggcgcc     300
atctacaacg gctacgacgt gctggacaac tggggccagg gcacactagt gaccgtgtcc     360
agcgccagca ccaagggccc cagcgtgttc cccctggccc ccagcagcaa gagcaccagc     420
ggcggcacag ccgccctggg ctgcctggtg aaggactact tccccgaacc ggtgaccgtg     480
tcctggaaca gcggagccct gaccagcggc gtgcacacct tccccgccgt gctgcagagc     540
agcggcctgt acagcctgag cagcgtggtg accgtgccca gcagcagcct gggcacccag     600
acctacatct gtaacgtgaa ccacaagccc agcaacacca aggtggacaa gaaggtggag     660
cccaagagct gtgacaagac ccacacctgc ccccctgcc ctgcccccga gctgctggga      720
ggccccagcg tgttcctgtt ccccccaag cctaaggaca ccctgatgat cagcagaacc      780
cccgaggtga cctgtgtggt ggtggatgtg agccacgagg accctgaggt gaagttcaac     840
tggtacgtgg acggcgtgga ggtgcacaat gccaagacca agcccaggga ggagcagtac     900
aacagcacct accgggtggt gtccgtgctg accgtgctgc accaggattg gctgaacggc     960
aaggagtaca agtgtaaggt gtccaacaag gccctgcctg cccctatcga gaaaaccatc    1020
agcaaggcca agggccagcc cagagagccc caggtgtaca ccctgccccc tagcagagat    1080
gagctgacca agaaccaggt gtccctgacc tgcctggtga agggcttcta ccccagcgac    1140
atcgccgtgg agtgggagag caacggccag cccgagaaca actacaagac cacccccct     1200
gtgctggaca gcgatggcag cttcttcctg tacagcaagc tgaccgtgga caagagcaga    1260
tggcagcagg gcaacgtgtt cagctgctcc gtgatgcacg aggccctgca caatcactac    1320
acccagaaga gcctgagcct gtcccctggc aag                                 1353
```

<210> SEQ ID NO 49
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Gly Ala Ile Tyr Asn Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 50
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 50

```
caggtgcagc tggtccagag cggcgccgaa gtgaagaagc ccggcagctc cgtgaaagtg     60

agctgcaagg gcagcggcta caccttcacc aactactgga tgcactgggt gaggcaggcc    120

cccggacagg gcctggagtg gatgggcgcc acctacaggg gccacagcga cacctactac    180

aaccagaagt tcaagggccg ggtgaccatc accgccgaca cgagcaccag caccgcctac    240

atggaactga gcagcctcag gagcgaggac accgctgtgt attactgcac caggggcgcc    300

atctacaacg gctacgacgt gctggacaac tggggccagg gcacactagt gaccgtgtcc    360

agcgccagca ccaagggccc cagcgtgttc cccctggccc ccagcagcaa gagcaccagc    420

ggcggcacag ccgccctggg ctgcctggtg aaggactact tccccgaacc ggtgaccgtg    480

tcctggaaca gcggagccct gaccagcggc gtgcacacct tccccgccgt gctgcagagc    540

agcggcctgt acagcctgag cagcgtggtg accgtgccca gcagcagcct gggcacccag    600

acctacatct gtaacgtgaa ccacaagccc agcaacacca aggtggacaa gaaggtggag    660

cccaagagct gtgacaagac ccacacctgc ccccctgcc ctgcccccga gctgctggga    720

ggccccagcg tgttcctgtt cccccccaag cctaaggaca ccctgatgat cagcagaacc    780

cccgaggtga cctgtgtggt ggtggatgtg agccacgagg accctgaggt gaagttcaac    840

tggtacgtgg acggcgtgga ggtgcacaat gccaagacca agcccaggga ggagcagtac    900

aacagcacct accgggtggt gtccgtgctg accgtgctgc accaggattg gctgaacggc    960

aaggagtaca agtgtaaggt gtccaacaag gccctgcctg cccctatcga gaaaaccatc   1020

agcaaggcca agggccagcc cagagagccc caggtgtaca ccctgccccc tagcagagat   1080

gagctgacca agaaccaggt gtccctgacc tgcctggtga agggcttcta ccccagcgac   1140

atcgccgtgg agtgggagag caacggccag cccgagaaca actacaagac caccccccct   1200

gtgctggaca gcgatggcag cttcttcctg tacagcaagc tgaccgtgga caagagcaga   1260

tggcagcagg gcaacgtgtt cagctgctcc gtgatgcacg aggccctgca caatcactac   1320

acccagaaga gcctgagcct gtcccctggc aag                                1353
```

```
<210> SEQ ID NO 51
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Ala Thr Tyr Arg Gly His Ser Asp Thr Tyr Tyr Asn Gln Lys Phe
    50                  55                  60

Lys Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asn Gly Tyr Asp Val Leu Asp Asn Trp Gly
            100                 105                 110

Gln Gly Thr Leu Val Thr Val Ser Ser Ala Ser Thr Lys Gly Pro Ser
```

```
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 52
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 52

```
caggtgcagc tggtccagag cggcgccgaa gtgaagaagc ccggcagctc cgtgaaagtg      60

agctgcaagg gcagcggcta caccttcacc aactactgga tgcactgggt gaggcaggcc     120
```

```
cccggacagg gcctggagtg gatcggcgcc acctacaggg gccacagcga cacctactac    180

aaccagaagt tcaagggccg ggcgaccctc accgccgaca cgagcaccag caccgcctac    240

atggaactga gcagcctcag gagcgaggac accgctgtgt attactgcac caggggcgcc    300

atctacaacg gctacgacgt gctggacaac tggggccagg gcacactagt gaccgtgtcc    360

agcgccagca ccaagggccc cagcgtgttc cccctggccc ccagcagcaa gagcaccagc    420

ggcggcacag ccgccctggg ctgcctggtg aaggactact tccccgaacc ggtgaccgtg    480

tcctggaaca gcggagccct gaccagcggc gtgcacacct tccccgccgt gctgcagagc    540

agcggcctgt acagcctgag cagcgtggtg accgtgccca gcagcagcct gggcacccag    600

acctacatct gtaacgtgaa ccacaagccc agcaacacca aggtggacaa gaaggtggag    660

cccaagagct gtgacaagac ccacacctgc ccccccctgcc ctgcccccga gctgctggga    720

ggccccagcg tgttcctgtt cccccccaag cctaaggaca ccctgatgat cagcagaacc    780

cccgaggtga cctgtgtggt ggtggatgtg agccacgagg accctgaggt gaagttcaac    840

tggtacgtgg acggcgtgga ggtgcacaat gccaagacca agcccaggga ggagcagtac    900

aacagcacct accgggtggt gtccgtgctg accgtgctgc accaggattg gctgaacggc    960

aaggagtaca agtgtaaggt gtccaacaag gccctgcctg cccctatcga gaaaaccatc   1020

agcaaggcca agggccagcc cagagagccc caggtgtaca ccctgccccc tagcagagat   1080

gagctgacca agaaccaggt gtccctgacc tgcctggtga agggcttcta ccccagcgac   1140

atcgccgtgg agtgggagag caacggccag cccgagaaca actacaagac caccccccct   1200

gtgctggaca gcgatggcag cttcttcctg tacagcaagc tgaccgtgga caagagcaga   1260

tggcagcagg gcaacgtgtt cagctgctcc gtgatgcacg aggccctgca caatcactac   1320

acccagaaga gcctgagcct gtcccctggc aag                                1353
```

<210> SEQ ID NO 53
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 53

```
Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 54
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 54

```
caggtgcagc tggtccagag cggcgccgaa gtgaagaagc ccggcagctc cgtgaaagtg      60

agctgcaagg gcagcggcta caccttcacc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca cgagcaccag caccgcctac     240

atggaactga gcagcctcag gagcgaggac accgctgtgt attactgcac caggggcgcc     300
```

atctacgacg gctacgacgt gctggacaac tggggccagg gcacactagt gaccgtgtcc 360
agcgccagca ccaagggccc cagcgtgttc cccctggccc ccagcagcaa gagcaccagc 420
ggcggcacag ccgccctggg ctgcctggtg aaggactact tccccgaacc ggtgaccgtg 480
tcctggaaca gcggagccct gaccagcggc gtgcacacct tccccgccgt gctgcagagc 540
agcggcctgt acagcctgag cagcgtggtg accgtgccca gcagcagcct gggcacccag 600
acctacatct gtaacgtgaa ccacaagccc agcaacacca aggtggacaa gaaggtggag 660
cccaagagct gtgacaagac ccacacctgc ccccctgcc ctgcccccga gctgctggga 720
ggccccagcg tgttcctgtt cccccccaag cctaaggaca ccctgatgat cagcagaacc 780
cccgaggtga cctgtgtggt ggtggatgtg agccacgagg accctgaggt gaagttcaac 840
tggtacgtgg acggcgtgga ggtgcacaat gccaagacca agcccaggga ggagcagtac 900
aacagcacct accgggtggt gtccgtgctg accgtgctgc accaggattg gctgaacggc 960
aaggagtaca agtgtaaggt gtccaacaag gccctgcctg cccctatcga gaaaaccatc 1020
agcaaggcca agggccagcc cagagagccc caggtgtaca ccctgccccc tagcagagat 1080
gagctgacca agaaccaggt gtccctgacc tgcctggtga agggcttcta ccccagcgac 1140
atcgccgtgg agtgggagag caacggccag cccgagaaca actacaagac cacccccct 1200 gtgctggaca gcgatggcag cttcttcctg tacagcaagc tgaccgtgga caagagcaga 1260
tggcagcagg gcaacgtgtt cagctgctcc gtgatgcacg aggccctgca caatcactac 1320
acccagaaga gcctgagcct gtcccctggc aag 1353

<210> SEQ ID NO 55
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 55

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asn Tyr
20 25 30

Trp Met His Trp Val Arg Gln Ala Pro Gly Gln Gly Leu Glu Trp Met
35 40 45

Gly Ala Thr Tyr Arg Gly His Ser Asp Thr Tyr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ala Ile Tyr Asp Gly Tyr Asp Val Leu Asp Asn Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

-continued

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 56
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 56

caggtgcagc tggtccagag cggcgccgaa gtgaagaagc ccggcagctc cgtgaaagtg      60

agctgcaagg ccagcggcgg caccttcagc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcgc caggggcgcc     300

atctacgacg gctacgacgt gctggacaac tggggccagg gcacactagt gaccgtgtcc     360

agcgccagca ccaagggccc cagcgtgttc cccctggccc ccagcagcaa gagcaccagc     420
```

-continued

```
ggcggcacag ccgccctggg ctgcctggtg aaggactact tccccgaacc ggtgaccgtg    480

tcctggaaca gcggagccct gaccagcggc gtgcacacct tccccgccgt gctgcagagc    540

agcggcctgt acagcctgag cagcgtggtg accgtgccca gcagcagcct gggcacccag    600

acctacatct gtaacgtgaa ccacaagccc agcaacacca aggtggacaa gaaggtggag    660

cccaagagct gtgacaagac ccacacctgc ccccctgcc ctgcccccga gctgctggga    720

ggccccagcg tgttcctgtt cccccccaag cctaaggaca ccctgatgat cagcagaacc    780

cccgaggtga cctgtgtggt ggtggatgtg agccacgagg accctgaggt gaagttcaac    840

tggtacgtgg acggcgtgga ggtgcacaat gccaagacca agcccaggga ggagcagtac    900

aacagcacct accgggtggt gtccgtgctg accgtgctgc accaggattg gctgaacggc    960

aaggagtaca agtgtaaggt gtccaacaag gccctgcctg cccctatcga gaaaaccatc   1020

agcaaggcca agggccagcc cagagagccc caggtgtaca ccctgccccc tagcagagat   1080

gagctgacca agaaccaggt gtccctgacc tgcctggtga agggcttcta ccccagcgac   1140

atcgccgtgg agtgggagag caacggccag cccgagaaca actacaagac cacccccct    1200

gtgctggaca gcgatggcag cttcttcctg tacagcaagc tgaccgtgga caagagcaga   1260

tggcagcagg gcaacgtgtt cagctgctcc gtgatgcacg aggccctgca caatcactac   1320

acccagaaga gcctgagcct gtcccctggc aag                                1353
```

<210> SEQ ID NO 57
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 57

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 58
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 58

```
caggtgcagc tggtccagag cggcgccgaa gtgaagaagc ccggcagctc cgtgaaagtg      60

agctgcaagg ccagcggcta caccttcacc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcgc caggggcgcc     300

atctacgacg gctacgacgt gctggacaac tggggccagg gcacactagt gaccgtgtcc     360

agcgccagca ccaagggccc cagcgtgttc cccctggccc ccagcagcaa gagcaccagc     420

ggcggcacag ccgccctggg ctgcctggtg aaggactact tccccgaacc ggtgaccgtg     480

tcctggaaca gcggagccct gaccagcggc gtgcacacct tccccgccgt gctgcagagc     540

agcggcctgt acagcctgag cagcgtggtg accgtgccca gcagcagcct gggcacccag     600
```

```
acctacatct gtaacgtgaa ccacaagccc agcaacacca aggtggacaa gaaggtggag    660

cccaagagct gtgacaagac ccacacctgc ccccctgcc ctgcccccga gctgctggga    720

ggccccagcg tgttcctgtt cccccccaag cctaaggaca ccctgatgat cagcagaacc    780

cccgaggtga cctgtgtggt ggtggatgtg agccacgagg accctgaggt gaagttcaac    840

tggtacgtgg acggcgtgga ggtgcacaat gccaagacca agcccaggga ggagcagtac    900

aacagcacct accgggtggt gtccgtgctg accgtgctgc accaggattg gctgaacggc    960

aaggagtaca agtgtaaggt gtccaacaag gccctgcctg cccctatcga gaaaaccatc   1020

agcaaggcca agggccagcc cagagagccc caggtgtaca ccctgccccc tagcagagat   1080

gagctgacca agaaccaggt gtccctgacc tgcctggtga agggcttcta ccccagcgac   1140

atcgccgtgg agtgggagag caacggccag cccgagaaca actacaagac cacccccccct   1200

gtgctggaca gcgatggcag cttcttcctg tacagcaagc tgaccgtgga caagagcaga   1260

tggcagcagg gcaacgtgtt cagctgctcc gtgatgcacg aggccctgca caatcactac   1320

acccagaaga gcctgagcct gtcccctggc aag                                1353


<210> SEQ ID NO 59
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

-continued

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 60
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 60

```
caggtgcagc tggtccagag cggcgccgaa gtgaagaagc ccggcagctc cgtgaaagtg      60

agctgcaagg ccagcggcta caccttcacc aactactgga tgcactgggt gaggcaggcc     120

cccggacagg gcctggagtg gatgggcgcc acctacaggg gccacagcga cacctactac     180

aaccagaagt tcaagggccg ggtgaccatc accgccgaca agagcaccag caccgcctac     240

atggaactga gcagcctcag gagcgaggac accgctgtgt attactgcac caggggcgcc     300

atctacgacg gctacgacgt gctggacaac tggggccagg gcacactagt gaccgtgtcc     360

agcgccagca ccaagggccc cagcgtgttc cccctggccc ccagcagcaa gagcaccagc     420

ggcggcacag ccgccctggg ctgcctggtg aaggactact tccccgaacc ggtgaccgtg     480

tcctggaaca gcggagccct gaccagcggc gtgcacacct tccccgccgt gctgcagagc     540

agcggcctgt acagcctgag cagcgtggtg accgtgccca gcagcagcct gggcacccag     600

acctacatct gtaacgtgaa ccacaagccc agcaacacca aggtggacaa gaaggtggag     660

cccaagagct gtgacaagac ccacacctgc cccccctgcc ctgcccccga gctgctggga     720
```

ggccccagcg tgttcctgtt cccccccaag cctaaggaca ccctgatgat cagcagaacc 780
cccgaggtga cctgtgtggt ggtggatgtg agccacgagg accctgaggt gaagttcaac 840
tggtacgtgg acggcgtgga ggtgcacaat gccaagacca agcccaggga ggagcagtac 900
aacagcacct accgggtggt gtccgtgctg accgtgctgc accaggattg gctgaacggc 960
aaggagtaca agtgtaaggt gtccaacaag gccctgcctg cccctatcga gaaaaccatc 1020
agcaaggcca agggccagcc cagagagccc caggtgtaca ccctgccccc tagcagagat 1080
gagctgacca agaaccaggt gtccctgacc tgcctggtga agggcttcta ccccagcgac 1140
atcgccgtgg agtgggagag caacggccag cccgagaaca actacaagac caccccccct 1200
gtgctggaca gcgatggcag cttcttcctg tacagcaagc tgaccgtgga caagagcaga 1260
tggcagcagg gcaacgtgtt cagctgctcc gtgatgcacg aggccctgca caatcactac 1320
acccagaaga gcctgagcct gtcccctggc aag 1353

<210> SEQ ID NO 61
<211> LENGTH: 451
<212> TYPE: PRT
<213> ORGANISM: Artificial Sequence
<220> FEATURE:
<223> OTHER INFORMATION: Humansed antibody sequence

<400> SEQUENCE: 61

Gln Val Gln Leu Val Gln Ser Gly Ala Glu Val Lys Lys Pro Gly Ser
1 5 10 15

Ser Val Lys Val Ser Cys Lys Gly Ser Gly Tyr Thr Phe Thr Asn Tyr
20 25 30

Trp Met His Trp Val Arg Gln Ala Pro Gly Gln Gly Leu Glu Trp Ile
35 40 45

Gly Ala Thr Tyr Arg Gly His Ser Asp Thr Tyr Tyr Asn Gln Lys Phe
50 55 60

Lys Gly Arg Ala Thr Leu Thr Ala Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Gly Ala Ile Tyr Asp Gly Tyr Asp Val Leu Asp Asn Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 62
<211> LENGTH: 1353
<212> TYPE: DNA
<213> ORGANISM: Artificial Sequence
<220> FEATURE:
<223> OTHER INFORMATION: Humansed antibody sequence

<400> SEQUENCE: 62

```
caggtgcagc tggtccagag cggcgccgaa gtgaagaagc ccggcagctc cgtgaaagtg     60

agctgcaagg gcagcggcta caccttcacc aactactgga tgcactgggt gaggcaggcc    120

cccggacagg gcctggagtg gatcggcgcc acctacaggg gccacagcga cacctactac    180

aaccagaagt tcaagggccg ggcgaccctc accgccgaca cgagcaccag caccgcctac    240

atggaactga gcagcctcag gagcgaggac accgctgtgt attactgcac caggggcgcc    300

atctacgacg gctacgacgt gctggacaac tggggccagg gcacactagt gaccgtgtcc    360

agcgccagca ccaagggccc cagcgtgttc cccctggccc ccagcagcaa gagcaccagc    420

ggcggcacag ccgccctggg ctgcctggtg aaggactact tccccgaacc ggtgaccgtg    480

tcctggaaca gcggagccct gaccagcggc gtgcacacct tccccgccgt gctgcagagc    540

agcggcctgt acagcctgag cagcgtggtg accgtgccca gcagcagcct gggcacccag    600

acctacatct gtaacgtgaa ccacaagccc agcaacacca aggtggacaa gaaggtggag    660

cccaagagct gtgacaagac ccacacctgc ccccctgcc ctgcccccga gctgctggga    720

ggccccagcg tgttcctgtt cccccccaag cctaaggaca ccctgatgat cagcagaacc    780

cccgaggtga cctgtgtggt ggtggatgtg agccacgagg accctgaggt gaagttcaac    840

tggtacgtgg acggcgtgga ggtgcacaat gccaagacca agcccaggga ggagcagtac    900
```

```
aacagcacct accgggtggt gtccgtgctg accgtgctgc accaggattg gctgaacggc    960

aaggagtaca agtgtaaggt gtccaacaag gccctgcctg cccctatcga gaaaaccatc   1020

agcaaggcca agggccagcc cagagagccc caggtgtaca ccctgccccc tagcagagat   1080

gagctgacca agaaccaggt gtccctgacc tgcctggtga agggcttcta ccccagcgac   1140

atcgccgtgg agtgggagag caacggccag cccgagaaca actacaagac cacccccccct   1200

gtgctggaca gcgatggcag cttcttcctg tacagcaagc tgaccgtgga caagagcaga   1260

tggcagcagg gcaacgtgtt cagctgctcc gtgatgcacg aggccctgca caatcactac   1320

acccagaaga gcctgagcct gtcccctggc aag                                1353
```

<210> SEQ ID NO 63
<211> LENGTH: 214
<212> TYPE: PRT
<213> ORGANISM: Artificial Sequence
<220> FEATURE:
<223> OTHER INFORMATION: Humansed antibody sequence

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 64
<211> LENGTH: 642
<212> TYPE: DNA
<213> ORGANISM: Artificial Sequence
<220> FEATURE:
<223> OTHER INFORMATION: Humansed antibody sequence

<400> SEQUENCE: 64

```
gacatccaga tgacccagag ccctagctca ctgagcgcca gcgtgggcga cagggtgacc      60

attacctgct ccgccagcca ggacatcagc aactacctga actggtacca gcagaagccc     120

ggcaaggccc ccaagctgct gatctactac acctccaacc tgcactccgg cgtgcccagc     180

aggttcagcg gaagcggcag cggcaccgat ttcaccctga ccatctccag cctgcagccc     240

gaggacttcg ccacctacta ctgccagcag tacaggaagc tcccctggac tttcggccag     300

ggcaccaaac tggagatcaa gcgtacggtg gccgccccca gcgtgttcat cttccccccc     360

agcgatgagc agctgaagag cggcaccgcc agcgtggtgt gtctgctgaa caacttctac     420

ccccgggagg ccaaggtgca gtggaaggtg gacaatgccc tgcagagcgg caacagccag     480

gagagcgtga ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac cggggcgagt gc                        642
```

```
<210> SEQ ID NO 65
<211> LENGTH: 214
<212> TYPE: PRT
<213> ORGANISM: Artificial Sequence
<220> FEATURE:
<223> OTHER INFORMATION: Humansed antibody sequence

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 66
<211> LENGTH: 642
<212> TYPE: DNA
<213> ORGANISM: Artificial Sequence
```

<220> FEATURE:
<223> OTHER INFORMATION: Humansed antibody sequence

<400> SEQUENCE: 66

```
gacatccaga tgacccagag ccctagctca ctgagcgcca gcgtgggcga cagggtgacc      60

attacctgct ccgccagcca ggacatcagc aactacctga actggtacca gcagaagccc     120

ggcaaggccc ccaagctgct gatctactac acctccaacc tgcactccgg cgtgcccagc     180

aggttcagcg gaagcggcag cggcaccgat tacaccctga ccatctccag cctgcagccc     240

gaggacttcg ccacctacta ctgccagcag tacaggaagc tcccctggac tttcggccag     300

ggcaccaaac tggagatcaa gcgtacggtg gccgccccca gcgtgttcat cttccccccc     360

agcgatgagc agctgaagag cggcaccgcc agcgtggtgt gtctgctgaa caacttctac     420

ccccgggagg ccaaggtgca gtggaaggtg gacaatgccc tgcagagcgg caacagccag     480

gagagcgtga ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac cggggcgagt gc                        642
```

<210> SEQ ID NO 67
<211> LENGTH: 214
<212> TYPE: PRT
<213> ORGANISM: Artificial Sequence
<220> FEATURE:
<223> OTHER INFORMATION: Humansed antibody sequence

<400> SEQUENCE: 67

```
Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Glu Leu Val Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 642
<212> TYPE: DNA
<213> ORGANISM: Artificial Sequence
<220> FEATURE:
<223> OTHER INFORMATION: Humansed antibody sequence

<400> SEQUENCE: 68
gacatccagc tgacccagag ccctagctca ctgagcgcca gcgtgggcga cagggtgacc 60
attacctgct ccgccagcca ggacatcagc aactacctga actggtacca gcagaagccc 120
ggcaaggccc ccgagctggt gatctactac acctccaacc tgcactccgg cgtgcccagc 180
aggttcagcg gaagcggcag cggcaccgat tacaccctga ccatctccag cctgcagccc 240
gaggacttcg ccacctacta ctgccagcag tacaggaagc tcccctggac tttcggccag 300
ggcaccaaac tggagatcaa gcgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 69
<211> LENGTH: 115
<212> TYPE: PRT
<213> ORGANISM: mus musculus

<400> SEQUENCE: 69

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Tyr Met Lys Trp Val Lys Gln Ser His Gly Lys Ser Leu Glu Trp Ile
35 40 45

Gly Glu Ile Tyr Pro Asn Asn Gly Gly Ile Thr Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Asn Gly Tyr Glu Phe Val Tyr Trp Gly Gln Gly Thr Leu Val Thr
100 105 110

Val Ser Ala
115

<210> SEQ ID NO 70
<211> LENGTH: 345
<212> TYPE: DNA
<213> ORGANISM: mus musculus

<400> SEQUENCE: 70
gaggtccagt tgcaacaatc tggacctgag ctggtgaagc ctggggcttc agtgaagata 60
tcctgtaagg cttctggata cacattcact gactactaca tgaagtgggt gaagcagagc 120
catggaaaga gccttgagtg gattggagag atttatccta ataatggtgg tattacctac 180
aaccagaagt tcaagggcaa ggccacattg actgtagaca agtcctccag cacagcctac 240

```
atggagctcc gcagcctgac atctgaggac tctgcagtct attactgtgc aaatggttac    300

gagtttgttt actggggcca agggactctg gtcactgtct ctgca                    345


<210> SEQ ID NO 71
<211> LENGTH: 108
<212> TYPE: PRT
<213> ORGANISM: mus musculus

<400> SEQUENCE: 71

Asp Ile Gln Met Thr Gln Thr Ala Ser Ser Leu Ser Ala Ser Leu Gly
 1               5                  10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg
            100                 105


<210> SEQ ID NO 72
<211> LENGTH: 324
<212> TYPE: DNA
<213> ORGANISM: mus musculus

<400> SEQUENCE: 72

gatatccaga tgacacagac tgcatcctcc ctgtctgcct ctctgggaga cagagtcacc     60

atcagttgca gtgcaagtca gggcattagc aattatttaa actggtatca gcagaaacca    120

gatggaactg ttaaactcct gatctattac acatcaagtt tacactcagg agtcccatca    180

aggttcagtg gcagtgggtc tgggacagat tattctctca ccatcagcaa cctggaacct    240

gaagatattg ccacttacta ttgtcagcag tatagtaagc ttccgtggac gttcggtgga    300

ggcaccaagc tggaaatcaa acgg                                           324


<210> SEQ ID NO 73
<211> LENGTH: 445
<212> TYPE: PRT
<213> ORGANISM: Artificial Sequence
<220> FEATURE:
<223> OTHER INFORMATION: Chimeric antibody sequence

<400> SEQUENCE: 73

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Glu Ile Tyr Pro Asn Asn Gly Gly Ile Thr Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Ala Asn Gly Tyr Glu Phe Val Tyr Trp Gly Gln Gly Thr Leu Val Thr
            100                 105                 110

Val Ser Ala Ala Lys Thr Thr Ala Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 74
<211> LENGTH: 1335
<212> TYPE: DNA
<213> ORGANISM: Artificial Sequence
<220> FEATURE:
<223> OTHER INFORMATION: Chimeric antibody sequence

<400> SEQUENCE: 74
gaggtccagt tgcaacaatc tggacctgag ctggtgaagc ctggggcttc agtgaagata 60
tcctgtaagg cttctggata cacattcact gactactaca tgaagtgggt gaagcagagc 120
catggaaaga gccttgagtg gattggagag atttatccta ataatggtgg tattacctac 180
aaccagaagt tcaagggcaa ggccacattg actgtagaca agtcctccag cacagcctac 240
atggagctcc gcagcctgac atctgaggac tctgcagtct attactgtgc aaatggttac 300
gagtttgttt actggggcca agggactctg gtcactgtct ctgcagccaa aacaacagcc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gccccccctg ccctgccccc gagctgctgg gaggccccag cgtgttcctg 720
ttccccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

<210> SEQ ID NO 75
<211> LENGTH: 214
<212> TYPE: PRT
<213> ORGANISM: Artificial Sequence
<220> FEATURE:
<223> OTHER INFORMATION: Chimeric antibody sequence

<400> SEQUENCE: 75

Asp Ile Gln Met Thr Gln Thr Ala Ser Ser Leu Ser Ala Ser Leu Gly
1 5 10 15

Asp Arg Val Thr Ile Ser Cys Ser Ala Ser Gln Gly Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Ser Leu His Ser Gly Val Pro Ser Arg Phe Ser Gly
50 55 60

Ser Gly Ser Gly Thr Asp Tyr Ser Leu Thr Ile Ser Asn Leu Glu Pro
65 70 75 80

Glu Asp Ile Ala Thr Tyr Tyr Cys Gln Gln Tyr Ser Lys Leu Pro Trp
85 90 95

Thr Phe Gly Gly Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 76
<211> LENGTH: 642
<212> TYPE: DNA
<213> ORGANISM: Artificial Sequence
<220> FEATURE:
<223> OTHER INFORMATION: Chimeric antibody sequence

<400> SEQUENCE: 76

gatatccaga tgacacagac tgcatcctcc ctgtctgcct ctctgggaga cagagtcacc      60

atcagttgca gtgcaagtca gggcattagc aattatttaa actggtatca gcagaaacca     120

gatggaactg ttaaactcct gatctattac acatcaagtt tacactcagg agtcccatca     180

aggttcagtg gcagtgggtc tgggacagat tattctctca ccatcagcaa cctggaacct     240

gaagatattg ccacttacta ttgtcagcag tatagtaagc ttccgtggac gttcggtgga     300

ggcaccaagc tggagctgaa acgtacggtg gccgccccca gcgtgttcat cttccccccc     360

agcgatgagc agctgaagag cggcaccgcc agcgtggtgt gtctgctgaa caacttctac     420

ccccgggagg ccaaggtgca gtggaaggtg gacaatgccc tgcagagcgg caacagccag     480

gagagcgtga ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac cggggcgagt gc                        642


<210> SEQ ID NO 77
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 77

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Glu Ile Tyr Pro Asn Asn Gly Gly Ile Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Gly Tyr Glu Phe Val Tyr Trp Gly Gln Gly Thr Leu Val Thr
            100                 105                 110

Val Ser Ser
        115


<210> SEQ ID NO 78
<211> LENGTH: 345
<212> TYPE: DNA
<213> ORGANISM: Artificial Sequence
<220> FEATURE:
<223> OTHER INFORMATION: Humansed antibody sequence

<400> SEQUENCE: 78

caggtgcagc tggtgcagag cggcgccgaa gtgaagaagc ccggctccag cgtgaaggtg      60

agctgcaagg ctagcggcgg caccttcagc gactactaca tgaagtgggt gaggcaggcc     120

cccggccagg gactggagtg gatgggcgag atctacccca acaacggggg catcacctac     180

aaccagaagt tcaagggcag ggtgaccatc accgccgaca aaagcaccag caccgcctac     240

atggaactga gcagcctgag gagcgaggac accgccgtgt actactgcgc caggggctac     300

gagttcgtgt attggggcca gggcacacta gtgaccgtgt ccagc                     345


<210> SEQ ID NO 79
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 79

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Met
        35                  40                  45

Gly Glu Ile Tyr Pro Asn Asn Gly Gly Ile Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Glu Phe Val Tyr Trp Gly Gln Gly Thr Leu Val Thr
            100                 105                 110

Val Ser Ser
        115


<210> SEQ ID NO 80
<211> LENGTH: 345
<212> TYPE: DNA
<213> ORGANISM: Artificial Sequence
<220> FEATURE:
<223> OTHER INFORMATION: Humansed antibody sequence

<400> SEQUENCE: 80

caggtgcagc tggtgcagag cggcgccgaa gtgaagaagc ccggctccag cgtgaaggtg      60

agctgcaagg ctagcggcta caccttcacc gactactaca tgaagtgggt gaggcaggcc     120

cccggccagg gactggagtg gatgggcgag atctacccca acaacggggg catcacctac     180

aaccagaagt tcaagggcag ggtgaccatc accgccgaca aaagcaccag caccgcctac     240
```

atggaactga gcagcctgag gagcgaggac accgccgtgt actactgcgc caggggctac 300
gagttcgtgt attggggcca gggcacacta gtgaccgtgt ccagc 345

<210> SEQ ID NO 81
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 81

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Met
35 40 45

Gly Glu Ile Tyr Pro Asn Asn Gly Gly Ile Thr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Asn Gly Tyr Glu Phe Val Tyr Trp Gly Gln Gly Thr Leu Val Thr
100 105 110

Val Ser Ser
115

<210> SEQ ID NO 82
<211> LENGTH: 345
<212> TYPE: DNA
<213> ORGANISM: Artificial Sequence
<220> FEATURE:
<223> OTHER INFORMATION: Humansed antibody sequence

<400> SEQUENCE: 82
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc caacggctac 300
gagttcgtgt attggggcca gggcacacta gtgaccgtgt ccagc 345

<210> SEQ ID NO 83
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 83

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Ile
35 40 45

```
Gly Glu Ile Tyr Pro Asn Asn Gly Gly Ile Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Tyr Glu Phe Val Tyr Trp Gly Gln Gly Thr Leu Val Thr
            100                 105                 110

Val Ser Ser
        115


<210> SEQ ID NO 84
<211> LENGTH: 345
<212> TYPE: DNA
<213> ORGANISM: Artificial Sequence
<220> FEATURE:
<223> OTHER INFORMATION: Humansed antibody sequence

<400> SEQUENCE: 84

caggtgcagc tggtgcagag cggcgccgaa gtgaagaagc ccggctccag cgtgaaggtg      60

agctgcaagg ctagcggcta caccttcacc gactactaca tgaagtgggt gaggcaggcc     120

cccggccagg gactggagtg gataggcgag atctacccca acaacggggg catcacctac     180

aaccagaagt tcaagggcag ggcgaccctc accgtcgaca aaagcaccag caccgcctac     240

atggaactga gcagcctgag gagcgaggac accgccgtgt actactgcgc caacggctac     300

gagttcgtgt attggggcca gggcacacta gtgaccgtgt ccagc                     345


<210> SEQ ID NO 85
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 85

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Met
        35                  40                  45

Gly Glu Ile Tyr Pro Asn Asn Gly Gly Ile Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Tyr Glu Phe Val Tyr Trp Gly Gln Gly Thr Leu Val Thr
            100                 105                 110

Val Ser Ser
        115


<210> SEQ ID NO 86
<211> LENGTH: 345
<212> TYPE: DNA
<213> ORGANISM: Artificial Sequence
<220> FEATURE:
<223> OTHER INFORMATION: Humansed antibody sequence
```

<400> SEQUENCE: 86
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc cgacggctac 300
gagttcgtgt attggggcca gggcacacta gtgaccgtgt ccagc 345

<210> SEQ ID NO 87
<211> LENGTH: 115
<212> TYPE: PRT
<213> ORGANISM: Artificial Sequence
<220> FEATURE:
<223> OTHER INFORMATION: Humansed antibody sequence

<400> SEQUENCE: 87

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Ile
35 40 45

Gly Glu Ile Tyr Pro Asn Asn Gly Gly Ile Thr Tyr Asn Gln Lys Phe
50 55 60

Lys Gly Arg Ala Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Asn Gly Tyr Glu Phe Asp Tyr Trp Gly Gln Gly Thr Leu Val Thr
100 105 110

Val Ser Ser
115

<210> SEQ ID NO 88
<211> LENGTH: 345
<212> TYPE: DNA
<213> ORGANISM: Artificial Sequence
<220> FEATURE:
<223> OTHER INFORMATION: Humansed antibody sequence

<400> SEQUENCE: 88
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gataggcgag atctacccca acaacggggg catcacctac 180
aaccagaagt tcaagggcag ggcgaccctc accgtcgaca aaagcaccag caccgcctac 240
atggaactga gcagcctgag gagcgaggac accgccgtgt actactgcgc caacggctac 300
gagttcgact attggggcca gggcacacta gtgaccgtgt ccagc 345

<210> SEQ ID NO 89
<211> LENGTH: 108
<212> TYPE: PRT
<213> ORGANISM: Artificial Sequence
<220> FEATURE:
<223> OTHER INFORMATION: Humansed antibody sequence

<400> SEQUENCE: 89

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Leu Glu Ile Lys Arg
            100                 105
```

<210> SEQ ID NO 90
<211> LENGTH: 324
<212> TYPE: DNA
<213> ORGANISM: Artificial Sequence
<220> FEATURE:
<223> OTHER INFORMATION: Humansed antibody sequence

<400> SEQUENCE: 90

```
gacatccaga tgacccagag cccctcaagc ctgagcgcca gcgtgggcga cagggtgact      60

atcacctgca gcgcctccca gggcatcagc aactacctga actggtacca gcagaagccc     120

ggcaaggccc ctaagctgct gatctactac accagcagcc tgcacagcgg cgtgcccagc     180

aggttctccg gcagcggcag cggaaccgac ttcaccctga ccattagcag cctccagccc     240

gaggacttcg ccacctacta ctgccagcag tacagcaagc tgccctggac cttcggccag     300

ggcaccaaac tggagatcaa gcgt                                            324
```

<210> SEQ ID NO 91
<211> LENGTH: 108
<212> TYPE: PRT
<213> ORGANISM: Artificial Sequence
<220> FEATURE:
<223> OTHER INFORMATION: Humansed antibody sequence

<400> SEQUENCE: 91

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Leu Glu Ile Lys Arg
            100                 105
```

<210> SEQ ID NO 92
<211> LENGTH: 324

<212> TYPE: DNA
<213> ORGANISM: Artificial Sequence
<220> FEATURE:
<223> OTHER INFORMATION: Humansed antibody sequence

<400> SEQUENCE: 92
gacatccaga tgacccagag cccctcaagc ctgagcgcca gcgtgggcga cagggtgact 60
atcacctgca gcgcctccca gggcatcagc aactacctga actggtacca gcagaagccc 120
ggcaaggccc ctaagctgct gatctactac accagcagcc tgcacagcgg cgtgcccagc 180
aggttctccg gcagcggcag cggaaccgac tacaccctga ccattagcag cctccagccc 240
gaggacttcg ccacctacta ctgccagcag tacagcaagc tgccctggac cttcggccag 300
ggcaccaaac tggagatcaa gcgt 324

<210> SEQ ID NO 93
<211> LENGTH: 5
<212> TYPE: PRT
<213> ORGANISM: mus musculus

<400> SEQUENCE: 93

Asp Tyr Tyr Met Lys
1 5

<210> SEQ ID NO 94
<211> LENGTH: 17
<212> TYPE: PRT
<213> ORGANISM: mus musculus

<400> SEQUENCE: 94

Glu Ile Tyr Pro Asn Asn Gly Gly Ile Thr Tyr Asn Gln Lys Phe Lys
1 5 10 15

Gly

<210> SEQ ID NO 95
<211> LENGTH: 6
<212> TYPE: PRT
<213> ORGANISM: mus musculus

<400> SEQUENCE: 95

Gly Tyr Glu Phe Val Tyr
1 5

<210> SEQ ID NO 96
<211> LENGTH: 11
<212> TYPE: PRT
<213> ORGANISM: mus musculus

<400> SEQUENCE: 96

Ser Ala Ser Gln Gly Ile Ser Asn Tyr Leu Asn
1 5 10

<210> SEQ ID NO 97
<211> LENGTH: 7
<212> TYPE: PRT
<213> ORGANISM: mus musculus

<400> SEQUENCE: 97

Tyr Thr Ser Ser Leu His Ser
1 5

<210> SEQ ID NO 98
<211> LENGTH: 9

<212> TYPE: PRT
<213> ORGANISM: mus musculus

<400> SEQUENCE: 98

Gln Gln Tyr Ser Lys Leu Pro Trp Thr
1 5

<210> SEQ ID NO 99
<211> LENGTH: 6
<212> TYPE: PRT
<213> ORGANISM: Artificial Sequence
<220> FEATURE:
<223> OTHER INFORMATION: Humansed antibody sequence

<400> SEQUENCE: 99

Gly Tyr Glu Phe Asp Tyr
1 5

<210> SEQ ID NO 100
<211> LENGTH: 445
<212> TYPE: PRT
<213> ORGANISM: Artificial Sequence
<220> FEATURE:
<223> OTHER INFORMATION: Humansed antibody sequence

<400> SEQUENCE: 100

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asp Tyr
20 25 30

Tyr Met Lys Trp Val Arg Gln Ala Pro Gly Gln Gly Leu Glu Trp Met
35 40 45

Gly Glu Ile Tyr Pro Asn Asn Gly Gly Ile Thr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Tyr Glu Phe Val Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

```
Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 101
<211> LENGTH: 1335
<212> TYPE: DNA
<213> ORGANISM: Artificial Sequence
<220> FEATURE:
<223> OTHER INFORMATION: Humansed antibody sequence

<400> SEQUENCE: 101

caggtgcagc tggtgcagag cggcgccgaa gtgaagaagc ccggctccag cgtgaaggtg     60

agctgcaagg ctagcggcgg caccttcagc gactactaca tgaagtgggt gaggcaggcc    120

cccggccagg gactggagtg gatgggcgag atctacccca acaacggggg catcacctac    180

aaccagaagt tcaagggcag ggtgaccatc accgccgaca aaagcaccag caccgcctac    240

atggaactga gcagcctgag gagcgaggac accgccgtgt actactgcgc caggggctac    300

gagttcgtgt attggggcca gggcacacta gtgaccgtgt ccagcgccag caccaagggc    360

cccagcgtgt tccccctggc ccccagcagc aagagcacca gcggcggcac agccgccctg    420

ggctgcctgg tgaaggacta cttccccgaa ccggtgaccg tgtcctggaa cagcggagcc    480

ctgaccagcg gcgtgcacac cttccccgcc gtgctgcaga gcagcggcct gtacagcctg    540

agcagcgtgg tgaccgtgcc cagcagcagc ctgggcaccc agacctacat ctgtaacgtg    600

aaccacaagc ccagcaacac caaggtggac aagaaggtgg agcccaagag ctgtgacaag    660

acccacacct gccccccctg ccctgccccc gagctgctgg gaggccccag cgtgttcctg    720

ttccccccca agcctaagga caccctgatg atcagcagaa cccccgaggt gacctgtgtg    780

gtggtggatg tgagccacga ggaccctgag gtgaagttca actggtacgt ggacggcgtg    840

gaggtgcaca atgccaagac caagcccagg gaggagcagt acaacagcac ctaccgggtg    900

gtgtccgtgc tgaccgtgct gcaccaggat tggctgaacg gcaaggagta caagtgtaag    960

gtgtccaaca aggccctgcc tgcccctatc gagaaaacca tcagcaaggc caagggccag   1020
```

```
cccagagagc cccaggtgta caccctgccc cctagcagag atgagctgac caagaaccag   1080

gtgtccctga cctgcctggt gaagggcttc taccccagcg acatcgccgt ggagtgggag   1140

agcaacggcc agcccgagaa caactacaag accaccccccc ctgtgctgga cagcgatggc   1200

agcttcttcc tgtacagcaa gctgaccgtg gacaagagca gatggcagca gggcaacgtg   1260

ttcagctgct ccgtgatgca cgaggccctg cacaatcact acacccagaa gagcctgagc   1320

ctgtcccctg gcaag                                                    1335
```

<210> SEQ ID NO 102
<211> LENGTH: 445
<212> TYPE: PRT
<213> ORGANISM: Artificial Sequence
<220> FEATURE:
<223> OTHER INFORMATION: Humansed antibody sequence

<400> SEQUENCE: 102

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Met
        35                  40                  45

Gly Glu Ile Tyr Pro Asn Asn Gly Gly Ile Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Glu Phe Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Asp Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 103
<211> LENGTH: 1335
<212> TYPE: DNA
<213> ORGANISM: Artificial Sequence
<220> FEATURE:
<223> OTHER INFORMATION: Humansed antibody sequence

<400> SEQUENCE: 103
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc caggggctac 300
gagttcgtgt attggggcca gggcacacta gtgaccgtgt ccagcgccag caccaagggc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gccccccctg ccctgccccc gagctgctgg gaggccccag cgtgttcctg 720
ttccccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

<210> SEQ ID NO 104
<211> LENGTH: 445
<212> TYPE: PRT
<213> ORGANISM: Artificial Sequence
<220> FEATURE:
<223> OTHER INFORMATION: Humansed antibody sequence

<400> SEQUENCE: 104

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Met
35 40 45

Gly Glu Ile Tyr Pro Asn Asn Gly Gly Ile Thr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Asn Gly Tyr Glu Phe Val Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser

```
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 105
<211> LENGTH: 1335
<212> TYPE: DNA
<213> ORGANISM: Artificial Sequence
<220> FEATURE:
<223> OTHER INFORMATION: Humansed antibody sequence

<400> SEQUENCE: 105

```
caggtgcagc tggtgcagag cggcgccgaa gtgaagaagc ccggctccag cgtgaaggtg     60

agctgcaagg ctagcggcta caccttcacc gactactaca tgaagtgggt gaggcaggcc    120

cccggccagg gactggagtg gatgggcgag atctacccca acaacggggg catcacctac    180

aaccagaagt tcaagggcag ggtgaccatc accgccgaca aaagcaccag caccgcctac    240

atggaactga gcagcctgag gagcgaggac accgccgtgt actactgcgc caacggctac    300

gagttcgtgt attggggcca gggcacacta gtgaccgtgt ccagcgccag caccaagggc    360

cccagcgtgt tcccccctggc ccccagcagc aagagcacca gcggcggcac agccgccctg    420

ggctgcctgg tgaaggacta cttccccgaa ccggtgaccg tgtcctggaa cagcggagcc    480

ctgaccagcg gcgtgcacac cttccccgcc gtgctgcaga gcagcggcct gtacagcctg    540

agcagcgtgg tgaccgtgcc cagcagcagc ctgggcaccc agacctacat ctgtaacgtg    600

aaccacaagc ccagcaacac caaggtggac aagaaggtgg agcccaagag ctgtgacaag    660

acccacacct gccccccctg ccctgccccc gagctgctgg gaggccccag cgtgttcctg    720

ttccccccca agcctaagga caccctgatg atcagcagaa cccccgaggt gacctgtgtg    780

gtggtggatg tgagccacga ggaccctgag gtgaagttca actggtacgt ggacggcgtg    840

gaggtgcaca atgccaagac caagcccagg gaggagcagt acaacagcac ctaccgggtg    900

gtgtccgtgc tgaccgtgct gcaccaggat tggctgaacg gcaaggagta caagtgtaag    960

gtgtccaaca aggccctgcc tgcccctatc gagaaaacca tcagcaaggc caagggccag   1020

cccagagagc cccaggtgta caccctgccc cctagcagag atgagctgac caagaaccag   1080

gtgtccctga cctgcctggt gaagggcttc taccccagcg acatcgccgt ggagtgggag   1140

agcaacggcc agcccgagaa caactacaag accacccccc ctgtgctgga cagcgatggc   1200

agcttcttcc tgtacagcaa gctgaccgtg gacaagagca gatggcagca gggcaacgtg   1260

ttcagctgct ccgtgatgca cgaggccctg cacaatcact acacccagaa gagcctgagc   1320

ctgtcccctg gcaag                                                    1335
```

<210> SEQ ID NO 106
<211> LENGTH: 445

<212> TYPE: PRT
<213> ORGANISM: Artificial Sequence
<220> FEATURE:
<223> OTHER INFORMATION: Humansed antibody sequence

<400> SEQUENCE: 106

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Ile
        35                  40                  45

Gly Glu Ile Tyr Pro Asn Asn Gly Gly Ile Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Tyr Glu Phe Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

```
<210> SEQ ID NO 107
<211> LENGTH: 1335
<212> TYPE: DNA
<213> ORGANISM: Artificial Sequence
<220> FEATURE:
<223> OTHER INFORMATION: Humansed antibody sequence

<400> SEQUENCE: 107

caggtgcagc tggtgcagag cggcgccgaa gtgaagaagc ccggctccag cgtgaaggtg     60

agctgcaagg ctagcggcta caccttcacc gactactaca tgaagtgggt gaggcaggcc    120

cccggccagg gactggagtg gataggcgag atctacccca acaacggggg catcacctac    180

aaccagaagt tcaagggcag ggcgaccctc accgtcgaca aaagcaccag caccgcctac    240

atggaactga gcagcctgag gagcgaggac accgccgtgt actactgcgc caacggctac    300

gagttcgtgt attggggcca gggcacacta gtgaccgtgt ccagcgccag caccaagggc    360

cccagcgtgt tccccctggc ccccagcagc aagagcacca gcggcggcac agccgccctg    420

ggctgcctgg tgaaggacta cttccccgaa ccggtgaccg tgtcctggaa cagcggagcc    480

ctgaccagcg gcgtgcacac cttccccgcc gtgctgcaga gcagcggcct gtacagcctg    540

agcagcgtgg tgaccgtgcc cagcagcagc ctgggcaccc agacctacat ctgtaacgtg    600

aaccacaagc ccagcaacac caaggtggac aagaaggtgg agcccaagag ctgtgacaag    660

acccacacct gccccccctg ccctgccccc gagctgctgg gaggccccag cgtgttcctg    720

ttccccccca agcctaagga caccctgatg atcagcagaa cccccgaggt gacctgtgtg    780

gtggtggatg tgagccacga ggaccctgag gtgaagttca actggtacgt ggacggcgtg    840

gaggtgcaca atgccaagac caagcccagg gaggagcagt acaacagcac ctaccgggtg    900

gtgtccgtgc tgaccgtgct gcaccaggat tggctgaacg gcaaggagta caagtgtaag    960

gtgtccaaca aggccctgcc tgcccctatc gagaaaacca tcagcaaggc caagggccag   1020

cccagagagc cccaggtgta caccctgccc cctagcagag atgagctgac caagaaccag   1080

gtgtccctga cctgcctggt gaagggcttc taccccagcg acatcgccgt ggagtgggag   1140

agcaacggcc agcccgagaa caactacaag accacccccc ctgtgctgga cagcgatggc   1200

agcttcttcc tgtacagcaa gctgaccgtg gacaagagca gatggcagca gggcaacgtg   1260

ttcagctgct ccgtgatgca cgaggccctg cacaatcact acacccagaa gagcctgagc   1320

ctgtcccctg gcaag                                                    1335
```

```
<210> SEQ ID NO 108
<211> LENGTH: 445
<212> TYPE: PRT
<213> ORGANISM: Artificial Sequence
<220> FEATURE:
<223> OTHER INFORMATION: Humansed antibody sequence

<400> SEQUENCE: 108

Gln Val Gln Leu Val Gln Ser Gly Ala Glu Val Lys Lys Pro Gly Ser
```

-continued

```
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Met
        35                  40                  45

Gly Glu Ile Tyr Pro Asn Asn Gly Gly Ile Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Tyr Glu Phe Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
435 440 445

<210> SEQ ID NO 109
<211> LENGTH: 1335
<212> TYPE: DNA
<213> ORGANISM: Artificial Sequence
<220> FEATURE:
<223> OTHER INFORMATION: Humansed antibody sequence

<400> SEQUENCE: 109
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gatgggcgag atctacccca acaacggggg catcacctac 180
aaccagaagt tcaagggcag ggtgaccatc accgccgaca aaagcaccag caccgcctac 240
atggaactga gcagcctgag gagcgaggac accgccgtgt actactgcgc cgacggctac 300
gagttcgtgt attggggcca gggcacacta gtgaccgtgt ccagcgccag caccaagggc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gccccccctg ccctgccccc gagctgctgg gaggccccag cgtgttcctg 720
ttccccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

<210> SEQ ID NO 110
<211> LENGTH: 445
<212> TYPE: PRT
<213> ORGANISM: Artificial Sequence
<220> FEATURE:
<223> OTHER INFORMATION: Humansed antibody sequence

<400> SEQUENCE: 110

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Ile
35 40 45

```
Gly Glu Ile Tyr Pro Asn Asn Gly Gly Ile Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Tyr Glu Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 111
<211> LENGTH: 1335
<212> TYPE: DNA

<213> ORGANISM: Artificial Sequence
<220> FEATURE:
<223> OTHER INFORMATION: Humansed antibody sequence

<400> SEQUENCE: 111
caggtgcagc tggtgcagag cggcgccgaa gtgaagaagc ccggctccag cgtgaaggtg 60
agctgcaagg ctagcggcta caccttcacc gactactaca tgaagtgggt gaggcaggcc 120
cccggccagg gactggagtg gataggcgag atctacccca acaacggggg catcacctac 180
aaccagaagt tcaagggcag ggcgaccctc accgtcgaca aaagcaccag caccgcctac 240
atggaactga gcagcctgag gagcgaggac accgccgtgt actactgcgc caacggctac 300
gagttcgact attggggcca gggcacacta gtgaccgtgt ccagcgccag caccaagggc 360
cccagcgtgt tccccctggc ccccagcagc aagagcacca gcggcggcac agccgccctg 420
ggctgcctgg tgaaggacta cttccccgaa ccggtgaccg tgtcctggaa cagcggagcc 480
ctgaccagcg gcgtgcacac cttccccgcc gtgctgcaga gcagcggcct gtacagcctg 540
agcagcgtgg tgaccgtgcc cagcagcagc ctgggcaccc agacctacat ctgtaacgtg 600
aaccacaagc ccagcaacac caaggtggac aagaaggtgg agcccaagag ctgtgacaag 660
acccacacct gccccccctg ccctgccccc gagctgctgg gaggccccag cgtgttcctg 720
ttccccccca agcctaagga caccctgatg atcagcagaa cccccgaggt gacctgtgtg 780
gtggtggatg tgagccacga ggaccctgag gtgaagttca actggtacgt ggacggcgtg 840
gaggtgcaca atgccaagac caagcccagg gaggagcagt acaacagcac ctaccgggtg 900
gtgtccgtgc tgaccgtgct gcaccaggat tggctgaacg gcaaggagta caagtgtaag 960
gtgtccaaca aggccctgcc tgcccctatc gagaaaacca tcagcaaggc caagggccag 1020
cccagagagc cccaggtgta caccctgccc cctagcagag atgagctgac caagaaccag 1080
gtgtccctga cctgcctggt gaagggcttc taccccagcg acatcgccgt ggagtgggag 1140
agcaacggcc agcccgagaa caactacaag accacccccc ctgtgctgga cagcgatggc 1200
agcttcttcc tgtacagcaa gctgaccgtg gacaagagca gatggcagca gggcaacgtg 1260
ttcagctgct ccgtgatgca cgaggccctg cacaatcact acacccagaa gagcctgagc 1320
ctgtcccctg gcaag 1335

<210> SEQ ID NO 112
<211> LENGTH: 214
<212> TYPE: PRT
<213> ORGANISM: Artificial Sequence
<220> FEATURE:
<223> OTHER INFORMATION: Humansed antibody sequence

<400> SEQUENCE: 112

Asp Ile Gln Met Thr Gln Ser Pro Ser Ser Leu Ser Ala Ser Val Gly
1 5 10 15

Asp Arg Val Thr Ile Thr Cys Ser Ala Ser Gln Gly Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Lys Leu Pro Trp
85 90 95

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 113
<211> LENGTH: 642
<212> TYPE: DNA
<213> ORGANISM: Artificial Sequence
<220> FEATURE:
<223> OTHER INFORMATION: Humansed antibody sequence

<400> SEQUENCE: 113

gacatccaga tgacccagag cccctcaagc ctgagcgcca gcgtgggcga cagggtgact      60

atcacctgca gcgcctccca gggcatcagc aactacctga actggtacca gcagaagccc     120

ggcaaggccc ctaagctgct gatctactac accagcagcc tgcacagcgg cgtgcccagc     180

aggttctccg gcagcggcag cggaaccgac ttcaccctga ccattagcag cctccagccc     240

gaggacttcg ccacctacta ctgccagcag tacagcaagc tgccctggac cttcggccag     300

ggcaccaaac tggagatcaa gcgtacggtg gccgccccca gcgtgttcat cttccccccc     360

agcgatgagc agctgaagag cggcaccgcc agcgtggtgt gtctgctgaa caacttctac     420

ccccgggagg ccaaggtgca gtggaaggtg gacaatgccc tgcagagcgg caacagccag     480

gagagcgtga ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac cggggcgagt gc                        642


<210> SEQ ID NO 114
<211> LENGTH: 214
<212> TYPE: PRT
<213> ORGANISM: Artificial Sequence
<220> FEATURE:
<223> OTHER INFORMATION: Humansed antibody sequence

<400> SEQUENCE: 114

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 115
<211> LENGTH: 642
<212> TYPE: DNA
<213> ORGANISM: Artificial Sequence
<220> FEATURE:
<223> OTHER INFORMATION: Humansed antibody sequence

<400> SEQUENCE: 115

gacatccaga tgacccagag cccctcaagc ctgagcgcca gcgtgggcga cagggtgact      60

atcacctgca gcgcctccca gggcatcagc aactacctga actggtacca gcagaagccc     120

ggcaaggccc ctaagctgct gatctactac accagcagcc tgcacagcgg cgtgcccagc     180

aggttctccg gcagcggcag cggaaccgac tacaccctga ccattagcag cctccagccc     240

gaggacttcg ccacctacta ctgccagcag tacagcaagc tgccctggac cttcggccag     300

ggcaccaaac tggagatcaa gcgtacggtg gccgccccca gcgtgttcat cttccccccc     360

agcgatgagc agctgaagag cggcaccgcc agcgtggtgt gtctgctgaa caacttctac     420

ccccgggagg ccaaggtgca gtggaaggtg gacaatgccc tgcagagcgg caacagccag     480

gagagcgtga ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac cggggcgagt gc                        642


<210> SEQ ID NO 116
<211> LENGTH: 118
<212> TYPE: PRT
<213> ORGANISM: mus musculus

<400> SEQUENCE: 116

Glu Val Gln Leu Gln Gln Ser Gly Pro Val Leu Val Lys Pro Gly Ala
1               5                   10                  15

Ser Val Lys Met Ser Cys Glu Ala Ser Gly Tyr Thr Phe Thr Asp Tyr
            20                  25                  30

Tyr Met Asn Trp Val Lys Gln Ser His Gly Lys Thr Leu Glu Trp Ile
        35                  40                  45
```

```
Gly Val Ile Asn Pro Tyr Asn Gly Gly Thr Asp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Ser Val Tyr Asp Tyr Pro Phe Asp Tyr Trp Gly Gln Gly Thr
            100                 105                 110

Leu Val Thr Val Ser Ser
        115


<210> SEQ ID NO 117
<211> LENGTH: 354
<212> TYPE: DNA
<213> ORGANISM: mus musculus

<400> SEQUENCE: 117

gaggtgcagc tgcagcagag cggccccgtg ctggtgaagc ctggagccag cgtgaaaatg      60

agctgcgaag ccagcggcta caccttcacc gactactaca tgaactgggt gaagcagagc     120

cacggcaaga ccctggagtg gatcggcgtg atcaacccct acaacggggg caccgactac     180

aaccagaagt tcaagggcaa ggccactctg accgtggaca agagctccag caccgcctac     240

atggaactga acagcctcac ctctgaggac agcgccgtct attactgcgc caggagcgtg     300

tacgactacc ccttcgacta ctggggccag ggcacactag tgaccgtgtc cagc           354


<210> SEQ ID NO 118
<211> LENGTH: 448
<212> TYPE: PRT
<213> ORGANISM: Artificial Sequence
<220> FEATURE:
<223> OTHER INFORMATION: Chimeric antibody sequence

<400> SEQUENCE: 118

Glu Val Gln Leu Gln Gln Ser Gly Pro Val Leu Val Lys Pro Gly Ala
 1               5                  10                  15

Ser Val Lys Met Ser Cys Glu Ala Ser Gly Tyr Thr Phe Thr Asp Tyr
            20                  25                  30

Tyr Met Asn Trp Val Lys Gln Ser His Gly Lys Thr Leu Glu Trp Ile
        35                  40                  45

Gly Val Ile Asn Pro Tyr Asn Gly Gly Thr Asp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Ser Val Tyr Asp Tyr Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 119
<211> LENGTH: 1344
<212> TYPE: DNA
<213> ORGANISM: Artificial Sequence
<220> FEATURE:
<223> OTHER INFORMATION: Chimeric antibody sequence

<400> SEQUENCE: 119
gaggtgcagc tgcagcagag cggccccgtg ctggtgaagc ctggagccag cgtgaaaatg 60
agctgcgaag ccagcggcta caccttcacc gactactaca tgaactgggt gaagcagagc 120
cacggcaaga ccctggagtg gatcggcgtg atcaacccct acaacggggg caccgactac 180
aaccagaagt tcaagggcaa ggccactctg accgtggaca agagctccag caccgcctac 240
atggaactga acagcctcac ctctgaggac agcgccgtct attactgcgc caggagcgtg 300
tacgactacc ccttcgacta ctggggccag ggcacactag tgaccgtgtc cagcgccagc 360
accaagggcc ccagcgtgtt ccccctggcc cccagcagca agagcaccag cggcggcaca 420
gccgccctgg gctgcctggt gaaggactac ttccccgaac cggtgaccgt gtcctggaac 480
agcggagccc tgaccagcgg cgtgcacacc ttccccgccg tgctgcagag cagcggcctg 540
tacagcctga gcagcgtggt gaccgtgccc agcagcagcc tgggcaccca gacctacatc 600

```
tgtaacgtga accacaagcc cagcaacacc aaggtggaca agaaggtgga gcccaagagc    660

tgtgacaaga cccacacctg ccccccctgc cctgcccccg agctgctggg aggccccagc    720

gtgttcctgt tcccccccaa gcctaaggac accctgatga tcagcagaac ccccgaggtg    780

acctgtgtgg tggtggatgt gagccacgag gaccctgagg tgaagttcaa ctggtacgtg    840

gacggcgtgg aggtgcacaa tgccaagacc aagcccaggg aggagcagta caacagcacc    900

taccgggtgg tgtccgtgct gaccgtgctg caccaggatt ggctgaacgg caaggagtac    960

aagtgtaagg tgtccaacaa ggccctgcct gcccctatcg agaaaaccat cagcaaggcc   1020

aagggccagc cccagagagcc ccaggtgtac accctgcccc ctagcagaga tgagctgacc  1080

aagaaccagg tgtccctgac ctgcctggtg aagggcttct accccagcga catcgccgtg   1140

gagtgggaga gcaacggcca gcccgagaac aactacaaga ccaccccccc tgtgctggac   1200

agcgatggca gcttcttcct gtacagcaag ctgaccgtgg acaagagcag atggcagcag   1260

ggcaacgtgt tcagctgctc cgtgatgcac gaggccctgc acaatcacta cacccagaag   1320

agcctgagcc tgtcccctgg caag                                          1344
```

```
<210> SEQ ID NO 120
<211> LENGTH: 111
<212> TYPE: PRT
<213> ORGANISM: mus musculus

<400> SEQUENCE: 120

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Thr Tyr Phe Cys Gln Gln Ser Ile
                85                  90                  95

Glu Asp Pro Arg Thr Phe Gly Gly Gly Thr Lys Leu Glu Ile Lys
            100                 105                 110
```

```
<210> SEQ ID NO 121
<211> LENGTH: 336
<212> TYPE: DNA
<213> ORGANISM: mus musculus

<400> SEQUENCE: 121

gacatcgtcc tgacccagag ccccgccagc ctggccgtga gcctgggcca gagggccaca     60

atcagctgca gggcctctga gtccgtgagc atccacggca cccacctgat gcactggtat    120

cagcagaagc ccggccagcc tcccaagctg ctgatctacg ccgccagcaa cctggagagc    180

ggcgtgcccg ctaggttcag cggaagcggc agcgagaccg acttcaccct gaacatccac    240

cccgtggagg aggaagacgc cgccacctac ttctgccagc agagcatcga ggaccccagg    300

accttcggcg gggcaccaa gctcgagatt aagcgt                               336
```

```
<210> SEQ ID NO 122
<211> LENGTH: 237
```

<212> TYPE: PRT
<213> ORGANISM: Artificial Sequence
<220> FEATURE:
<223> OTHER INFORMATION: Chimeric antibody sequence

<400> SEQUENCE: 122

```
Met Gly Trp Ser Cys Ile Ile Leu Phe Leu Val Ala Thr Ala Thr Gly
 1               5                  10                  15

Val His Ser Asp Ile Val Leu Thr Gln Ser Pro Ala Ser Leu Ala Val
            20                  25                  30

Ser Leu Gly Gln Arg Ala Thr Ile Ser Cys Arg Ala Ser Glu Ser Val
        35                  40                  45

Ser Ile His Gly Thr His Leu Met His Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Ala Arg Phe Ser Gly Ser Gly Ser Glu Thr Asp Phe Thr Leu
                85                  90                  95

Asn Ile His Pro Val Glu Glu Glu Asp Ala Ala Thr Tyr Phe Cys Gln
            100                 105                 110

Gln Ser Ile Glu Asp Pro Arg Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 123
<211> LENGTH: 711
<212> TYPE: DNA
<213> ORGANISM: Artificial Sequence
<220> FEATURE:
<223> OTHER INFORMATION: Chimeric antibody sequence

<400> SEQUENCE: 123

```
atgggctggt cctgcatcat cctgtttctg gtggccaccg ccaccggcgt gcacagcgac     60

atcgtcctga cccagagccc cgccagcctg gccgtgagcc tgggccagag ggccacaatc    120

agctgcaggg cctctgagtc cgtgagcatc cacggcaccc acctgatgca ctggtatcag    180

cagaagcccg gccagcctcc caagctgctg atctacgccg ccagcaacct ggagagcggc    240

gtgcccgcta ggttcagcgg aagcggcagc gagaccgact tcaccctgaa catccacccc    300

gtggaggagg aagacgccgc cacctacttc tgccagcaga gcatcgagga ccccaggacc    360

ttcggcgggg gcaccaagct cgagattaag cgtacggtgg ccgcccccag cgtgttcatc    420

ttccccccca gcgatgagca gctgaagagc ggcaccgcca gcgtggtgtg tctgctgaac    480

aacttctacc cccgggaggc caaggtgcag tggaaggtgg acaatgccct gcagagcggc    540
```

aacagccagg agagcgtgac cgagcaggac agcaaggact ccacctacag cctgagcagc 600
accctgaccc tgagcaaggc cgactacgag aagcacaagg tgtacgcctg tgaggtgacc 660
caccagggcc tgtccagccc cgtgaccaag agcttcaacc ggggcgagtg c 711

<210> SEQ ID NO 124
<211> LENGTH: 119
<212> TYPE: PRT
<213> ORGANISM: mus musculus

<400> SEQUENCE: 124

Glu Val Gln Leu Gln Gln Ser Gly Pro Glu Leu Val Lys Pro Gly Thr
1 5 10 15

Ser Val Lys Ile Pro Cys Lys Thr Ser Gly Tyr Ile Phe Thr Asp Tyr
20 25 30

Ser Ile Asp Trp Val Lys Gln Ser His Gly Lys Ser Leu Glu Trp Ile
35 40 45

Gly Asp Ile Asp Pro Asn Tyr Gly Asp Pro Ile Tyr Asn His Lys Phe
50 55 60

Lys Gly Lys Ala Thr Leu Thr Val Asp Arg Ser Ser Ser Thr Ala Tyr
65 70 75 80

Met Glu Leu Arg Ser Leu Thr Ser Glu Asp Thr Ala Val Tyr Phe Cys
85 90 95

Ala Arg Arg Ala Thr Gly Thr Asp Trp Phe Ala Phe Trp Gly Gln Gly
100 105 110

Thr Leu Val Thr Val Ser Ser
115

<210> SEQ ID NO 125
<211> LENGTH: 357
<212> TYPE: DNA
<213> ORGANISM: mus musculus

<400> SEQUENCE: 125
gaggtgcagc tgcagcagag cggccccgag ctggtgaaac ccggcaccag cgtgaagatc 60
ccctgcaaga cctctggcta catcttcacc gactacagca tcgactgggt gaagcagagc 120
cacggcaagt ctctggagtg gattggggac atcgacccca actacggcga ccccatctac 180
aaccacaagt tcaagggcaa ggccaccctg accgtggaca ggagcagcag caccgcctac 240
atggaactca ggagcctgac cagcgaggac accgccgtgt atttttgcgc caggagggcc 300
accggcactg attggttcgc cttctggggc cagggcacac tagtgaccgt gtccagc 357

<210> SEQ ID NO 126
<211> LENGTH: 449
<212> TYPE: PRT
<213> ORGANISM: Artificial Sequence
<220> FEATURE:
<223> OTHER INFORMATION: Chimeric antibody sequence

<400> SEQUENCE: 126

Glu Val Gln Leu Gln Gln Ser Gly Pro Glu Leu Val Lys Pro Gly Thr
1 5 10 15

Ser Val Lys Ile Pro Cys Lys Thr Ser Gly Tyr Ile Phe Thr Asp Tyr
20 25 30

Ser Ile Asp Trp Val Lys Gln Ser His Gly Lys Ser Leu Glu Trp Ile
35 40 45

Gly Asp Ile Asp Pro Asn Tyr Gly Asp Pro Ile Tyr Asn His Lys Phe

```
    50                  55                  60

Lys Gly Lys Ala Thr Leu Thr Val Asp Arg Ser Ser Ser Thr Ala Tyr
65                  70                  75                  80

Met Glu Leu Arg Ser Leu Thr Ser Glu Asp Thr Ala Val Tyr Phe Cys
                85                  90                  95

Ala Arg Arg Ala Thr Gly Thr Asp Trp Phe Ala Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 127
<211> LENGTH: 1347
```

<212> TYPE: DNA
<213> ORGANISM: Artificial Sequence
<220> FEATURE:
<223> OTHER INFORMATION: Chimeric antibody sequence

<400> SEQUENCE: 127
gaggtgcagc tgcagcagag cggccccgag ctggtgaaac ccggcaccag cgtgaagatc 60
ccctgcaaga cctctggcta catcttcacc gactacagca tcgactgggt gaagcagagc 120
cacggcaagt ctctggagtg gattggggac atcgacccca actacggcga ccccatctac 180
aaccacaagt tcaagggcaa ggccaccctg accgtggaca ggagcagcag caccgcctac 240
atggaactca ggagcctgac cagcgaggac accgccgtgt atttttgcgc caggagggcc 300
accggcactg attggttcgc cttctggggc cagggcacac tagtgaccgt gtccagcgcc 360
agcaccaagg gccccagcgt gttccccctg gcccccagca gcaagagcac cagcggcggc 420
acagccgccc tgggctgcct ggtgaaggac tacttccccg aaccggtgac cgtgtcctgg 480
aacagcggag ccctgaccag cggcgtgcac accttccccg ccgtgctgca gagcagcggc 540
ctgtacagcc tgagcagcgt ggtgaccgtg cccagcagca gcctgggcac ccagacctac 600
atctgtaacg tgaaccacaa gcccagcaac accaaggtgg acaagaaggt ggagcccaag 660
agctgtgaca agacccacac ctgccccccc tgccctgccc ccgagctgct gggaggcccc 720
agcgtgttcc tgttcccccc caagcctaag gacaccctga tgatcagcag aacccccgag 780
gtgacctgtg tggtggtgga tgtgagccac gaggaccctg aggtgaagtt caactggtac 840
gtggacggcg tggaggtgca caatgccaag accaagccca gggaggagca gtacaacagc 900
acctaccggg tggtgtccgt gctgaccgtg ctgcaccagg attggctgaa cggcaaggag 960
tacaagtgta aggtgtccaa caaggccctg cctgccccta tcgagaaaac catcagcaag 1020
gccaagggcc agcccagaga gccccaggtg tacaccctgc cccctagcag agatgagctg 1080
accaagaacc aggtgtccct gacctgcctg gtgaagggct tctaccccag cgacatcgcc 1140
gtggagtggg agagcaacgg ccagcccgag aacaactaca agaccacccc ccctgtgctg 1200
gacagcgatg gcagcttctt cctgtacagc aagctgaccg tggacaagag cagatggcag 1260
cagggcaacg tgttcagctg ctccgtgatg cacgaggccc tgcacaatca ctacacccag 1320
aagagcctga gcctgtcccc tggcaag 1347

<210> SEQ ID NO 128
<211> LENGTH: 108
<212> TYPE: PRT
<213> ORGANISM: mus musculus

<400> SEQUENCE: 128

Asp Ile Gln Met Thr Gln Ser Pro Ala Ser Leu Ser Val Ser Val Gly
1 5 10 15

Glu Thr Val Thr Ile Thr Cys Arg Ala Ser Glu Asn Ile Tyr Asn Asn
20 25 30

Leu Ala Trp Tyr Gln Gln Lys Gln Gly Lys Ser Pro Gln Leu Leu Val
35 40 45

Tyr Ala Ala Thr Ile Leu Ala Asp Gly Val Pro Ser Arg Phe Ser Gly
50 55 60

Ser Gly Ser Gly Thr Gln Tyr Ser Leu Lys Ile Asn Ser Leu Gln Ser
65 70 75 80

Gly Asp Phe Gly Thr Tyr Tyr Cys Gln His Phe Trp Gly Thr Pro Leu
85 90 95

```
Thr Phe Gly Ala Gly Thr Lys Leu Glu Leu Lys Arg
            100                 105


<210> SEQ ID NO 129
<211> LENGTH: 324
<212> TYPE: DNA
<213> ORGANISM: mus musculus

<400> SEQUENCE: 129

gacatccaga tgacccagag ccccgctagc ctcagcgtgt ccgtcggcga gaccgtgacc     60

atcacctgca gggccagcga gaacatctac aacaacctgg cctggtatca gcagaagcag    120

ggcaaaagcc cccagctgct ggtgtacgcc gccaccattc tggccgacgg cgtgcccagc    180

aggttctctg gaagcggcag cggcacccag tacagcctga agatcaacag cctgcagagc    240

ggggacttcg gcacctacta ctgccagcac ttctggggca ctcccctgac cttcggagcc    300

ggcaccaagc tggagctgaa gcgt                                            324


<210> SEQ ID NO 130
<211> LENGTH: 214
<212> TYPE: PRT
<213> ORGANISM: Artificial Sequence
<220> FEATURE:
<223> OTHER INFORMATION: Chimeric antibody sequence

<400> SEQUENCE: 130

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Asn Asn
            20                  25                  30

Leu Ala Trp Tyr Gln Gln Lys Gln Gly Lys Ser Pro Gln Leu Leu Val
        35                  40                  45

Tyr Ala Ala Thr Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Gly Asp Phe Gly Thr Tyr Tyr Cys Gln His Phe Trp Gly Thr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 131
<211> LENGTH: 642
<212> TYPE: DNA
```

<213> ORGANISM: Artificial Sequence
<220> FEATURE:
<223> OTHER INFORMATION: Chimeric antibody sequence

<400> SEQUENCE: 131
gacatccaga tgacccagag ccccgctagc ctcagcgtgt ccgtcggcga gaccgtgacc 60
atcacctgca gggccagcga gaacatctac aacaacctgg cctggtatca gcagaagcag 120
ggcaaaagcc cccagctgct ggtgtacgcc gccaccattc tggccgacgg cgtgcccagc 180
aggttctctg gaagcggcag cggcacccag tacagcctga agatcaacag cctgcagagc 240
ggggacttcg gcacctacta ctgccagcac ttctggggca ctcccctgac cttcggagcc 300
ggcaccaagc tggagctgaa gcgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 132
<211> LENGTH: 118
<212> TYPE: PRT
<213> ORGANISM: mus musculus

<400> SEQUENCE: 132

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Ile Ile His Pro Asn Ser Gly Ser Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Ile Tyr Asp Tyr Pro Phe Ala Tyr Trp Gly Gln Gly Thr
100 105 110

Leu Val Thr Val Ser Ser
115

<210> SEQ ID NO 133
<211> LENGTH: 354
<212> TYPE: DNA
<213> ORGANISM: mus musculus

<400> SEQUENCE: 133
caggtgcagc tccagcagcc cggagccgaa ctggtgaagc ccggagccag cgtcaaactg 60
tcctgcaagg ccagcggcta caccttcacc aactactgga tgcactgggt gaagcagagg 120
cccggccagg gcctggagtg gatcggcatc atccacccca acagcgggag caccaactac 180
aacgagaagt tcaagagcaa ggccaccctg accgtggaca agagcagcag cactgcctac 240
atgcagctga gcagcctgac cagcgaggac agcgctgtgt actactgcgc caggggcatc 300
tacgactacc ccttcgccta ttggggccag ggcacactag tgaccgtgtc cagc 354

<210> SEQ ID NO 134
<211> LENGTH: 448
<212> TYPE: PRT
<213> ORGANISM: Artificial Sequence
<220> FEATURE:
<223> OTHER INFORMATION: Chimeric antibody sequence

<400> SEQUENCE: 134

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Ile Ile His Pro Asn Ser Gly Ser Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Ile Tyr Asp Tyr Pro Phe Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 135
<211> LENGTH: 1344
<212> TYPE: DNA
<213> ORGANISM: Artificial Sequence
<220> FEATURE:
<223> OTHER INFORMATION: Chimeric antibody sequence

<400> SEQUENCE: 135

caggtgcagc tccagcagcc cggagccgaa ctggtgaagc ccggagccag cgtcaaactg     60

tcctgcaagg ccagcggcta caccttcacc aactactgga tgcactgggt gaagcagagg    120

cccggccagg gcctggagtg gatcggcatc atccacccca acagcgggag caccaactac    180

aacgagaagt tcaagagcaa ggccaccctg accgtggaca agagcagcag cactgcctac    240

atgcagctga gcagcctgac cagcgaggac agcgctgtgt actactgcgc caggggcatc    300

tacgactacc ccttcgccta ttggggccag ggcacactag tgaccgtgtc cagcgccagc    360

accaagggcc ccagcgtgtt cccccctggcc cccagcagca agagcaccag cggcggcaca    420

gccgccctgg gctgcctggt gaaggactac ttccccgaac cggtgaccgt gtcctggaac    480

agcggagccc tgaccagcgg cgtgcacacc ttccccgccg tgctgcagag cagcggcctg    540

tacagcctga gcagcgtggt gaccgtgccc agcagcagcc tgggcaccca gacctacatc    600

tgtaacgtga accacaagcc cagcaacacc aaggtggaca agaaggtgga gcccaagagc    660

tgtgacaaga cccacacctg cccccccctgc cctgccccccg agctgctggg aggccccagc    720

gtgttcctgt tccccccccaa gcctaaggac accctgatga tcagcagaac ccccgaggtg    780

acctgtgtgg tggtggatgt gagccacgag gaccctgagg tgaagttcaa ctggtacgtg    840

gacggcgtgg aggtgcacaa tgccaagacc aagcccaggg aggagcagta caacagcacc    900

taccgggtgg tgtccgtgct gaccgtgctg caccaggatt ggctgaacgg caaggagtac    960

aagtgtaagg tgtccaacaa ggccctgcct gcccctatcg agaaaaccat cagcaaggcc   1020

aagggccagc ccagagagcc ccaggtgtac accctgcccc ctagcagaga tgagctgacc   1080

aagaaccagg tgtccctgac ctgcctggtg aagggcttct accccagcga catcgccgtg   1140

gagtgggaga gcaacggcca gcccgagaac aactacaaga ccaccccccc tgtgctggac   1200

agcgatggca gcttcttcct gtacagcaag ctgaccgtgg acaagagcag atggcagcag   1260

ggcaacgtgt tcagctgctc cgtgatgcac gaggccctgc acaatcacta cacccagaag   1320

agcctgagcc tgtcccctgg caag                                           1344
```

```
<210> SEQ ID NO 136
<211> LENGTH: 112
<212> TYPE: PRT
<213> ORGANISM: mus musculus

<400> SEQUENCE: 136
```

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Thr Tyr Phe Cys Gln Gln Ser Ile
                85                  90                  95

Glu Asp Pro Tyr Thr Phe Gly Gly Gly Thr Lys Leu Glu Ile Lys Arg
            100                 105                 110
```

<210> SEQ ID NO 137
<211> LENGTH: 336
<212> TYPE: DNA
<213> ORGANISM: mus musculus

<400> SEQUENCE: 137

```
gacatcgtgc tgacccagtc tcccgctagc ctggccgtgt ctctgggcca gagggccaca     60

atcagctgca gggccagcga gagcgtcagc attcacggca cccacctgat gcactggtac    120

cagcagaagc ccggccagcc tcccaagctc ctgatctacg ccgccagcaa cctggaaagc    180

ggagtgcccg ccaggttcag cggcagcggc tccgagaccg acttcaccct gaacatccac    240

cccgtggagg aggaggacgc cgccacctac ttctgccagc agagcatcga ggacccctac    300

accttcggcg gcggcaccaa gctggagatc aagcgt                              336
```

<210> SEQ ID NO 138
<211> LENGTH: 218
<212> TYPE: PRT
<213> ORGANISM: Artificial Sequence
<220> FEATURE:
<223> OTHER INFORMATION: Chimeric antibody sequence

<400> SEQUENCE: 138

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Thr Tyr Phe Cys Gln Gln Ser Ile
                85                  90                  95

Glu Asp Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 139
<211> LENGTH: 654
<212> TYPE: DNA
<213> ORGANISM: Artificial Sequence
<220> FEATURE:
<223> OTHER INFORMATION: Chimeric antibody sequence

<400> SEQUENCE: 139

gacatcgtgc tgacccagtc tcccgctagc ctggccgtgt ctctgggcca gagggccaca      60

atcagctgca gggccagcga gagcgtcagc attcacggca cccacctgat gcactggtac     120

cagcagaagc ccggccagcc tcccaagctc ctgatctacg ccgccagcaa cctggaaagc     180

ggagtgcccg ccaggttcag cggcagcggc tccgagaccg acttcaccct gaacatccac     240

cccgtggagg aggaggacgc cgccacctac ttctgccagc agagcatcga ggacccctac     300

accttcggcg gcggcaccaa gctggagatc aagcgtacgg tggccgcccc cagcgtgttc     360

atcttccccc ccagcgatga gcagctgaag agcggcaccg ccagcgtggt gtgtctgctg     420

aacaacttct acccccggga ggccaaggtg cagtggaagg tggacaatgc cctgcagagc     480

ggcaacagcc aggagagcgt gaccgagcag gacagcaagg actccaccta cagcctgagc     540

agcaccctga ccctgagcaa ggccgactac gagaagcaca aggtgtacgc ctgtgaggtg     600

acccaccagg gcctgtccag ccccgtgacc aagagcttca accggggcga gtgc           654


<210> SEQ ID NO 140
<211> LENGTH: 120
<212> TYPE: PRT
<213> ORGANISM: mus musculus

<400> SEQUENCE: 140

Glu Val Lys Leu Leu Gln Ser Gly Gly Gly Leu Val Gln Pro Gly Gly
 1               5                  10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Arg Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Val Phe Tyr Tyr Asp Tyr Glu Gly Ala Met Asp Tyr Trp Gly Gln
            100                 105                 110

Gly Thr Ser Val Thr Val Ser Ser
        115                 120
```

<210> SEQ ID NO 141
<211> LENGTH: 360
<212> TYPE: DNA
<213> ORGANISM: mus musculus

<400> SEQUENCE: 141
gaggtgaagc ttctccagtc tggaggtggc ctggtgcagc ctggaggatc cctgaaactc 60
tcctgtgcag cctcaggaat cgattttagt agatactgga tgagttgggt tcggcgggct 120
ccagggaaag gactagaatg gattggagaa attaatccag ataggagtac aatcaactat 180
gcaccatctc taaaggataa attcatcatc tccagagaca acgccaaaaa tacgctgtac 240
ctgcaaatga gcaaagtgag atctgaggac acagcccttt attactgtgc agttttctac 300
tatgattacg agggtgctat ggactactgg ggtcaaggaa cctcagtcac cgtctcctca 360

<210> SEQ ID NO 142
<211> LENGTH: 450
<212> TYPE: PRT
<213> ORGANISM: Artificial Sequence
<220> FEATURE:
<223> OTHER INFORMATION: Chimeric antibody sequence

<400> SEQUENCE: 142

Glu Val Lys Leu Leu Gln Ser Gly Gly Gly Leu Val Gln Pro Gly Gly
1 5 10 15

Ser Leu Lys Leu Ser Cys Ala Ala Ser Gly Ile Asp Phe Ser Arg Tyr
20 25 30

Trp Met Ser Trp Val Arg Arg Ala Pro Gly Lys Gly Leu Glu Trp Ile
35 40 45

Gly Glu Ile Asn Pro Asp Arg Ser Thr Ile Asn Tyr Ala Pro Ser Leu
50 55 60

Lys Asp Lys Phe Ile Ile Ser Arg Asp Asn Ala Lys Asn Thr Leu Tyr
65 70 75 80

Leu Gln Met Ser Lys Val Arg Ser Glu Asp Thr Ala Leu Tyr Tyr Cys
85 90 95

Ala Val Phe Tyr Tyr Asp Tyr Glu Gly Ala Met Asp Tyr Trp Gly Gln
100 105 110

Gly Thr Ser Val Thr Val Ser Ser Ala Lys Thr Thr Ala Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 143
<211> LENGTH: 1350
<212> TYPE: DNA
<213> ORGANISM: Artificial Sequence
<220> FEATURE:
<223> OTHER INFORMATION: Chimeric antibody sequence

<400> SEQUENCE: 143

```
gaggtgaagc ttctccagtc tggaggtggc ctggtgcagc ctggaggatc cctgaaactc     60

tcctgtgcag cctcaggaat cgattttagt agatactgga tgagttgggt tcggcgggct    120

ccagggaaag gactagaatg gattggagaa attaatccag ataggagtac aatcaactat    180

gcaccatctc taaaggataa attcatcatc tccagagaca acgccaaaaa tacgctgtac    240

ctgcaaatga gcaaagtgag atctgaggac acagcccttt attactgtgc agttttctac    300

tatgattacg agggtgctat ggactactgg ggtcaaggaa cctcagtcac cgtctcctca    360

gccaaaacaa cagcccccag cgtgttcccc ctggccccca gcagcaagag caccagcggc    420

ggcacagccg ccctgggctg cctggtgaag gactacttcc ccgaaccggt gaccgtgtcc    480

tggaacagcg gagccctgac cagcggcgtg cacaccttcc ccgccgtgct gcagagcagc    540

ggcctgtaca gcctgagcag cgtggtgacc gtgcccagca gcagcctggg cacccagacc    600

tacatctgta acgtgaacca caagcccagc aacaccaagg tggacaagaa ggtggagccc    660

aagagctgtg acaagaccca cacctgcccc ccctgccctg cccccgagct gctgggaggc    720

cccagcgtgt tcctgttccc ccccaagcct aaggacaccc tgatgatcag cagaaccccc    780

gaggtgacct gtgtggtggt ggatgtgagc cacgaggacc ctgaggtgaa gttcaactgg    840

tacgtggacg gcgtggaggt gcacaatgcc aagaccaagc ccagggagga gcagtacaac    900

agcacctacc gggtggtgtc cgtgctgacc gtgctgcacc aggattggct gaacggcaag    960
```

```
gagtacaagt gtaaggtgtc caacaaggcc ctgcctgccc ctatcgagaa aaccatcagc   1020

aaggccaagg gccagcccag agagccccag gtgtacaccc tgccccctag cagagatgag   1080

ctgaccaaga accaggtgtc cctgacctgc ctggtgaagg gcttctaccc cagcgacatc   1140

gccgtggagt gggagagcaa cggccagccc gagaacaact acaagaccac ccccctgtg    1200

ctggacagcg atggcagctt cttcctgtac agcaagctga ccgtggacaa gagcagatgg   1260

cagcagggca acgtgttcag ctgctccgtg atgcacgagg ccctgcacaa tcactacacc   1320

cagaagagcc tgagcctgtc ccctggcaag                                    1350


<210> SEQ ID NO 144
<211> LENGTH: 108
<212> TYPE: PRT
<213> ORGANISM: mus musculus

<400> SEQUENCE: 144

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Phe Pro Phe
                85                  90                  95

Thr Phe Gly Ser Gly Thr Lys Leu Glu Ile Lys Arg
            100                 105


<210> SEQ ID NO 145
<211> LENGTH: 324
<212> TYPE: DNA
<213> ORGANISM: mus musculus

<400> SEQUENCE: 145

gacattgtga tgacccagtc tcaaaaattc atgtccacat cagtaggaga cagggtcagc     60

gtcacctgca aggccagtca gaatgtggat actaatgtag cctggtatca acaaaaacca    120

gggcaatctc ctaaagcact gatttactcg gcatcctacc ggttcagtgg agtccctgat    180

cgcttcacag gcagtggatc tgggacagat ttcactctca ccatcagcaa tgtgcagtct    240

gaagacttgg cagagtattt ctgtcagcaa tataacagct ttccattcac gttcggctcg    300

gggacaaagt tggaaataaa acgt                                           324


<210> SEQ ID NO 146
<211> LENGTH: 214
<212> TYPE: PRT
<213> ORGANISM: Artificial Sequence
<220> FEATURE:
<223> OTHER INFORMATION: Chimeric antibody sequence

<400> SEQUENCE: 146

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Asp Thr Asn
            20                  25                  30
```

Val Ala Trp Tyr Gln Gln Lys Pro Gly Gln Ser Pro Lys Ala Leu Ile
35 40 45

Tyr Ser Ala Ser Tyr Arg Phe Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Phe Pro Phe
85 90 95

Thr Phe Gly Ser Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 147
<211> LENGTH: 642
<212> TYPE: PRT
<213> ORGANISM: Artificial Sequence
<220> FEATURE:
<223> OTHER INFORMATION: Chimeric antibody sequence

<400> SEQUENCE: 147

Gly Ala Cys Ala Thr Thr Gly Thr Gly Ala Thr Gly Ala Cys Cys Cys
1 5 10 15

Ala Gly Thr Cys Thr Cys Ala Ala Ala Ala Ala Thr Thr Cys Ala Thr
20 25 30

Gly Thr Cys Cys Ala Cys Ala Thr Cys Ala Gly Thr Ala Gly Gly Ala
35 40 45

Gly Ala Cys Ala Gly Gly Gly Thr Cys Ala Gly Cys Gly Thr Cys Ala
50 55 60

Cys Cys Thr Gly Cys Ala Ala Gly Gly Cys Cys Ala Gly Thr Cys Ala
65 70 75 80

Gly Ala Ala Thr Gly Thr Gly Gly Ala Thr Ala Cys Thr Ala Ala Thr
85 90 95

Gly Thr Ala Gly Cys Cys Thr Gly Gly Thr Ala Thr Cys Ala Ala Cys
100 105 110

Ala Ala Ala Ala Ala Cys Cys Ala Gly Gly Gly Cys Ala Ala Thr Cys
115 120 125

Thr Cys Cys Thr Ala Ala Ala Gly Cys Ala Cys Thr Gly Ala Thr Thr
130 135 140

Thr Ala Cys Thr Cys Gly Gly Cys Ala Thr Cys Cys Thr Ala Cys Cys
145 150 155 160

Gly Gly Thr Thr Cys Ala Gly Thr Gly Gly Ala Gly Thr Cys Cys Cys
165 170 175

-continued

```
Thr Gly Ala Thr Cys Gly Cys Thr Thr Cys Ala Cys Ala Gly Gly Cys
            180                 185                 190

Ala Gly Thr Gly Gly Ala Thr Cys Thr Gly Gly Gly Ala Cys Ala Gly
        195                 200                 205

Ala Thr Thr Thr Cys Ala Cys Thr Cys Thr Cys Ala Cys Cys Ala Thr
    210                 215                 220

Cys Ala Gly Cys Ala Ala Thr Gly Thr Gly Cys Ala Gly Thr Cys Thr
225                 230                 235                 240

Gly Ala Ala Gly Ala Cys Thr Thr Gly Gly Cys Ala Gly Ala Gly Thr
                245                 250                 255

Ala Thr Thr Thr Cys Thr Gly Thr Cys Ala Gly Cys Ala Ala Thr Ala
            260                 265                 270

Thr Ala Ala Cys Ala Gly Cys Thr Thr Thr Cys Cys Ala Thr Thr Cys
        275                 280                 285

Ala Cys Gly Thr Thr Cys Gly Gly Cys Thr Cys Gly Gly Gly Gly Ala
    290                 295                 300

Cys Ala Ala Ala Gly Thr Thr Gly Gly Ala Ala Ala Thr Ala Ala Ala
305                 310                 315                 320

Ala Cys Gly Thr Ala Cys Gly Gly Thr Gly Gly Cys Cys Gly Cys Cys
                325                 330                 335

Cys Cys Cys Ala Gly Cys Gly Thr Gly Thr Thr Cys Ala Thr Cys Thr
            340                 345                 350

Thr Cys Cys Cys Cys Cys Cys Cys Ala Gly Cys Gly Ala Thr Gly Ala
        355                 360                 365

Gly Cys Ala Gly Cys Thr Gly Ala Ala Gly Ala Gly Cys Gly Gly Cys
    370                 375                 380

Ala Cys Cys Gly Cys Cys Ala Gly Cys Gly Thr Gly Gly Thr Gly Thr
385                 390                 395                 400

Gly Thr Cys Thr Gly Cys Thr Gly Ala Ala Cys Ala Ala Cys Thr Thr
                405                 410                 415

Cys Thr Ala Cys Cys Cys Cys Cys Gly Gly Gly Ala Gly Gly Cys Cys
            420                 425                 430

Ala Ala Gly Gly Thr Gly Cys Ala Gly Thr Gly Gly Ala Ala Gly Gly
        435                 440                 445

Thr Gly Gly Ala Cys Ala Ala Thr Gly Cys Cys Cys Thr Gly Cys Ala
    450                 455                 460

Gly Ala Gly Cys Gly Gly Cys Ala Ala Cys Ala Gly Cys Cys Ala Gly
465                 470                 475                 480

Gly Ala Gly Ala Gly Cys Gly Thr Gly Ala Cys Cys Gly Ala Gly Cys
                485                 490                 495

Ala Gly Gly Ala Cys Ala Gly Cys Ala Ala Gly Gly Ala Cys Thr Cys
            500                 505                 510

Cys Ala Cys Cys Thr Ala Cys Ala Gly Cys Cys Thr Gly Ala Gly Cys
        515                 520                 525

Ala Gly Cys Ala Cys Cys Cys Thr Gly Ala Cys Cys Cys Thr Gly Ala
    530                 535                 540

Gly Cys Ala Ala Gly Gly Cys Cys Gly Ala Cys Thr Ala Cys Gly Ala
545                 550                 555                 560

Gly Ala Ala Gly Cys Ala Cys Ala Ala Gly Gly Thr Gly Thr Ala Cys
                565                 570                 575

Gly Cys Cys Thr Gly Thr Gly Ala Gly Gly Thr Gly Ala Cys Cys Cys
            580                 585                 590
```

Ala Cys Cys Ala Gly Gly Gly Cys Cys Thr Gly Thr Cys Cys Ala Gly
595 600 605

Cys Cys Cys Cys Gly Thr Gly Ala Cys Cys Ala Ala Gly Ala Gly Cys
610 615 620

Thr Thr Cys Ala Ala Cys Cys Gly Gly Gly Gly Cys Gly Ala Gly Thr
625 630 635 640

Gly Cys

<210> SEQ ID NO 148
<211> LENGTH: 118
<212> TYPE: PRT
<213> ORGANISM: mus musculus

<400> SEQUENCE: 148

Pro Val Gln Leu Gln Gln Pro Gly Thr Glu Leu Val Arg Pro Gly Thr
1 5 10 15

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Val Ile Asp Pro Ser Asp Ser Tyr Thr Asn Tyr Asn Gln Lys Phe
50 55 60

Lys Gly Lys Ala Thr Leu Thr Val Asp Thr Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gln Val Phe Asp Tyr Pro Met Asp Tyr Trp Gly Gln Gly Thr
100 105 110

Ser Val Thr Val Ser Ser
115

<210> SEQ ID NO 149
<211> LENGTH: 354
<212> TYPE: DNA
<213> ORGANISM: mus musculus

<400> SEQUENCE: 149
ccggtccaac tgcagcagcc tgggactgag ctggtgaggc ctgggacttc agtgaagttg 60
tcctgcaagg cttctggcta caccttcacc agctactgga tgcactgggt aaagcagagg 120
cctggacaag gccttgagtg gatcggagtg attgatcctt ctgatagtta tactaactac 180
aatcaaaagt tcaagggcaa ggccacattg actgtagaca catcctccag cacagcctac 240
atgcagctca gcagcctgac atctgaggac tctgcggtct attactgtgc aagacaggtg 300
tttgactatc ctatggacta ctggggtcaa ggaacctcag tcaccgtctc ctca 354

<210> SEQ ID NO 150
<211> LENGTH: 448
<212> TYPE: PRT
<213> ORGANISM: Artificial Sequence
<220> FEATURE:
<223> OTHER INFORMATION: Chimeric antibody sequence

<400> SEQUENCE: 150

Pro Val Gln Leu Gln Gln Pro Gly Thr Glu Leu Val Arg Pro Gly Thr
1 5 10 15

Ser Val Lys Leu Ser Cys Lys Ala Ser Gly Tyr Thr Phe Thr Ser His
20 25 30

-continued

```
Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Val Phe Asp Tyr Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 151
<211> LENGTH: 1344
<212> TYPE: DNA
<213> ORGANISM: Artificial Sequence
<220> FEATURE:
<223> OTHER INFORMATION: Chimeric antibody sequence

<400> SEQUENCE: 151
ccggtccaac tgcagcagcc tgggactgag ctggtgaggc ctgggacttc agtgaagttg 60
tcctgcaagg cttctggcta caccttcacc agccactgga tgcactgggt aaagcagagg 120
cctggacaag gccttgagtg gatcggagtg attgatcctt ctgatagtta tactaactac 180
aatcaaaagt tcaagggcaa ggccacattg actgtagaca catcctccag cacagcctac 240
atgcagctca gcagcctgac atctgaggac tctgcggtct attactgtgc aagacaggtg 300
tttgactatc ctatggacta ctggggtcaa ggaacactag tgaccgtgtc cagcgccagc 360
accaagggcc ccagcgtgtt ccccctggcc cccagcagca agagcaccag cggcggcaca 420
gccgccctgg gctgcctggt gaaggactac ttccccgaac cggtgaccgt gtcctggaac 480
agcggagccc tgaccagcgg cgtgcacacc ttccccgccg tgctgcagag cagcggcctg 540
tacagcctga gcagcgtggt gaccgtgccc agcagcagcc tgggcaccca gacctacatc 600
tgtaacgtga accacaagcc cagcaacacc aaggtggaca agaaggtgga gcccaagagc 660
tgtgacaaga cccacacctg ccccccctgc cctgccccg agctgctggg aggccccagc 720
gtgttcctgt tcccccccaa gcctaaggac accctgatga tcagcagaac ccccgaggtg 780
acctgtgtgg tggtggatgt gagccacgag gaccctgagg tgaagttcaa ctggtacgtg 840
gacggcgtgg aggtgcacaa tgccaagacc aagcccaggg aggagcagta caacagcacc 900
taccgggtgg tgtccgtgct gaccgtgctg caccaggatt ggctgaacgg caaggagtac 960
aagtgtaagg tgtccaacaa ggccctgcct gcccctatcg agaaaaccat cagcaaggcc 1020
aagggccagc ccagagagcc ccaggtgtac accctgcccc ctagcagaga tgagctgacc 1080
aagaaccagg tgtccctgac ctgcctggtg aagggcttct accccagcga catcgccgtg 1140
gagtgggaga gcaacggcca gcccgagaac aactacaaga ccaccccccc tgtgctggac 1200
agcgatggca gcttcttcct gtacagcaag ctgaccgtgg acaagagcag atggcagcag 1260
ggcaacgtgt tcagctgctc cgtgatgcac gaggccctgc acaatcacta cacccagaag 1320
agcctgagcc tgtcccctgg caag 1344

<210> SEQ ID NO 152
<211> LENGTH: 112
<212> TYPE: PRT
<213> ORGANISM: mus musculus

<400> SEQUENCE: 152

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Ser Ile His
20 25 30

Gly Thr His Leu Met His Trp Tyr Gln Gln Lys Pro Gly Gln Pro Pro
35 40 45

Lys Leu Leu Ile Tyr Ala Ala Ser Asn Leu Glu Ser Gly Val Pro Ala
50 55 60

Arg Phe Ser Gly Ser Gly Ser Glu Thr Asp Phe Thr Leu Asn Ile His
65 70 75 80

Pro Val Glu Glu Glu Asp Ala Ala Thr Tyr Phe Cys Gln Gln Ser Ile

```
                85                  90                  95

Glu Asp Pro Trp Thr Phe Gly Gly Gly Thr Lys Leu Glu Ile Lys Arg
            100                 105                 110


<210> SEQ ID NO 153
<211> LENGTH: 336
<212> TYPE: DNA
<213> ORGANISM: mus musculus

<400> SEQUENCE: 153

gacattgtgc tgacccaatc tccagcttct ttggctgtgt ctctagggca gagggccacc      60

atctcctgca gagccagtga aagtgtcagt attcatggta ctcatttaat gcactggtac     120

caacagaaac caggacagcc acccaaactc ctcatctatg ctgcatccaa cctagaatct     180

ggagtccctg ccaggttcag tggcagtggg tctgagacag acttcaccct caacatccat     240

cctgtggagg aggaggatgc tgcaacctat ttctgtcagc aaagtattga ggatccgtgg     300

acgttcggtg gaggcaccaa gctggaaatc aaacgt                               336


<210> SEQ ID NO 154
<211> LENGTH: 218
<212> TYPE: PRT
<213> ORGANISM: Artificial Sequence
<220> FEATURE:
<223> OTHER INFORMATION: Chimeric antibody sequence

<400> SEQUENCE: 154

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Thr Tyr Phe Cys Gln Gln Ser Ile
                85                  90                  95

Glu Asp Pro Trp Thr Phe Gly Gly Gly Thr Lys Leu Glu Ile Asn Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 155
```

<211> LENGTH: 654
<212> TYPE: DNA
<213> ORGANISM: Artificial Sequence
<220> FEATURE:
<223> OTHER INFORMATION: Chimeric antibody sequence

<400> SEQUENCE: 155

```
gacattgtgc tgacccaatc tccagcttct ttggctgtgt ctctagggca gagggccacc     60

atctcctgca gagccagtga aagtgtcagt attcatggta ctcatttaat gcactggtac    120

caacagaaac caggacagcc acccaaactc ctcatctatg ctgcatccaa cctagaatct    180

ggagtccctg ccaggttcag tggcagtggg tctgagacag acttcaccct caacatccat    240

cctgtggagg aggaggatgc tgcaacctat ttctgtcagc aaagtattga ggatccgtgg    300

acgttcggtg gaggcaccaa gctggaaatc aatcgtacgg tggccgcccc cagcgtgttc    360

atcttccccc ccagcgatga gcagctgaag agcggcaccg ccagcgtggt gtgtctgctg    420

aacaacttct acccccggga ggccaaggtg cagtggaagg tggacaatgc cctgcagagc    480

ggcaacagcc aggagagcgt gaccgagcag gacagcaagg actccaccta cagcctgagc    540

agcaccctga ccctgagcaa ggccgactac gagaagcaca aggtgtacgc ctgtgaggtg    600

acccaccagg gcctgtccag ccccgtgacc aagagcttca accggggcga gtgc          654
```

<210> SEQ ID NO 156
<211> LENGTH: 118
<212> TYPE: PRT
<213> ORGANISM: mus musculus

<400> SEQUENCE: 156

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Ser Ile Tyr Asp Tyr Tyr Phe Asp Tyr Trp Gly Gln Gly Thr
            100                 105                 110

Thr Leu Thr Val Ser Ser
        115
```

<210> SEQ ID NO 157
<211> LENGTH: 354
<212> TYPE: DNA
<213> ORGANISM: mus musculus

<400> SEQUENCE: 157

```
caggttcaac tgcagcagtc tggggctgag ctggtgaggc ctggggcttc agtgacgctg     60

tcctgcaagg cttcgggcta cacatttact gactatgaaa tgcactgggt gaagcagaca    120

cctgtgcatg gcctggaatg gattggagct attgatcctg aaactggtgg tactgcctac    180

aatcagaagt tcaagggcaa ggccatactg actgcagaca aatcctccag cacagcctac    240

atggagctcc gcagcctgac atctgaggac tctgccgtct attactgtac aagatcgatt    300
```

tatgattact actttgacta ctggggccaa ggcaccactc tcacagtctc ctca 354

<210> SEQ ID NO 158
<211> LENGTH: 448
<212> TYPE: PRT
<213> ORGANISM: Artificial Sequence
<220> FEATURE:
<223> OTHER INFORMATION: Chimeric antibody sequence

<400> SEQUENCE: 158

Gln Val Gln Leu Gln Gln Ser Gly Ala Glu Leu Val Arg Pro Gly Ala
1 5 10 15

Ser Val Thr Leu Ser Cys Lys Ala Ser Gly Tyr Thr Phe Thr Asp Tyr
20 25 30

Glu Met His Trp Val Lys Gln Thr Pro Val His Gly Leu Glu Trp Ile
35 40 45

Gly Ala Ile Asp Pro Glu Thr Gly Gly Thr Ala Tyr Asn Gln Lys Phe
50 55 60

Lys Gly Lys Ala Ile Leu Thr Ala Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Thr Arg Ser Ile Tyr Asp Tyr Tyr Phe Asp Tyr Trp Gly Gln Gly Thr
100 105 110

Thr Leu Thr Val Ser Ser Ala Lys Thr Thr Pro Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

```
Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 159
<211> LENGTH: 1344
<212> TYPE: DNA
<213> ORGANISM: Artificial Sequence
<220> FEATURE:
<223> OTHER INFORMATION: Chimeric antibody sequence

<400> SEQUENCE: 159

caggttcaac tgcagcagtc tggggctgag ctggtgaggc ctggggcttc agtgacgctg      60

tcctgcaagg cttcgggcta cacatttact gactatgaaa tgcactgggt gaagcagaca     120

cctgtgcatg gcctggaatg gattggagct attgatcctg aaactggtgg tactgcctac     180

aatcagaagt tcaagggcaa ggccatactg actgcagaca aatcctccag cacagcctac     240

atggagctcc gcagcctgac atctgaggac tctgccgtct attactgtac aagatcgatt     300

tatgattact actttgacta ctggggccaa ggcaccactc tcacagtctc ctcagccaaa     360

acgacacccc ccagcgtgtt ccccctggcc cccagcagca agagcaccag cggcggcaca     420

gccgccctgg gctgcctggt gaaggactac ttccccgaac cggtgaccgt gtcctggaac     480

agcggagccc tgaccagcgg cgtgcacacc ttccccgccg tgctgcagag cagcggcctg     540

tacagcctga gcagcgtggt gaccgtgccc agcagcagcc tgggcaccca gacctacatc     600

tgtaacgtga accacaagcc cagcaacacc aaggtggaca agaaggtgga gcccaagagc     660

tgtgacaaga cccacacctg ccccccctgc cctgcccccg agctgctggg aggccccagc     720

gtgttcctgt tccccccaa gcctaaggac accctgatga tcagcagaac ccccgaggtg     780

acctgtgtgg tggtggatgt gagccacgag gaccctgagg tgaagttcaa ctggtacgtg     840

gacggcgtgg aggtgcacaa tgccaagacc aagcccaggg aggagcagta caacagcacc     900

taccgggtgg tgtccgtgct gaccgtgctg caccaggatt ggctgaacgg caaggagtac     960

aagtgtaagg tgtccaacaa ggccctgcct gcccctatcg agaaaaccat cagcaaggcc    1020

aagggccagc ccagagagcc ccaggtgtac accctgcccc ctagcagaga tgagctgacc    1080

aagaaccagg tgtccctgac ctgcctggtg aagggcttct accccagcga catcgccgtg    1140

gagtgggaga gcaacggcca gcccgagaac aactacaaga ccaccccccc tgtgctggac    1200

agcgatggca gcttcttcct gtacagcaag ctgaccgtgg acaagagcag atggcagcag    1260

ggcaacgtgt tcagctgctc cgtgatgcac gaggccctgc acaatcacta cacccagaag    1320

agcctgagcc tgtcccctgg caag                                           1344


<210> SEQ ID NO 160
<211> LENGTH: 112
<212> TYPE: PRT
<213> ORGANISM: mus musculus
```

<400> SEQUENCE: 160

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Ser Ile His
20 25 30

Gly Thr His Leu Met His Trp Tyr Gln Gln Lys Pro Gly Gln Pro Pro
35 40 45

Lys Leu Leu Ile Tyr Ala Ala Ser Asn Leu Glu Ser Gly Val Pro Ala
50 55 60

Arg Phe Ser Gly Gly Gly Ser Glu Thr Asp Phe Thr Leu Asn Ile His
65 70 75 80

Pro Val Glu Glu Glu Asp Gly Ala Thr Tyr Phe Cys Gln Gln Ser Ile
85 90 95

Glu Tyr Pro Arg Thr Phe Gly Gly Gly Thr Lys Leu Glu Ile Asn Arg
100 105 110

<210> SEQ ID NO 161
<211> LENGTH: 336
<212> TYPE: DNA
<213> ORGANISM: mus musculus

<400> SEQUENCE: 161
gacattgtgc tgacccaatc tccagcttct ttggctgtgt ctctagggca gagggccacc 60
atctcctgca gagccagtga aagtgtcagt attcatggta ctcatttaat gcactggtac 120
caacagaaac caggacagcc acccaaactc ctcatctatg ctgcatccaa cctagaatct 180
ggagtccctg ccaggttcag tggcggtggg tctgagacag acttcaccct caacatccat 240
cctgtggagg aggaggatgg tgcaacctat ttctgtcagc aaagtattga gtatcctcgg 300
acgttcggtg gaggcaccaa gctggaaatc aatcgt 336

<210> SEQ ID NO 162
<211> LENGTH: 218
<212> TYPE: PRT
<213> ORGANISM: Artificial Sequence
<220> FEATURE:
<223> OTHER INFORMATION: Chimeric antibody sequence

<400> SEQUENCE: 162

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Ser Ile His
20 25 30

Gly Thr His Leu Met His Trp Tyr Gln Gln Lys Pro Gly Gln Pro Pro
35 40 45

Lys Leu Leu Ile Tyr Ala Ala Ser Asn Leu Glu Ser Gly Val Pro Ala
50 55 60

Arg Phe Ser Gly Gly Gly Ser Glu Thr Asp Phe Thr Leu Asn Ile His
65 70 75 80

Pro Val Glu Glu Glu Asp Gly Ala Thr Tyr Phe Cys Gln Gln Ser Ile
85 90 95

Glu Tyr Pro Arg Thr Phe Gly Gly Gly Thr Lys Leu Glu Ile Asn Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 163
<211> LENGTH: 654
<212> TYPE: DNA
<213> ORGANISM: Artificial Sequence
<220> FEATURE:
<223> OTHER INFORMATION: Chimeric antibody sequence

<400> SEQUENCE: 163
gacattgtgc tgacccaatc tccagcttct ttggctgtgt ctctagggca gagggccacc 60
atctcctgca gagccagtga aagtgtcagt attcatggta ctcatttaat gcactggtac 120
caacagaaac caggacagcc acccaaactc ctcatctatg ctgcatccaa cctagaatct 180
ggagtccctg ccaggttcag tggcggtggg tctgagacag acttcaccct caacatccat 240
cctgtggagg aggaggatgg tgcaacctat ttctgtcagc aaagtattga gtatcctcgg 300
acgttcggtg gaggcaccaa gctggaaatc aatcgtacgg tggccgcccc cagcgtgttc 360
atcttccccc ccagcgatga gcagctgaag agcggcaccg ccagcgtggt gtgtctgctg 420
aacaacttct acccccggga ggccaaggtg cagtggaagg tggacaatgc cctgcagagc 480
ggcaacagcc aggagagcgt gaccgagcag gacagcaagg actccaccta cagcctgagc 540
agcaccctga ccctgagcaa ggccgactac gagaagcaca aggtgtacgc ctgtgaggtg 600
acccaccagg gcctgtccag ccccgtgacc aagagcttca accggggcga gtgc 654

<210> SEQ ID NO 164
<211> LENGTH: 5
<212> TYPE: PRT
<213> ORGANISM: mus musculus

<400> SEQUENCE: 164

Asp Tyr Tyr Asn Met
1 5

<210> SEQ ID NO 165
<211> LENGTH: 16
<212> TYPE: PRT
<213> ORGANISM: mus musculus

<400> SEQUENCE: 165

Val Ile Asn Pro Tyr Asn Gly Gly Thr Asp Tyr Asn Gln Lys Phe Gly
1 5 10 15

<210> SEQ ID NO 166
<211> LENGTH: 9
<212> TYPE: PRT
<213> ORGANISM: mus musculus

<400> SEQUENCE: 166

Ser Val Tyr Asp Tyr Pro Phe Asp Tyr
1 5

<210> SEQ ID NO 167
<211> LENGTH: 15
<212> TYPE: PRT
<213> ORGANISM: mus musculus

<400> SEQUENCE: 167

```
Arg Ala Ser Glu Ser Val Ser Ile His Gly Thr His Leu Met His
 1               5                  10                  15
```

<210> SEQ ID NO 168
<211> LENGTH: 7
<212> TYPE: PRT
<213> ORGANISM: mus musculus

<400> SEQUENCE: 168

```
Ala Ala Ser Asn Leu Glu Ser
 1               5
```

<210> SEQ ID NO 169
<211> LENGTH: 9
<212> TYPE: PRT
<213> ORGANISM: mus musculus

<400> SEQUENCE: 169

```
Gln Gln Ser Ile Glu Asp Pro Arg Thr
 1               5
```

<210> SEQ ID NO 170
<211> LENGTH: 5
<212> TYPE: PRT
<213> ORGANISM: mus musculus

<400> SEQUENCE: 170

```
Asp Tyr Ser Ile Asp
 1               5
```

<210> SEQ ID NO 171
<211> LENGTH: 17
<212> TYPE: PRT
<213> ORGANISM: mus musculus

<400> SEQUENCE: 171

```
Asp Ile Asp Pro Asn Tyr Gly Asp Pro Ile Tyr Asn His Lys Phe Lys
 1               5                  10                  15

Gly
```

<210> SEQ ID NO 172
<211> LENGTH: 10
<212> TYPE: PRT
<213> ORGANISM: mus musculus

<400> SEQUENCE: 172

```
Arg Ala Thr Gly Thr Asp Trp Phe Ala Phe
 1               5                  10
```

<210> SEQ ID NO 173
<211> LENGTH: 11
<212> TYPE: PRT
<213> ORGANISM: mus musculus

<400> SEQUENCE: 173

```
Arg Ala Ser Glu Asn Ile Tyr Asn Asn Leu Ala
 1               5                  10
```

<210> SEQ ID NO 174
<211> LENGTH: 7
<212> TYPE: PRT
<213> ORGANISM: mus musculus

<400> SEQUENCE: 174

Ala Ala Thr Ile Leu Ala Asp
1 5

<210> SEQ ID NO 175
<211> LENGTH: 9
<212> TYPE: PRT
<213> ORGANISM: mus musculus

<400> SEQUENCE: 175

Gln His Phe Trp Gly Thr Pro Leu Thr
1 5

<210> SEQ ID NO 176
<211> LENGTH: 5
<212> TYPE: PRT
<213> ORGANISM: mus musculus

<400> SEQUENCE: 176

Asn Tyr Trp Met His
1 5

<210> SEQ ID NO 177
<211> LENGTH: 17
<212> TYPE: PRT
<213> ORGANISM: mus musculus

<400> SEQUENCE: 177

Ile Ile His Pro Asn Ser Gly Ser Thr Asn Tyr Asn Glu Lys Phe Lys
1 5 10 15

Ser

<210> SEQ ID NO 178
<211> LENGTH: 9
<212> TYPE: PRT
<213> ORGANISM: mus musculus

<400> SEQUENCE: 178

Gly Ile Tyr Asp Tyr Pro Phe Ala Tyr
1 5

<210> SEQ ID NO 179
<211> LENGTH: 15
<212> TYPE: PRT
<213> ORGANISM: mus musculus

<400> SEQUENCE: 179

Arg Ala Ser Glu Ser Val Ser Ile His Gly Thr His Leu Met His
1 5 10 15

<210> SEQ ID NO 180
<211> LENGTH: 7
<212> TYPE: PRT
<213> ORGANISM: mus musculus

<400> SEQUENCE: 180

Ala Ala Ser Asn Leu Glu Ser
1 5

<210> SEQ ID NO 181
<211> LENGTH: 9
<212> TYPE: PRT
<213> ORGANISM: mus musculus

<400> SEQUENCE: 181

Gln Gln Ser Ile Glu Asp Pro Tyr Thr
1 5

<210> SEQ ID NO 182
<211> LENGTH: 5
<212> TYPE: PRT
<213> ORGANISM: mus musculus

<400> SEQUENCE: 182

Arg Tyr Trp Met Ser
1 5

<210> SEQ ID NO 183
<211> LENGTH: 17
<212> TYPE: PRT
<213> ORGANISM: mus musculus

<400> SEQUENCE: 183

Glu Ile Asn Pro Asp Arg Ser Thr Ile Asn Tyr Ala Pro Ser Leu Lys
1 5 10 15

Asp

<210> SEQ ID NO 184
<211> LENGTH: 11
<212> TYPE: PRT
<213> ORGANISM: mus musculus

<400> SEQUENCE: 184

Phe Tyr Tyr Asp Tyr Glu Gly Ala Met Asp Tyr
1 5 10

<210> SEQ ID NO 185
<211> LENGTH: 11
<212> TYPE: PRT
<213> ORGANISM: mus musculus

<400> SEQUENCE: 185

Lys Ala Ser Gln Asn Val Asp Thr Asn Val Ala
1 5 10

<210> SEQ ID NO 186
<211> LENGTH: 7
<212> TYPE: PRT
<213> ORGANISM: mus musculus

<400> SEQUENCE: 186

Ser Ala Ser Tyr Arg Phe Ser
1 5

<210> SEQ ID NO 187
<211> LENGTH: 9
<212> TYPE: PRT
<213> ORGANISM: mus musculus

<400> SEQUENCE: 187

Gln Gln Tyr Asn Ser Phe Pro Phe Thr
1 5

<210> SEQ ID NO 188
<211> LENGTH: 5
<212> TYPE: PRT
<213> ORGANISM: mus musculus

<400> SEQUENCE: 188

Ser Tyr Trp Met His
1 5

<210> SEQ ID NO 189
<211> LENGTH: 17
<212> TYPE: PRT
<213> ORGANISM: mus musculus

<400> SEQUENCE: 189

Val Ile Asp Pro Ser Asp Ser Tyr Thr Asn Tyr Asn Gln Lys Phe Lys
1 5 10 15

Gly

<210> SEQ ID NO 190
<211> LENGTH: 9
<212> TYPE: PRT
<213> ORGANISM: mus musculus

<400> SEQUENCE: 190

Gln Val Phe Asp Tyr Pro Met Asp Tyr
1 5

<210> SEQ ID NO 191
<211> LENGTH: 15
<212> TYPE: PRT
<213> ORGANISM: mus musculus

<400> SEQUENCE: 191

Arg Ala Ser Glu Ser Val Ser Ile His Gly Thr His Leu Met His
1 5 10 15

<210> SEQ ID NO 192
<211> LENGTH: 7
<212> TYPE: PRT
<213> ORGANISM: mus musculus

<400> SEQUENCE: 192

Ala Ala Ser Asn Leu Glu Ser
1 5

<210> SEQ ID NO 193
<211> LENGTH: 9
<212> TYPE: PRT
<213> ORGANISM: mus musculus

<400> SEQUENCE: 193

Gln Gln Ser Ile Glu Asp Pro Trp Thr
1 5

<210> SEQ ID NO 194
<211> LENGTH: 5
<212> TYPE: PRT
<213> ORGANISM: mus musculus

<400> SEQUENCE: 194

Asp Tyr Glu Met His
1 5

-continued

<210> SEQ ID NO 195
<211> LENGTH: 17
<212> TYPE: PRT
<213> ORGANISM: mus musculus

<400> SEQUENCE: 195

```
Ala Ile Asp Pro Glu Thr Gly Gly Thr Ala Tyr Asn Gln Lys Phe Lys
 1               5                  10                  15

Gly
```

<210> SEQ ID NO 196
<211> LENGTH: 9
<212> TYPE: PRT
<213> ORGANISM: mus musculus

<400> SEQUENCE: 196

```
Ser Ile Tyr Asp Tyr Tyr Phe Asp Tyr
 1               5
```

<210> SEQ ID NO 197
<211> LENGTH: 15
<212> TYPE: PRT
<213> ORGANISM: mus musculus

<400> SEQUENCE: 197

```
Arg Ala Ser Glu Ser Val Ser Ile His Gly Thr His Leu Met His
 1               5                  10                  15
```

<210> SEQ ID NO 198
<211> LENGTH: 7
<212> TYPE: PRT
<213> ORGANISM: mus musculus

<400> SEQUENCE: 198

```
Ala Ala Ser Asn Leu Glu Ser
 1               5
```

<210> SEQ ID NO 199
<211> LENGTH: 9
<212> TYPE: PRT
<213> ORGANISM: mus musculus

<400> SEQUENCE: 199

```
Gln Gln Ser Ile Glu Tyr Pro Arg Thr
 1               5
```

B CELL MATURATION ANTIGEN (BCMA) BINDING PROTEINS

This application is a continuation of International Application No. PCT/EP2012/059762, filed May 24, 2012 which is incorporated herein by reference. This application claims priority to and benefit of U.S. Provisional Application No. 61/490,732 filed on May 27, 2011 which is incorporated by reference in its entirety.

FIELD OF THE INVENTION

The present invention relates to antigen binding proteins and fragments thereof that specifically bind B cell maturation antigen (BCMA) and in particular human BCMA (hBCMA).

The present invention also concerns methods of treating diseases or disorders with said antigen binding fragments, pharmaceutical compositions comprising said antigen binding fragments and methods of manufacture. Other embodiments of the present invention will be apparent from the description below.

Applicants incorporate by reference the material in the sequence listing in the ASCII text file, named PB64476T_US_Sequence_Listing__1379514, created on Mar. 12, 2013, which is 242 kilobytes in size.

BACKGROUND OF THE INVENTION

BCMA (CD269 or TNFRSF17) is a member of the TNF receptor superfamily. It is a non-glycosylated integral membrane receptor for the ligands BAFF and APRIL. BCMA's ligands can also bind additional receptors: TACI (Transmembrane Activator and Calcium modulator and cyclophilin ligand Interactor), which binds APRIL and BAFF; as well as BAFF-R (BAFF Receptor or BR3), which shows restricted but high affinity for BAFF. Together, these receptors and their corresponding ligands regulate different aspects of humoral immunity, B-cell development and homeostasis.

BCMA's expression is typically restricted to the B-cell lineage and is reported to increase in terminal B-cell differentiation. BCMA is expressed by human plasma blasts, plasma cells from tonsils, spleen and bone marrow, but also by tonsillar memory B cells and by germinal centre B cells, which have a TACI-BAFFR low phenotype (Darce et al, 2007). BCMA is virtually absent on naïve and memory B-cells (Novak et al., 2004a and b). The BCMA antigen is expressed on the cell surface so is accessible to the antibody, but is also expressed in the golgi. As suggested by its expression profile, BCMA signalling, typically linked with B-cell survival and proliferation, is important in the late stages of B-cell differentiation, as well as the survival of long lived bone marrow plasma cells (O'Connor et al., 2004) and plasmablasts (Avery et al., 2003). Furthermore, as BCMA binds APRIL with high affinity, the BCMA-APRIL signalling axis is suggested to predominate at the later stages of B-cell differentiation, perhaps being the most physiologically relevant interaction.

Multiple Myeloma (MM) is a clonal B-cell malignancy that occurs in multiple sites within the bone marrow before spreading to the circulation; either de novo, or as a progression from monoclonal gammopathy of undetermined significance (MGUS). It is commonly characterised by increases in paraprotein and osteoclast activity, as well as hypercalcaemia, cytopenia, renal dysfunction, hyperviscosity and peripheral neuropathy. Decreases in both normal antibody levels and numbers of neutrophils are also common, leading to a life threatening susceptibility to infection. BCMA has been implicated in the growth and survival of myeloma cell lines in vitro (Novak et al., 2004a and b; Moreaux et al., 2004).

BCMA expression (both transcript and protein) is reported to correlate with disease progression in MM. Using Affymetrix microarrays, it was demonstrated that the TACI and BCMA genes were over-expressed in Multiple Myeloma Cells (MMC) compared with their normal counterparts (Moreaux et al, 2004). Gene expression analysis has been used to compare human myeloma cells with purified plasma cells from patients with MGUS and from normal bone marrow as well as with primary tumour cells from B-cell lineage leukaemias (Bellucci et al, 2005). The BCMA gene was highly expressed in all myeloma samples. Although purified plasma cells from patients with MGUS had lower expression of BCMA, there was no significant difference when compared with the expression found in normal plasma cells or myeloma cells. In contrast, BCMA expression was significantly lower in B-cell Chronic Lymphocytic Leukaemia (CLL), pre-B Acute Lymphocytic Leukaemia (ALL) and T-cell ALL (T-ALL). Mouse models that transgenically overexpress BAFF or APRIL have a significant increase in B-cell lymphomas (Batten et al., 2004-BAFF; Planelles et al., 2004-APRIL). In humans, excess BAFF and APRIL have been detected in the sera and micro-environments of patients with a number of B-cell malignancies, as well as other B-cell disorders.

All patent and literature references disclosed within the present specification are expressly and entirely incorporated herein by reference.

Multiple myeloma cell line H929 or ARH77-hBCMA 10B5 BCMA expressing transfectant cells were stained with either murine anti BCMA antibodies (solid histogram) or murine IgG2a isotype control (open histograms). Cells were analysed by FACS to detect antibody bound to the cells.

Figure 5:
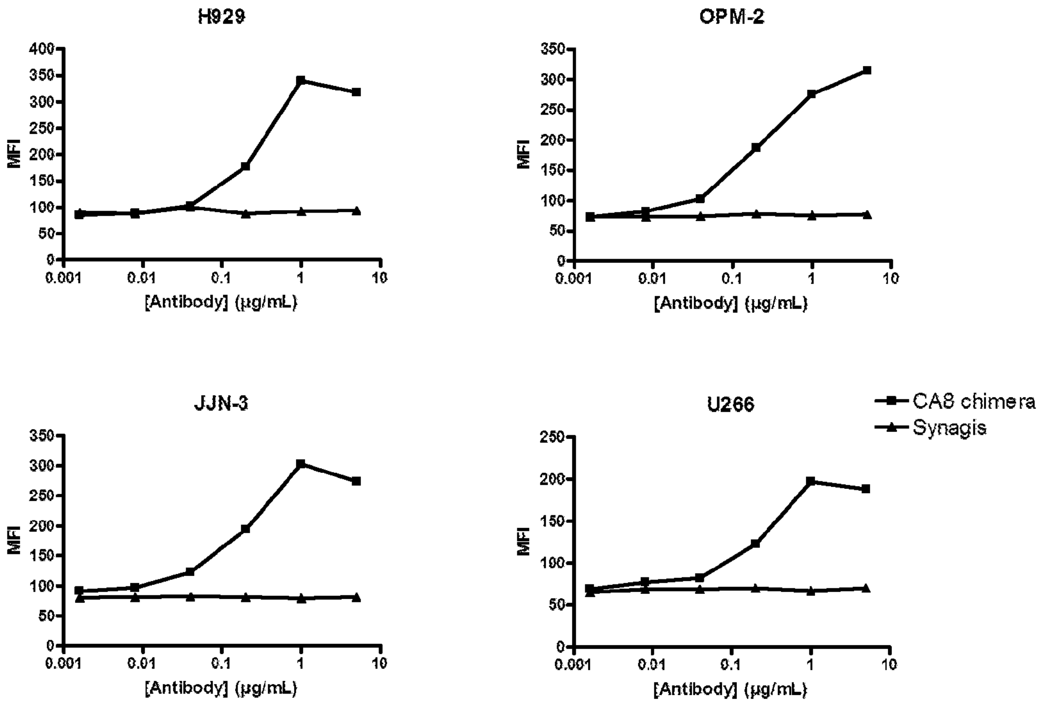

FIG. 5: Cell binding assay—Figure showing binding of chimeric CA8 to a panel of multiple myeloma cell lines as determined by FACS. Binding to H929, OPM-2, JJN-3 and U266 was tested by flow cytometry and mean fluorescence intensity (MFI) values measured to determine binding. Synagis was used as an irrelevant isotype control.

Figure 6A:
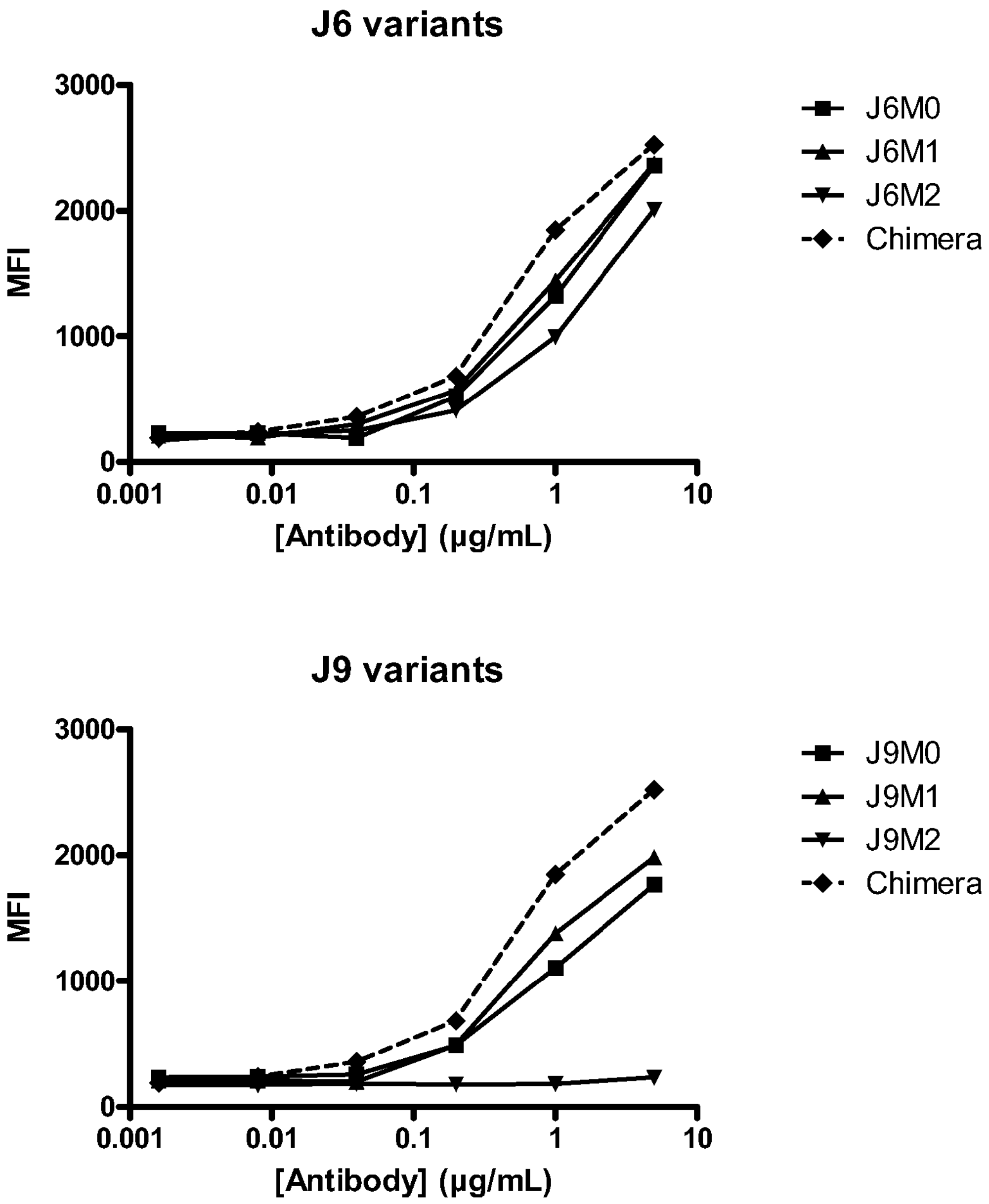
Figure 6B:
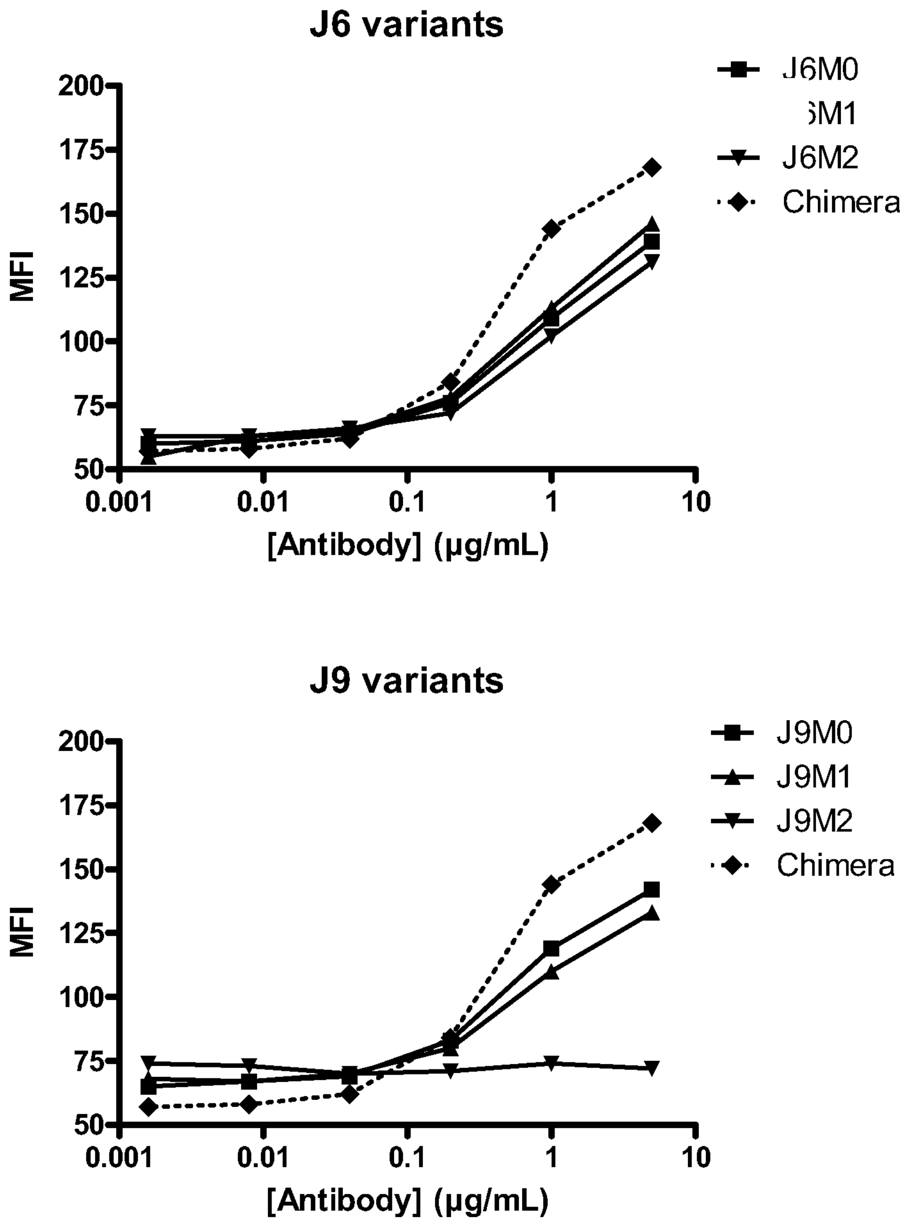

FIG. 6: Cell binding assay—Figure showing binding curves of humanised CA8 variants to BCMA transfected ARH77 cells (A) and multiple myeloma H929 cells (B) as determined by FACS.

Humanised variants J6M0, J6M1, J6M2, J9M0, J9M1 and J9M2 were tested by flow cytometry and mean fluorescence intensity (MFI) values measured to determine binding compared to the CA8 chimera.

Figure 7A:
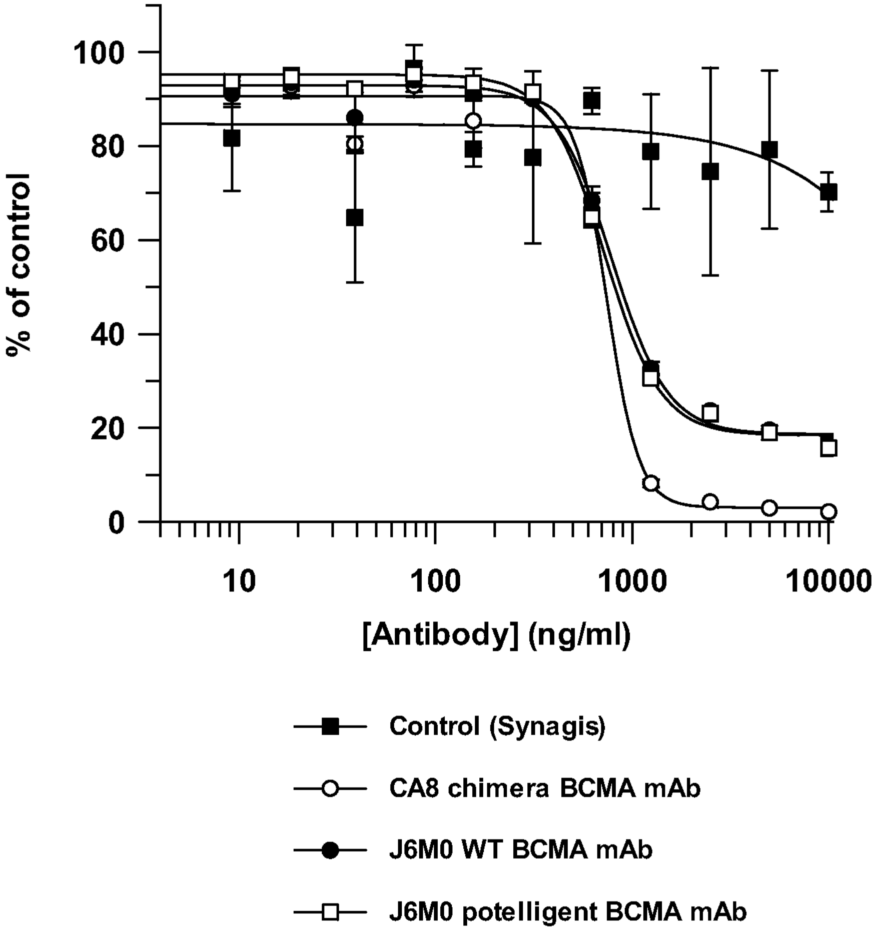
Figure 7B:
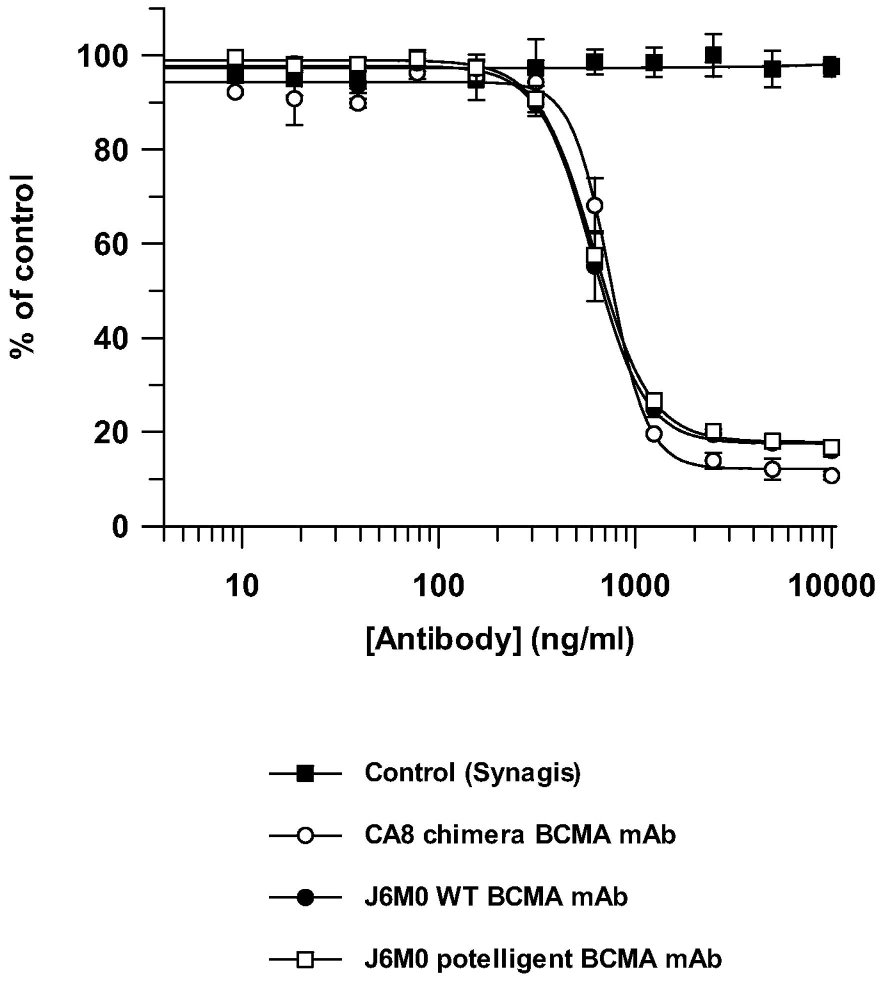

FIG. 7: Ligand neutralisation assays—

(A and B) Figure showing the ability of CA8 and J6M0 to neutralise binding of recombinant BAFF or APRIL to recombinant BCMA coated on an ELISA plate. OD values were used to calculate the antibody mediated inhibition of the maximal signal achieved by the relevant ligand alone binding to recombinant BCMA. Data is reported as percentage inhibition of the maximal signal. Antibodies tested were chimeric CA8 and humanised CA8 version J6M0 in both wild type and afucosylated (Potelligent) form.

(A) Neutralisation of BAFF ligand binding; (B)—Neutralisation APRIL ligand binding.

(C)—Figure showing the ability of J6M0 BCMA antibody in inhibition of BAFF or APRIL induced phosphorylation of NFKappaB in H929 cells. H-929 cells were washed 3 times to remove any sBCMA and resuspended in serum free medium. J6M0 potelligent antibody was added to a 96 well plate to give a final well concentrations up to 100 ug/ml along with BAFF or APRIL ligand to give a final well concentration of 0.6 or 0.2 ug/ml respectively. H-929 cells were then plated at 7.5×104 cells/well in serum free medium. 30 minutes later the cells were lysed and phosphorylated NFkappaB levels measured using a MSD pNFkappaB assay. MSD reader 502819. This is data from one independent experiments. Each data point is the mean/sd of two replicates.

Figure 8A:
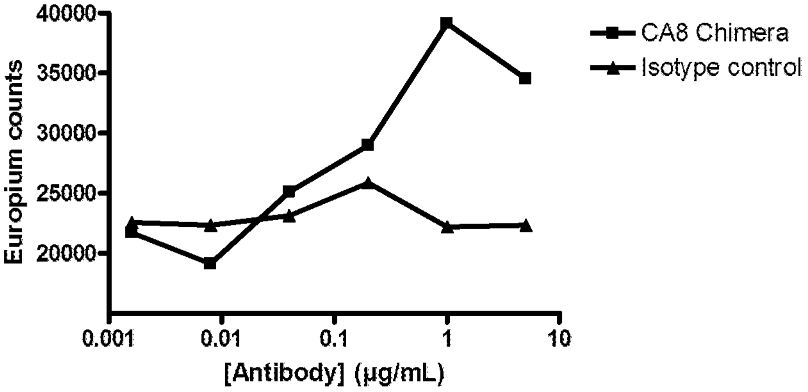
Figure 8B:
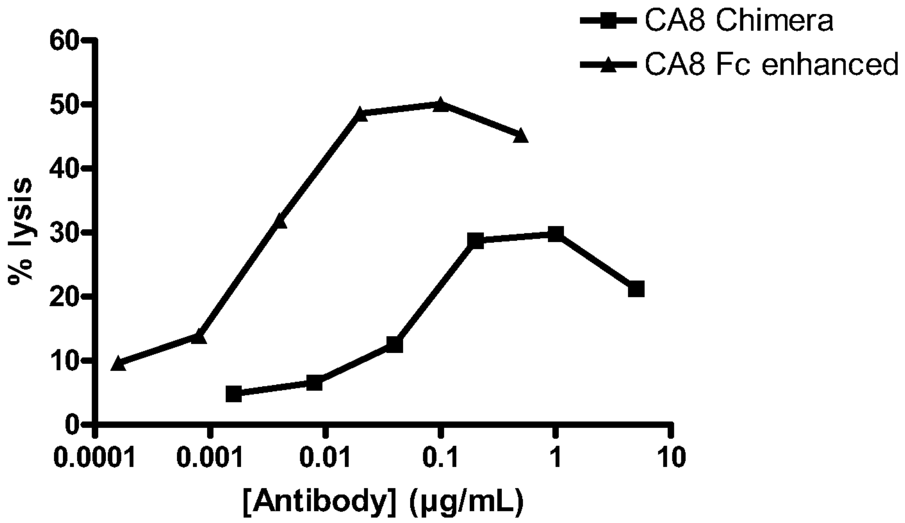

FIG. 8: ADCC assay—Figure showing ADCC activity of chimeric CA8 and defucosylated (Fc enhanced) CA8 with target cells expressing BCMA.

Human NK cells were incubated with europium labelled ARH77 10B5 BCMA transfected target cells in the presence of varying concentrations of antibody. Europium release from the target cells was measured and specific lysis calculated. (A) ADCC dose response curves of chimeric CA8 compared to isotype control. (B) ADCC dose response curves for chimeric CA8 and defucosylated chimeric CA8 (Fc enhanced), against the BCMA expressing cell line ARH77 10B5.

Figure 9:
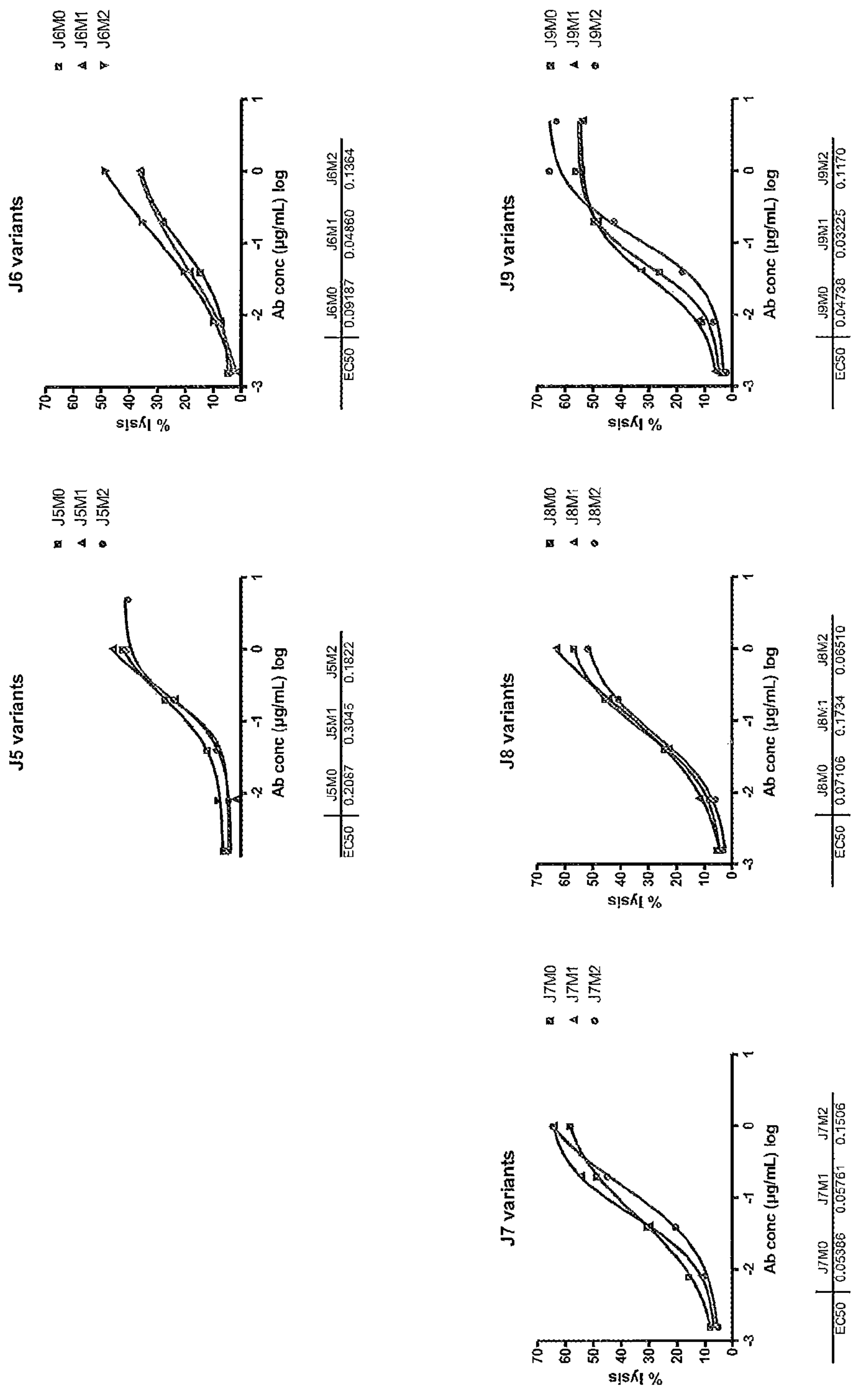

FIG. 9: ADCC assay—Figure showing ADCC assay on CA8 humanised antibodies using ARH77 BCMA expressing target cells.

Human PBMC were incubated with europium labelled ARH77 BCMA transfected target cells in the presence of a range of concentrations of the J5, J6, J7, J8 or J9 series of humanised CA8 antibodies. Europium release from the target cells was measured and specific lysis calculated. EC50 values are shown in ug/ml.

Figure 10:
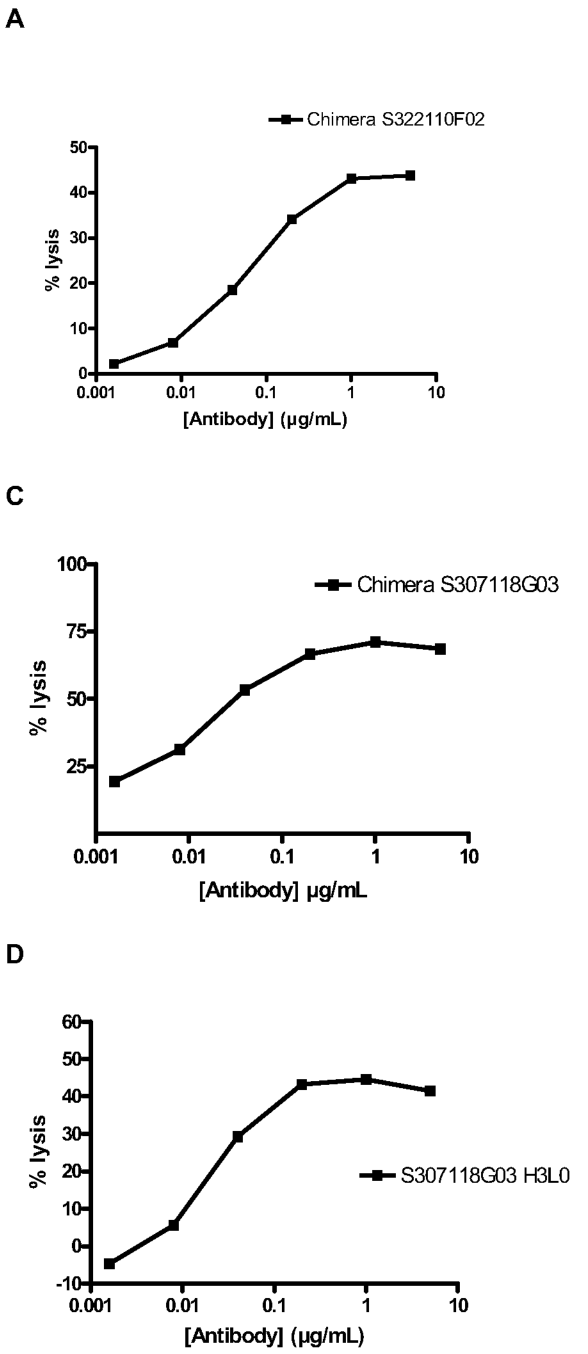

FIG. 10: ADCC assay—Figure showing ADCC activity of chimeric, S332121F02 (A), S3322110D07 (B) S307118G03 (C) and humanised S307118G03 H3L0 (D) against ARH7710B5 target cells with purified NK cells as effector cells. Human NK target cells were incubated with europium labelled ARH77 10B5 BCMA transfected target cells in the presence of varying concentrations of antibody. Europium release from the target cells was measured and specific lysis calculated.

Figure 11:
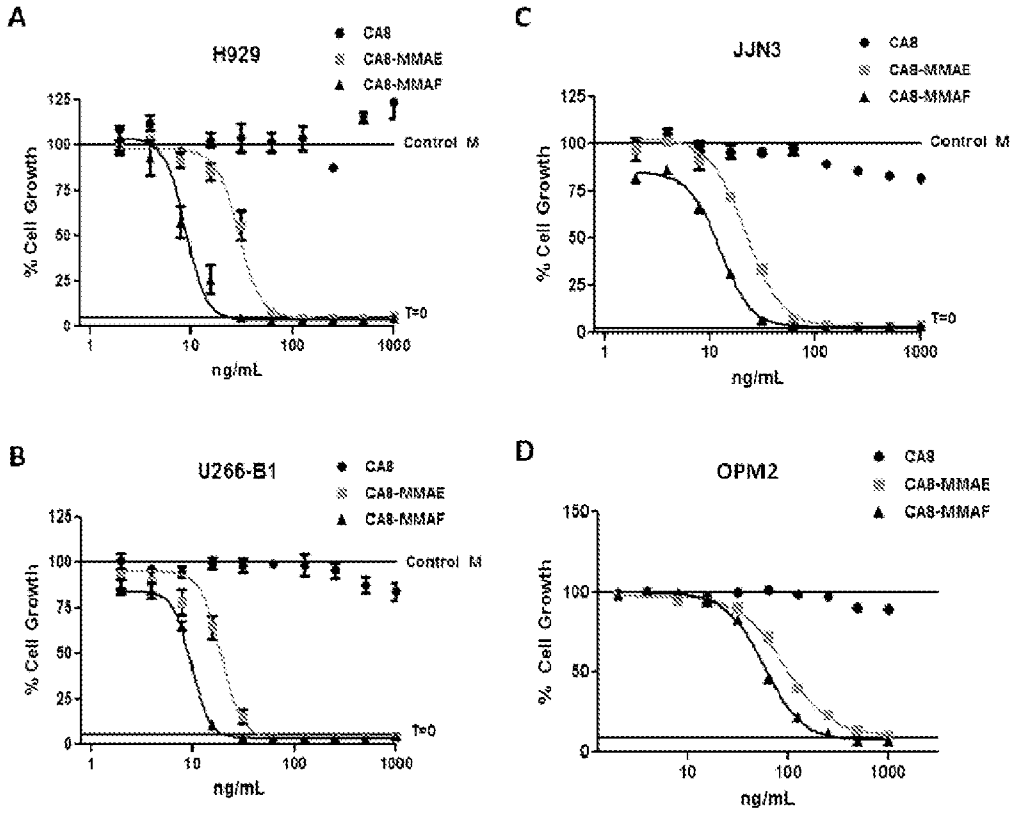

FIG. 11: Viability assay dose response curves—Figure showing dose response curves in a cell viability assay for chimeric CA8 antibody, chimeric CA8-vcMMAE and chimeric CA8-mcMMAF antibody-drug conjugates in human multiple myeloma cell lines (A) NCI-H929 (B) U266-B1 (C) JJN3 and (D) OPM2. Antibody was added to the cells and the number of viable cells after 96 hours measured using Cellti-terGlo.Data points represent the mean of triplicate CellTiter-Glo measurements. Error bars represent standard error.

Figure 12A:
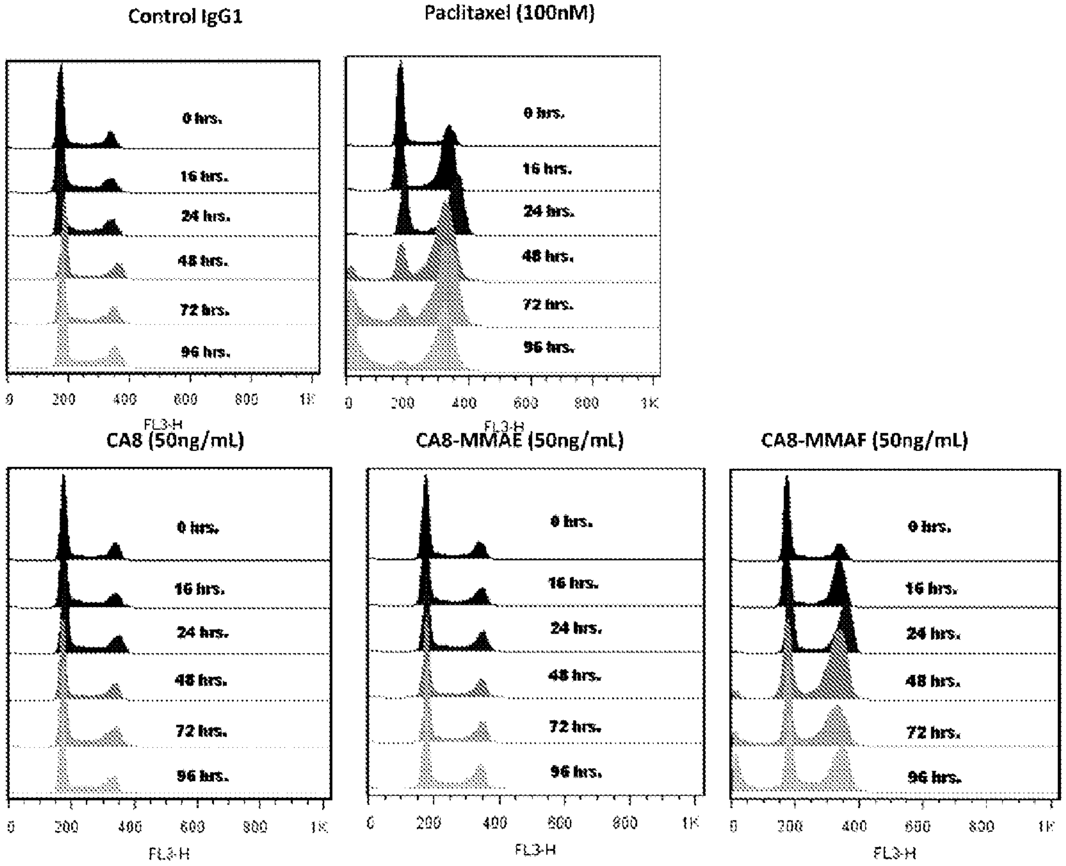
Figure 12B:
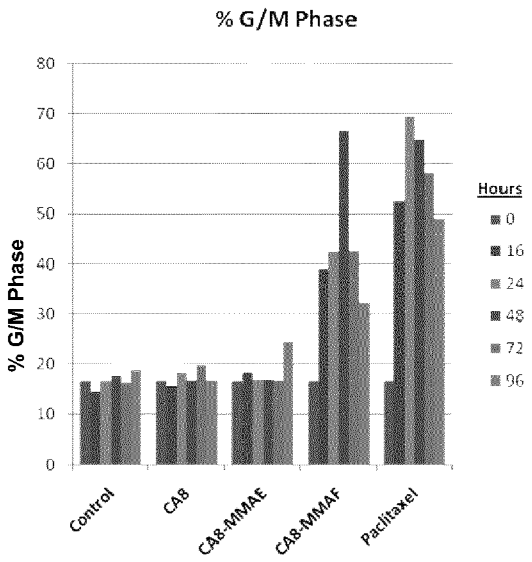
Figure 12C:
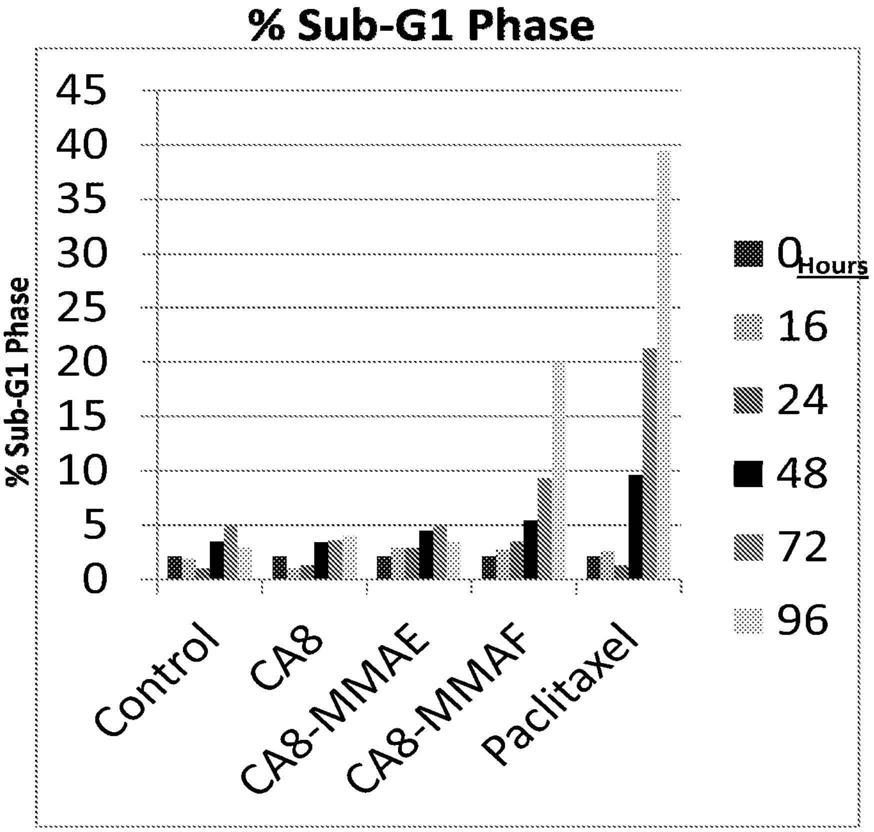

FIG. 12: Impact of CA8 chimeric antibody on cell cycle.

(A) Cell cycle histograms of NCI-H929 cells treated with unconjugated chimeric CA8, chimeric CA8-vcMMAE ADC or chimeric CA8-mcMMAF ADC at 50 ng/mL for the time-points indicated. Pactitaxel (100 nM) was used as a positive control for G2/M cell cycle arrest and cell death. Control human IgG1 was used as a negative control. Cell cycle analysis was carried out at the times shown on the graphs.

(B) Quantification of the 4N DNA cell population indicative of G2/M arrest and (C) sub-2N DNA cell population indicative of cell death for each of the treatments indicated. Cells were seeded in 12-well plates ($2\times10^5$ cells per well in 1 mL of RPMI+10% FBS). Antibody or ADC was added 6 hours after cell seeding.

Figure 13A:
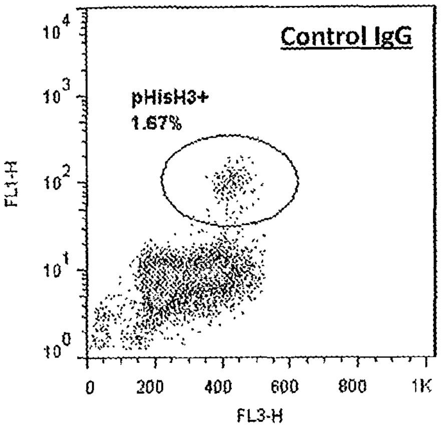
Figure 13B:
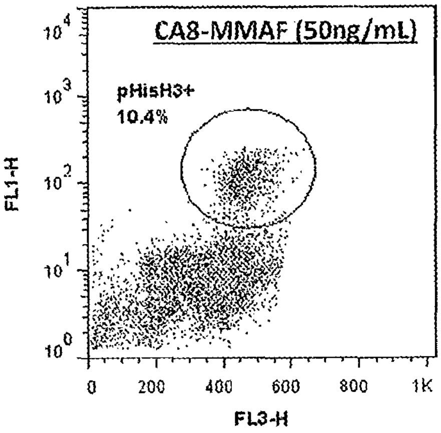
Figure 13C:
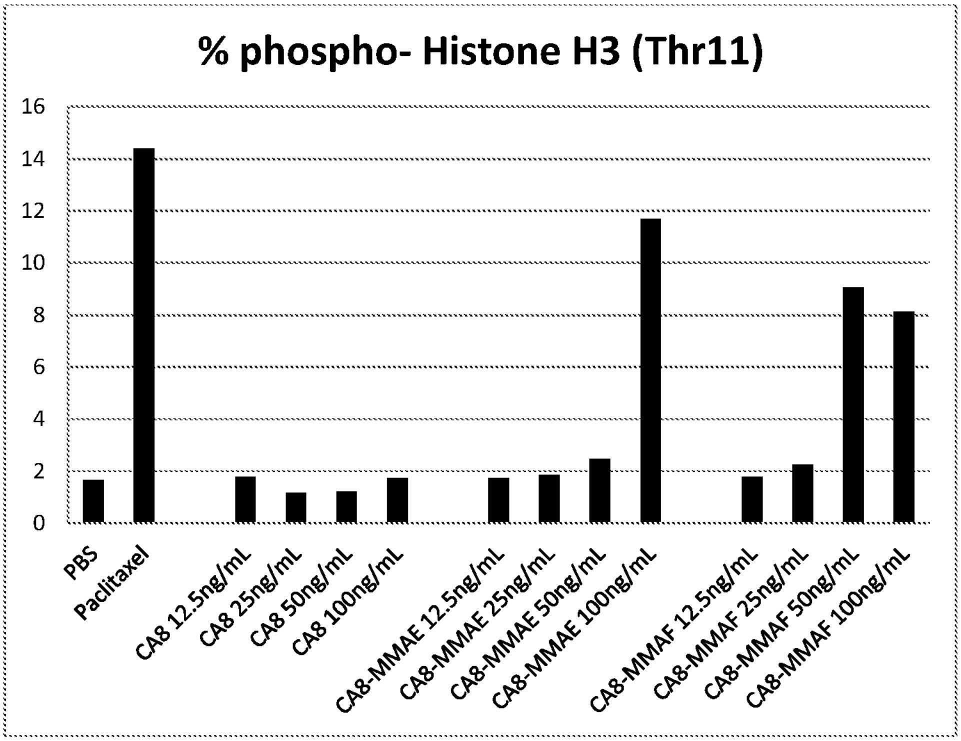

FIG. 13: Impact of chimeric CA8 on phospho-histone H3. Chimeric CA8 ADC treatment results in increased phospho-Histone H3 staining of NCI-H929 cells. (A,B) Dot plots of cells stained with propidium iodide to measure DNA content (FL3-H) x-axis and anti-phospho-Histone H3 (Thr11) antibody (FL1-H) y-axis after treatment with either Control IgG (A) or chimeric CA8-mcMMAF (B). (C) Quantification of phospho-Histone H3 positive NCI-H929 cells after a 48 hour treatment with the indicated concentrations of chimeric CA8 ADCs. Pactitaxel (100 nM) was used as a positive control for mitotic arrest and control chimera IgG1 was used as a negative control. Cells were seeded in 12-well plates ($2\times10^5$ cells per well in 1 mL of RPMI+10% FBS). Antibody or ADC was added 6 hours after cell seeding.

Figure 14A:
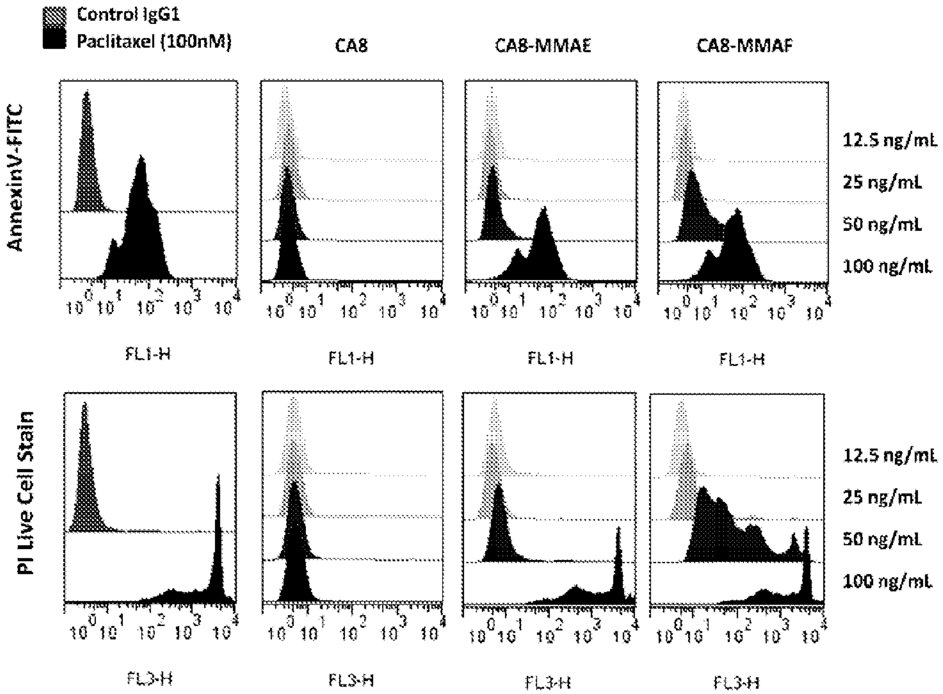
Figure 14B:
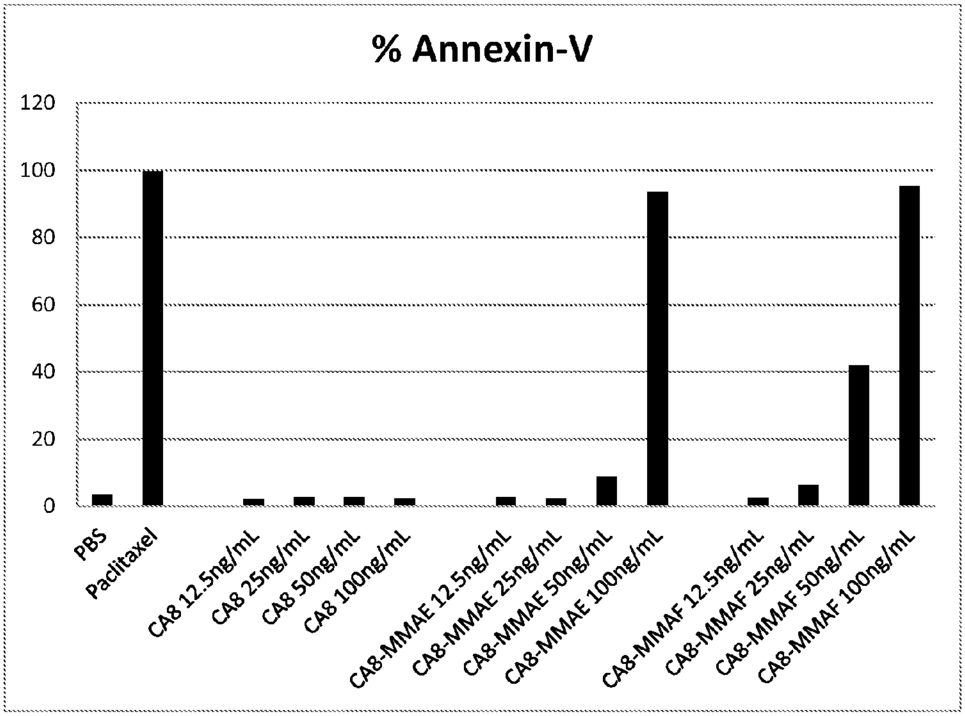

FIG. 14: Impact of chimeric CA8 on Annexin-V. Chimeric CA8 ADC treatment results in increased Annexin-V staining of NCI-H929 cells.

(A) Histograms of Annexin-V-FITC (FL1-H; top panels) and Live cell propidium iodide staining (FL3-H; bottom panels) after treatment with increasing concentrations of chimeric CA8 ADCs (B) Quantification of Annexin-V positive NCI-H929 cells after a 96 hour treatment with the indicated concentrations of chimeric CA8 ADCs. Pactitaxel (100 nM) was used as a positive control for apoptosis and control chimera IgG1 was used as a negative control. Cells were seeded in 12-well plates ($2\times10^5$ cells per well in 1 mL of RPMI+10% FBS). Antibody or ADC was added 6 hours after cell seeding.

Figure 15:
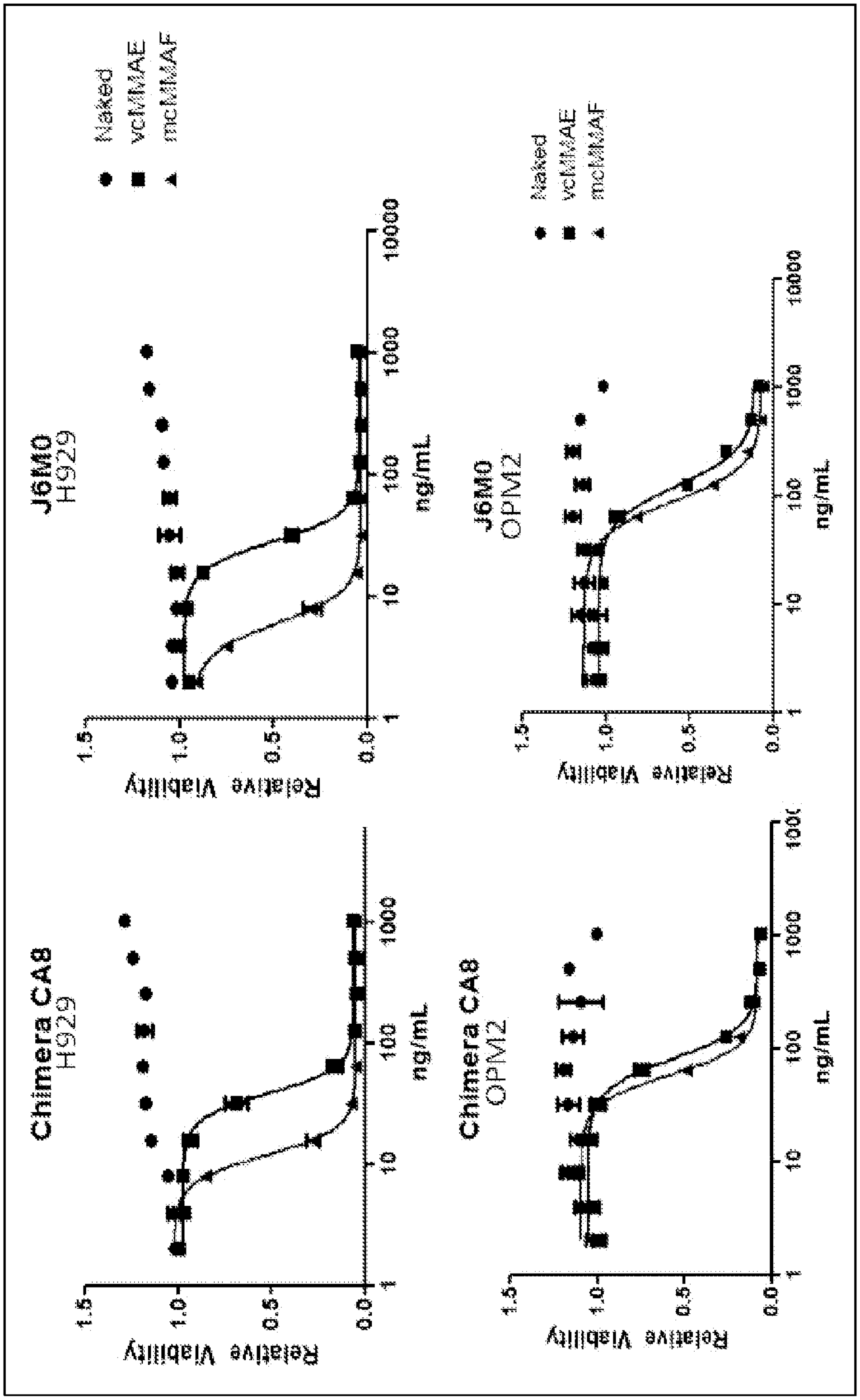

FIG. 15: Viability assay dose response curves—Figure showing dose response curves for the unconjugated (Naked) and vcMMAE and mcMMAF antibody-drug conjugates of chimeric CA8 or humanized J6M0 antibodies. Antibody drug conjugates were tested against human multiple myeloma cell lines NCI-H929 and OPM2.

Figure 16:
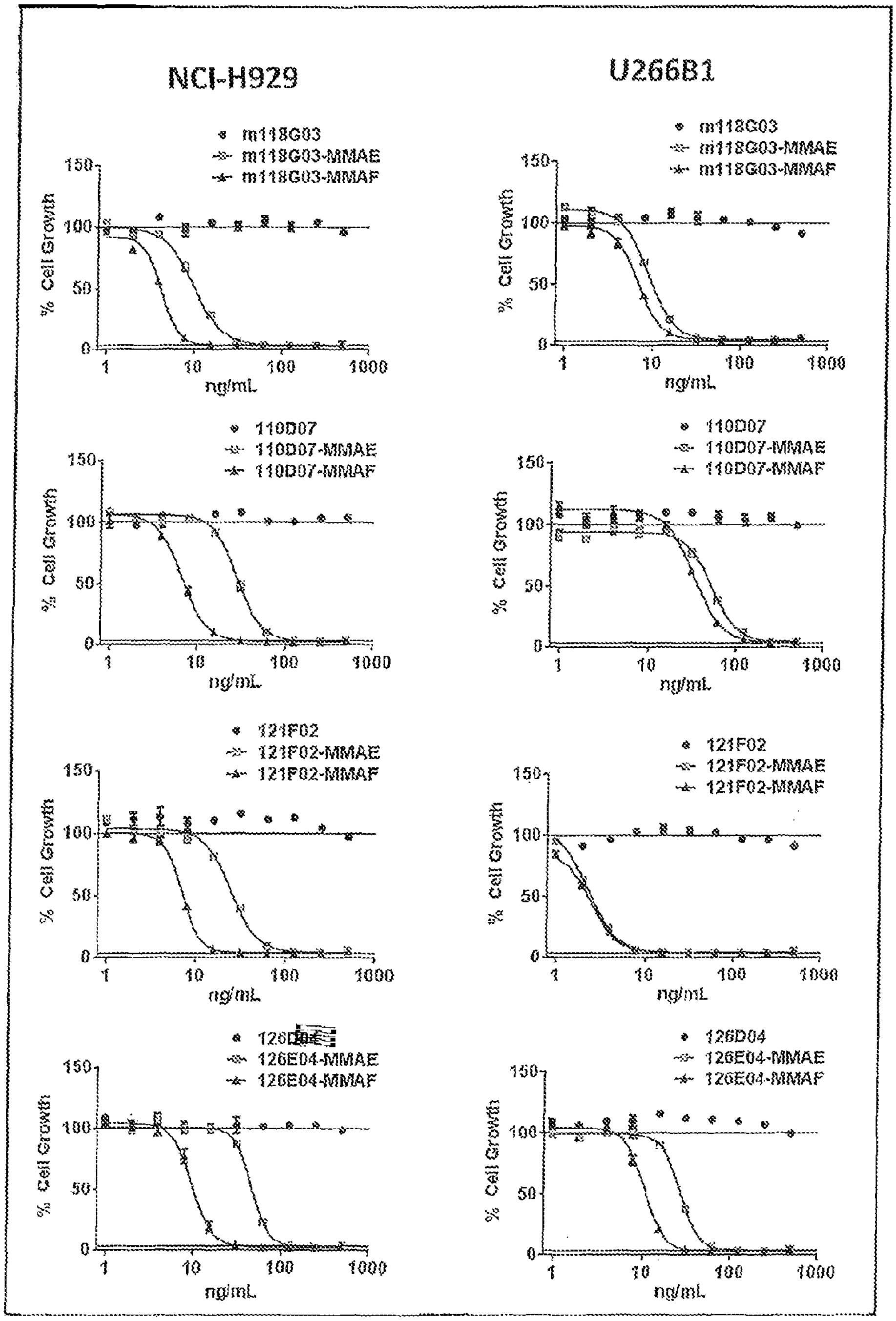

FIG. 16: Viability assay dose response curves—Figure showing dose response curves for the unconjugated antibodies, vcMMAE and mcMMAF antibody-drug conjugates of murine anti-BCMA antibodies S332121F02, S322110D07, S332126E04 and S307118G03 in human multiple myeloma cell lines NCI-H929 and U266-B1.

Figure 17:
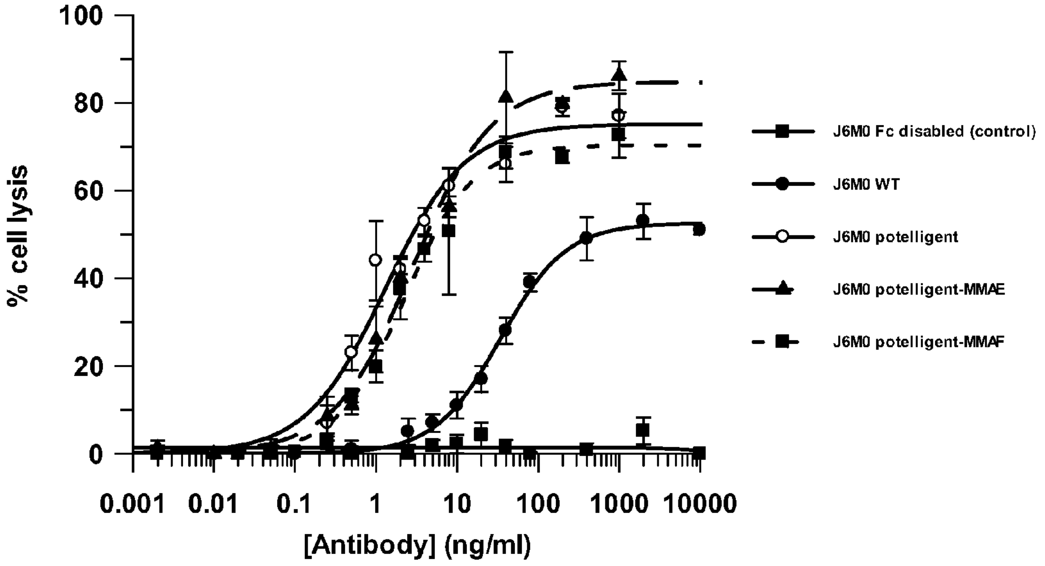

FIG. 17 ADCC activity of ADC J6M0 molecules—Figure showing ADCC assay on J6M0 antibodies using ARH77 BCMA expressing target cells. Human PBMC were incubated with europium labelled ARH77 BCMA transfected target cells in the presence of a range of concentrations of J6M0 WT and potelligent BCMA antibodies conjugated to MMAE, MMAF, or unconjugated Europium release was monitored on the Victor 2 1420 multilabel reader.

Figure 18A:
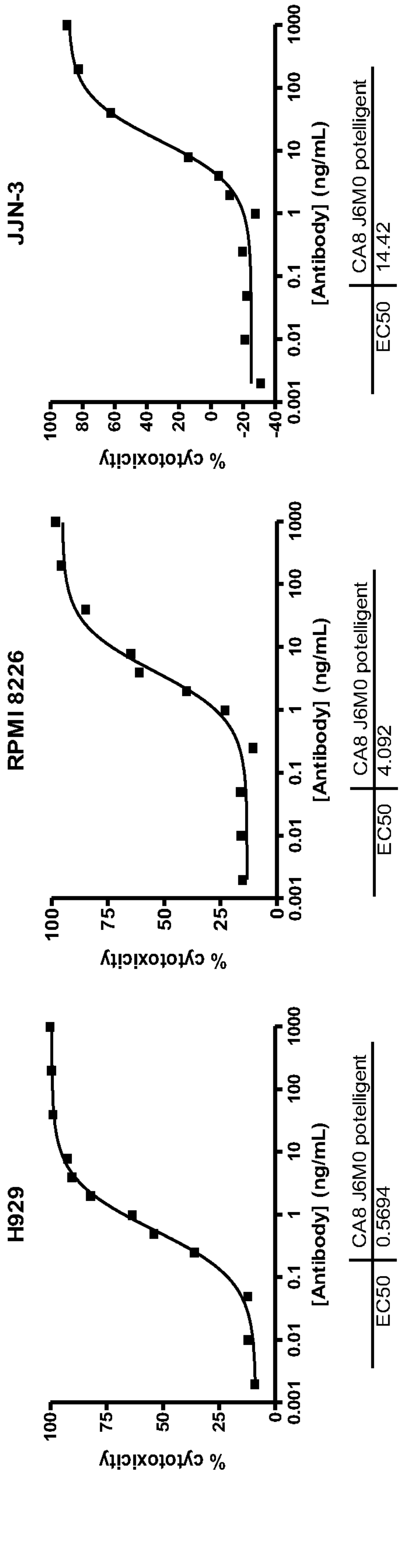
Figure 18B:
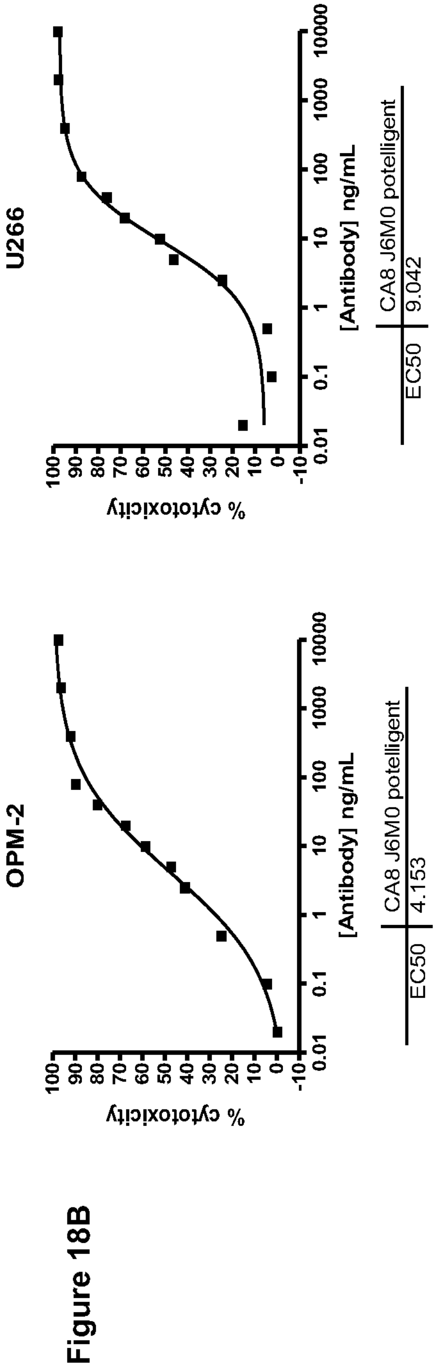

FIGS. 18A and 18B ADCC dose response curves of CA8 J6M0 Potelligent against a panel of 5 multiple myeloma lines—Human PBMC were incubated with multiple myeloma target cells in the presence of varying concentrations of CA8 J6M0 potelligent antibody at an E:T ratio of 50:1 for 18 hours. The percentage of target cells remaining in the effecter plus target mixture was then measured by FACS using a fluorescently labelled anti-CD138 antibody to detect the target cells and the percent cytotoxicity calculated. [A]) Example dose response curves for CA8 J6M0 potelligent against the five multiple myeloma cell lines tested. Each data point is from a singlicate value.

Figure 19:
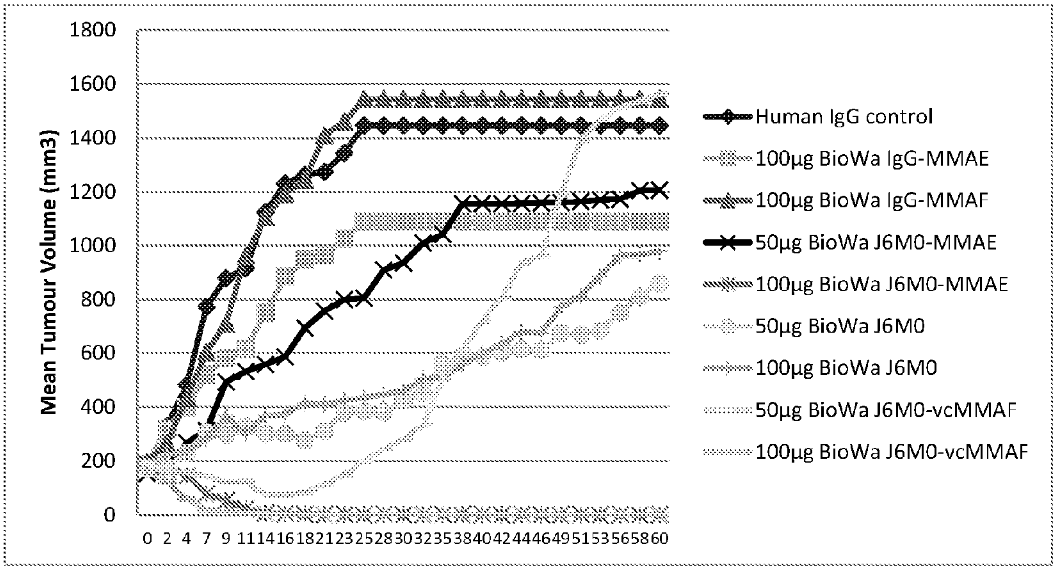
Figure 20:
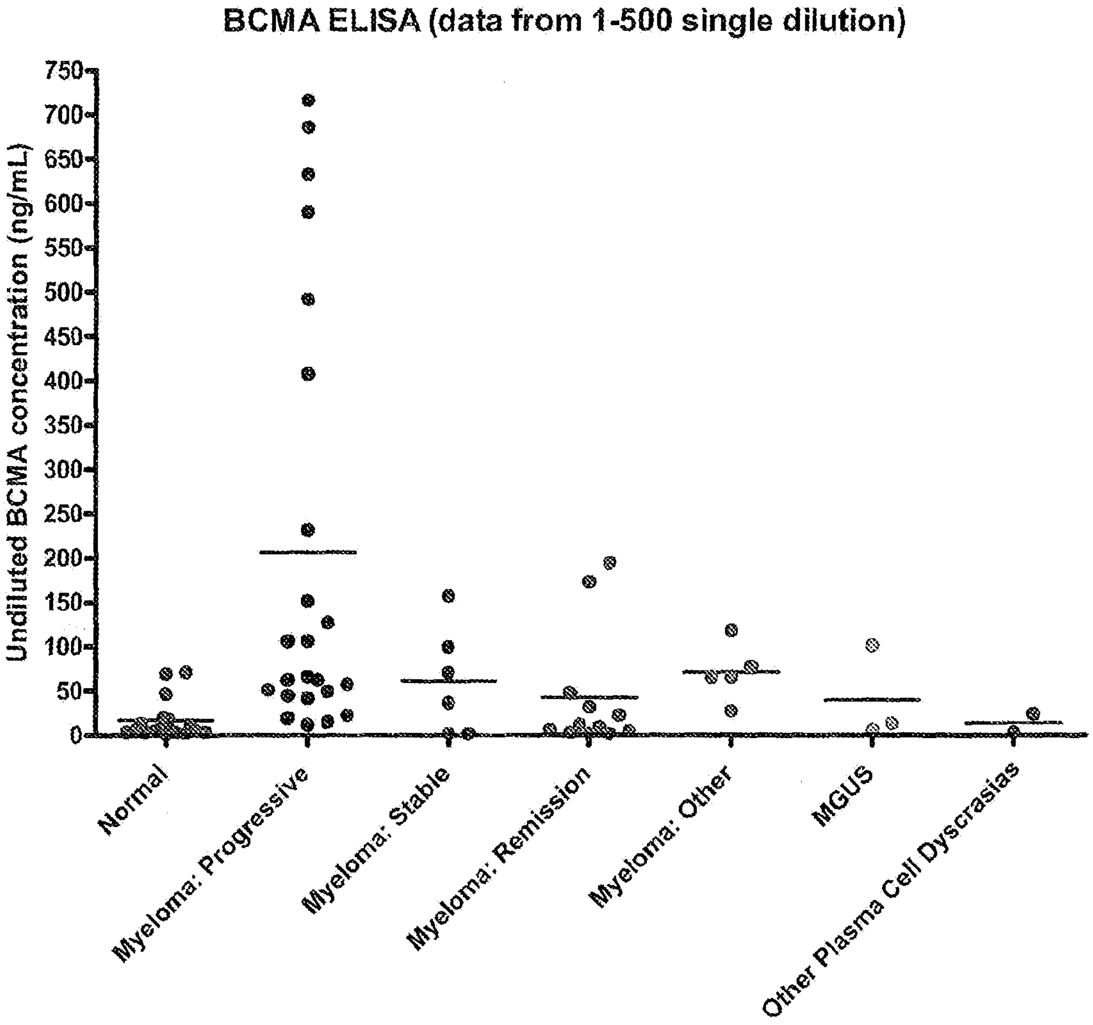

FIG. 19 Effect of dose escalation of J6M0 and drug conjugated J6M0 on the growth and establishment of NCIH929 cells in CB.17 SCID mice Calculated tumour volumes of NCI-H929 tumours in CB17 SCID mice following twice weekly intraperitoneal dosing of either 50 or 100 ug J6M0 anti-BCMA or IgG1 isotype control unconjugated, or conjugated to MMAE or MMAF for 2 weeks. Data points represent mean tumour volume of n=5 per group FIG. 20-Determination of soluble BCMA levels in serum from healthy volunteers and myeloma patients. Serum samples were collected from MM patient samples were from a variety of stages (progressive disease, remission, relapsed, newly diagnosed, and others). The samples shown in the figure are those from serum diluted 1/500 prior to the assay.

A Human BCMA/TNFRSF17 sandwich ELISA kit from R& D Systems which measures soluble human BCMA levels was used to detect BCMA following the standard protocol provided with the kit.

SUMMARY OF THE INVENTION

The present invention provides antigen binding proteins which bind to membrane bound targets and wherein the antigen binding protein is capable of internalisation. In a further embodiment there is provided an immunoconjugate comprising the antigen binding protein of the present invention and a cytotoxic agent. In a further embodiment the antigen binding protein has ADCC effector function for example the antigen binding protein has enhanced ADCC effector function.

The present invention provides antigen binding proteins which specifically bind to BCMA, for example antibodies which specifically bind to BCMA and which inhibit the binding of BAFF and/or APRIL to the BCMA receptor. The present invention also provides antigen binding proteins which specifically bind to BCMA and which inhibits the binding of BAFF and/or APRIL to BCMA wherein the antigen binding protein is capable of binding to FcγRIIIA or is capable of FcγRIIIA mediated effector function.

The antigen binding proteins of the present invention specifically bind to BCMA and inhibit the binding of BAFF and/or APRIL to BCMA wherein the antigen binding protein has enhanced binding to FcγRIIIA or has enhanced FcγRIIIA mediated effector function. In one embodiment the antigen binding protein is capable of internalisation.

In one aspect of the invention there is provided an antigen binding protein according to the invention as herein described which binds to non-membrane bound BCMA, for example to serum BCMA.

In one embodiment of the present invention there is provided an immunoconjugate comprising the antigen binding protein of the present invention and a cytotoxic agent. In a further embodiment the antigen binding proteins are conjugated to a toxin such as an auristatin. In yet a further embodiment the drug conjugate is vcMMAE or mcMMAF.

The antigen binding proteins of the present invention are related to, or derived from a murine monoclonal antibody CA8. The CA8 murine heavy chain variable region amino acid sequence is provided as SEQ ID NO. 7 and the CA8 murine light chain variable region amino acid sequence is provided as SEQ ID NO. 9.

The antigen binding proteins of the present invention are related to, or derived from a murine monoclonal antibody S336105A07. The S336105A07 murine heavy chain variable region amino acid sequence is provided as SEQ ID NO. 140 and the S336105A07 murine light chain variable region amino acid sequence is provided as SEQ ID NO. 144.

Other murine monoclonal antibodies from which antigen binding proteins of the present invention may also be derived are included in Table C.

The heavy chain variable regions (VH) of the present invention may comprise the following CDRs or variants of these CDR's (as defined by Kabat (Kabat et al; Sequences of proteins of Immunological Interest NIH, 1987)):

CDRH1 is provided as SEQ ID NO. 1 or SEQ ID NO. 182
CDRH2 is provided as SEQ ID NO. 2 or SEQ ID NO. 183
CDRH3 is provided as SEQ ID NO. 3 or SEQ ID NO. 184

The light chain variable regions (VL) of the present invention may comprise the following CDRs or variants of these CDR's (as defined by Kabat (Kabat et al; Sequences of proteins of Immunological Interest NIH, 1987)):

CDRL1 is provided as SEQ ID NO. 4 or SEQ ID NO. 185
CDRL2 is provided as SEQ ID NO. 5 or SEQ ID NO. 186
CDRL3 is provided as SEQ ID NO. 6 or SEQ ID NO. 187

The invention also provides a polynucleotide sequence encoding a heavy chain variable region of any of the antigen-binding proteins described herein, and a polynucleotide encoding a light chain variable region of any of the antigen-binding proteins described herein.

The invention also provides a polynucleotide sequence encoding a heavy chain of any of the antigen-binding proteins described herein, and a polynucleotide encoding a light chain of any of the antigen-binding proteins described herein.

Such polynucleotides represent the coding sequence which corresponds to the equivalent polypeptide sequences, however it will be understood that such polynucleotide sequences could be cloned into an expression vector along with a start codon, an appropriate signal sequence and a stop codon.

The invention also provides a recombinant transformed or transfected host cell comprising one or more polynucleotides encoding a heavy chain and/or a light chain of any of the antigen-binding proteins described herein.

The invention further provides a method for the production of any of the antigen-binding proteins described herein which method comprises the step of culturing a host cell comprising a first and second vector, said first vector comprising a polynucleotide encoding a heavy chain of any of the antigen-binding proteins described herein and said second vector comprising a polynucleotide encoding a light chain of any of the antigen-binding proteins described herein, in a suitable culture media, for example serum-free culture media.

The invention further provides a pharmaceutical composition comprising an antigen-binding protein as described herein and a pharmaceutically acceptable carrier.

In a further aspect, the present invention provides a method of treatment or prophylaxis of a disease or disorder responsive to inhibiting or blocking BCMA such as the modulation of the interaction between BCMA and its ligands, BAFF or APRIL which method comprises the step of administering to said patient a therapeutically effective amount of the antigen binding protein thereof as described herein.

It is therefore an object of the present invention to provide a therapeutic approach to the treatment of B cell related disorders or diseases such as antibody mediated or plasma cell mediated diseases or plasma cell malignancies such as for example Multiple Myeloma (MM). In particular it is an object of the present invention to provide antigen binding proteins, especially antibodies that specifically bind BCMA (e.g.

hBCMA) and modulate (i.e. inhibit or block) the interaction between BCMA and its ligands such as BAFF and/or APRIL in the treatment of diseases and disorders responsive to modulation of that interaction.

In another aspect of the present invention there is provided a method of treating a human patient afflicted with a B cell related disorders or diseases such as antibody mediated or plasma cell mediated diseases or plasma cell malignancies such as for example Multiple Myeloma (MM) which method comprises the step of administering to said patient a therapeutically effective amount of the antigen binding protein as described herein.

In another aspect of the present invention there is provided a method of treating a human patient afflicted with Rheumatoid Arthritis, Psoriasis, Type 1 Diabetes Mellitus or Multiple Sclerosis which method comprises the step of administering to said patient a therapeutically effective amount of the antigen binding protein as described herein.

DETAILED DESCRIPTION OF THE INVENTION

The present invention provides antigen binding proteins which bind to membrane bound targets and wherein the antigen binding protein is capable of internalisation. In a further embodiment there is provided an immunoconjugate comprising the antigen binding protein of the present invention and a cytotoxic agent. In a further embodiment the antigen binding protein has ADCC effector function for example the antigen binding protein has enhanced ADCC effector function.

In one such embodiment there is provided antigen binding proteins or fragments thereof which specifically bind to BCMA, for example which specifically binds human BCMA (hBCMA) and which inhibit the binding of BAFF and/or APRIL to the BCMA receptor.

In a further embodiment the antigen binding proteins or fragments of the present invention specifically bind to BCMA and inhibit the binding of BAFF and/or APRIL to BCMA wherein the antigen binding proteins or fragments thereof have the ability to bind to FcγRIIIA and mediate FcgRIIIA mediated effector functions, or have enhanced FcγRIIIA mediated effector function. In one embodiment of the invention as herein provided the antigen binding proteins are capable of internalisation.

In one aspect of the invention there is provided an antigen binding protein according to the invention as herein described which binds to non-membrane bound BCMA, for example to serum BCMA.

In one aspect of the invention there is provided an antigen binding protein as herein described wherein the antigen binding protein comprises CDRH3 of SEQ ID NO. 3 or a variant of SEQ ID NO. 3.

In a further aspect of the invention there is provided an antigen binding protein as herein described wherein the antigen binding protein further comprises one or more of: CDR H1 of SEQ. ID. NO: 1, CDRH2: SEQ. ID. NO: 2: CDRL1: SEQ. ID. NO: 4, CDRL2: SEQ. ID. NO: 5 and/or CDRL3: SEQ. ID. NO: 6 and or variants thereof.

In one aspect of the invention there is provided an antigen binding protein as herein described wherein the antigen binding protein comprises CDRH3 of SEQ ID NO. 184 or a variant of SEQ ID NO. 184.

In a further aspect of the invention there is provided an antigen binding protein as herein described wherein the antigen binding protein further comprises one or more of: CDR H1 of SEQ. ID. NO: 182, CDRH2: SEQ. ID. NO: 183: CDRL1: SEQ. ID. NO: 185, CDRL2: SEQ. ID. NO: 186 and/or CDRL3: SEQ. ID. NO: 187 and or variants thereof.

In yet a further aspect the antigen binding protein comprises CDR H3 of SEQ. ID. NO: 3: CDRH2: SEQ. ID. NO: 2: CDR H1 of SEQ. ID. NO:1: CDRL1: SEQ. ID. NO: 4: CDRL2: SEQ. ID. NO: 5 and CDRL3: SEQ. ID. NO: 6.

In yet a further aspect the antigen binding protein comprises CDR H3 of SEQ. ID. NO: 184: CDRH2: SEQ. ID. NO: 183: CDR H1 of SEQ. ID. NO:182: CDRL1: SEQ. ID. NO: 185: CDRL2: SEQ. ID. NO: 186 and CDRL3: SEQ. ID. NO: 187.

The antigen binding proteins of the present invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

The constant region is selected according to any functionality required e.g. an IgG1 may demonstrate lytic ability through binding to complement and/or will mediate ADCC (antibody dependent cell cytotoxicity).

The antigen binding proteins of the present invention are derived from the murine antibody having the variable regions as described in SEQ ID NO:7 and SEQ ID NO:9 or non-murine equivalents thereof, such as rat, human, chimeric or humanised variants thereof, for example they are derived from the antibody having the variable heavy chain sequences as described in SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29 and/or the variable light chain sequences as described in SEQ ID NO:31, SEQ ID NO:33 and/or SEQ ID NO:35.

In another embodiment the antigen binding proteins of the present invention are derived from an antibody having the variable heavy chain sequences as described in SEQ ID NO:116 or SEQ ID NO:118 and/or the variable light chain sequences as described in SEQ ID NO:120, or SEQ ID NO:122.

In another embodiment the antigen binding proteins of the present invention are derived from an antibody having the variable heavy chain sequences as described in SEQ ID NO:140 and/or the variable light chain sequences as described in SEQ ID NO:144.

In one aspect of the invention there is provided an antigen binding protein comprising an isolated heavy chain variable domain selected from any one of the following: SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:116 or SEQ ID NO:118.

In another aspect of the invention there is provided an antigen binding protein comprising an isolated light chain variable domain selected from any one of the following: SEQ ID NO:31, SEQ ID NO:33 or SEQ ID NO:35, SEQ ID NO:120 or SEQ ID NO:122.

In a further aspect of the invention there is provided an antigen binding protein comprising an isolated heavy chain variable domain selected from any one of the following: SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29 and an isolated light chain variable domain selected from any one of the following: SEQ ID NO:31, SEQ ID NO:33 and/or SEQ ID NO:35.

In one aspect the antigen binding protein of the present invention comprises a heavy chain variable region encoded by SEQ. ID. NO:23 and a light chain variable region encoded by SEQ. ID. NO:31 In one aspect the antigen binding protein of the present invention comprises a heavy chain variable region encoded by SEQ. ID. NO:27 and a light chain variable region encoded by SEQ. ID. NO:31. In one aspect the antigen binding protein of the present invention comprises a heavy chain variable region encoded by SEQ. ID. NO:29 and a light chain variable region encoded by SEQ. ID. NO:31.

In one aspect the antigen binding protein of the present invention comprises a heavy chain variable region encoded by SEQ. ID. NO:116 and a light chain variable region encoded by SEQ. ID. NO:120

In one aspect the antigen binding protein of the present invention comprises a heavy chain variable region encoded by SEQ. ID. NO:118 and a light chain variable region encoded by SEQ. ID. NO:122

In one aspect there is provided a polynucleotide encoding an isolated variable heavy chain said polynucleotide comprising SEQ. ID. NO. 12, or SEQ. ID. NO. 14, or SEQ. ID. NO. 16, or SEQ. ID. NO. 18, or SEQ. ID. NO. 20, or SEQ. ID. NO. 22, or SEQ. ID. NO. 24, or SEQ. ID. NO. 26, or SEQ. ID. NO. 28, or SEQ. ID. NO. 30 or SEQ. ID. NO. 117 or SEQ. ID. NO. 119 or SEQ. ID. NO. 141.

In one aspect there is provided a polynucleotide encoding an isolated variable light chain said polynucleotide comprising SEQ. ID. NO. 32, or SEQ. ID. NO. 34, or SEQ. ID. NO. 36 or SEQ. ID. NO. 121 or SEQ. ID. NO. 123 or SEQ. ID. NO. 145.

In a further aspect there is provided a polynucleotide encoding an isolated variable heavy chain said polynucleotide comprising SEQ. ID. NO. 24, or SEQ. ID. NO. 28 or SEQ. ID. NO. 30 and a polynucleotide encoding an isolated variable light chain said polynucleotide comprising SEQ. ID. NO. 32, or SEQ. ID. NO. 34.

In yet a further aspect there is provided a polynucleotide encoding an isolated variable heavy chain said polynucleotide comprising SEQ. ID. NO. 24 and a polynucleotide encoding an isolated variable light chain said polynucleotide comprising SEQ. ID. NO. 32.

In yet a further aspect there is provided a polynucleotide encoding an isolated variable heavy chain said polynucleotide comprising SEQ. ID. NO. 117 and a polynucleotide encoding an isolated variable light chain said polynucleotide comprising SEQ. ID. NO. 121.

In yet a further aspect there is provided a polynucleotide encoding an isolated variable heavy chain said polynucleotide comprising SEQ. ID. NO. 119 and a polynucleotide encoding an isolated variable light chain said polynucleotide comprising SEQ. ID. NO. 123.

In yet a further aspect there is provided a polynucleotide encoding an isolated variable heavy chain said polynucleotide comprising SEQ. ID. NO. 141 and a polynucleotide encoding an isolated variable light chain said polynucleotide comprising SEQ. ID. NO. 145.

In a further aspect the antigen binding protein may comprise any one of the variable heavy chains as described herein in combination with any one of the light chains as described herein.

In one aspect the antigen binding protein is an antibody or antigen binding fragment thereof comprising one or more CDR's according to the invention described herein, or one or both of the heavy or light chain variable domains according to the invention described herein. In one embodiment the antigen binding protein binds primate BCMA. In one such embodiment the antigen binding protein additionally binds non-human primate BCMA, for example cynomolgus macaque monkey BCMA.

In another aspect the antigen binding protein is selected from the group consisting of a dAb, Fab, Fab', $F(ab')_2$, Fv, diabody, triabody, tetrabody, miniantibody, and a minibody.

In one aspect of the present invention the antigen binding protein is a humanised or chimaeric antibody, in a further aspect the antibody is humanised.

In one aspect the antibody is a monoclonal antibody.

In one aspect of the present invention there is provided an antibody with the heavy chain sequence as set forth in SEQ ID NO: 55 or SEQ ID NO: 59 or SEQ ID NO: 61.

In one aspect of the present invention there is provided an antibody with the light chain sequence as set forth in SEQ ID NO: 63 or SEQ ID NO: 65.

In a further aspect of the invention there is provided an antibody with the heavy chain sequence of SEQ ID NO: 55 and a light chain sequence as set forth in SEQ ID NO: 63.

In one embodiment there is provided an antigen binding protein which competes with an antigen binding protein of the invention as herein described. In one such embodiment there is therefore provided an antigen binding protein which competes with an antigen binding protein which comprises the heavy chain variable sequence of SEQ ID NO 23 and the light chain variable region of SEQ ID NO 31.

In a further embodiment there is therefore provided an antigen binding protein which competes with an antigen binding protein which comprises a heavy chain variable sequence selected from one of SEQ ID NO 27, SEQ ID NO 29, SEQ ID NO 116, SEQ ID NO 118 and SEQ ID NO 140 and a light chain variable region selected from one of SEQ ID NO 31, SEQ ID NO 120, SEQ ID NO 122 and SEQ ID NO 144.

In another aspect the antigen binding protein binds to human BCMA with high affinity for example when measured by Biacore the antigen binding protein binds to human BCMA with an affinity of 20 nM or less or an affinity of 15 nM or less or an affinity of 5 nM or less or an affinity of 1000 pM or less or an affinity of 500 pM or less or an affinity of 400 pM or less, or 300 pM or less or for example about 120 pM. In a further embodiment the antigen binding protein binds to human BCMA when measured by Biacore of between about 100 pM and about 500 pM or between about 100 pM and about 400 pM, or between about 100 pM and about 300 pM. In one embodiment of the present invention the antigen binding protein binds BCMA with an affinity of less than 150 pm.

In one such embodiment, this is measured by Biacore, for example as set out in Example 4.

In another aspect the antigen binding protein binds to human BCMA and neutralises the binding of the ligands BAFF and/or APRIL to the BCMA receptor in a cell neutralisation assay wherein the antigen binding protein has an 1050 of between about 1 nM and about 500 nM, or between about 1 nM and about 100 nM, or between about 1 nM and about 50 nM, or between about 1 nM and about 25 nM, or between about 5 nM and about 15 nM. In a further embodiment of the present invention the antigen binding protein binds BCMA and neutralises BCMA in a cell neutralisation assay wherein the antigen binding protein has an 1050 of about 10 nM.

In one such embodiment, this is measured by a cell neutralisation assay, for example as set out in Example 4.6.

The antigen binding proteins, for example antibodies of the present invention may be produced by transfection of a host cell with an expression vector comprising the coding sequence for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of *E. Coli* may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns.

Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of *E. Coli* used for expression are well-known as host cells in the field of biotechnology. Various strains of *B. Subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium precipitation, affinity columns, column chromatography, gel electrophoresis and the like. Such techniques are within the skill of the art and do not limit this invention. For example, preparations of altered antibodies are described in WO 99/58679 and WO 96/16990. Yet another method of expression of the antigen binding proteins may utilize expression in a transgenic animal, such as described in U.S. Pat. No. 4,873,316. This relates to an expression system using the animals casein promoter which when transgenically incorporated into a mammal permits the female to produce the desired recombinant protein in its milk.

In a further embodiment of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-BCMA antibody of the present invention which binds to and neutralises the activity of human BCMA which method comprises the steps of;

providing a first vector encoding a heavy chain of the antibody;

providing a second vector encoding a light chain of the antibody;

transforming a mammalian host cell (e.g. CHO) with said first and second vectors;

culturing the host cell of step (c) under conditions conducive to the secretion of the antibody from said host cell into said culture media;

recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to BCMA. Additionally, other in vitro assays may also be used to verify neutralizing efficacy prior to subsequent human clinical studies performed to evaluate the persistence of the antibody in the body despite the usual clearance mechanisms.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks or once every 3 weeks) over an extended time period (e.g. four to six months) maybe required to achieve maximal therapeutic efficacy.

In one embodiment of the present invention there is provided a recombinant transformed, transfected or transduced host cell comprising at least one expression cassette, for example where the expression cassette comprises a polynucleotide encoding a heavy chain of an antigen binding protein according to the invention described herein and further comprises a polynucleotide encoding a light chain of an antigen binding protein according to the invention described herein or where there are two expression cassettes and the $1^{st}$ encodes the light chain and the second encodes the heavy chain. For example in one embodiment the first expression cassette comprises a polynucleotide encoding a heavy chain of an antigen binding protein comprising a constant region or antigen binding fragment thereof which is linked to a constant region according to the invention described herein and further comprises a second cassette comprising a polynucleotide encoding a light chain of an antigen binding protein comprising a constant region or antigen binding fragment thereof which is linked to a constant region according to the invention described herein for example the first expression cassette comprises a polynucleotide encoding a heavy chain selected from SEQ. ID. NO:56, or SEQ. ID. NO: 60 or SEQ. ID. NO: 62 and a second expression cassette comprising a polynucleotide encoding a light chain selected from SEQ. ID. NO: 64 or SEQ. ID. NO: 66.

In another embodiment of the invention there is provided a stably transformed host cell comprising a vector comprising one or more expression cassettes encoding a heavy chain and/or a light chain of the antibody comprising a constant region or antigen binding fragment thereof which is linked to a constant region as described herein. For example such host cells may comprise a first vector encoding the light chain and a second vector encoding the heavy chain, for example the first vector encodes a heavy chain selected from SEQ. ID. NO: 55, or SEQ. ID. NO: 59 or SEQ. ID. NO: 61 and a second vector encoding a light chain for example the light chain of SEQ ID NO: 63 or SEQ. ID. NO: 65. In one such example the first vector encodes a heavy chain selected from SEQ. ID. NO: 55 and a second vector encoding a light chain for example the light chain of SEQ ID NO: 63.

In another embodiment of the present invention there is provided a host cell according to the invention described herein wherein the cell is eukaryotic, for example where the cell is mammalian. Examples of such cell lines include CHO or NS0.

In another embodiment of the present invention there is provided a method for the production of an antibody comprising a constant region or antigen binding fragment thereof which is linked to a constant region according to the invention described herein which method comprises the step of culturing a host cell in a culture media, for example serum-free culture media.

In another embodiment of the present invention there is provided a method according to the invention described herein wherein said antibody is further purified to at least 95% or greater (e.g. 98% or greater) with respect to said antibody containing serum-free culture media.

In yet another embodiment there is provided a pharmaceutical composition comprising an antigen binding protein and a pharmaceutically acceptable carrier.

In another embodiment of the present invention there is provided a kit-of-parts comprising the composition according to the invention described herein described together with instructions for use.

The mode of administration of the therapeutic agent of the invention may be any suitable route which delivers the agent to the host. The antigen binding proteins, and pharmaceutical compositions of the invention are particularly useful for parenteral administration, i.e., subcutaneously (s.c.), intrathecally, intraperitoneally, intramuscularly (i.m.) or intravenously (i.v.). In one such embodiment the antigen binding proteins of the present invention are administered intravenously or subcutaneously.

Therapeutic agents of the invention may be prepared as pharmaceutical compositions containing an effective amount of the antigen binding protein of the invention as an active ingredient in a pharmaceutically acceptable carrier. In one embodiment the prophylactic agent of the invention is an aqueous suspension or solution containing the antigen binding protein in a form ready for injection. In one embodiment the suspension or solution is buffered at physiological pH. In one embodiment the compositions for parenteral administration will comprise a solution of the antigen binding protein of the invention or a cocktail thereof dissolved in a pharmaceutically acceptable carrier. In one embodiment the carrier is an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding protein of the invention in such pharmaceutical formulation can vary widely, i.e., from less than about 0.5%, usually at or at least about 1% to as much as about 15 or 20% by weight and will be selected primarily based on fluid volumes, viscosities, etc., according to the particular mode of administration selected.

Thus, a pharmaceutical composition of the invention for intravenous infusion could be made up to contain about 250 ml of sterile Ringer's solution, and about 1 to about 30 or 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, 15$^{th}$ ed., Mack Publishing Company, Easton, Pa. For the preparation of intravenously administrable antigen binding protein formulations of the invention see Lasmar U and Parkins D "The formulation of Biopharmaceutical products", Pharma. Sci. Tech. today, page 129-137, Vol. 3 (3$^{rd}$ Apr. 2000); Wang, W "Instability, stabilisation and formulation of liquid protein pharmaceuticals", Int. J. Pharm 185 (1999) 129-188; Stability of Protein Pharmaceuticals Part A and Bed Ahern T. J., Manning M. C., New York, N.Y.: Plenum Press (1992); Akers, M. J. "Excipient-Drug interactions in Parenteral Formulations", J. Pharm Sci 91 (2002) 2283-2300; Imamura, K et al "Effects of types of sugar on stabilization of Protein in the dried state", J Pharm Sci 92 (2003) 266-274; Izutsu, Kkojima, S. "Excipient crystallinity and its protein-structure-stabilizing effect during freeze-drying", J. Pharm. Pharmacol, 54 (2002) 1033-1039; Johnson, R, "Mannitol-sucrose mixtures-versatile formulations for protein peroxidise19g19n", J. Pharm. Sci, 91 (2002) 914-922; and Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

In one embodiment the therapeutic agent of the invention, when in a pharmaceutical preparation, is present in unit dose forms. The appropriate therapeutically effective dose will be determined readily by those of skill in the art. Suitable doses may be calculated for patients according to their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg. To effectively treat conditions such as Multiple myeloma, SLE or IPT in a human, suitable doses may be within the range of about 0.1 to about 1000 mg, for example about 0.1 to about 500 mg, for example about 500 mg, for example about 0.1 to about 100 mg, or about 0.1 to about 80 mg, or about 0.1 to about 60 mg, or about 0.1 to about 40 mg, or for example about 1 to about 100 mg, or about 1 to about 50 mg, of an antigen binding protein of this invention, which may be administered parenterally, for example subcutaneously, intravenously or intramuscularly. Such dose may, if necessary, be repeated at appropriate time intervals selected as appropriate by a physician.

The antigen binding proteins described herein can be lyophilized for storage and reconstituted in a suitable carrier prior to use. This technique has been shown to be effective with conventional immunoglobulins and art-known peroxidise and reconstitution techniques can be employed.

In another aspect of the invention there is provided an antigen binding protein as herein described for use in a medicament.

In one aspect of the present invention there is provided an antigen binding protein according to the invention as herein described for use in the treatment of rheumatoid arthitis, Type 1 Diabetes Mellitus, multiple sclerosis or psoriasis wherein said method comprises the step of administering to said patient a therapeutically effective amount of the antigen binding protein as described herein.

In one embodiment of the present invention, methods are provided for treating cancer in a human comprising administering to said human an antigen binding protein that specifically binds to BCMA. In some instances the antigen binding protein is part of an immunoconjugate.

In another aspect of the present invention there is provided an antigen binding protein according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, Extramedullary), Lymphoplasmacytic lymphoma (LPL), Waldenström's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the antigen binding protein as described herein.

B-cell disorders can be divided into defects of B-cell development/immunoglobulin production (immunodeficiencies) and excessive/uncontrolled proliferation (lymphomas, leukemias). As used herein, B-cell disorder refers to both types of diseases, and methods are provided for treating B-cell disorders with an antigen binding protein.

In a particular aspect, the disease or disorder is selected from the group consisting of Multiple Myeloma (MM), Chronic Lymphocytic Leukaemia (CLL), Solitary Plasmacytoma (Bone, Extramedullary), Waldenström's Macroglobulinemia.

In one aspect of the present invention the disease is Multiple Myeloma, Smoldering Multiple Myeloma (SMM) or Solitary Plasmacytoma (Bone, Extramedullary).

In one aspect of the present invention the disease is Multiple Myeloma.

In one aspect of the present invention the disease is Systemic lupus erythematosus (SLE)

In one aspect of the present invention the disease is Idiopathic thrombocytopenic purpura (ITP)

Use of the antigen binding protein as described herein in the manufacture of a medicament for the treatment of diseases and disorders as described herein is also provided.

For example in one aspect of the invention there is provided the use of the antigen binding protein as described herein for use in the treatment or prophylaxis of diseases and disorders responsive to modulation (such as inhibiting or blocking) of the interaction between BCMA and the ligands BAFF and APRIL.

In another aspect of the invention there is provided the use of the antigen binding protein as described herein for use in the treatment or prophylaxis of an antibody mediated or plasma cell mediated disease or disorder selected from rheumatoid arthitis, Type 1 Diabeted Mellitus, multiple sclerosis or psoriasis.

In another aspect of the invention there is provided the use of the antigen binding protein as described herein for use in the treatment or prophylaxis of an antibody mediated or plasma cell mediated disease or disorder selected from Multiple Myeloma (MM), chronic lymphocytic leukemia (CLL), Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering to said patient a therapeutically effective amount of the antigen binding protein as described herein.

In one aspect, the invention provides a pharmaceutical composition comprising an antigen binding protein of the present invention or a functional fragment thereof and a pharmaceutically acceptable carrier for treatment or prophylaxis of rheumatoid arthitis, Type 1 Diabetes Mellitus, multiple sclerosis or psoriasis or an antibody mediated or plasma cell mediated disease or disorder selected from selected from Multiple Myeloma (MM), chronic lymphocytic leukemia (CLL), Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering to said patient a therapeutically effective amount of the antigen binding protein as described herein.

In another embodiment of the present invention there is provided a method of treating a human patient afflicted with rheumatoid arthitis, Type 1 Diabetes Mellitus, multiple sclerosis or psoriasis or an antibody mediated or plasma cell mediated disorder or disease which method comprises the step of administering a therapeutically effective amount of the antigen binding protein according to the invention as described herein, for example there is provided a method of treating a human patient afflicted with an antibody mediated or plasma cell mediated disease or disorder selected from In another aspect of the present invention there is provided an antigen binding protein according to the invention as herein described for use in the treatment of an antibody mediated or plasma cell mediated disease or disorder selected from Multiple Myeloma (MM), Chronic Lymphocytic Leukaemia (CLL) Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia with BCMA expression or any diseases in which patients develop neutralising antibodies to recombinant protein replacement therapy wherein said method comprises the step of administering a pharmaceutical composition comprising an antigen binding protein according to the invention herein in combination with a pharmaceutically acceptable carrier.

In a further embodiment there is provided a method of treating a human patient afflicted with Multiple Myeloma (MM).

Definitions

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenström's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The term "antigen binding protein" as used herein refers to antibodies, antibody fragments and other protein constructs which are capable of binding to and neutralising human BCMA.

The terms Fv, Fc, Fd, Fab, or F(ab)2 are used with their standard meanings (see, e.g., Harlow et al., Antibodies A Laboratory Manual, Cold Spring Harbor Laboratory, (1988)).

The term "antibody" is used herein in the broadest sense and specifically covers monoclonal antibodies (including full length monoclonal antibodies), polyclonal antibodies, multispecific antibodies (e.g. bispecific antibodies)

The term "monoclonal antibody" as used herein refers to an antibody obtained from a population of substantially homogenous antibodies i.e. the individual antibodies comprising the population are identical except for possible naturally occurring mutations that may be present in minor amounts. Monoclonal antibodies are highly specific being directed against a single antigenic binding site. Furthermore, in contrast to polyclonal antibody preparations which typically include different antibodies directed against different determinants (epitopes), each monoclonal antibody is directed against a single determinant on the antigen.

A "chimeric antibody" refers to a type of engineered antibody in which a portion of the heavy and/or light chain is identical with or homologous to corresponding sequences in antibodies derived from a particular donor antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al. *Proc. Natl. Acad. Sci. USA* 81:6851-6855) (1984)).

A "humanised antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

For nucleic acids, the term "substantial identity" indicates that two nucleic acids, or designated sequences thereof, when optimally aligned and compared, are identical, with appropriate nucleotide insertions or deletions, in at least about 80% of the nucleotides, at least about 90% to about 95%, or at least about 98% to about 99.5% of the nucleotides. Alternatively, substantial identity exists when the segments will hybridize under selective hybridization conditions, to the complement of the strand. "Identity," means, for polynucleotides and polypeptides, as the case may be, the comparison calculated using an algorithm provided in (1) and (2) below:

(1) Identity for polynucleotides is calculated by multiplying the total number of nucleotides in a given sequence by the integer defining the percent identity divided by 100 and then subtracting that product from said total number of nucleotides in said sequence, or:

$$nn \leq xn-(xn \cdot y),$$

wherein nn is the number of nucleotide alterations, xn is the total number of nucleotides in a given sequence, y is 0.95 for 95%, 0.97 for 97% or 1.00 for 100%, and · is the symbol for the multiplication operator, and wherein any non-integer product of xn and y is rounded down to the nearest integer prior to subtracting it from xn. Alterations of a polynucleotide sequence encoding a polypeptide may create nonsense, missense or frameshift mutations in this coding sequence and thereby alter the polypeptide encoded by the polynucleotide following such alterations.

(2) Identity for polypeptides is calculated by multiplying the total number of amino acids by the integer defining the percent identity divided by 100 and then subtracting that product from said total number of amino acids, or:

$$na \leq xa-(xa \cdot y),$$

wherein na is the number of amino acid alterations, xa is the total number of amino acids in the sequence, y is 0.95 for 95%, 0.97 for 97% or 1.00 for 100%, and · is the symbol for the multiplication operator, and wherein any non-integer product of xa and y is rounded down to the nearest integer prior to subtracting it from xa For nucleotide and amino acid sequences, the term “identical” indicates the degree of identity between two nucleic acid or amino acid sequences when optimally aligned and compared with appropriate insertions or deletions.

“Isolated” means altered “by the hand of man” from its natural state, has been changed or removed from its original environment, or both. For example, a polynucleotide or a polypeptide naturally present in a living organism is not “isolated,” but the same polynucleotide or polypeptide separated from the coexisting materials of its natural state is “isolated”, including but not limited to when such polynucleotide or polypeptide is introduced back into a cell, even if the cell is of the same species or type as that from which the polynucleotide or polypeptide was separated.

Throughout the present specification and the accompanying claims the term “comprising” and “comprises” incorporates “consisting of” and “consists of”. That is, these words are intended to convey the possible inclusion of other elements or integers not specifically recited, where the context allows.

The term “specifically binds” as used throughout the present specification in relation to antigen binding proteins of the invention means that the antigen binding protein binds human BCMA (hBCMA) with no or insignificant binding to other human proteins. The term however does not exclude the fact that antigen binding proteins of the invention may also be cross-reactive with other forms of BCMA, for example primate BCMA. For example in one embodiment the antigen binding protein does not bind to TACI or BAFF-R.

The term “inhibits” as used throughout the present specification in relation to antigen binding proteins of the invention means that the biological activity of BCMA is reduced in the presence of the antigen binding proteins of the present invention in comparison to the activity of BCMA in the absence of such antigen binding proteins. Inhibition may be due but not limited to one or more of blocking ligand binding, preventing the ligand activating the receptor, and/or down regulating the BCMA. Inhibits can also refer to an antigen binding protein binding to BCMA and causing cell apoptosis or ADCC. The antibodies of the invention may neutralise the activity of the BCMA ligands BAFF and/or APRIL binding to BCMA. Levels of neutralisation can be measured in several ways, for example by use of the assays as set out in the examples below, for example in 4.4 in an H929 cell NFkB signalling assay. The BCMA ligands BAFF and APRIL are able to induce NFkB signalling and downstream events following binding to BCMA. The neutralisation of BCMA in this assay is measured by assessing the ability of anti-BCMA monoclonal antibodies to inhibit BAFF or APRIL driven NFkB induction.

If an antibody or antigen binding fragment thereof is capable of neutralisation then this is indicative of inhibition of the interaction between human BAFF or APRIL and BCMA. Antibodies which are considered to have neutralising activity against human BCMA would have an 1050 of less than 30 micrograms/ml, or less than 20 micrograms/ml, or less than 10 micrograms/ml, or less than 5 micrograms/ml or less than 1 micrograms/ml or less than 0.1 micrograms/ml in the H929 stimulation assay as set out in Example 4.4

“CDRs” are defined as the complementarity determining region amino acid sequences of an antibody which are the hypervariable domains of immunoglobulin heavy and light chains. There are three heavy chain and three light chain CDRs (or CDR regions) in the variable portion of an immunoglobulin. Thus, “CDRs” as used herein may refer to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The CDR sequences of antibodies can be determined by the Kabat numbering system (Kabat et al; (Sequences of proteins of Immunological Interest NIH, 1987), alternatively they can be determined using the Chothia numbering system (Al-Lazikani et al., (1997) JMB 273, 927-948), the contact definition method (MacCallum R. M., and Martin A. C. R. and Thornton J. M, (1996), Journal of Molecular Biology, 262 (5), 732-745) or any other established method for numbering the residues in an antibody and determining CDRs known to the skilled man in the art Other numbering conventions for CDR sequences available to a skilled person include “AbM” (University of Bath) and “contact” (University College London) methods. The minimum overlapping region using at least two of the Kabat, Chothia, AbM and contact methods can be determined to provide the “minimum binding unit”. The minimum binding unit may be a sub-portion of a CDR.

Table A below represents one definition using each numbering convention for each CDR or binding unit. The Kabat numbering scheme is used in Table X to number the variable domain amino acid sequence. It should be noted that some of the CDR definitions may vary depending on the individual publication used.

TABLE A

| | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Throughout this specification, amino acid residues in antibody sequences are numbered according to the Kabat scheme. Similarly, the terms “CDR”, “CDRL1”, “CDRL2”, “CDRL3”, “CDRH1”, “CDRH2”, “CDRH3” follow the Kabat numbering system as set forth in Kabat et al; Sequences of proteins of Immunological Interest NIH, 1987.

The terms "Variant" refers to at least one, two or three amino acid changes in the sequence. These amino acid changes may be deletion, substitution or addition but are preferably substitution. In one such embodiment the substitutions are conservative substitutions.

In an alternative embodiment the variant sequence contains at least one substitution whilst retaining the canonical of the antigen binding protein.

The complementarity determining regions (CDRs) L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and e.g. conserved glycines. The CDRs of antibody sequences can be assigned to canonical classes by comparing the sequences to the key residue templates and scoring each template using identity or similarity matrices.

The terms "VH" and "VL" are used herein to refer to the heavy chain variable domain and light chain variable domain respectively of an antibody.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein "VH includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; 29eroxidise29g (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a numer of loops at the open end of the conical structure which can be engineered to bind to different target antigens. Anticalins are between 160-180 amino acids in size, and are derived from lipocalins. For further details see Biochim Biophys Acta 1482: 337-350 (2000), US7250297B1 and US20070224633

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A Transferrin is a monomeric serum transport glycoprotein. Transferrins can be engineered to bind different target antigens by insertion of peptide sequences in a permissive surface loop. Examples of engineered transferrins scaffolds include the Trans-body. For further details see J. Biol. Chem. 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the $10^{th}$ domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include up to 25 amino acids without affecting the overall fold of the microprotein. For further details of engineered knottin domains, see WO2008098796.

Other epitope binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

As used herein, the term "antigen-binding site" refers to a site on a protein which is capable of specifically binding to antigen, this may be a single domain, for example an epitope-binding domain, or it may be paired VH/VL domains as can be found on a standard antibody. In some embodiments of the invention single-chain Fv (ScFv) domains can provide antigen-binding sites.

The terms "mAbdAb" and dAbmAb" are used herein to refer to antigen-binding proteins of the present invention. The two terms can be used interchangeably, and are intended to have the same meaning as used herein.

The term "antigen binding protein" as used herein refers to antibodies, antibody fragments for example a domain antibody (dAb), ScFv, Fab, Fab2, and other protein constructs. Antigen binding molecules may comprise at least one Ig variable domain, for example antibodies, domain antibodies (dAbs), Fab, Fab', F(ab')2, Fv, ScFv, diabodies, mAbdAbs, affibodies, heteroconjugate antibodies or bispecific antibodies. In one embodiment the antigen binding molecule is an antibody. In another embodiment the antigen binding molecule is a dAb, i.e. an immunoglobulin single variable domain such as a VH, VHH or VL that specifically binds an antigen or epitope independently of a different V region or domain. Antigen binding molecules may be capable of binding to two targets, i.e. they may be dual targeting proteins. Antigen binding molecules may be a combination of antibodies and antigen binding fragments such as for example, one or more domain antibodies and/or one or more ScFvs linked to a monoclonal antibody. Antigen binding molecules may also comprise a non-Ig domain for example a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; 32eroxidise32g (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to OSM. As used herein "antigen binding protein" will be capable of antagonising and/or neutralising human OSM. In addition, an antigen binding protein may inhibit and or block OSM activity by binding to OSM and preventing a natural ligand from binding and/or activating the gp130 receptor.

The term "Effector Function" as used herein is meant to refer to one or more of Antibody dependant cell mediated cytotoxic activity (ADCC), Complement-dependant cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antigen binding protein bound to antigen and the formation of the Fc/Fcγ complex induces a range of effects including cytotoxicity, immune cell activation, phagocytosis and release of inflammatory cytokines.

The interaction between the constant region of an antigen binding protein and various Fc receptors (FcR) is believed to mediate the effector functions of the antigen binding protein. Significant biological effects can be a consequence of effector functionality, in particular, antibody-dependent cellular cytotoxicity (ADCC), fixation of complement (complement dependent cytotoxicity or CDC), and half-life/clearance of the antigen binding protein. Usually, the ability to mediate effector function requires binding of the antigen binding protein to an antigen and not all antigen binding proteins will mediate every effector function.

Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p6591-6604; Chappel et al, 1993 The Journal of Biological Chemistry, Vol 268, p25124-25131; Lazar et al, 2006 PNAS, 103; 4005-4010. Examples of assays to determine CDC function include that described in 1995 J Imm Meth 184:29-38.

Some isotypes of human constant regions, in particular IgG4 and IgG2 isotypes, essentially lack the functions of a) activation of complement by the classical pathway; and b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS 1991, 88; 9036-9040;

Burton and Woof, Adv. Immunol. 1992, 51; 1-84; Morgan et al., Immunology 1995, 86; 319-324; Hezareh et al., J. Virol. 2001, 75 (24); 12161-12168).

In one embodiment of the present invention there is provided an antigen binding protein comprising a constant region such that the antigen binding protein has reduced ADCC and/or complement activation or effector functionality. In one such embodiment the heavy chain constant region may comprise a naturally disabled constant region of IgG2 or IgG4 isotype or a mutated IgG1 constant region. Examples of suitable modifications are described in EP0307434. One example comprises the substitutions of alanine residues at positions 235 and 237 (EU index numbering).

Human IgG1 constant regions containing specific mutations or altered glycosylation on residue Asn297 have also been described to enhance binding to Fc receptors. In some cases these mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and 1332E and A330L. In one embodiment the antigen binding protein of the invention herein described is mutated at positions 239 and 332, for example S239D and 1332E or in a further embodiment it is mutated at three or more positions selected from 239 and 332 and 330, for example S239D and 1332E and A330L. (EU index numbering).

In an alternative embodiment of the present invention, there is provided an antigen binding protein comprising a heavy chain constant region with an altered glycosylation profile such that the antigen binding protein has enhanced effector function. For example, wherein the antigen binding protein has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125, all of which can be applied to the antigen binding proteins of the present invention.

The present invention also provides a method for the production of an antigen binding protein according to the invention comprising the steps of:

a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein.

Such methods for the production of antigen binding proteins can be performed, for example, using the POTELLIGENT™ technology system available from BioWa, Inc. (Princeton, N.J.) in which CHOK1 SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. Nos. 7,214,775, 6,946,292, WO0061739 and WO0231240 all of which are incorporated herein by reference. Those of ordinary skill in the art will also recognize other appropriate systems.

In one embodiment of the present invention there is provided an antigen binding protein comprising a chimaeric heavy chain constant region for example an antigen binding protein comprising a chimaeric heavy chain constant region with at least one CH2 domain from IgG3 such that the antigen binding protein has enhanced effector function, for example wherein it has enhanced ADCC or enhanced CDC, or enhanced ADCC and CDC functions. In one such embodiment, the antigen binding protein may comprise one CH2 domain from IgG3 or both CH2 domains may be from IgG3.

Also provided is a method of producing an antigen binding protein according to the invention comprising the steps of:

a) culturing a recombinant host cell comprising an expression vector comprising an isolated nucleic acid as described herein wherein the expression vector comprises a nucleic acid sequence encoding an Fc domain having both IgG1 and IgG3 Fc domain amino acid residues; and b) recovering the antigen binding protein.

Such methods for the production of antigen binding proteins can be performed, for example, using the COMPLEGENT™ technology system available from BioWa, Inc. (Princeton, N.J.) and Kyowa Hakko Kogyo (now, Kyowa Hakko Kirin Co., Ltd.) Co., Ltd. In which a recombinant host cell comprising an expression vector in which a nucleic acid sequence encoding a chimeric Fc domain having both IgG1 and IgG3 Fc domain amino acid residues is expressed to produce an antigen binding protein having enhanced complement dependent cytotoxicity (CDC) activity that is increased relative to an otherwise identical antigen binding protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

It will be apparent to those skilled in the art that such modifications may not only be used alone but may be used in combination with each other in order to further enhance effector function. In one such embodiment of the present invention there is provided an antigen binding protein comprising a heavy chain constant region which comprises a mutated and chimaeric heavy chain constant region for example wherein an antigen binding protein comprising at least one CH2 domain from IgG3 and one CH2 domain from IgG1, wherein the IgG1 CH2 domain has one or more mutations at positions selected from 239 and 332 and 330 (for example the mutations may be selected from S239D and 1332E and A330L) such that the antigen binding protein has enhanced effector function, for example wherein it has one or more of the following functions, enhanced ADCC or enhanced CDC, for example wherein it has enhanced ADCC and enhanced CDC. In one embodiment the IgG1 CH2 domain has the mutations S239D and I332E.

In an alternative embodiment of the present invention there is provided an antigen binding protein comprising a chimaeric heavy chain constant region and which has an altered glycosylation profile. In one such embodiment the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC In an alternative embodiment the antigen binding protein has at least one IgG3 CH2 domain and at least one heavy chain constant domain from IgG1 wherein both IgG CH2 domains are mutated in accordance with the limitations described herein.

In one aspect of the invention there is provided a method of producing an antigen binding protein according to the invention described herein comprising the steps of:

a) culturing a recombinant host cell containing an expression vector containing an isolated nucleic acid as described herein, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and b) recovering the antigen binding protein.

Such methods for the production of antigen binding proteins can be performed, for example, using the ACCRETAMAB™ technology system available from BioWa, Inc. (Princeton, N.J.) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide In yet another embodiment of the present invention there is provided an antigen binding protein comprising a mutated and chimeric heavy chain constant region wherein said antigen binding protein has an altered glycosylation profile such that the antigen binding protein has enhanced effector function, for example wherein it has one or more of the following functions, enhanced ADCC or enhanced CDC. In one embodiment the mutations are selected from positions 239 and 332 and 330, for example the mutations are selected from S239D and I332E and A330L. In a further embodiment the heavy chain constant region comprises at least one CH2 domain from IgG3 and one Ch2 domain from IgG1. In one embodiment the heavy chain constant region has an altered glycosylation profile such that the ratio of fucose to mannose is 0.8:3 or less for example the antigen binding protein is defucosylated, so that said antigen binding protein has an enhanced effector function in comparison with an equivalent non-chimaeric antigen binding protein or with an immunoglobulin heavy chain constant region lacking said mutations and altered glycosylation profile.

Immunoconjugates

Also provided is an immunoconjugate (interchangeably referred to as "antibody-drug conjugates," or "ADCs") comprising an antigen binding protein according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al. (2005) Nature Biotechnology 23(9):1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342).

In one embodiment, the present invention includes immunoconjugates having the following general structure:

$$ABP\text{-}((\text{Linker})_n\text{-}Ctx)_m$$

Wherein ABP is an antigen binding protein

Linker is either absent or any a cleavable or non-cleavable linker described herein Ctx is any cytotoxic agent described herein n is 0, 1, 2, or 3 and m is 1, 2, 3, 4, 5, 6, 7, 8, 9 or 10.

Examples of antibodies linked by an MC linker with auristatins such as MMAE and MMAF are depicted in the following structures:

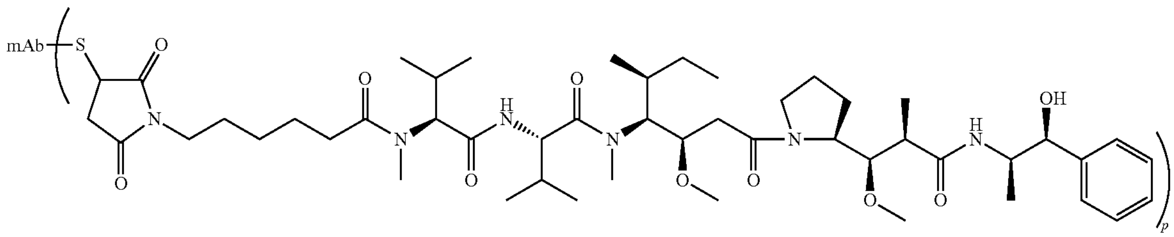

or

L-MC-MMAE

-continued

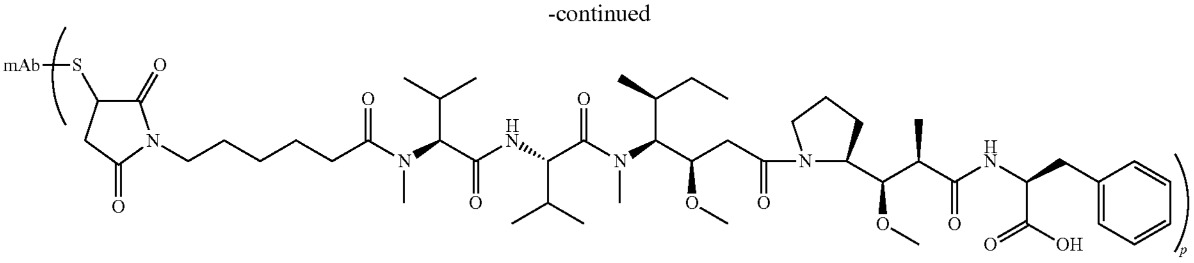

L-MC-MMAF

In certain embodiments, an immunoconjugate comprises an antigen binding protein, including but not limited to, an antibody and a chemotherapeutic agent or other toxin. Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{211}At$, $^{212}Bi$, $^{131}I$, $^{131}In$, $^{90}Y$, and $^{186}Re$.

Antigen binding proteins of the present invention may also be conjugated to one or more toxins, including, but not limited to, a calicheamicin, maytansinoids, dolastatins, aurostatins, a trichothecene, and CC1065, and the derivatives of these toxins that have toxin activity. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a vinca alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. Antitubulin agent include dimethylvaline-valine-dolaisoleuine-dolaproine-phenylalanine-p-phenylened-iamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

Antibody drug conjugates were produced by conjugating the small molecule anti-tubulin agent monomethylauristatin E (MMAE) or monomethylauristatin F (MMAF) to the antibodies. In the case of MMAE the linker consists of a thiol-reactive maleimide, a caproyl spacer, the dipeptide valine-citrulline, and p-aminobenzyloxycarbonyl, a self-immolative fragmenting group. In the case of MMAF a protease-resistant maleimidocaproyl linker is used. The conjugation process leads to heterogeneity in drug-antibody attachment, varying in both the number of drugs bound to each antibody molecule (mole ratio [MR]), and the site of attachment. The most prevalent species is the material with an MR=4; less prevalent are materials with MR of 0, 2, 6, and 8. The overall average drug-to-antibody MR is approximately 4.

Production of Immunoconjugates

The points of attachment are cysteines produced by mild reduction of the interchain disulfides of the antibody which is carried out whilst antibodies are immobilised on Protein G affinity resin (thus enabling the use of large reagent excesses without intermediate purifications). While immobilized, a large excess of TCEP will fully reduce the interchain disulfides but has no impact upon the binding of the antibody to the resin.

The number of thiols per antibody generated by this procedure depends upon the source and isotype of the antibodies. For example, human (and mouse-human chimeric) IgG1 s have 4 reducible disulfides, and thus generate 8 thiols upon full reduction, whereas murine IgG1 s have 5 reducible disulfides and produce 10 thiols. If ADCs with the maximal drug loading (e.g., 10 drugs per antibody for the murine IgG1 s) are desired, then the maleimido-drug-linker can simply be added to the immobilized antibodies in sufficient excess to ensure complete conjugation. However, ADCs with fewer drugs per antibody can also be prepared from fully reduced antibodies by including a biologically inert capping agent such as N-ethyl maleimide (NEM) which occupies some of the available thiols on the antibody. When the maleimido-drug-linker and the capping agent are added simultaneously to the fully reduced antibody and in large excess (at least 3-fold), the two maleimide electrophiles compete for the limiting number of available thiols. In this fashion, the drug loading is determined by the relative thiol reaction rates of the drug-linker and capping agent, and thus can be considered to be under kinetic control. The relative reaction rates of maleimido-drug-linkers do vary significantly, and thus the molar ratio of drug-linker to NEM present in a reaction mix must be determined empirically to arrive at a panel of ADCs with a desired level of drug loading. The mole fraction of the drug linkers SGD-1006 (vcMMAE) and SGD-1269 (mcMMAF) in NEM mixtures which yield ADCs with approximately 4 drugs per antibody are summarized in Table 2 for common human and murine IgG isotypes.

Auristatins and Dolastatins

In some embodiments, the immunoconjugate comprises an antigen binding protein or antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965). The dolastatin or auristatin (which are pentapeptide derivatives of dolastatins) drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Pat. No. 7,498,298, the disclosure of which is expressly incorporated by reference in its entirety. As used herein, the abbreviation "MMAE" refers to monomethyl auristatin E. As used herein the abbreviation "MMAF" refers to dovaline-valine-dolaisoleuine-dolaproine-phenylalanine.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides," volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al. (1989) J. Am. Chem. Soc. 111:5463-5465; Pettit et al. (1998) Anti-Cancer Drug Design 13:243-277; Pettit, G. R., et al. Synthesis, 1996, 719-725; and Pettit et al. (1996) J. Chem. Soc. Perkin Trans. 15:859-863. See also Doronina (2003) Nat Biotechnol 21(7):778-784; "Monomethylvaline Compounds Capable of Conjugation to Ligands," U.S. Pat. No. 7,498,298, filed Nov. 5, 2004, hereby incorporated by reference in its entirety (disclosing, e.g., linkers and methods of preparing monomethylvaline compounds such as MMAE and MMAF conjugated to linkers). Biologically active organic compounds which act as cytotoxic agents, specifically pentapeptides, are disclosed in U.S. Pat. Nos. 6,884,869; 7,498,298; 7,098,308; 7,256,257; and 7,423,116. Monoclonal antibodies linked with MMAE and MMAF as well as various derivatives of auristatins and methods of making them are described in U.S. Pat. No. 7,964,566. Examples of auristatins include MMAE and MMAF the structures of which are shown below:

Maytansine and Maytansinoids

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Highly cytotoxic maytansinoid drugs drugs can be prepared from ansamitocin precursors produced by fermentation of microorganisms such as Actinosynnema. Methods for isolating ansamitocins are described in U.S. Pat. No. 6,573,074. Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Maytansinoids are maytansinol and maytansinol analogues modified in the aromatic ring or at other positions of the maytansinol molecule, such as various maytansinol esters. Methods for preparing matansinoids for linkage with antibodies are disclosed in U.S. Pat. Nos. 6,570,024 and 6,884,874.

Calicheamicin

The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001,

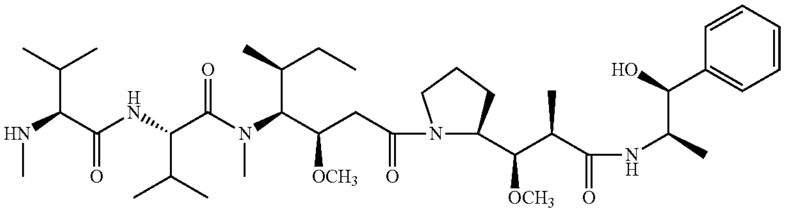

MMAE

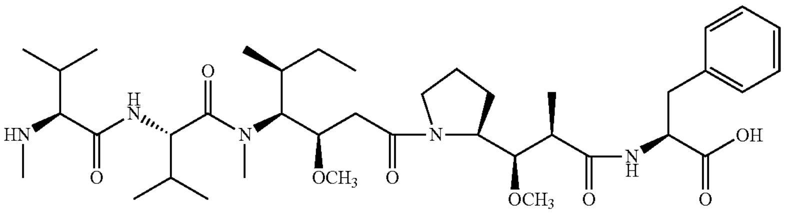

MMAF 5,877,296 (all to American Cyanamid Company). Structural analogues of calicheamicin which may be used include, but are not limited to, .gamma.1I, .alpha.2I, .alpha.3I, N-acetyl-.gamma.1I, PSAG and .theta.I1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al. (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Preparation of ADCs

In antibody drug conjugates, the antibody can be conjugated directly to the cytotoxic agent or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

Bristol-Myers Squibb has described particular lysosomal enzyme-cleavable antitumor drug conjugates. See, for example, U.S. Pat. No. 6,214,345. Seattle Genetics has published applications U.S. Pat. Appl. 2003/0096743 and U.S. Pat. Appl. 2003/0130189, which describe p-aminobenzylethers in drug delivery agents. The linkers described in these applications are limited to aminobenzyl ether compositions.

Conjugates of the antigen binding protein and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Additionally the linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Pat. No. 7,498,298, filed Nov. 5, 2004, the contents of which are hereby incorporated by reference in its entirety.

Linkers may also comprises amino acids and/or amino acid analogs. Amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Antigen binding proteins and antibodies may be made reactive for conjugation with linker reagents. Nucleophilic groups on antibodies include, but are not limited to: (i) N-terminal amine groups, (ii) side chain amine groups, e.g., lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antigen binding proteins and antibodies may also be modified to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehydes can be reacted with a drug moiety or linker nucleophile. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers may be cleavable by enzymes that are present cells. For example, a peptidyl linker that is cleavable by the thiol-dependent protease cathepsin-B, which is highly expressed in cancerous tissue, can be used (e.g., a Phe-Leu or a Gly-Phe-Leu-Gly (SEQ ID NO:50) linker). Other such linkers are described, e.g., in U.S. Pat. No. 6,214,345. In specific embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.) In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of ADC or ADC derivative, are cleaved when the ADC or ADC derivative present in an extracellular environment (e.g., in plasma). Whether a linker is not substantially sensitive to the extracellular environment can be determined, for example, by incubating independently with plasma both (a) the ADC or ADC derivative (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the antigen binding protein or antibody or derivative thereof (i.e., in the milieu of the ADC or ADC derivative as described herein).

A variety of linkers that can be used with the present compositions and methods are described in WO 2004010957 entitled "Drug Conjugates and Their Use for Treating Cancer, An Autoimmune Disease or an Infectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

Alternatively, a fusion protein comprising the antigen binding protein and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

The term "Non Human antibody or antibody fragment thereof" as used herein is meant to refer to antibodies or fragments thereof which originate from any species other than human wherein human includes chimeric antibodies.

The term "donor antibody" refers to an antibody (monoclonal, and/or recombinant) which contributes the amino acid sequences of its variable domains, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. The human antibody is the acceptor antibody. The term "Human acceptor sequence" as used herein is meant to refer to a framework of an antibody or antibody fragment thereof comprising the amino acid sequence of a VH or VL framework derived from a human antibody or antibody fragment thereof or a human consensus sequence framework into which CDR's from a non-human species may be incorporated.

The term "incorporation" of CDR's or hypervariable regions as used herein encompasses any means by which the non-human CDR's are situated with the human acceptor framework. It will be appreciated that this can be achieved in various ways, for example, nucleic acids encoding the desired amino acid sequence can be generated by mutating nucleic acids encoding the non-human variable domain sequence so that the framework residues thereof are changed to human acceptor framework residues, or by mutating nucleic acid encoding the human variable domain sequence so that the CDR's are changed to non-human residues, or by synthesizing nucleic acids encoding the desired sequence. In one embodiment the final sequence is generated in silico.

The present invention is now described by way of example only. The appended claims may include a generalisation of one of more of the following examples.

EXAMPLES

Example 1

Monoclonal Antibody Generation and Selection 1.1 Immunisation Strategies

The anti human BCMA mAb murine parental CA8 was identified from hybridomas derived from mice immunized with full length human BCMA. A BALB/c mouse was immunized i.p. with 25 μg of recombinant (rBCMA) protein combined with CFA. The mouse was boosted three times at one-month intervals with 25 μg of full length rBCMA protein+10 μg monophosphoryl lipid A-stable emulsion (MPL-SE) (Corixa Corporation, Seattle, Wash.) and given a pre-fusion boost of 30 μg rBCMA protein i.v. 3 days prior to fusion. Hybridomas were either generated and cloned using the CloneCell-HY hybridoma cloning kit (StemCell Technologies, Vancouver, BC) or using a conventional method. In the conventional method, B cells from the spleens of the immunized animals were fused with Sp2/0 myeloma cells in the presence of PEG (Sigma-Aldrich, St. Louis, Mo.). After overnight recovery, fused cells were plated at limiting dilution in 96-well plates and subjected to hypoxanthine-aminopterin-thymidine selection. Hybridoma culture supernatants were examined for the presence of anti-BCMA antibodies by ELISA and flow cytometry The anti human BCMA mAb murine parental S307118G03 was identified from hybridomas derived from SJL mice immunized with recombinant human BCMA/TNFRSF17-Fc chimera (R&D 193-Fc) using the RIMMS method (Rapid immunisation multiple sites). At Day 0, 5 ug protein per mouse was emulsified in AS02a adjuvant at 2 sites on back (over haunches and over shoulders) and subjacent to the major lymph nodes at 4 sites on front. On day 6 and day 11 2.5 ug protein per mouse in RIBI adjuvant was injected subjacent to the major lymph nodes at 4 sites on front. On day 14 the animals were sacrificed. The lymph nodes and spleen were excised, disrupted and a PEG1500 induced somatic cell fusion performed using a 3:1 ratio with mouse myeloma cells X63 AG8 653.GFP.BcI-2.11 (BioCat 112754; R17209/58). The fusion was plated out into 10×96 well plates and screened directly from these.

The anti human BCMA mAb murine parental S336105A07 was identified from hybridomas derived from identical immunisations. The lymph nodes and spleen were excised at day 14, disrupted, and a Cytopulse electrofusion was performed using a 1:1 ratio with mouse myeloma cells X63 AG8 653.GFP.BcI-2.11 (BioCat 112754; R17209/58). The fusion was plated out into omnitrays containing semi solid medium prior to picking into 10×96 well plates and was screened directly from these 5 days later.

The anti human BCMA murine parental mAbs S332121F02 and S332126E04 were identified from hybridomas derived from SJL mice immunized with recombinant Fc fusion of the extracellular domain of human BCMA (4-53) BCMA using the RIMMS method (Rapid immunisation). At Day 0, 5 ug protein per mouse was emulsified in AS02a adjuvant at 2 sites on back (over haunches and over shoulders) and subjacent to the major lymph nodes at 4 sites on front. On day 6 5 ug recombinant cyno BCMA-Fc protein per mouse in RIBI adjuvant was injected subjacent to the major lymph nodes at 4 sites on front. On day 11 2.5 ug recombinant human BCMA-Fc and 2.5 ug recombinant cyno BCMA-Fc per mouse in RIBI adjuvant was injected subjacent to the major lymph nodes at 4 sites on front. On day 14 the animals were sacrificed and cells treated as for S307118G03.

The anti human BCMA murine parental mAb S322110D07 was identified from hybridomas derived from SJL mice immunised with recombinant Fc fusion of the extracellular domain of human BCMA (4-53) in complex with recombinant human April (R&D 5860-AP/CF) premixed at 1:1 molar ratio. The mice were immunized i.p. with 5 ug April/Cyno BCMA-Fc complex in PBS, suspended in RIBI adjuvant, 100 ul dose per mouse and boosted 3 times at 3-4 week intervals with 2.5 ug April/Cyno BCMA-Fc complex in PBS, suspended in RIBI adjuvant, 100 ul dose per mouse injected via intraperitoneal route and given a pre-fusion boost of the same immunogen 1 day prior to fusion and treated as for S307118G03.

The anti human BCMA mAb murine parental 5335115G01 and 5335122F05 were identified from hybridomas derived from SJL mice immunized with a mixture of recombinant Fc fusion of the extracellular domain of human BCMA (4-53) and recombinant Fc fusion of the extracellular domain of cyno BCMA (4-52) using the RIMMS method (Rapid immunisation multiple sites). At Day 0, 2, 5 ug of each protein per mouse was emulsified in AS02a adjuvant and injected at 2 sites on the back (over haunches and over shoulders) and subjacent to the major lymph nodes at 4 sites on front. On day 6 and day 11 2.5 ug of each protein per mouse in RIBI adjuvant was injected subjacent to the major lymph nodes at 4 sites on front. On day 14 the animals were sacrificed. The lymph nodes and spleen were excised, disrupted and a Cytopulse electrofusion was performed using a 1:1 ratio with mouse myeloma cells X63 AG8 653.GFP.Bcl-2.11 (BioCat 112754; R17209/58). The fusion was plated out into omnitrays containing semi solid medium prior to picking into 32×96 well plates and was screened directly from these 5 days later.

Example 2

Humanisation 2.1 Cloning of CA8 Hybridoma Variable Regions

Total RNA was extracted from CA8 hybridoma cells, heavy and light variable domain cDNA sequence was then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions. Reverse primers specific for IgG1, IgG2a and IgG2b were used in this case as the isotype was unknown. To design the primers, DNA multiple sequence alignments of the leader sequences of the mouse $V_H$ and $V_k$ genes were generated.

2.2 Cloning of Chimeric CA8

The DNA expression constructs encoding the chimeric antibody were prepared de novo by build-up of overlapping oligonucleotides including restriction sites for cloning into mammalian expression vectors as well as a human signal sequence. HindIII and SpeI restriction sites were introduced to frame the VH domain containing the signal sequence for cloning into mammalian expression vectors containing the human γ1 constant region. HindIII and BsiWI restriction sites were introduced to frame the VL domain containing the signal sequence for cloning into mammalian expression vector containing the human kappa constant region.

2.3 Cloning of the Humanised CA8 Variants

The DNA expression constructs encoding the humanised antibody variants were prepared de novo by build-up of overlapping oligonucleotides including restriction sites for cloning into mammalian expression vectors as well as a human signal sequence. HindIII and SpeI restriction sites were introduced to frame the VH domain containing the signal sequence for cloning into mammalian expression vectors containing the human γ1 constant region. HindIII and BsiWI restriction sites were introduced to frame the VL domain containing the signal sequence for cloning into mammalian expression vector containing the human kappa constant region.

2.4 Expression of the Recombinant CA8 Antibodies (Including Antibody Quantification)

Expression plasmids encoding the heavy and light chains respectively were transiently co-transfected into HEK 293 6E cells and expressed at small scale to produce antibody. Antibodies were quantified by ELISA. ELISA plates were coated with anti human IgG (Sigma 13382) at 1 mg/ml and blocked with blocking solution (4% BSA in Tris buffered saline). Various dilutions of the tissue culture supernatants were added and the plate was incubated for 1 hour at room temperature. Dilutions of a known standard antibody were also added to the plate. The plate was washed in TBST and binding was detected by the addition of a peroxidise labelled anti human kappa light chain antibody (Sigma A7164) at a dilution of 1/1000 in blocking solution. The plate was incubated for 1 hour at room temp before washing in TBST. The plate was developed by addition of OPD substrate (Sigma P9187) and colour development stopped by addition of 2M H2SO4. Absorbance was measured at 490 nm and a standard curve plotted using data for the known standard dilutions. The standard curve was used to estimate the concentration of antibody in the tissue culture supernatants. Larger scale antibody preparations were purified using protein A and concentrations were measured using a Nanodrop (Thermo Scientific).

TABLE 1

Design of CA8 variable heavy and light humanised variants

| Humanised VH | Template | Backmutations (Kabat#) |
|---|---|---|
| J0 | Straight graft of CA8 VH CDRs onto IGHV1_69 + JH1 minigene | None |
| J1 | J0 | G27Y. S30T |
| J2 | J1 | A93T |
| J3 | J2 | A24G. K73T |
| J4 | J3 | M48I. V67A. |
| J5 | J3 | N99D |
| J6 | J0 | N99D |
| J7 | J1 | N99D |
| J8 | J2 | N99D |
| J9 | J4 | N99D |
| M0 | Straight graft of CA8 VL CDRs onto IGKV1_39 + JK2 minigene | None |
| M1 | M0 | F71Y |
| M2 | M1 | M4L. K45E. |

2.5 Defucosylated Antibody Production

To generate defucosylated antibodies the heavy and light chains respectively were co-transfected into CHO DG44 MS705 BioWa cells and expressed at scale to produce antibody. Briefly, 30 μg DNA was linearised overnight with Not1, the DNA was ethanol precipitated and re-dissolved in TE buffer. From culture, 2.4×107 BioWa DG44 cells were obtained and washed in 14 ml of warmed PBS-sucrose. The cells were spun and the pellet resuspended in 1.6 ml of PBS-sucrose. Half (0.8 ml) of aforementioned cells, suspended in PBS-sucrose, were added to a BioRad cuvette with the 30 μg of linearised DNA (in 50 μl TE buffer). A BioRad GenePulser was programmed to 380V with a capacitance of 25 μF and the cuvette was entered for electroporation. The resulting 850 ul of electroporated cells and DNA were added to (80 ml) warmed SFM512 medium (including phenol red, 2×HT (nucleosides), glutamax and Gibco supplement4). Finally, the resulting 80 ml of cell suspension was transferred (150 μl/well) to each well of one of 4×96-well plates. After 48 hours, the medium was changed to nucleoside free by removing approximately 130 μl of conditioned and replacing with 150 μl of fresh selection medium SFM512 medium (including phenol red and glutamax). Every 3-4 days, 130-150 μl of conditioned medium was removed and replaced with fresh, selection medium. Wells were monitored for colour change and assayed for IgG concentration as discussed previously.

2.6 Additional Antibodies—Cloning of Hybridoma Variable Regions

Total RNA was extracted from S307118G03, S332121F02, S332126E04, S322110D07, S336105A07, S335115G01 and S335122F05 hybridoma cells. Heavy and light variable domain cDNA sequence was then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, in this case isotype IgG2a. Primers were designed based on a strategy described by Jones and Bendig (Bio/Technology 9:88, 1991). RT-PCR was carried out for both V-region sequences to enable subsequent verification of the correct V-region sequences. DNA sequence data was obtained for the V-region products generated by the RT-PCR.

2.7 Additional Antibodies—Cloning of the Chimeras

The DNA expression constructs encoding the chimeric antibodies were prepared de novo by infusion advantage PCR cloning (Clonetech) of the V-gene PCR products into mammalian expression vectors. This cloning method enabled fusion the murine variable regions to human IgG1 H chain and kappa L chain constant regions.

2.8 S307118G03—Cloning of the Humanized Variants

Cloning was carried out as for paragraph 2.3.

2.9 S307118G03 Expression of the Recombinant Antibodies

Expression plasmids encoding the relevant heavy and light chains (listed in Table 8 below) were transiently co-transfected into HEK 293 6E cells and expressed at small scale to produce antibody. The antibodies were Protein A purified from the supernatants and quantified using the Nanodrop spectrophotometer.

8 below) were transiently co-transfected into HEK 293 6E cells and expressed at small scale to produce antibody. The antibodies were Protein A purified from the supernatants and quantified using the Nanodrop spectrophotometer.

Example 3

Conjugation of Antibodies to vcMMAE and mcMMAF to Form Antibody Drug Conjugates (ADC)

TABLE B

Chemical structures of drug-linkers

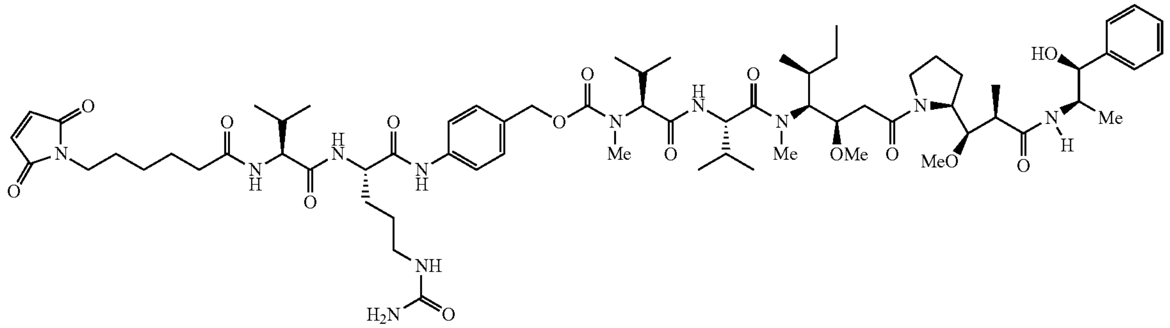

SGD-1006 (vcMMAE)

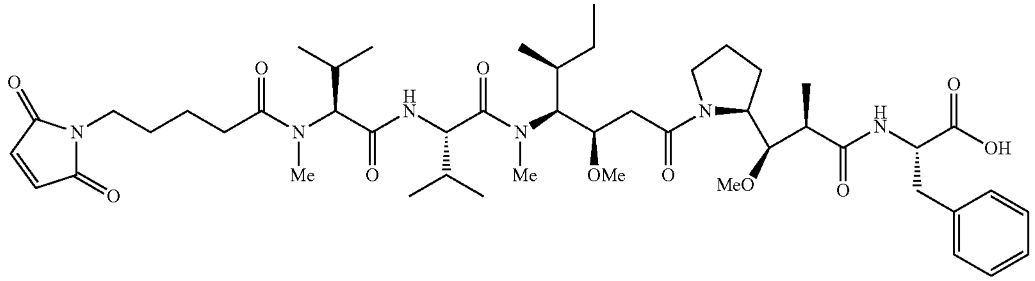

SGD-1269 (mcMMAF)

Gammabind Plus Protein G Sepharose (GE Healthcare) resin slurry (75 uL) was added to a each well of a deep well (2 mL capacity) filter plate. The antibodies to be conjugated were grouped by species and isotype and up to 0.5 mg of each antibody transferred to each well of the plate. Each antibody was transferred to two separate wells to facilitate the preparation of two conjugates, with the drug-linkers SGD-1006 and SGD-1269. The filter plate was then shaken at 1200 RPM for 2 hours at 5° C. to bind the antibodies to the resin. The filter plate was then centrifuged at 500×g for 3 minutes to ensure complete pulldown of all fluids and resin to the bottom of the each well.

The bound antibodies were then reduced by adding 500 uL of 10 mM TCEP in 100 mM KPO4, 150 mM NaCl, pH 7, 1 mM EDTA and shaking for 30 minutes at 22° C. Following reduction, the plate was again centrifuged to remove the TCEP solution and subsequently washed with PBS+1 mM EDTA, 1 mL per well. The wash solution was removed by centrifugation and the process repeated 3 times for a total of 4 washes. The bound and reduced antibodies were then conjugated using a mixture of NEM and drug linker prepared in accordance with the mole fractions indicated in Table 2.

TABLE 2

| Antibody (species/isotype) | Reducible Disulfides | SGD-1006 mole fraction | SGD-1269 mole fraction |
|---|---|---|---|
| Human IgG1* | 4 | 0.675 | 0.688 |
| Murine IgG1 | 5 | 0.500 | 0.586 |
| Murine IgG2a | 5 | 0.500 | 0.586 |
| Murine IgG2b | 6 | 0.463 | 0.481 |

*also for murine/human IgG1 chimerics

Separate mixtures of NEM and drug linker were thus prepared for each antibody species/isotype using 10 mM DMSO stock solutions of SGD-1006, SGD-1269 (See Table B) and NEM. When mixed at the appropriate ratio the total maleimide concentration was therefore still 10 mM, and this value was used to calculate the volume of maleimide solution to be added to each well. For example for a murine IgG1 with 5 reducible disulfides (10 available thiols when reduced) 0.5 mg of antibody at 150 kD is 3.33 nmol corresponding to 33.3 nmol of thiol. A 3-fold excess is therefore 100 nmol of total maleimide or 10 μL of the 10 mM drug linker/NEM mix. For the SGD-1269 conjugate this mix would then be prepared with 5.86 μL of SGD-1269 and 4.14 μL of NEM. The maleimide mix would then be diluted into 500 μL of PBS prior to addition to the immobilized reduced antibody. In practice, since multiple antibodies of each isotype were conjugated simultaneously a single SGD-1269/NEM mixed solution for each isotype was prepared by multiplying the number of wells containing that isotype by 10 μL per well then diluting into a volume of PBS equal to 500 μL times the number of wells. In like fashion a total of eight drug-linker/NEM mixes were prepared—four with SGD-1006 and four with SGD-1269—and diluted into PBS. These mixes were then added to the reduced antibodies (500 μL per well) and the plate was shaken for 30 minutes at 22° C. The plate was then centrifuged as above to remove the excess reaction solution, and subsequently washed 4 times with PBS as before. The bound ADCs were then eluted by adding 200 uL of 50 mM glycine pH 2.5 to each well and shaking the plate for 3 minutes at 1200 RPM. While shaking 20 uL of neutralization buffer (1M potassium phosphate, pH 7.4, 500 mM NaCl, 0.2% Tween-20) was added to each well of a 1 mL collection plate. The ADCs were then eluted into the collection plate by spinning at 1500×g for 6 minutes. The collection plate was then shaken briefly to ensure complete mixing of the neutralization buffer.

The concentration of each ADC was then determined with an absorbance plate reader by transferring the solutions into a UV assay plate (Costar model 3635, Corning) and measuring the optical density at 280 nm. An average IgG extinction coefficient of 1.45 mL mg-1 cm-1 was used to provide an adequate estimation of ADC concentration across the panel. To confirm successful conjugation, a reversed phase protein HPLC method (described below) was used to estimate the drug loading of the isotype controls. For the plate containing the humanization variants of CA8 this method was used to estimate the loading of all ADCs directly.

The reversed phase protein chromatography method for determining drug loading employs the PLRP-S polymeric stationary phase (Agilent Technologies). Since the antibodies were fully reduced during the conjugation process all of the antibody subunits elute from the column as single polypeptide chains allowing the subpopulations of light and heavy chain species with varying levels of drug loading to be evaluated separately. Thus, the analysis of these data allow for the calculation of the average light chain drug loading and the average heavy chain drug loading as independent factors which can then be combined to determine average antibody drug loading with the basic knowledge that each antibody is comprised of two light and two heavy chains. The chromatographic conditions were as follows: A PRLP-S column, 1000 Å, 50×2.1 mm, 8 um particle size (Agilent Technologies) with water+0.05% TFA as mobile phase A and acetonitrile+0.01% TFA as mobile phase B; elution with a linear gradient of 27% B to 42% B in 12.5 minutes.

Anti-BCMA antibodies were conjugated with SGD-1006 and SGD-1269 in three separate batches over a period of seven months. In the first batch a total of 29 antibodies were conjugated (resulting in 58 ADCs). The drug loading of each isotype control determined by PLRP chromatography and the data are summarized in Table 3.

TABLE 3

| Isotype | SGD-1006 loading | SGD-1269 loading |
|---|---|---|
| cIgG1 (control P) | 4.23 | 4.35 |
| cIgG1 (control M) | 4.42 | 4.41 |
| mIgG1 | 4.26 | 4.04 |
| mIgG2a | 4.51 | 4.57 |
| mIgG2b | 4.39 | 4.18 |

For the second batch an additional 25 antibodies were conjugated (resulting in 50 ADCs). The drug loading of each isotype control was again determined by PLRP chromatography and the data are summarized in Table 4.

TABLE 4

| Isotype | SGD-1006 loading | SGD-1269 loading |
|---|---|---|
| cIgG1 | 3.96 | 3.78 |
| mIgG1 | 3.95 | 3.32 |
| mIgG2a | 4.53 | 3.60 |
| mIgG2b | 4.32 | 3.49 |

In the third batch 30 antibodies were conjugated (resulting in 60 ADCs), including 13 humanized variants of CA8. In this final batch, the drug loading of all ADCs were determined and are summarized in the following two plate maps. (Table 5 & 6)

TABLE 5

| | drug loading | | | | | | | | | |
|---|---|---|---|---|---|---|---|---|---|---|
| | 1 | 2 | 3 | 4 | 5 | 6 | 7 | 8 | 9 | 10 |
| A | 3.7 | 4.0 | 3.6 | 3.8 | 3.8 | 3.5 | 3.9 | 2.8 | 3.8 | 3.8 |
| B | 3.7 | 3.6 | 3.5 | 3.7 | 4.0 | 3.4 | 3.7 | 3.3 | 3.8 | 3.9 |
| C | 3.6 | 3.8 | 3.5 | 3.7 | 3.6 | 3.3 | 3.8 | 4.7 | 3.8 | 3.7 |
| D | 3.4 | 3.6 | 3.6 | 3.9 | 3.9 | 3.4 | 3.2 | 4.8 | 3.8 | 3.9 |
| E | 3.9 | | 3.8 | 3.9 | 3.4 | 3.6 | | 3.3 | 3.7 | 3.4 |
| F | 3.7 | | | 4.0 | 3.6 | 3.5 | | | 3.8 | 3.7 |
| G | 3.6 | | | 3.6 | | 3.4 | | | 3.7 | |
| H | | | | 3.6 | | | | | 3.6 | |
| | SGD-1006 (vc-MMAE) ADCs | | | | | SGD-1269 (mc-MMAF) ADCs | | | | |
| | 3.7 | 3.8 | 3.6 | 3.8 | | 3.4 | 3.7 | 3.8 | 3.7 | |
| | 4.1% | 5.1% | 3.4% | 4.8% | | 2.8% | 8.5% | 24.1% | 3.4% | |

TABLE 6

| | mIgG1 | mIgG2a | mIgG2b | humanized | | mIgG1 | mIgG2a | mIgG2b | humanized | |
|---|---|---|---|---|---|---|---|---|---|---|
| | 1 | 2 | 3 | 4 | 5 | 6 | 7 | 8 | 9 | 10 |
| A | control | control | control | CA8 J6M0 | CA8 J8M2 | control | control | control | CA8 J6M0 | CA8 J8M2 |
| B | S336106D07 | S336105A07 | S336107G08 | CA8 J6M1 | CA8 J9M0 | S336106D07 | S336105A07 | S336107G08 | CA8 J6M1 | CA8 J9M0 |
| C | S335115G03 | S335122F05 | S336104A09 | CA8 J6M2 | CA8 J9M1 | S335115G03 | S335122F05 | S336104A09 | CA8 J6M2 | CA8 J9M1 |
| D | S335115G01 | S335128A12 | S335107H11 | CA8 J7M0 | CA8 J9M2 | S335115G01 | S335128A12 | S335107H11 | CA8 J7M0 | CA8 J9M2 |
| E | S335106E08 | | S335119E11 | CA8 J7M1 | CA8 Fc ENH | S335106E08 | | S335119E11 | CA8 J7M1 | CA8 Fc ENH |
| F | S335132E01 | | | CA8 J7M2 | GRITS28785 | S335132E01 | | | CA8 J7M2 | GRITS28785 |
| G | S341106G02 | | | CA8 J8M0 | | S341106G02 | | | CA8 J8M0 | |
| H | | | | CA8 J8M1 | | | | | CA8 J8M1 | |
| | SGD-1006 (vc-MMAE) ADCs | | | | | SGD-1269 (mc-MMAF) ADCs | | | | |

Mean drug loading and % CV are indicated for each isotype series at the bottom. An uncharacteristically large variability in drug loading was observed for the SGD-1269 ADCs prepared with mIgG2b antibodies; the reason for this is unclear. Also, the Fc-enhanced CA8 antibodies yielded somewhat lower drug loading levels than the other CA8 human variants; to address this, additional Fc-enhanced CA8 was conjugated in a solution-phase reaction to better match the drug loading achieved for the other antibodies.

Example 4

Binding Data 4.1 FMAT Binding Assay to Show Binding of Chimeric CA8 to Cells Expressing Human or Cyno BCMA.

Cryopreserved transfected human, cyno BCMA and mock transfected HEK293 cells were recovered from LN2 storage. Assay wells were prepared with human chimeric CA8 antibody, at a range of different concentrations, mixed with human BCMA HEK293, cyno BCMA HEK293 and mock transfected cells respectively. Anti-human IgG FMAT Blue secondary conjugate was added for detection of human chimeric CA8. The assay plates were left for a minimum of 90 minutes before the result was read on the ABI8200 (FMAT) plate reader.

This showed that the CA8 antibody in chimeric form binds well to both human and cyno BCMA proteins expressed on HEK293 cells.

Figure 1:
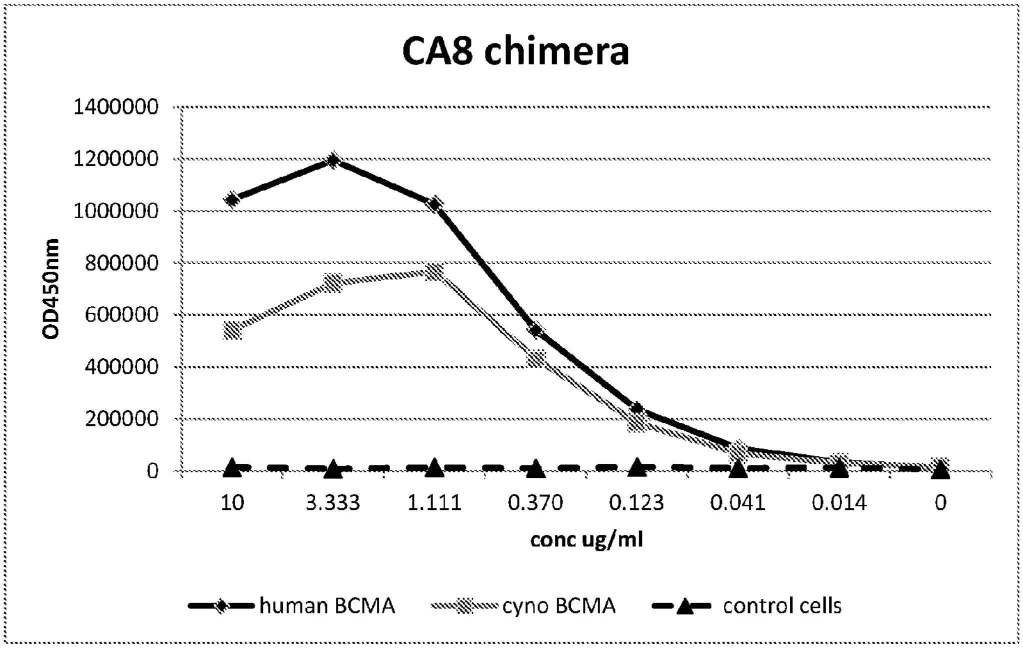
FIG. 1: FMAT Binding Assay—Figure showing the results of the FMAT assay for CA8 antibody binding to human and cyno BCMA expressing HEK293 cells. Human chimeric CA8 binds well to human and cyno BCMA expressing cells.

Results are shown in FIG. 1.

Figure 2:
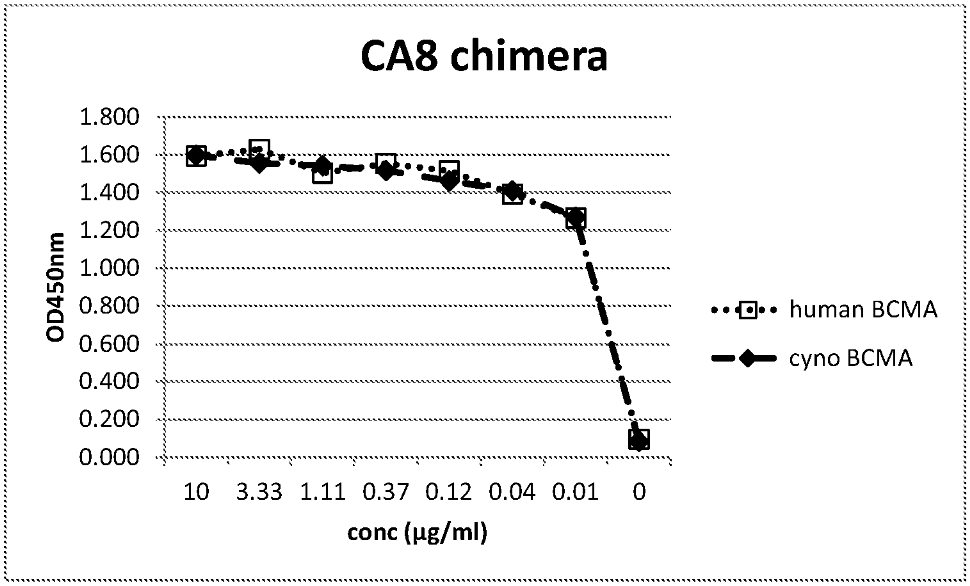
FIG. 2: ELISA Binding Assay—Figure showing the ELISA results for CA8 antibodies binding to human and cyno BCMA recombinant proteins. This clearly shows that human chimeric CA8 antibodies bind to human and cyno BCMA proteins equally.

4.2 ELISA Experiment Showing Binding of Chimeric CA8 to Recombinant BCMA Protein Chimeric CA8 antibodies were tested for binding to human BCMA and cyno BCMA expressed as Fc fusions. Human BCMA-Fc and cyno BCMA-Fc were coated to ELISA plates and the plates were blocked using BSA to reduce non specific binding. CA8 chimeric antibodies were added in a concentration range from 5 ug/ml to 0.1 ug/ml to the human and cyno BCMA coated ELISA plates. Any bound human chimeric CA8 antibody was detected using anti-human IgG HRP conjugated secondary antibody as appropriate. HRP substrate (TMB) was added to develop the ELISA. This showed that CA8 antibody binds to recombinant human and cyno BCMA in an ELISA assay. Results are shown in FIG. 2.

4.3 Biacore Experiment to Show CA8 Antibody Binding to BCMA and TACI Proteins to Determine Cross Reactivity with TACI Protein.

CA8 chimera antibody was injected and captured on protein A. (A protein A derivitised sensorchip was used). Residual protein A binding was blocked with an injection of a high concentration of human IgG solution. BCMA-Fc, TACI-Fc or BAFF-R-Fc solutions were then tested for binding to the antibody. The 3 proteins were injected in sequence and binding events were measured. The surface was regenerated between injection of each protein.

Sensorgrams were analysed in the Biaevaluation program. Double reference subtraction was done to remove instrument noise and any non-specific binding from the sensorgram curves.

This showed that CA8 was specific for binding to BCMA binding and not to TACI and BAFFR.

Figure 3:
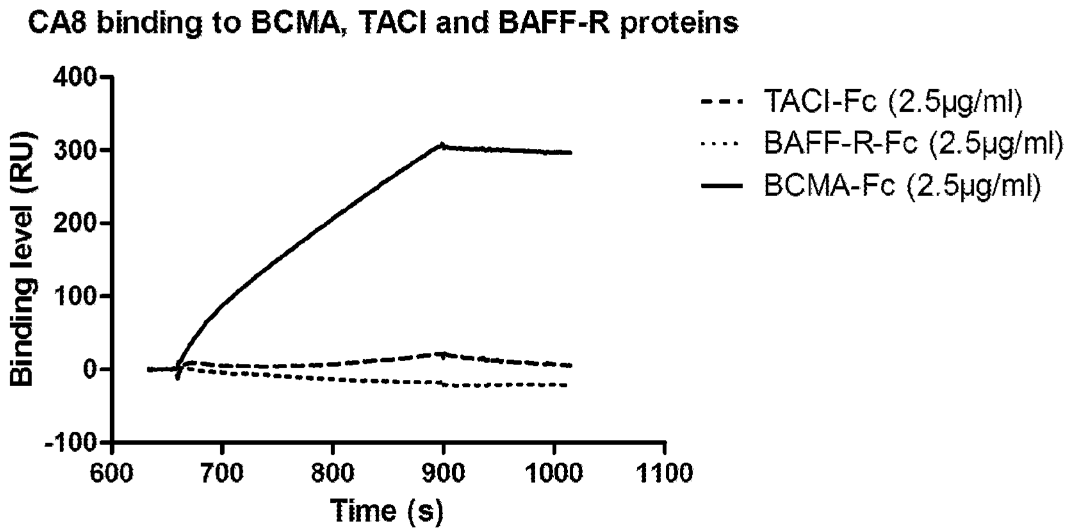
FIG. 3: BiaCore Binding Assay—Figure showing the binding of CA8 to BCMA-Fc, TACI-Fc and BAFF-R-Fc proteins in the Biacore experiment. CA8 chimera antibody does not bind to TACI or BAFF-R proteins.

Binding of the CA8 antibody to BCMA-Fc, TACI-Fc and BAFF-R-Fc was plotted out as shown in FIG. 3.

4.4 Cell Binding and Neutralisation Data 4.4.1 Binding of Murine Anti BCMA Antibodies to Multiple Myeloma Cells and BCMA Expressing Cells Multiple myeloma cell line H929 and ARH77-hBCMA 10B5 BCMA expressing transfectant cells were stained with murine S332211D07, S3332121F02 or S332126E04 or murine isotype control at 5 pg/mL. Multiple myeloma cell line H929 was stained with murine S307118G03. Cells were incubated for 20 mins at room temperature (RT) and then washed with FACS buffer (PBS+0.5% BSA+0.1% sodium azide) to remove unbound antibody. Cells were incubated with a secondary PE labelled anti-mouse IgG antibody for 15 minutes at RT and then washed with FACS buffer to remove unbound antibody. Cells were analysed by FACS to detect antibody bound to the cells.

Figure 4:
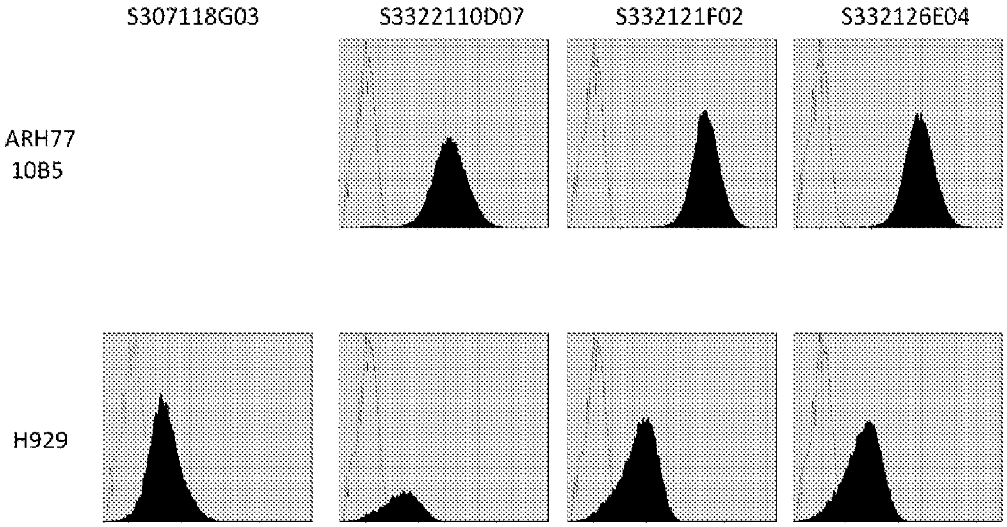
FIG. 4: Cell binding assay—Figure showing binding of murine S307118G03, S3222110D07, S332121F02 and S332126E04 to H929 multiple myeloma cells and S3322110D07, S332121F02 and S332126E04 to the BCMA transfected ARH77 cells as determined by FACS.

The results (FIG. 4) showed that all 4 murine antibodies bound to the H929 multiple myeloma cell line and the three antibodies tested on ARH77 BCMA transfected cells bound to these.

4.4.2 Binding Curve of Chimeric CA8 to Multiple Myeloma Cells as Determined by FACS A panel of multiple myeloma cell lines were used to determine the binding of chimeric CA8. Cell lines H929, OPM-2, JJN-3 and U266 were stained with either chimeric CA8 or irrelevant antibody (Synagis) at varying concentrations for 20 minutes at RT. Cells were then washed with FACS buffer (PBS+0.5% BSA+0.1% sodium azide) to remove unbound antibody. Cells were incubated with a secondary PE labelled anti-human IgG antibody for 15 minutes at RT and then washed with FACS buffer to remove unbound antibody. Cells were analysed by FACS and mean fluorescence intensity (MFI) values measured to determine binding.

Result:s showed that chimeric CA8 bound to multiple myeloma cell lines H929, OPM-2, JJN-3 & U266 in a dose dependent manner (FIG. 5).

4.4.3 Binding of Humanised CA8 to BCMA Transfected Cells as Determined by FACS

ARH77-hBCMA 10B5 BCMA expressing transfectant cells or H929 cells were stained with either chimeric CA8 or humanised variants of CA8 designated J6M0, J6M1, J6M2, J9M0, J9M1, J9M2 at varying concentrations for 20 minutes at RT. Cells were then washed with FACS buffer (PBS+0.5% BSA+0.1% sodium azide) to remove unbound antibody. Cells were incubated with a secondary PE labelled anti-human IgG antibody for 15 minutes at RT and then washed with FACS buffer to remove unbound antibody. Cells were analysed by FACS and mean fluorescence intensity (MFI) values measured to determine binding.

Results showed that chimeric CA8 and all antibodies tested apart from J9M2 bound to ARH77-hBCMA 10B5 BCMA expressing transfectant cells and H929 cells in a dose dependent manner (FIG. 6).

4.5 Demonstration of Ability of CA8 and the Humanised Version J6M0 to Neutralise Binding of BAFF or APRIL to Recombinant BCMA.

The aim of this assay was to assess the ability of antibody CA8, and humanised version J6M0 in both wild type and afucosylated (Potelligent) form, at various concentrations, to neutralise the binding ability of either BCMA ligand, BAFF or APRIL.

96 well flat bottomed plates were coated overnight with 1 μg/mL solution of recombinant human BCMA Fc 4-53 in PBS. Following a wash step using 0.05% TWEEN20, plates were blocked with 2% Bovine Serum Albumin solution in PBS for 1 hour at room temperature. Plates were washed as before and 40 μL of each antibody (murine IgG, murine CA8, and chimeric CA8), starting at 10 μg/mL, titrated at 1 in 2 in duplicate was added to the relevant wells and incubated for 1 hour at room temperature. 40 μL of 2% BSA was added to the relevant control wells. 10 μL of either recombinant human BAFF (2149-BF/CF, R&D Systems) or recombinant human APRIL (5860-AP/CF, R&D Systems) was added at 30 ng/mL and 750 ng/mL respectively, giving a final concentration of 6 ng/mL and 150 ng/mL respectively in each well. Equivalent volume of 2% BSA was added to the relevant control wells. Plates were allowed to incubate for 2 hours at room temperature, after which they were washed as before. Biotinylated anti-human ligand (BAFF BAF124 or APRIL BAF884, R&D Systems) was added to the relevant wells at 50 ng/mL and incubated for 1 hour. Following a wash step, 50 μL of a 1:4000 dilution of Streptavidin-HRP (Amersham RPN4401) was added to each well and incubated for 30 minutes at room temperature. The wash process was repeated again followed by the addition of 100 μL of Tetramethylbenzidine substrate solution (T8665, Sigma) into each well. Plates were incubated for 20-25 minutes at room temperature, wrapped in foil. The reaction was stopped with the addition of 100 μL of 1M $H_2SO_4$. Optical density was determined at 450 nm using Spectromax reader. See FIGS. 7A and B.

In a plate based assay for neutralisation of binding of BAFF or APRIL to BCMA, the EC50 values calculated for chimeric CA8 were 0.695 μg/mL and 0.773 μg/mL respectively. The values for the humanised J6M0 were 0.776 ng/ml and 0.630 ng/ml. The vaues for the J6M0 potelligent version were 0.748 and 0.616 ng/ml respectively.

4.6 Effect of Chimerised CA8 and Humanised J6M0 BCMA Antibody on BAFF or APRIL Induced Phosphorylation Of NFkB in H929 Cells.

In one set of experiments, H-929 cells were plated at 75,000 cells/well in a 96 well plate in serum free medium. The chimeric CA8 antibody was added 24 hours later to give final well concentrations up to 200 ug/ml. Ten minutes later, BAFF or APRIL ligand were added to the cells to give final well concentrations of 0.6 or 0.3 ug/ml respectively. After 30 minutes the cells were lysed and phosphorylated NfkappaB levels measured using a MSD pNFkappaB assay.

The chimeric BCMA antibody CA8 neutralised both BAFF and APRIL induced NfkappaB cell signalling in H-929 cells. It was particularly potent at neutralising BAFF induced NfkappaB cell signalling in this cell type with a mean IC50 of 10 nM, compared to 257 nM for APRIL induced NfkappaB cell signalling.

Meaned Data for 2 Experiments

IC50s were 10 nM for BAFF induced NfkappaB neutralisation and 257 nM for April induced NfkappaB neutralisation (mean of 2 independent experiments) are shown in Table 7.

TABLE 7

| | BAFF induced IC50 | | APRIL induced IC50 | |
|---|---|---|---|---|
| | ug/ml | nM | ug/ml | nM |
| BCMA antibody CA8 | 1.5 | 10 | 38.5 | 256.7 |

Figure 7C:
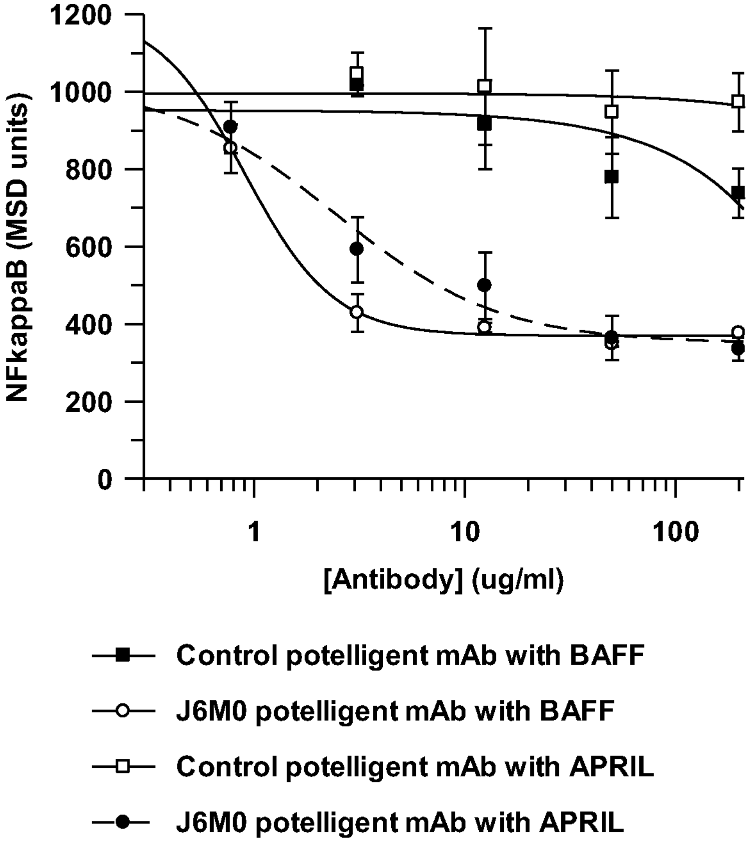

A further set of experiments were carried out to aim to understand why there was such a discrepancy between the potency in neutralisation of APRIL and BAFF in the cell based system. Following the discovery of the soluble form of BCMA the experimental design was changed to include a step where the H929 cells were washed prior to the assay to reduce the interference from the antibody binding to soluble BCMA. H-929 cells were washed 3 times to remove any sBCMA and resuspended in serum free medium. J6M0 potelligent antibody was added to a 96 well plate to give a final well concentrations up to 100 ug/ml along with BAFF or APRIL ligand to give a final well concentration of 0.6 or 0.2 ug/ml respectively. H-929 cells were then plated at 7.5×104 cells/well in serum free medium. 30 minutes later the cells were lysed and phosphorylated NFkappaB levels measured using a MSD pNFkappaB assay. This is data from one experiment. Each data point is the mean/sd of two replicates. The data from this experiment is shown in FIG. 7*c*. The IC50s for inhibition of BAFF and APRIL signalling were determined as 0.91 ug/ml and 2.43 ug/ml respectively.

4.7 ProteOn Analysis of Anti-BCMA CA8 Chimeric and Humanised Constructs

The initial screen of CA8 chimeric and humanised variants was carried out on the ProteOn XPR36 (Biorad). The method was as follows; Protein A was immobilised on a GLC chip (Biorad, Cat No: 176-5011) by primary amine coupling, CA8 variants were then captured on this surface and recombinant human BCMA (in house or commercial US Biological, B0410) materials (run 2 only)) passed over at 256, 64, 16, 4, 1 nM with a 0 nM injection (i.e. buffer alone) used to double reference the binding curves, the buffer used is the HBS-EP buffer. 50 mM NaOH was used to regenerate the capture surface. The data was fitted to the 1:1 model using the analysis software inherent to the ProteOn XPR36. Run 1 corresponds to the first screen of humanised CA8 variants (J0 to J5 series) and run 2 to the second screen of humanised CA8 variants (J5 to J9 series). Both runs were carried out at 25° C.

The data obtained from run1 are set out in Table 8 and data from run 2 are set in Table 9 Several molecules in the Run 2 (Table 09) failed to give affinity values measurable by ProteOn, this was due to the off-rate being beyond the sensitivity of the machine in this assay, this does however indicate that all these molecules bind tightly to recombinant human BCMA. From Run 1 the data indicates that some constructs did not show any binding to recombinant cyno BCMA.

TABLE 8

Run 1-Kinetics analyses of anti-BCMA molecules against Recombinant Human BCMA

| | Human in house BCMA | | | Cyno in house BCMA | | |
|---|---|---|---|---|---|---|
| Sample name | ka | kd | KD (nM) | ka | kd | KD (nM) |
| CA8 humanised J5M0 | 2.16E+05 | 1.88E−05 | 0.087 | 3.25E+05 | 8.14E−06 | 0.025 |
| CA8 humanised J5M2 | 2.67E+05 | 3.21E−05 | 0.12 | 4.30E+05 | 4.70E−05 | 0.109 |
| CA8 humanised J5M1 | 2.97E+05 | 4.32E−05 | 0.145 | 4.81E+05 | 5.41E−05 | 0.112 |
| CA8 humanised J4M1 | 2.54E+05 | 7.04E−05 | 0.278 | 3.50E+05 | 7.10E−05 | 0.203 |
| CA8 humanised J4M2 | 2.51E+05 | 7.06E−05 | 0.281 | 3.44E+05 | 6.15E−05 | 0.179 |
| CA8 humanised J0M2 | 2.25E+05 | 6.97E−05 | 0.31 | 3.26E+05 | 1.84E−04 | 0.563 |
| CA8 humanised J3M2 | 2.66E+05 | 9.64E−05 | 0.362 | 3.69E+05 | 5.87E−05 | 0.159 |
| CA8 humanised J0M1 | 2.31E+05 | 8.60E−05 | 0.373 | 3.32E+05 | 1.67E−04 | 0.503 |
| CA8 humanised J0M0 | 2.45E+05 | 1.06E−04 | 0.435 | 3.58E+05 | 2.32E−04 | 0.648 |
| CA8 humanised J3M1 | 2.85E+05 | 1.25E−04 | 0.438 | 4.04E+05 | 7.93E−05 | 0.196 |
| CA8 humanised J2M2 | 2.05E+05 | 9.87E−05 | 0.482 | 2.98E+05 | 3.17E−05 | 0.106 |
| CA8 Chimera | 2.41E+05 | 1.25E−04 | 0.519 | 3.82E+05 | 1.74E−04 | 0.457 |
| CA8 humanised J2M1 | 2.04E+05 | 1.72E−04 | 0.842 | 2.96E+05 | 6.46E−05 | 0.218 |
| CA8 humanised J4M0 | 2.42E+05 | 2.20E−04 | 0.906 | 3.34E+05 | 2.89E−04 | 0.866 |
| CA8 humanised J1M2 | 2.15E+05 | 2.46E−04 | 1.14 | 3.19E+05 | 9.67E−05 | 0.303 |
| CA8 humanised J3M0 | 2.08E+05 | 2.85E−04 | 1.37 | 2.93E+05 | 1.54E−04 | 0.526 |
| CA8 humanised J1M1 | 2.27E+05 | 3.43E−04 | 1.51 | 3.33E+05 | 1.47E−04 | 0.442 |
| CA8 humanised J2M0 | 1.95E+05 | 3.77E−04 | 1.94 | 2.81E+05 | 1.51E−04 | 0.538 |
| CA8 humanised J1M0 | 1.78E+05 | 5.02E−04 | 2.82 | 2.47E+05 | 2.10E−04 | 0.849 |
| S307118G03 Chimera | 4.75E+05 | 1.95E−03 | 4.11 | No | Analysable | Binding |
| S307118G03 humanised H3L1 | 4.69E+05 | 2.28E−03 | 4.86 | No | Analysable | Binding |
| S307118G03 humanised H3L0 | 2.86E+05 | 1.52E−03 | 5.31 | No | Analysable | Binding |
| S307118G03 humanised H2L0 | 3.78E+05 | 2.41E−03 | 6.36 | No | Analysable | Binding |
| S307118G03 humanised H2L1 | 3.38E+05 | 2.15E−03 | 6.37 | No | Analysable | Binding |
| S307118G03 humanised H4L1 | No | Analysable | Binding | No | Analysable | Binding |

TABLE 9

Run 2-Kinetics analyses of anti-BCMA molecules against Recombinant Human BCMA
For antibodies J8M0, J9M0, J8M1, J9M2, J7M2, J5M0, J7M1, J7M0, J8M2, J9M1, J5M2, J5M1 the off rate was beyond the sensitivity of the assay hence no data shown.

| | Human in house BCMA | | | commercial human BCMA | | | Cyno in house BCMA | | |
|---|---|---|---|---|---|---|---|---|---|
| Sample Name | ka | kd | KD (nM) | ka | kd | KD (nM) | ka | kd | KD (nM) |
| CA8 Chimera | 2.51E+05 | 1.03E−04 | 0.412 | 7.05E+05 | 9.79E−05 | 0.139 | 5.89E+04 | 1.21E−04 | 2.060 |
| CA8 humanised J6M1 | 2.17E+05 | 2.70E−05 | 0.124 | 5.92E+05 | 3.75E−05 | 0.063 | 4.88E+04 | 2.58E−04 | 5.300 |
| CA8 humanised J6M0 | 2.40E+05 | 7.40E−05 | 0.308 | 6.23E+05 | 5.37E−05 | 0.086 | 5.64E+04 | 3.18E−04 | 5.630 |
| CA8 humanised J6M2 | 2.01E+05 | 4.06E−05 | 0.202 | 5.63E+05 | 3.97E−05 | 0.071 | 4.41E+04 | 3.02E−04 | 6.860 |
| S307118G03 H5L0 | No Analysable Binding | | | V weak signal | | | No | Analysable | Binding |
| S307118G03 H5L1 | No Analysable Binding | | | V weak signal | | | No | Analysable | Binding |
| S307118G03Chimera | 4.79E+05 | 1.65E−03 | 3.44 | 1.55E+06 | 1.48E−03 | 0.956 | No | Analysable | Binding |

4.8 BIAcore Analysis of Anti-BCMA CA8 Chimeric and Humanised Constructs (J7 to J9 Series)

Protein A was immobilised on a CM5 chip (GE Healthcare, Cat No: BR-1005-30) by primary amine coupling and this surface was then used to capture the antibody molecules. Recombinant human BCMA (US Biological, B0410) was used as analyte at 256 nM, 64 nM, 16 nM, 4 nM and 1 nM. Regeneration of the capture surface was carried out using 50 mM NaOH. All binding curves were double referenced with a buffer injection (i.e. 0 nM) and the data was fitted to the using the 1:1 model inherent to T100 evaluation software. The run was carried out at 37° C., using HBS-EP as the running buffer.

The results showed the molecules tested with the exception of J9M2 bind to recombinant human BCMA, with similar affinity as the chimeric molecule. Data generated from this experiment are presented in table 10.

TABLE 10

Kinetics analysis of anti-BCMA humanised molecules against Recombinant Human BCMA

| | Human commercial BCMA | | | Cyno in house BCMA | | |
|---|---|---|---|---|---|---|
| Sample name | ka | kd | KD (nM) | ka | kd | KD (nM) |
| CA8 humanised J9M1 | 1.96E+07 | 3.50E−04 | 0.018 | 6.77E+05 | 2.99E−04 | 0.442 |

TABLE 10-continued

Kinetics analysis of anti-BCMA humanised molecules against Recombinant Human BCMA

| | Human commercial BCMA | | | Cyno in house BCMA | | |
|---|---|---|---|---|---|---|
| Sample name | ka | kd | KD (nM) | ka | kd | KD (nM) |
| CA8 humanised J9M0 | 4.95E+06 | 1.74E−04 | 0.035 | 7.03E+05 | 3.24E−04 | 0.46 |
| CA8 Chimera | 3.27E+07 | 1.18E−03 | 0.036 | 1.15E+06 | 3.49E−04 | 0.305 |
| CA8 humanised J8M1 | 2.66E+06 | 1.34E−04 | 0.05 | 2.82E+05 | 3.62E−04 | 1.284 |
| CA8 humanised J8M0 | 2.44E+06 | 1.26E−04 | 0.052 | 3.89E+05 | 4.18E−04 | 1.076 |
| CA8 humanised J7M1 | 2.35E+06 | 1.31E−04 | 0.056 | 3.70E+05 | 3.91E−04 | 1.057 |
| CA8 humanised J8M2 | 2.63E+06 | 1.50E−04 | 0.057 | 3.83E+05 | 5.06E−04 | 1.324 |
| CA8 humanised J7M2 | 2.37E+06 | 1.35E−04 | 0.057 | 3.46E+05 | 4.47E−04 | 1.293 |
| CA8 humanised J7M0 | 2.36E+06 | 1.51E−04 | 0.064 | 3.21E+05 | 3.67E−04 | 1.143 |
| CA8 humanised J9M2 | No | Analysable | Binding | 4.88E+05 | 2.52E−04 | 0.515 |

4.9 BIAcore analysis of anti-BCMA CA8 chimeric and humanised constructs J6M0 and J9M0 Protein A was immobilised on a CM5 chip (GE Healthcare, Cat No: BR-1005-30) by primary amine coupling and this surface was then used to capture the antibody molecules. Recombinant human BCMA (US Biological, B0410) was used as analyte at 256 nM, 64 nM, 16 nM, 4 nM and 1 nM. Regeneration of the capture surface was carried out using 50 mM NaOH. All binding curves were double referenced with a buffer injection (i.e. 0 nM) the data was fitted to the using the 1:1 model inherent to T100 evaluation software. The run was carried out at 25° C. and 37° C. for experiment 1 and only 37° C. for experiment 2 using HBS-EP as the running buffer.

The both runs identified J9M0 as the best molecule in term of overall affinity to human BCMA. Data generated from this experiment are presented in table 11.

4.10. ProteOn Analysis of New Anti-BCMA Chimeric Constructs

The initial screen of the new chimeric variants from the second batch of hybridomas was carried out on the ProteOn XPR36 (Biorad). The method was as follows; Protein A was immobilised on a GLM chip (Biorad, Cat No: 176-5012) by primary amine coupling, anti-BCMA variants were then captured on this surface and recombinant human BCMA (in house material) passed over at 256, 64, 16, 4, 1 nM with a 0 nM injection (i.e. buffer alone) used to double reference the binding curves, the buffer used is the HBS-EP buffer. Regeneration of the capture surface was carried out using 50 mM NaOH. The data was fitted to the 1:1 model using the analysis software inherent to the ProteOn XPR36. The run was carried out at 25° C.

Data generated from this experiment are presented in table 12.

TABLE 11

Kinetics analyses of anti-BCMA humanised molecules against Human BCMA

| | Human commercial BCMA | | | | | | | | |
|---|---|---|---|---|---|---|---|---|---|
| | 25° C. | | | 37° C. | | | | | |
| | Experiment 1 | | | Experiment 1 | | | Experiment 2 | | |
| Sample | ka | kd | KD (nM) | ka | kd | KD (nM) | ka | kd | KD (nM) |
| J9M0 | 1.59E+06 | 3.38E−05 | 0.021 | 3.75E+06 | 1.58E−04 | 0.042 | 3.62E+06 | 1.89E−04 | 0.052 |
| J6M0 | 1.01E+06 | 1.22E−04 | 0.121 | 2.12E+06 | 1.48E−03 | 0.698 | 3.78E+06 | 1.88E−03 | 0.498 |
| Chimera CA8 | 1.88E+06 | 2.63E−04 | 0.140 | 1.72E+07 | 8.72E−04 | 0.051 | 1.88E+07 | 1.04E−03 | 0.055 |

TABLE 12

| Kinetics analyses of anti-BCMA humanised molecules against Human BCMA | | | |
|---|---|---|---|
| | In house human BCMA | | |
| Sample name | ka | kd | KD (nM) |
| S332110D07 | 3.11E+05 | 3.77E−03 | 12.100 |
| S332121F02 | 3.73E+05 | 6.45E−03 | 17.300 |

Example 5

Cell Killing Assays 5.1 ADCC Potencies of Chimeric CA8 and Defucosylated Chimeric CA8 Version in ARH77 Cells Expressing BCMA Human natural killer (NK) cells were incubated with europium labelled ARH77 BCMA transfected target cells (10B5) in the presence of varying concentrations of antibody at an E:T ratio of 5:1 for 2 hours. Europium release from the target cells was measured and specific lysis calculated. Result: Chimeric CA8 and defucosylated chimeric CA8 killed BCMA expressing target cells via ADCC. The defucosylated chimeric antibody showed more potent ADCC activity, as measured by a higher percent lysis achieved with all the target cells tested and a ten-fold lower $EC_{50}$ on the high BCMA expressing target cell line 10B5, compared to the parent chimeric antibody. See FIGS. 8A and 8B.

5.2 ADCC Activity of CA8 Humanised Antibodies Using ARH77 BCMA Expressing Target Cells and PBMC as Effectors Human PBMC were incubated with europium labelled ARH77 BCMA transfected target cells (10B5) in the presence of varying concentrations of humanised versions of CA8 antibody (5 ug/ml to 0.005 ug/ml) at an E:T ratio of 5:1 for 2 hours. Europium release from the target cells was measured and specific lysis calculated.

Result:

Result: All the J5, J6, J7 J8 & J9 series of humanised variants of CA8 showed ADCC activity against the ARH77 high BCMA expressing cell line 10B5 in a dose dependent manner. ADCC was at a similar level as that found in the experiments using chimeric CA8 molecule. See FIG. 9.

5.3 ADCC Potencies of Chimeric S322110F02, S322110D07 and S307118G03 and Humanised S307118G03 H3L0 Against ARH77 10B5 Cells Expressing BCMA with Purified NK Cells as Effector Cells Human natural killer (NK) target cells were incubated with europium labelled ARH77 BCMA transfected target cells (10B5) in the presence of varying concentrations of antibody at an E:T ratio of 5:1 for 2 hours. Europium release from the target cells was measured and specific lysis calculated. Result: all 4 antibodies tested showed ADCC activity against ARH77 10B5 cells. See FIG. 10.

5.4 Antibody-Drug Conjugate (ADC) Activity of Chimeric CA8 ADCs.

Measuring ADC activity of chimeric CA8 antibody, chimeric CA8-mcMMAF antibody drug conjugates and chimeric CA8-vcMMAE antibody drug conjugates against human multiple myeloma cell lines. Muliple Myeloma cell lines were treated with chimeric CA8 antibody-drug conjugates to determine the ADC concentrations required for growth inhibition and death.

The antibody drug conjugates tested were added to wells containing multiple myeloma cells at concentrations ranging from 1 ug/ml to 5 ng/ml. The plates were incubated at 37° C. for 96 hours at which point viable cells were quantitated using Cell titre Glo. The unconjugated chimeric CA8 antibody showed no significant growth inhibitory activity at the antibody concentrations that were tested. The chimeric CA8-mcMMAF antibody-drug conjugate showed greater growth inhibitory activity than the chimeric CA8-vcMMAE antibody-drug conjugate in all 4 of the multiple myeloma cell lines that were tested. See FIG. 11 and Table 13

TABLE 13

| $IC_{50}$ values represented in ng/mL for the chimeric CA8-vcMMAE and the chimeric CA8-mcMMAF antibody-drug conjugates in 4 different multiple myeloma cell lines | | |
|---|---|---|
| | $IC_{50}$ (ng/mL) | |
| Multiple Myeloma cell lines | CA8 chimera - vcMMAE | CA8 chimera - mcMMAF |
| NCI-H929 | 29.5 | 8.8 |
| U266-B1 | 18.9 | 9.7 |
| JJN3 | 21.8 | 12.4 |
| OPM2 | 92.7 | 58.1 |

5.5 Measuring Cell Cycle Arrest Activity of Chimeric CA8 Antibody, Chimeric CA8-mcMMAF Antibody Drug Conjugates and Chimeric CA8-vcMMAE Antibody Drug Conjugates Against Human Multiple Myeloma Cell Line H929.

To determine the mechanism that chimeric CA8 Antibody Drug Conjugates (ADC's) cause growth inhibition in multiple myeloma cells, the cell cycle of NCI-H929 cells was monitored by measuring cellular DNA content through fixed cell propidium iodide staining at multiple timepoints following chimeric CA8 antibody and chimeric CA8 ADC treatment.

At the chimeric CA8 ADC concentration tested (50 ng/mL), the chimeric CA8-mcMMAF ADC caused significant G2/M cell cycle arrest (4N DNA content) which peaked at 48 hours. At the later timepoints 48, 72 and 96 hours, treatment with the chimeric CA8-mcMMAF ADC resulted in accumulation of a cell population with sub-2N DNA content, which is representative of cell death. At the 50 ng/mL concentration tested the chimeric CA8-vcMMAE ADC had no significant effect on G2/M cell cycle arrest or sub-G1 accumulation. See FIG. 12.

5.6 Phospho-Histone-H3 (Thr11) Staining as a Marker for Chimeric CA8-mcMMAF Antibody Drug conjugate and chimeric CA8-vcMMAE antibody drug conjugate induced mitotic arrest.

To determine if the accumulation of cells with 4N DNA content is a specific result of mitotic arrest induced by the chimeric CA8 ADCs NCI-H929 cells were stained with an anti-phospho-Histone H3 antibody following treatment with increasing concentrations of unconjugated chimeric CA8, chimeric CA8-vcMMAE or chimeric CA8-mcMMAF for 48 hours.

Treatment with chimeric CA8 ADCs resulted in a dose-dependent accumulation of NCI-H929 cells that stained positive for 65eroxidi-Histone H3 (Thr11), a specific marker of mitotic cells. The chimeric CA8-mcMMAF ADC caused accumulation of 65eroxidi-Histone H3 positive cells at lower concentrations than the chimeric CA8-vcMMAE ADC. See FIG. 13.

5.7 Measuring Apoptosis in NCI-H929 Cells in Response to Chimeric CA8 ADCs by Staining for Annexin V.

To determine if the accumulation of cells with sub-2N DNA content is a specific result of apoptosis induced by the chimeric CA8 ADCs, NCI-H929 cells were stained with an anti-Annexin-V antibody following treatment with increasing concentrations of unconjugated chimeric CA8, chimeric CA8-vcMMAE or chimeric CA8-mcMMAF for 48 hours. Treatment with chimeric CA8 ADCs resulted in a dose-dependent accumulation of NCI-H929 cells that stained positive for Annexin-V, a specific marker of apoptosis. The chimeric CA8-mcMMAF ADC caused accumulation of Annexin-V positive cells at lower concentrations than the chimeric CA8-vcMMAE ADC. See FIG. 14.

5.8 Antibody-Drug Conjugate (ADC) Activity of Humanised Variants of CA8 Anti-BCMA Antibody-Drug Conjugates.

Cells were plated in 96-well plates (4,000 cells per well in 100 uL of RPMI+10% FBS) Naked antibody or ADC was added 6 hours after cell seeding and plates were incubated for 144 hours. Growth inhibition in the presence of the antibodies or ADCs was measured at 144 hours using Cell Titre glo. Data points represent the mean of triplicate CellTiterGlo measurements. Error bars represent standard error.

Multiple Myeloma cell lines NCI-H929 and OPM2 were treated with humanized CA8 anti-BCMA antibody-drug conjugates to determine the ADC concentrations required for growth inhibition and death. The mcMMAF and vcMMAE antibody-drug conjugate forms of these antibodies showed significant growth inhibitory activity comparable to that found with the CA8 chimera. Variant J6M0 showed higher potency than the chimera and data is shown in FIG. 15 in H929 cells and OPM2 cells. The mcMMAF antibody-drug conjugate showed greater growth inhibitory activity than the vcMMAE antibody-drug conjugate for all antibodies in both cell lines tested. Results for all humanized variants are shown in Table 14.

TABLE 14

$IC_{50}$ values represented in ng/mL for the anti BCMA antibody-drug conjugates in NCI-H929 and U266-B1 cells

| | NCI-H929 | | OPM2 | |
|---|---|---|---|---|
| | mcMMAF Average IC50 (ng/mL) | vcMMAE Average IC50 (ng/mL) | mcMMAF Average IC50 (ng/mL) | vcMMAE Average IC50 (ng/mL) |
| CA8 chimera | 11.64 | 37.96 | 57.04 | 80.01 |
| CA8 J6M0 | 5.97 | 27.67 | 87.22 | 121.2 |
| CA8 J6M1 | 14.6 | 51.89 | 205.6 | 239.9 |
| CA8 J6M2 | 9.5 | 39.71 | 112.9 | 144.7 |
| CA8 J7M0 | 18.97 | 52.25 | 93.27 | 127.1 |
| CA8 J7M1 | 17.87 | 43.97 | 95.35 | 107.5 |
| CA8 J7M2 | 31.63 | 55.13 | 102.6 | 115.9 |
| CA8 J8M0 | 15.67 | 59.94 | 89.95 | 132 |
| CA8 J8M1 | 17.04 | 46.55 | 82.96 | 115.8 |
| CA8 J8M2 | 15.08 | 55.98 | 72.63 | 124.5 |
| CA8 J9M0 | 14.95 | 48.5 | 58.6 | 109.8 |
| CA8 J9M1 | 15.19 | 55.1 | 55.88 | 115 |
| CA8 J9M2 | 20.87 | 55.77 | 80.35 | 111.7 |

5.9 Antibody-Drug Conjugate (ADC) Activity of Other Murine Anti-BCMA Antibody-Drug Conjugates.

Cells were plated in 96-well plates (4,000 cells per well in 100 uL of RPMI+10% FBS) Antibody or ADC was added 6 hours after cell seeding and plates were incubated for 144 hours. Growth inhibition in the presence of the ADCs was measured at 144 hours using Cell Titre glo. The mean of triplicate CellTiterGlo measurements are shown. Table 15a and 15b are from experiments carried out at different times on different series of antibodies. Multiple Myeloma cell lines NCI-H929 and U266-B1 were used for antibodies in Table 15a.

The mcMMAF and vcMMAE antibody-drug conjugate forms of murine antibodies S322110D07, S332121F02 and S332136E04 showed significant growth inhibitory activity. The mcMMAF antibody-drug conjugate showed greater growth inhibitory activity than the vcMMAE antibody-drug conjugate in all of the murine anti-BCMA antibodies tested where activity was seen. IC50 figures are shown in Table 15a. See FIG. 16 for dose response curves for these three antibodies and also S107118G03. Error bars represent standard error. NCI-H929, U266-B1, JJN3 and OPM2 cells for antibodies in Table 15b were treated with a different series of murine anti-BCMA antibody-drug conjugates to determine the ADC concentrations required for growth inhibition and death. 1050 figures are shown in Table 15b. All 5 antibodies shown on the table had significant ADC activity.

TABLE 15a $IC_{50}$ values represented in ng/mL for the anti BCMA antibody-drug conjugates in NCI-H929 and U266-B1 cells

| | IC50 (ng/mL) | | | |
|---|---|---|---|---|
| | NCI-H929 | | U226-B1 | |
| Antibody | -vcMMAE | -mcMMAF | -vcMMAE | -mcMMAF |
| S322110D07 mIgG1 | 28.4 | 6.7 | 53.3 | 33.3 |
| S332121F02 mIgG1 | 24.5 | 7 | 2.3 | 2.5 |
| S332126E04 mIgG1 | 46.8 | 9.7 | 27.1 | 10.6 |

TABLE 15B $IC_{50}$ values represented in ng/mL for the anti BCMA antibody-drug conjugates in NCI-H929, U266-B1, JJN3 and OPM2 cells

| Average IC50 | NCI-H929 | | U266B1 | | JJN3 | | OPM2 | |
|---|---|---|---|---|---|---|---|---|
| (ng/mL) | vcMMAE | mcMMAF | vcMMAE | mcMMAF | vcMMAE | mcMMAF | vcMMAE | mcMMAF |
| S335115G01 | 14.9 | 4.2 | 38.8 | 18.5 | 73.9 | 45.8 | 162.4 | 197.2 |
| S336105A07 | 17.8 | 5.1 | 21.4 | 9.3 | 54.2 | 23.2 | 95.5 | 73.7 |
| S335122F05 | 10.9 | 4.2 | 21.1 | 14.1 | 29.5 | 25.5 | 98.4 | 128.7 |
| S335106E08 | 19.2 | 7.9 | 36.8 | 32.6 | 189.8 | 214.1 | 243.9 | 307.5 |
| S335128A12 | 86.3 | 28.3 | 101.8 | 104.1 | >500 | >500 | >500 | >500 |

5.10 ADCC Potency of Conjugated, Afucosylated J6M0 (Potelligent)

Afucosylated J6M0 conjugated to MMAE or MMAF was tested in ADCC assays using BCMA transfectants to ensure that its ADCC activity was not compromised by the conjugation. Europium labelled ARH77-10B5 cells were incubated with various J6M0 WT and Potelligent BCMA antibodies at concentrations up to 10000 ng/ml for 30 minutes prior to the addition of PBMCs (PBMC: target cell ratio 50:1). Two hours later an aliquot of cell media was sampled and mixed with enhancement solution. After 30 minutes on a plate shaker, europium release was monitored on the Victor 2 1420 multilabel reader. Datapoints represent means of triplicate values. This data is representative of 2 experiments.

There were no significant differences in ADCC potency between the unconjugated and ADC forms of J6M0 Potelligent. In the same experiment a wild type version of J6M0 was included to show how the potency compares to the afucosylated version. As expected, defucosylation resulted in a lower EC50 and higher maximal lysis. No lysis was observed with the Fc disabled form of J6M0. (FIG. 17)

5.11 ADCC Potency of Afucosylated J6M0 on MM Cell Lines

Human PBMC were incubated with multiple myeloma target cells at an E:T ratio of 50:1 in presence of varying concentrations of afucosylated (Potelligent) J6M0 The percentage of target cells remaining in the effector+target cell mixture after 18 hours was measured by FACS using a fluorescently labelled anti-CD138 antibody to detect the target cells and the percent lysis calculated. This is representative of several experiments.

J6M0 Potelligent antibody showed ADCC activity against all five multiple myeloma target cell lines tested. This was important to test since earlier studies were carried out using transfected cells. Results are shown in FIG. 18. Full dataset with multiple donors is shown in Table 16 The potencies were all in a similar range as those found with the transfectants. The ADCC activity was not directly related to BCMA surface expression on these cell lines.

TABLE 16

$EC_{50}$ values generated on 13 independent assays using 11 donors (designated A-K) across the five multiple myeloma cell lines.

| | $EC_{50}$ (ng/mL) | | | | |
|---|---|---|---|---|---|
| Donor | H929 | RPMI 8226 | JJN-3 | OPM-2 | U266 |
| A | 1.43 | NA | 1.64 | NA | NA |
| B | 0.57 | NA | NA | NA | NA |
| C | 0.73 | NA | 1.01 | NA | NA |
| C | 1.81 | NA | NA | NA | NA |
| A | 2.05 | NA | NA | NA | NA |
| D | NA | 4.09 | NA | NA | NA |
| E | NA | NA | 14.4 | NA | NA |
| F | 2.18 | NA | NA | NA | NA |
| G | NA | NA | 26.3 | NA | NA |
| H | 4.79 | NA | 111.3 | NA | NA |
| I | NA | NA | 40.1 | NA | NA |
| J | 2.19 | 20.4 | 4.89 | NA | NA |
| K | ND | ND | 4.52 | 4.15 | 9.04 |

Example 6

Xenograft Data 6.1 Murine xenografts of human MM cell lines were tested to ensure that antibody potency detected in vitro can also be demonstrated in vivo. The cell line selected for xenograft studies was NCI-H929 which is sensitive to ADC and ADCC killing in vitro. Studies were carried out in immunocompromised CB.17 SCID mice which lack T and B cells but maintain NK cells to allow for ADCC activity. However it should be noted that although human IgG1 can engage murine Fc receptors, the Potelligent enhancement does not improve the affinity as it does with human Fc receptors.

6.2 Impact of Unconjugated and MMAE or MMAF Conjugated J6M0 on NCI-H929 Tumour Growth.

In order to independently analyze both the ADCC and ADC activities of J6M0 we tested J6M0 antibody in the presence and absence of MMAF or MMAE conjugation. By testing the unconjugated J6M0, any anti-tumour effects could be attributed to some combination of ADDC and functional inhibitory activity.

Mice with NCI-H929 tumours that had reached a volume of 200 $mm^3$ on average were treated with a human IgG1 control or the J6M0 antibody (unconjugated, MMAE or MMAF) twice weekly at a dose of 50 ug or 100 ug, for 2 weeks. Results from this study show that a 100 ug dose of the J6M0-MMAF conjugate resulted in elimination of tumours in those mice which have completed the dosing. The J6M0-MMAF mice were maintained for 40 days after the last dose with no recurrence of tumour occurring. These results from this experiment demonstrate that MMAF conjugation had increased anti-tumour activity over both unconjugated J6M0 antibody and J6MO-MMAE conjugate See FIG. 19.

Example 7

Evaluation of Soluble BCMA Levels from MM Patient Serum 7.1 It is currently unknown whether BCMA is present extracellularly and can be detected in the blood. In this work, we determined the serum level of human BCMA from MM patients. Serum samples from 54 MM and plasma cell dyscrasia patients and 20 normal control samples were analyzed by ELISA. Human Subject Approval was obtained from Western Institutional Review Board.

7.2 Assessment of Serum Human BCMA Levels

Blood, from patients and normal controls in the clinic, were collected in serum collection tubes. MM patient samples were from a variety of stages (progressive disease, remission, relapsed, newly diagnosed, and others). The Blood samples were spun at 10,000 rpm for 10 minutes and serum transferred into sterile micro-centrifuge plastic tubes.

A Human BCMA/TNFRSF17 ELISA kit from R& D Systems (catalog # DY193E) which measures soluble human BCMA levels was used to detect BCMA following the standard protocol supplied with the kit.

Briefly, 96 well micro-plates were coated with 100 ul per well capture antibody and incubated overnight at 4° C. The plates were washed three times with wash buffer (0.05% Tween 20 in PBS, pH 7.2) and blocked with 300 ul of 1% BSA in PBS at room temperature for 2 hours. The plates were washed three times with washing buffer. 100 ul of serum sample or standard was added into each well and incubated for 2 hours at room temperature. The plates were washed three times with washing buffer and then 100 ul of the detection antibody was added to each well and incubated 2 hours at room temperature. 100 ul of Streptavidin-HRP was added in each well after washing plates three times and incubated in dark room for 20 minutes. The plates were washed three times and added 50 ul stop solution and then determined by microplate reader with 570 nM wavelength.

A series of assays were carried out in order to determine the serum dilution factor appropriate for the levels of BCMA which were present. A dilution factor of 1:500 was found to be suitable for the majority of samples and is the dilution factor used in the data shown in FIG. 20. The full data set is shown in Table 17.

Patient and normal control serum samples diluted and run in triplicates had BCMA levels determined. The serum levels of BCMA were significantly elevated in the sera from MM patients compared with normal controls in this study. When the disease subset was divided further there was a trend towards elevated serum levels of BCMA in the sera from progressing MM patients compared with those in remission. This is the first report identifying serum BCMA in any human disease and suggests that these levels may be a novel biomarker for monitoring disease status and therapeutic response of MM patients and for other patients with plasma cell mediated diseases.

TABLE 17

Figures represent serum concentration of soluble BCMA in ng/ml calculated from samples diluted at 1/50, 1/500 and 1/5000. P values were calculated using the one tailed T-Test and 95% significance values are below the table.

| | Normal | Myeloma: Progressive | Myeloma: Stable | Myeloma: Remission | Myeloma: Other | MGUS | Other Plasma Cell Dyscrasias |
|---|---|---|---|---|---|---|---|
| 1-5000 | | | | | | | |
| Mean | 14.130 | 500.804 | 154.762 | 151.201 | 94.457 | 84.912 | 22.838 |
| 1-500 Triplicate | | | | | | | |
| Mean | 15.901 | 215.877 | 81.135 | 43.294 | 97.584 | 53.894 | 22.838 |
| 1-500 Single | | | | | | | |
| Mean | 16.620 | 207.028 | 61.576 | 42.796 | 71.372 | 40.623 | 14.099 |
| 1-50 Trial 1 | | | | | | | |
| Mean | 25.568 | 129.544 | 41.983 | 40.507 | 65.120 | 42.067 | 51.650 |
| 1-50 Trial 2 | | | | | | | |
| Mean | 17.160 | 119.220 | 34.567 | 34.264 | 54.780 | 26.333 | 51.650 |

P-Values (One Tailed T-Test, 95% Significance)
~1-500 Single
Normal vs Progressive: p = .0010*
Progressive vs Remission: p = .0146*
~1-500 Triplicate
Normal vs Progressive: p = .0004*
Progressive vs Remission: p = .0091*
~1-50 Trial 1
Normal vs Progressive: p = .0171*
Progressive vs Remission: p = .0777
~1-50 Trial 2
Normal vs Progressive: p = .0184*
Progressive vs Remission: p = .0876
* shows significance

TABLE C

Sequence Summary

| Description | Amino acid sequence | Polynucleotide sequence |
|---|---|---|
| CA8 CDRH1 | SEQ. I.D. NO: 1 | n/a |
| CA8 CDRH2 | SEQ. I.D. NO: 2 | n/a |
| CA8 CDRH3 | SEQ. I.D. NO: 3 | n/a |
| CA8 CDRL1 | SEQ. I.D. NO: 4 | n/a |
| CA8 CDRL2 | SEQ. I.D. NO: 5 | n/a |
| CA8 CDRL3 | SEQ. I.D. NO: 6 | n/a |
| CA8 $V_H$ domain (murine) | SEQ. I.D. NO: 7 | SEQ. I.D. NO: 8 |
| CA8 $V_L$ domain (murine) | SEQ. I.D. NO: 9 | SEQ. I.D. NO: 10 |
| CA8 Humanised $V_H$ J0 | SEQ. I.D. NO: 11 | SEQ. I.D. NO: 12 |
| CA8 Humanised $V_H$ J1 | SEQ. I.D. NO: 13 | SEQ. I.D. NO: 14 |
| CA8 Humanised $V_H$ J2 | SEQ. I.D. NO: 15 | SEQ. I.D. NO: 16 |
| CA8 Humanised $V_H$ J3 | SEQ. I.D. NO: 17 | SEQ. I.D. NO: 18 |
| CA8 Humanised $V_H$ J4 | SEQ. I.D. NO: 19 | SEQ. I.D. NO: 20 |
| CA8 Humanised $V_H$ J5 | SEQ. I.D. NO: 21 | SEQ. I.D. NO: 22 |
| CA8 Humanised $V_H$ J6 | SEQ. I.D. NO: 23 | SEQ. I.D. NO: 24 |
| CA8 Humanised $V_H$ J7 | SEQ. I.D. NO: 25 | SEQ. I.D. NO: 26 |
| CA8 Humanised $V_H$ J8 | SEQ. I.D. NO: 27 | SEQ. I.D. NO: 28 |
| CA8 Humanised $V_H$ J9 | SEQ. I.D. NO: 29 | SEQ. I.D. NO: 30 |
| CA8 Humanised $V_L$ M0 | SEQ. I.D. NO: 31 | SEQ. I.D. NO: 32 |

TABLE C-continued

Sequence Summary

| Description | Amino acid sequence | Polynucleotide sequence |
|---|---|---|
| CA8 Humanised $V_L$ M1 | SEQ. I.D. NO: 33 | SEQ. I.D. NO: 34 |
| CA8 Humanised $V_L$ M2 | SEQ. I.D. NO: 35 | SEQ. I.D. NO: 36 |
| Human BCMA CD33-hBCMA ECD (1-53) TEV-Fc | SEQ. I.D. NO: 37 | SEQ. I.D. NO: 38 |
| Human BCMA CD33-hBCMA ECD (4-53) TEV-Fc | SEQ. I.D. NO: 39 | SEQ. I.D. NO: 40 |
| Cyno BCMA CD33 cyno BCMA ECD (4-52) TEV-Fc | SEQ. I.D. NO: 41 | SEQ. I.D. NO: 42 |
| CA8 J0 Humanised heavy chain | SEQ. I.D. NO: 43 | SEQ. I.D. NO: 44 |
| CA8 J1 Humanised heavy chain | SEQ. I.D. NO: 45 | SEQ. I.D. NO: 46 |
| CA8 J2 Humanised heavy chain | SEQ. I.D. NO: 47 | SEQ. I.D. NO: 48 |
| CA8 J3 Humanised heavy chain | SEQ. I.D. NO: 49 | SEQ. I.D. NO: 50 |
| CA8 J4 Humanised heavy chain | SEQ. I.D. NO: 51 | SEQ. I.D. NO: 52 |
| CA8 J5 Humanised heavy chain | SEQ. I.D. NO: 53 | SEQ. I.D. NO: 54 |
| CAS J6 Humanised heavy chain | SEQ. I.D. NO: 55 | SEQ. I.D. NO: 56 |
| CAS J7 Humanised heavy chain | SEQ. I.D. NO: 57 | SEQ. I.D. NO: 58 |
| CAS J8 Humanised heavy chain | SEQ. I.D. NO: 59 | SEQ. I.D. NO: 60 |
| CAS J9 Humanised heavy chain | SEQ. I.D. NO: 61 | SEQ. I.D. NO: 62 |
| CAS M0 Humanised light chain | SEQ. I.D. NO: 63 | SEQ. I.D. NO: 64 |
| CAS M1 Humanised light chain | SEQ. I.D. NO: 65 | SEQ. I.D. NO: 66 |
| CAS M2 Humanised light chain | SEQ. I.D. NO: 67 | SEQ. I.D. NO: 68 |
| S307118G03 $V_H$ domain (murine) | SEQ. I.D. NO: 69 | SEQ. I.D. NO: 70 |
| S307118G03 $V_L$ domain (murine) | SEQ. I.D. NO: 71 | SEQ. I.D. NO: 72 |
| S307118G03 heavy chain (chimeric) | SEQ. I.D. NO: 73 | SEQ. I.D. NO: 74 |
| S307118G03 light chain(chimeric) | SEQ. I.D. NO: 75 | SEQ. I.D. NO: 76 |
| S307118G03 Humanised $V_H$ H0 | SEQ. I.D. NO: 77 | SEQ. I.D. NO: 78 |
| S307118G03 Humanised $V_H$ H1 | SEQ. I.D. NO: 79 | SEQ. I.D. NO: 80 |
| S307118G03 humanised $V_H$ H2 | SEQ. I.D. NO: 81 | SEQ. I.D. NO: 82 |
| S307118G03 humanised $V_H$ H3 | SEQ. I.D. NO: 83 | SEQ. I.D. NO: 84 |
| S307118G03 humanised $V_H$ H4 | SEQ. I.D. NO: 85 | SEQ. I.D. NO: 86 |
| S307118G03 humanised $V_H$ H5 | SEQ. I.D. NO: 87 | SEQ. I.D. NO: 88 |
| S307118G03 humanised $V_L$ L0 | SEQ. I.D. NO: 89 | SEQ. I.D. NO: 90 |
| S307118G03 humanised $V_L$ L1 | SEQ. I.D. NO: 91 | SEQ. I.D. NO: 92 |
| S307118G03 CDRH1 | SEQ. I.D. NO: 93 | |
| S307118G03 CDRH2 | SEQ. I.D. NO: 94 | |
| S307118G03 CDRH3 | SEQ. I.D. NO: 95 | |
| S307118G03 CDRL1 | SEQ. I.D. NO: 96 | |
| S307118G03 CDRL2 | SEQ. I.D. NO: 97 | |
| S307118G03 CDRL3 | SEQ. I.D. NO: 98 | |
| S307118G03 humanised H5 CDRH3 | SEQ. I.D. NO: 99 | |
| S307118G03 H0 Humanised heavy chain | SEQ. I.D. NO: 100 | SEQ. I.D. NO: 101 |
| S307118G03 H1 humanised heavy chain | SEQ. I.D. NO: 102 | SEQ. I.D. NO: 103 |
| S307118G03 H2 humanised heavy chain | SEQ. I.D. NO: 104 | SEQ. I.D. NO: 105 |
| S307118G03 H3 humanised heavy chain | SEQ. I.D. NO: 106 | SEQ. I.D. NO: 107 |
| S307118G03 H4 humanised heavy chain | SEQ. I.D. NO: 108 | SEQ. I.D. NO: 109 |
| S307118G03 H5 humanised heavy chain | SEQ. I.D. NO: 110 | SEQ. I.D. NO: 111 |
| S307118G03 L0 humanised light chain | SEQ. I.D. NO: 112 | SEQ. I.D. NO: 113 |
| S307118G03L1 humanised light chain | SEQ. I.D. NO: 114 | SEQ. I.D. NO: 115 |
| S332121F02 murine variable heavy chain | SEQ. I.D. NO: 116 | SEQ. I.D. NO: 117 |
| S332121F02 chimeric variable heavy chain | SEQ. I.D. NO: 118 | SEQ. I.D. NO: 119 |
| S332121F02 murine variable light chain | SEQ. I.D. NO: 120 | SEQ. I.D. NO: 121 |
| S332121F02 chimeric variable light chain | SEQ. I.D. NO: 122 | SEQ. I.D. NO: 123 |
| S322110D07 murine variable heavy chain | SEQ. I.D. NO: 124 | SEQ. I.D. NO: 125 |
| S322110D07 chimeric heavy chain | SEQ. I.D. NO: 126 | SEQ. I.D. NO: 127 |
| S322110D07 murine variable light chain | SEQ. I.D. NO: 128 | SEQ. I.D. NO: 129 |
| S322110D07 chimeric light chain | SEQ. I.D. NO: 130 | SEQ. I.D. NO: 131 |
| S332126E04 murine variable heavy chain | SEQ. I.D. NO: 132 | SEQ. I.D. NO: 133 |
| S332126E04 Chimeric heavy chain | SEQ. I.D. NO: 134 | SEQ. I.D. NO: 135 |
| S332126E04 murine variable light chain | SEQ. I.D. NO: 136 | SEQ. I.D. NO: 137 |
| S332126E04 Chimeric light chain | SEQ. I.D. NO: 138 | SEQ. I.D. NO: 139 |
| S336105A07 murine variable heavy chain | SEQ. I.D. NO: 140 | SEQ. I.D. NO: 141 |
| S336105A07 Chimeric heavy chain | SEQ. I.D. NO: 142 | SEQ. I.D. NO: 143 |
| S336105A07 murine variable light chain | SEQ. I.D. NO: 144 | SEQ. I.D. NO: 145 |
| S336105A07 chimeric light chain | SEQ. I.D. NO: 146 | SEQ. I.D. NO: 147 |
| S335115G01 murine variable heavy chain | SEQ. I.D. NO: 148 | SEQ. I.D. NO: 149 |
| S335115G01 Chimeric heavy chain | SEQ. I.D. NO: 150 | SEQ. I.D. NO: 151 |
| S335115G01 murine variable light chain | SEQ. I.D. NO: 152 | SEQ. I.D. NO: 153 |
| S335115G01 Chimeric light chain | SEQ. I.D. NO: 154 | SEQ. I.D. NO: 155 |
| S335122F05 murine variable heavy chain | SEQ. I.D. NO: 156 | SEQ. I.D. NO: 158 |
| S335122F05 Chimeric heavy chain | SEQ. I.D. NO: 158 | SEQ. I.D. NO: 159 |
| S335122F05 murine variable light chain | SEQ. I.D. NO: 160 | SEQ. I.D. NO: 161 |
| S335122F05 Chimeric light chain | SEQ. I.D. NO: 162 | SEQ. I.D. NO: 163 |
| S332121F02 CDRH1 | SEQ. I.D. NO: 164 | |
| S332121F02 CDRH2 | SEQ. I.D. NO: 165 | |
| S332121F02 CDRH3 | SEQ. I.D. NO: 166 | |

TABLE C-continued

| Sequence Summary | | |
|---|---|---|
| Description | Amino acid sequence | Polynucleotide sequence |
| S332121F02 CDRL1 | SEQ. I.D. NO: 167 | |
| S332121F02 CDRL2 | SEQ. I.D. NO: 168 | |
| S332121F02 CDRL3 | SEQ. I.D. NO: 169 | |
| S322110D07 CDRH1 | SEQ. I.D. NO: 170 | |
| S322110D07 CDRH2 | SEQ. I.D. NO: 171 | |
| S322110D07 CDRH3 | SEQ. I.D. NO: 172 | |
| S322110D07 CDRL1 | SEQ. I.D. NO: 173 | |
| S322110D07 CDRL2 | SEQ. I.D. NO: 174 | |
| S322110D07 CDRL3 | SEQ. I.D. NO: 175 | |
| S332126E04 CDRH1 | SEQ. I.D. NO: 176 | |
| S332126E04 CDRH2 | SEQ. I.D. NO: 177 | |
| S332126E04 CDRH3 | SEQ. I.D. NO: 178 | |
| S332126E04 CDRL1 | SEQ. I.D. NO: 179 | |
| S332126E04 CDRL2 | SEQ. I.D. NO: 180 | |
| S332126E04 CDRL3 | SEQ. I.D. NO: 181 | |
| S336105A07 CDRH1 | SEQ. I.D. NO: 182 | |
| S336105A07 CDRH2 | SEQ. I.D. NO: 183 | |
| S336105A07 CDRH3 | SEQ. I.D. NO: 184 | |
| S336105A07 CDRL1 | SEQ. I.D. NO: 185 | |
| S336105A07 CDRL2 | SEQ. I.D. NO: 186 | |
| S336105A07 CDRL3 | SEQ. I.D. NO: 187 | |
| S335115G01 CDRH1 | SEQ. I.D. NO: 188 | |
| S335115G01 CDRH2 | SEQ. I.D. NO: 189 | |
| S335115G01 CDRH3 | SEQ. I.D. NO: 190 | |
| S335115G01 CDRL1 | SEQ. I.D. NO: 191 | |
| S335115G01 CDRL2 | SEQ. I.D. NO: 192 | |
| S335115G01 CDRL3 | SEQ. I.D. NO: 193 | |
| S335122F05 CDRH1 | SEQ. I.D. NO: 194 | |
| S335122F05 CDRH2 | SEQ. I.D. NO: 195 | |
| S335122F05 CDRH3 | SEQ. I.D. NO: 196 | |
| S335122F05 CDRL1 | SEQ. I.D. NO: 197 | |
| S335122F05 CDRL2 | SEQ. I.D. NO: 198 | |
| S335122F05 CDRL3 | SEQ. I.D. NO: 199 | |

SEQUENCE LISTING

SEQ ID 1 - CA8 CDRH1
NYWMH

SEQ ID 2 - CA8 CDRH2
ATYRGHSDTYYNQKFKG

SEQ ID 3 - CA8 CDRH3
GAIYNGYDVLDN

SEQ ID 4 - CA8 CDRL1
SASQDISNYLN

SEQ ID 5 - CA8 CDRL2
YTSNLHS

SEQ ID 6 - CA8 CDRL3
QQYRKLPWT

SEQ ID 7 - CA8 $V_H$ domain (murine)
EVQLQQSGAVLARPGASVKMSCKGSGYTFTNYWMHWVKQRPGQGLEWIGATYRGHSDTYYNQKF
KGKAKLTAVTSTSTAYMELSSLTNEDSAVYYCTRGAIYNGYDVLDNWGQGTLVTVSS SEQ ID 8 - CA8 $V_H$ domain (murine) (Polynucleotide)
GAGGTGCAGCTGCAGCAGAGCGGCGCCGTGCTGGCCAGGCCCGGAGCTAGCGTGAAGATGAG
CTGCAAGGGCAGCGGCTACACCTTCACCAACTACTGGATGCACTGGGTGAAACAGAGGCCCGG
CCAGGGACTGGAGTGGATCGGCGCCACCTACAGGGGCCACAGCGACACCTACTACAACCAGAA
GTTCAAGGGCAAGGCCAAGCTGACCGCCGTGACCTCAACCAGCACCGCCTACATGGAACTGAG
CAGCCTGACCAACGAGGACAGCGCCGTCTATTACTGCACCAGGGGCGCCATCTACAACGGCTA
CGACGTGCTGGACAATTGGGGCCAGGGAACACTAGTGACCGTGTCCAGC SEQ ID 9 - CA8 $V_L$ domain (murine)
DIQLTQTTSSLSASLGDRVTISCSASQDISNYLNWYQQKPDGTVELVIYYTSNLHSGVPSRFSGSGSG
TDYSLTIGYLEPEDVATYYCQQYRKLPWTFGGGSKLEIKR -continued

SEQUENCE LISTING

SEQ ID 10 - CA8 $V_L$ domain (murine) (Polynucleotide)
GATATCCAGCTGACCCAGACCACAAGCAGCCTGAGCGCCTCCCTGGGCGACAGGGTGACCATT
AGCTGCAGCGCCAGCCAGGACATCAGCAACTACCTGAACTGGTACCAGCAGAAGCCCGACGGC
ACCGTGGAGCTCGTGATCTACTACACCTCCAACCTGCACAGCGGCGTGCCCAGCAGGTTCTCTG
GCAGCGGCAGCGGCACCGACTACAGCCTGACCATCGGCTATCTGGAGCCCGAGGACGTCGCCA
CCTACTACTGCCAGCAGTACAGGAAGCTGCCCTGGACCTTCGGCGGAGGCTCTAAGCTGGAGA
TTAAGCGT SEQ ID 11 - CA8 Humanised $V_H$ J0
QVQLVQSGAEVKKPGSSVKVSCKASGGTFSNYWMHWVRQAPGQGLEWMGATYRGHSDTYYNQK
FKGRVTITADKSTSTAYMELSSLRSEDTAVYYCARGAIYNGYDVLDNWGQGTLVTVSS SEQ ID 12 - CA8 Humanised $V_H$ J0 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCGGCACCTTCAGCAACTACTGGATGCACTGGGTGAGGCAGGCCCCCG
GACAGGGCCTGGAGTGGATGGGCGCCACCTACAGGGGCCACAGCGACACCTACTACAACCAGA
AGTTCAAGGGCCGGGTGACCATCACCGCCGACAAGAGCACCAGCACCGCCTACATGGAACTGA
GCAGCCTCAGGAGCGAGGACACCGCTGTGTATTACTGCGCCAGGGGCGCCATCTACAACGGCT
ACGACGTGCTGGACAACTGGGGCCAGGGCACACTAGTGACCGTGTCCAGC SEQ ID 13 - CA8 Humanised $V_H$ J1
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCARGAIYNGYDVLDNWGQGTLVTVSS SEQ ID 14 - CA8 Humanised $V_H$ J1 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCGCCAGGGGCGCCATCTACAACGGCTA
CGACGTGCTGGACAACTGGGGCCAGGGCACACTAGTGACCGTGTCCAGC SEQ ID 15 - CA8 Humanised $V_H$ J2
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCTRGAIYNGYDVLDNWGQGTLVTVSS SEQ ID 16 - CA8 Humanised $V_H$ J2 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCACCAGGGGCGCCATCTACAACGGCTA
CGACGTGCTGGACAACTGGGGCCAGGGCACACTAGTGACCGTGTCCAGC SEQ ID 17 - CA8 Humanised $V_H$ J3
QVQLVQSGAEVKKPGSSVKVSCKGSGYTFTNYWMHWVRQAPGQGLEWMGATYRGHSDTYYNQK
FKGRVTITADTSTSTAYMELSSLRSEDTAVYYCTRGAIYNGYDVLDNWGQGTLVTVSS SEQ ID 18 - CA8 Humanised $V_H$ J3 (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACACGAGCACCAGCACCGCCTACATGGAACTGAG
CAGCCTCAGGAGCGAGGACACCGCTGTGTATTACTGCACCAGGGGCGCCATCTACAACGGCTA
CGACGTGCTGGACAACTGGGGCCAGGGCACACTAGTGACCGTGTCCAGC SEQ ID 19 - CA8 Humanised $V_H$ J4
QVQLVQSGAEVKKPGSSVKVSCKGSGYTFTNYWMHWVRQAPGQGLEWIGATYRGHSDTYYNQKF
KGRATLTADTSTSTAYMELSSLRSEDTAVYYCTRGAIYNGYDVLDNWGQGTLVTVSS SEQ ID 20 - CA8 Humanised $V_H$ J4 (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATCGGCGCCACCTACAGGGGCCACAGCGACACCTACTACAACCAGAA
GTTCAAGGGCCGGGCGACCCTCACCGCCGACACGAGCACCAGCACCGCCTACATGGAACTGAG
CAGCCTCAGGAGCGAGGACACCGCTGTGTATTACTGCACCAGGGGCGCCATCTACAACGGCTA
CGACGTGCTGGACAACTGGGGCCAGGGCACACTAGTGACCGTGTCCAGC SEQ ID 21 - CA8 Humanised $V_H$ J5
QVQLVQSGAEVKKPGSSVKVSCKGSGYTFTNYWMHWVRQAPGQGLEWMGATYRGHSDTYYNQK
FKGRVTITADTSTSTAYMELSSLRSEDTAVYYCTRGAIYDGYDVLDNWGQGTLVTVSS SEQ ID 22 - CA8 Humanised $V_H$ J5 (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACACGAGCACCAGCACCGCCTACATGGAACTGAG -continued

SEQUENCE LISTING

CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGC

SEQ ID 23 - CA8 Humanised $V_H$ J6
QVQLVQSGAEVKKPGSSVKVSCKASGGTFSNYWMHWVRQAPGQGLEWMGATYRGHSDTYYNQK
FKGRVTITADKSTSTAYMELSSLRSEDTAVYYCARGAIYDGYDVLDNWGQGTLVTVSS SEQ ID 24 - CA8 Humanised $V_H$ J6 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCGGCACCTTCAGCAACTACTGGATGCACTGGGTGAGGCAGGCCCCCG
GACAGGGCCTGGAGTGGATGGGCGCCACCTACAGGGGCCACAGCGACACCTACTACAACCAGA
AGTTCAAGGGCCGGGTGACCATCACCGCCGACAAGAGCACCAGCACCGCCTACATGGAACTGA
GCAGCCTCAGGAGCGAGGACACCGCTGTGTATTACTGCGCCAGGGGCGCCATCTACGACGGCT
ACGACGTGCTGGACAACTGGGGCCAGGGCACACTAGTGACCGTGTCCAGC SEQ ID 25 - CA8 Humanised $V_H$ J7
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCARGAIYDGYDVLDNWGQGTLVTVSS SEQ ID 26 - CA8 Humanised $V_H$ J7 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCGCCAGGGGCGCCATCTACGACGGCTA
CGACGTGCTGGACAACTGGGGCCAGGGCACACTAGTGACCGTGTCCAGC SEQ ID 27 - CA8 Humanised $V_H$ J8
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCTRGAIYDGYDVLDNWGQGTLVTVSS SEQ ID 28 - CA8 Humanised $V_H$ J8 (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGC SEQ ID 29 - CA8 Humanised $V_H$ J9
QVQLVQSGAEVKKPGSSVKVSCKGSGYTFTNYWMHWVRQAPGQGLEWIGATYRGHSDTYYNQKF
KGRATLTADTSTSTAYMELSSLRSEDTAVYYCTRGAIYDGYDVLDNWGQGTLVTVSS SEQ ID 30 - CA8 Humanised $V_H$ J9 (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATCGGCGCCACCTACAGGGGCCACAGCGACACCTACTACAACCAGAA
GTTCAAGGGCCGGGCGACCCTCACCGCCGACACGAGCACCAGCACCGCCTACATGGAACTGAG
CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGC SEQ ID 31 - CA8 Humanised $V_L$ M0
DIQMTQSPSSLSASVGDRVTITCSASQDISNYLNWYQQKPGKAPKLLIYYTSNLHSGVPSRFSGSGS
GTDFTLTISSLQPEDFATYYCQQYRKLPWTFGQGTKLEIKR SEQ ID 32 - CA8 Humanised $V_L$ M0 (Polynucleotide)
GACATCCAGATGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCAAGCTGCTGATCTACTACACCTCCAACCTGCACTCCGGCGTGCCCAGCAGGTTCAGCG
GAAGCGGCAGCGGCACCGATTTCACCCTGACCATCTCCAGCCTGCAGCCCGAGGACTTCGCCA
CCTACTACTGCCAGCAGTACAGGAAGCTCCCCTGGACTTTCGGCCAGGGCACCAAACTGGAGAT
CAAGCGT SEQ ID 33 - CA8 Humanised $V_L$ M1
DIQMTQSPSSLSASVGDRVTITCSASQDISNYLNWYQQKPGKAPKLLIYYTSNLHSGVPSRFSGSGS
GTDYTLTISSLQPEDFATYYCQQYRKLPWTFGQGTKLEIKR SEQ ID 34 - CA8 Humanised $V_L$ M1 (Polynucleotide)
GACATCCAGATGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCAAGCTGCTGATCTACTACACCTCCAACCTGCACTCCGGCGTGCCCAGCAGGTTCAGCG
GAAGCGGCAGCGGCACCGATTACACCCTGACCATCTCCAGCCTGCAGCCCGAGGACTTCGCCA
CCTACTACTGCCAGCAGTACAGGAAGCTCCCCTGGACTTTCGGCCAGGGCACCAAACTGGAGAT
CAAGCGT -continued

SEQUENCE LISTING

SEQ ID 35 - CA8 Humanised $V_L$ M2
DIQLTQSPSSLSASVGDRVTITCSASQDISNYLNWYQQKPGKAPELVIYYTSNLHSGVPSRFSGSGSG
TDYTLTISSLQPEDFATYYCQQYRKLPWTFGQGTKLEIKR SEQ ID 36 - CA8 Humanised $V_L$ M2 (Polynucleotide)
GACATCCAGCTGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCGAGCTGGTGATCTACTACACCTCCAACCTGCACTCCGGCGTGCCCAGCAGGTTCAGC
GGAAGCGGCAGCGGCACCGATTACACCCTGACCATCTCCAGCCTGCAGCCCGAGGACTTCGCC
ACCTACTACTGCCAGCAGTACAGGAAGCTCCCCTGGACTTTCGGCCAGGGCACCAAACTGGAGA
TCAAGCGT SEQ ID 37 - Human BCMA CD33-hBCMA ECD (1-53) TEV-Fc
MPLLLLLPLLWAGALAMLQMAGQCSQNEYFDSLLHACIPCQLRCSSNTPPLTCQRYCNASVTNSVKG
TNSGENLYFQGDPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID 38 - Human BCMA CD33-hBCMA ECD (1-53) TEV-Fc (Polynucleotide)
ATGCCGCTGCTGCTACTGCTGCCCCTGCTGTGGGCAGGGGCGCTAGCTATGCTGCAGATGGCC
GGCCAGTGCAGCCAGAACGAGTACTTCGACAGCCTGCTGCACGCCTGCATCCCCTGCCAGCTG
AGATGCAGCAGCAACACACCTCCTCTGACCTGCCAGAGATACTGCAACGCCAGCGTGACCAACA
GCGTGAAGGGCACCAACTCCGGAGAGAACCTGTACTTCCAAGGGGATCCCAAATCTTGTGACAA
AACTCACACATGCCCACCGTGCCCAGCACCTGAACTCCTGGGGGGACCGTCAGTCTTCCTCTTC
CCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCAT
AATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCC
TCCCAGCCCCCATCGAGAAAACCATCTCCAAAGCCAAAGGGCAGCCCCGAGAGCCACAGGTGT
ACACCCTGCCCCCATCCCGGGATGAGCTGACCAAGAACCAGGTCAGCCTGACCTGCCTGGTCA
AAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCATGAGGCTCTGCA
CAACCACTACACGCAGAAGAGCCTCTCCCTGTCTCCGGGTAAA SEQ ID 39 - Human BCMA CD33-hBCMA ECD (4-53) TEV-Fc
MPLLLLLPLLWAGALAMAGQCSQNEYFDSLLHACIPCQLRCSSNTPPLTCQRYCNASVTNSVKGTNS
GENLYFQGDPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK SEQ ID 40 - Human BCMA CD33-hBCMA ECD (4-53) TEV-Fc (Polynucleotide)
ATGCCGCTGCTGCTACTGCTGCCCCTGCTGTGGGCAGGGGCGCTAGCTATGGCCGGCCAGTGC
AGCCAGAACGAGTACTTCGACAGCCTGCTGCACGCCTGCATCCCCTGCCAGCTGAGATGCAGC
AGCAACACACCTCCTCTGACCTGCCAGAGATACTGCAACGCCAGCGTGACCAACAGCGTGAAGG
GCACCAACTCCGGAGAGAACCTGTACTTCCAAGGGGATCCCAAATCTTGTGACAAAACTCACAC
ATGCCCACCGTGCCCAGCACCTGAACTCCTGGGGGGACCGTCAGTCTTCCTCTTCCCCCCAAAA
CCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTCCTCACCGTCCTG
CACCAGGACTGGCTGAATGGCAAGGAGTACAAGTGCAAGGTCTCCAACAAAGCCCTCCCAGCC
CCCATCGAGAAAACCATCTCCAAAGCCAAAGGGCAGCCCCGAGAGCCACAGGTGTACACCCTG
CCCCCATCCCGGGATGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTCTGCACAACCACTAC
ACGCAGAAGAGCCTCTCCCTGTCTCCGGGTAAA SEQ ID 41 - Cynomolgous BCMA CD33 cyno BCMA ECD (4-52) TEV-Fc
MPLLLLLPLLWAGALAMARQCSQNEYFDSLLHDCKPCQLRCSSTPPLTCQRYCNASMTNSVKGMNS
GENLYFQGDPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK SEQ ID 42 - Cynomolgous BCMA CD33 cyno BCMA ECD (4-52) TEV-Fc (Polynucleotide)
ATGCCGCTGCTGCTACTGCTGCCCCTGCTGTGGGCAGGGGCGCTAGCTATGGCCAGACAGTGC
AGCCAGAACGAGTACTTCGACAGCCTGCTGCACGACTGCAAGCCCTGCCAGCTGAGATGCAGC
AGCACACCTCCTCTGACCTGCCAGAGATACTGCAACGCCAGCATGACCAACAGCGTGAAGGGCA
TGAACTCCGGAGAGAACCTGTACTTCCAAGGGGATCCCAAATCTTGTGACAAAACTCACACATGC
CCACCGTGCCCAGCACCTGAACTCCTGGGGGGACCGTCAGTCTTCCTCTTCCCCCCAAAACCCA
AGGACACCCTCATGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCAGCCCCCATC -continued

SEQUENCE LISTING

GAGAAAACCATCTCCAAAGCCAAAGGGCAGCCCCGAGAGCCACAGGTGTACACCCTGCCCCCA
TCCCGGGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTC
CCGTGCTGGACTCCGACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACAACCACTACACGCAG
AAGAGCCTCTCCCTGTCTCCGGGTAAA

SEQ ID 43 - CA8 J0 Humanised heavy chain
QVQLVQSGAEVKKPGSSVKVSCKASGGTFSNYWMHWVRQAPGQGLEWMGATYRGHSDTYYNQK
FKGRVTITADKSTSTAYMELSSLRSEDTAVYYCARGAIYNGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 44 - CA8 J0 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCGGCACCTTCAGCAACTACTGGATGCACTGGGTGAGGCAGGCCCCCG
GACAGGGCCTGGAGTGGATGGGCGCCACCTACAGGGGCCACAGCGACACCTACTACAACCAGA
AGTTCAAGGGCCGGGTGACCATCACCGCCGACAAGAGCACCAGCACCGCCTACATGGAACTGA
GCAGCCTCAGGAGCGAGGACACCGCTGTGTATTACTGCGCCAGGGGCGCCATCTACAACGGCT
ACGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 45 - CA8 J1 Humanised heavy chain
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCARGAIYNGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 46 - CA8 J1 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCGCCAGGGGCGCCATCTACAACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 47 - CA8 J2 Humanised heavy chain
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCTRGAIYNGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL -continued

SEQUENCE LISTING

GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK

SEQ ID 48 - CA8 J2 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCACCAGGGGCGCCATCTACAACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 49 - CA8 J3 Humanised heavy chain
QVQLVQSGAEVKKPGSSVKVSCKGSGYTFTNYWMHWVRQAPGQGLEWMGATYRGHSDTYYNQK
FKGRVTITADTSTSTAYMELSSLRSEDTAVYYCTRGAIYNGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 50 - CA8 J3 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACACGAGCACCAGCACCGCCTACATGGAACTGAG
CAGCCTCAGGAGCGAGGACACCGCTGTGTATTACTGCACCAGGGGCGCCATCTACAACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 51 - CA8 J4 Humanised heavy chain
QVQLVQSGAEVKKPGSSVKVSCKGSGYTFTNYWMHWVRQAPGQGLEWIGATYRGHSDTYYNQKF
KGRATLTADTSTSTAYMELSSLRSEDTAVYYCTRGAIYNGYDVLDNWGQGTLVTVSSASTKGPSVFP
LAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID 52 - CA8 J4 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATCGGCGCCACCTACAGGGGCCACAGCGACACCTACTACAACCAGAA
GTTCAAGGGCCGGGCGACCCTCACCGCCGACACGAGCACCAGCACCGCCTACATGGAACTGAG
CAGCCTCAGGAGCGAGGACACCGCTGTGTATTACTGCACCAGGGGCGCCATCTACAACGGCTA -continued

SEQUENCE LISTING

CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG

SEQ ID 53 - CA8 J5 Humanised heavy chain
QVQLVQSGAEVKKPGSSVKVSCKGSGYTFTNYWMHWVRQAPGQGLEWMGATYRGHSDTYYNQK
FKGRVTITADTSTSTAYMELSSLRSEDTAVYYCTRGAIYDGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 54 - CA8 J5 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACACGAGCACCAGCACCGCCTACATGGAACTGAG
CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 55 - CA8 J6 Humanised heavy chain
QVQLVQSGAEVKKPGSSVKVSCKASGGTFSNYWMHWVRQAPGQGLEWMGATYRGHSDTYYNQK
FKGRVTITADKSTSTAYMELSSLRSEDTAVYYCARGAIYDGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 56 - CA8 J6 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCGGCACCTTCAGCAACTACTGGATGCACTGGGTGAGGCAGGCCCCCG
GACAGGGCCTGGAGTGGATGGGCGCCACCTACAGGGGCCACAGCGACACCTACTACAACCAGA
AGTTCAAGGGCCGGGTGACCATCACCGCCGACAAGAGCACCAGCACCGCCTACATGGAACTGA
GCAGCCTCAGGAGCGAGGACACCGCTGTGTATTACTGCGCCAGGGGCGCCATCTACGACGGCT
ACGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA -continued

SEQUENCE LISTING

TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG

SEQ ID 57 - CA8 J7 Humanised heavy chain
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCARGAIYDGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 58 - CA8 J7 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCGCCAGGGGCGCCATCTACGACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 59 - CA8 J8 Humanised heavy chain
QVQLVQSGAEVKKPGSSVKVSCKASGYTFTNYWMHWVRQAPGQGLEWMGATYRGHSDTYYNQK
FKGRVTITADKSTSTAYMELSSLRSEDTAVYYCTRGAIYDGYDVLDNWGQGTLVTVSSASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID 60 - CA8 J8 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGCCAGCGGCTACACCTTCACCAACTACTGGATGCACTGGGTGAGGCAGGCCCCCGG
ACAGGGCCTGGAGTGGATGGGCGCCACCTACAGGGGCCACAGCGACACCTACTACAACCAGAA
GTTCAAGGGCCGGGTGACCATCACCGCCGACAAGAGCACCAGCACCGCCTACATGGAACTGAG
CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 61 - CA8 J9 Humanised heavy chain
QVQLVQSGAEVKKPGSSVKVSCKGSGYTFTNYWMHWVRQAPGQGLEWIGATYRGHSDTYYNQKF
KGRATLTADTSTSTAYMELSSLRSEDTAVYYCTRGAIYDGYDVLDNWGQGTLVTVSSASTKGPSVFP
LAPSSKSTSGGTAALGCLVKDYFPEPVTVSWNSGALTSGVHTFPAVLQSSGLYSLSSVVTVPSSSLG -continued

SEQUENCE LISTING

TQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK

SEQ ID 62 - CA8 J9 Humanised heavy chain (Polynucleotide)
CAGGTGCAGCTGGTCCAGAGCGGCGCCGAAGTGAAGAAGCCCGGCAGCTCCGTGAAAGTGAG
CTGCAAGGGCAGCGGCTACACCTTCACCAACTACTGGATGCACTGGGTGAGGCAGGCCCCCGG
ACAGGGCCTGGAGTGGATCGGCGCCACCTACAGGGGCCACAGCGACACCTACTACAACCAGAA
GTTCAAGGGCCGGGCGACCCTCACCGCCGACACGAGCACCAGCACCGCCTACATGGAACTGAG
CAGCCTCAGGAGCGAGGACACCGCTGTGTATTACTGCACCAGGGGCGCCATCTACGACGGCTA
CGACGTGCTGGACAACTGGGGCCAGGGCACACTAGTGACCGTGTCCAGCGCCAGCACCAAGG
GCCCCAGCGTGTTCCCCCTGGCCCCCAGCAGCAAGAGCACCAGCGGCGGCACAGCCGCCCTG
GGCTGCCTGGTGAAGGACTACTTCCCCGAACCGGTGACCGTGTCCTGGAACAGCGGAGCCCTG
ACCAGCGGCGTGCACACCTTCCCCGCCGTGCTGCAGAGCAGCGGCCTGTACAGCCTGAGCAGC
GTGGTGACCGTGCCCAGCAGCAGCCTGGGCACCCAGACCTACATCTGTAACGTGAACCACAAG
CCCAGCAACACCAAGGTGGACAAGAAGGTGGAGCCCAAGAGCTGTGACAAGACCCACACCTGC
CCCCCCTGCCCTGCCCCCGAGCTGCTGGGAGGCCCCAGCGTGTTCCTGTTCCCCCCCAAGCCT
AAGGACACCCTGATGATCAGCAGAACCCCCGAGGTGACCTGTGTGGTGGTGGATGTGAGCCAC
GAGGACCCTGAGGTGAAGTTCAACTGGTACGTGGACGGCGTGGAGGTGCACAATGCCAAGACC
AAGCCCAGGGAGGAGCAGTACAACAGCACCTACCGGGTGGTGTCCGTGCTGACCGTGCTGCAC
CAGGATTGGCTGAACGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTGTACACCCTGCCCC
CTAGCAGAGATGAGCTGACCAAGAACCAGGTGTCCCTGACCTGCCTGGTGAAGGGCTTCTACCC
CAGCGACATCGCCGTGGAGTGGGAGAGCAACGGCCAGCCCGAGAACAACTACAAGACCACCCC
CCCTGTGCTGGACAGCGATGGCAGCTTCTTCCTGTACAGCAAGCTGACCGTGGACAAGAGCAGA
TGGCAGCAGGGCAACGTGTTCAGCTGCTCCGTGATGCACGAGGCCCTGCACAATCACTACACC
CAGAAGAGCCTGAGCCTGTCCCCTGGCAAG SEQ ID 63 - CA8 M0 Humanised light chain
DIQMTQSPSSLSASVGDRVTITCSASQDISNYLNWYQQKPGKAPKLLIYYTSNLHSGVPSRFSGSGS
GTDFTLTISSLQPEDFATYYCQQYRKLPWTFGQGTKLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC SEQ ID 64 - CA8 M0 Humanised light chain (Polynucleotide)
GACATCCAGATGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCAAGCTGCTGATCTACTACACCTCCAACCTGCACTCCGGCGTGCCCAGCAGGTTCAGCG
GAAGCGGCAGCGGCACCGATTTCACCCTGACCATCTCCAGCCTGCAGCCCGAGGACTTCGCCA
CCTACTACTGCCAGCAGTACAGGAAGCTCCCCTGGACTTTCGGCCAGGGCACCAAACTGGAGAT
CAAGCGTACGGTGGCCGCCCCCAGCGTGTTCATCTTCCCCCCCAGCGATGAGCAGCTGAAGAG
CGGCACCGCCAGCGTGGTGTGTCTGCTGAACAACTTCTACCCCCGGGAGGCCAAGGTGCAGTG
GAAGGTGGACAATGCCCTGCAGAGCGGCAACAGCCAGGAGAGCGTGACCGAGCAGGACAGCA
AGGACTCCACCTACAGCCTGAGCAGCACCCTGACCCTGAGCAAGGCCGACTACGAGAAGCACA
AGGTGTACGCCTGTGAGGTGACCCACCAGGGCCTGTCCAGCCCCGTGACCAAGAGCTTCAACC
GGGGCGAGTGC SEQ ID 65 - CA8 M1 Humanised light chain
DIQMTQSPSSLSASVGDRVTITCSASQDISNYLNWYQQKPGKAPKLLIYYTSNLHSGVPSRFSGSGS
GTDYTLTISSLQPEDFATYYCQQYRKLPWTFGQGTKLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC SEQ ID 66 - CA8 M1 Humanised light chain (Polynucleotide)
GACATCCAGATGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCAAGCTGCTGATCTACTACACCTCCAACCTGCACTCCGGCGTGCCCAGCAGGTTCAGCG
GAAGCGGCAGCGGCACCGATTACACCCTGACCATCTCCAGCCTGCAGCCCGAGGACTTCGCCA
CCTACTACTGCCAGCAGTACAGGAAGCTCCCCTGGACTTTCGGCCAGGGCACCAAACTGGAGAT
CAAGCGTACGGTGGCCGCCCCCAGCGTGTTCATCTTCCCCCCCAGCGATGAGCAGCTGAAGAG
CGGCACCGCCAGCGTGGTGTGTCTGCTGAACAACTTCTACCCCCGGGAGGCCAAGGTGCAGTG
GAAGGTGGACAATGCCCTGCAGAGCGGCAACAGCCAGGAGAGCGTGACCGAGCAGGACAGCA
AGGACTCCACCTACAGCCTGAGCAGCACCCTGACCCTGAGCAAGGCCGACTACGAGAAGCACA
AGGTGTACGCCTGTGAGGTGACCCACCAGGGCCTGTCCAGCCCCGTGACCAAGAGCTTCAACC
GGGGCGAGTGC SEQ ID 67 - CA8 M2 Humanised light chain
DIQLTQSPSSLSASVGDRVTITCSASQDISNYLNWYQQKPGKAPELVIYYTSNLHSGVPSRFSGSGSG
TDYTLTISSLQPEDFATYYCQQYRKLPWTFGQGTKLEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSS
PVTKSFNRGEC SEQ ID 68 - CA8 M2 Humanised light chain (Polynucleotide)
GACATCCAGCTGACCCAGAGCCCTAGCTCACTGAGCGCCAGCGTGGGCGACAGGGTGACCATT
ACCTGCTCCGCCAGCCAGGACATCAGCAACTACCTGAACTGGTACCAGCAGAAGCCCGGCAAG
GCCCCCGAGCTGGTGATCTACTACACCTCCAACCTGCACTCCGGCGTGCCCAGCAGGTTCAGC -continued

SEQUENCE LISTING

GGAAGCGGCAGCGGCACCGATTACACCCTGACCATCTCCAGCCTGCAGCCCGAGGACTTCGCC
ACCTACTACTGCCAGCAGTACAGGAAGCTCCCCTGGACTTTCGGCCAGGGCACCAAACTGGAGA
TCAAGCGTACGGTGGCCGCCCCCAGCGTGTTCATCTTCCCCCCCAGCGATGAGCAGCTGAAGA
GCGGCACCGCCAGCGTGGTGTGTCTGCTGAACAACTTCTACCCCCGGGAGGCCAAGGTGCAGT
GGAAGGTGGACAATGCCCTGCAGAGCGGCAACAGCCAGGAGAGCGTGACCGAGCAGGACAGC
AAGGACTCCACCTACAGCCTGAGCAGCACCCTGACCCTGAGCAAGGCCGACTACGAGAAGCAC
AAGGTGTACGCCTGTGAGGTGACCCACCAGGGCCTGTCCAGCCCCGTGACCAAGAGCTTCAAC
CGGGGCGAGTGC

SEQ ID 69 - S307118G03 mouse variable heavy
EVQLQQSGPELVKPGASVKISCKASGYTFTDYYMKWVKQSHGKSLEWIGEIYPNNGGITYNQKFKGK
ATLTVDKSSSTAYMELRSLTSEDSAVYYCANGYEFVYWGQGTLVTVSA SEQ ID 70 - S307118G03 mouse variable heavy (DNA sequence)
GAGGTCCAGTTGCAACAATCTGGACCTGAGCTGGTGAAGCCTGGGGCTTCAGTGAAGATATCCT
GTAAGGCTTCTGGATACACATTCACTGACTACTACATGAAGTGGGTGAAGCAGAGCCATGGAAA
GAGCCTTGAGTGGATTGGAGAGATTTATCCTAATAATGGTGGTATTACCTACAACCAGAAGTTCA
AGGGCAAGGCCACATTGACTGTAGACAAGTCCTCCAGCACAGCCTACATGGAGCTCCGCAGCCT
GACATCTGAGGACTCTGCAGTCTATTACTGTGCAAATGGTTACGAGTTTGTTTACTGGGGCCAAG
GGACTCTGGTCACTGTCTCTGCA SEQ ID 71 - S307118G03 mouse variable light
DIQMTQTASSLSASLGDRVTISCSASQGISNYLNWYQQKPDGTVKLLIYYTSSLHSGVPSRFSGSGSG
TDYSLTISNLEPEDIATYYCQQYSKLPWTFGGGTKLEIKR SEQ ID 72 - S307118G03 mouse variable light (DNA sequence)
GATATCCAGATGACACAGACTGCATCCTCCCTGTCTGCCTCTCTGGGAGACAGAGTCACCATCA
GTTGCAGTGCAAGTCAGGGCATTAGCAATTATTTAAACTGGTATCAGCAGAAACCAGATGGAACT
GTTAAACTCCTGATCTATTACACATCAAGTTTACACTCAGGAGTCCCATCAAGGTTCAGTGGCAG
TGGGTCTGGGACAGATTATTCTCTCACCATCAGCAACCTGGAACCTGAAGATATTGCCACTTACT
ATTGTCAGCAGTATAGTAAGCTTCCGTGGACGTTCGGTGGAGGCACCAAGCTGGAAATCAAACGG SEQ ID 73 - S307118G03 chimeric heavy chain
EVQLQQSGPELVKPGASVKISCKASGYTFTDYYMKWVKQSHGKSLEWIGEIYPNNGGITYNQKFKGK
ATLTVDKSSSTAYMELRSLTSEDSAVYYCANGYEFVYWGQGTLVTVSAAKTTAPSVFPLAPSSKSTS
GGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK SEQ ID 74 - S307118G03 chimeric heavy chain (DNA sequence)
GAGGTCCAGTTGCAACAATCTGGACCTGAGCTGGTGAAGCCTGGGGCTTCAGTGAAGATATCCT
GTAAGGCTTCTGGATACACATTCACTGACTACTACATGAAGTGGGTGAAGCAGAGCCATGGAAA
GAGCCTTGAGTGGATTGGAGAGATTTATCCTAATAATGGTGGTATTACCTACAACCAGAAGTTCA
AGGGCAAGGCCACATTGACTGTAGACAAGTCCTCCAGCACAGCCTACATGGAGCTCCGCAGCCT
GACATCTGAGGACTCTGCAGTCTATTACTGTGCAAATGGTTACGAGTTTGTTTACTGGGGCCAAG
GGACTCTGGTCACTGTCTCTGCAGCCAAAACAACAGCCCCCAGCGTGTTCCCCCTGGCCCCCAG
CAGCAAGAGCACCAGCGGCGGCACAGCCGCCCTGGGCTGCCTGGTGAAGGACTACTTCCCCGA
ACCGGTGACCGTGTCCTGGAACAGCGGAGCCCTGACCAGCGGCGTGCACACCTTCCCCGCCGT
GCTGCAGAGCAGCGGCCTGTACAGCCTGAGCAGCGTGGTGACCGTGCCCAGCAGCAGCCTGG
GCACCCAGACCTACATCTGTAACGTGAACCACAAGCCCAGCAACACCAAGGTGGACAAGAAGGT
GGAGCCCAAGAGCTGTGACAAGACCCACACCTGCCCCCCCTGCCCTGCCCCCGAGCTGCTGGG
AGGCCCCAGCGTGTTCCTGTTCCCCCCCAAGCCTAAGGACACCCTGATGATCAGCAGAACCCCC
GAGGTGACCTGTGTGGTGGTGGATGTGAGCCACGAGGACCCTGAGGTGAAGTTCAACTGGTAC
GTGGACGGCGTGGAGGTGCACAATGCCAAGACCAAGCCCAGGGAGGAGCAGTACAACAGCACC
TACCGGGTGGTGTCCGTGCTGACCGTGCTGCACCAGGATTGGCTGAACGGCAAGGAGTACAAG
TGTAAGGTGTCCAACAAGGCCCTGCCTGCCCCTATCGAGAAAACCATCAGCAAGGCCAAGGGCC
AGCCCAGAGAGCCCCAGGTGTACACCCTGCCCCCTAGCAGAGATGAGCTGACCAAGAACCAGG
TGTCCCTGACCTGCCTGGTGAAGGGCTTCTACCCCAGCGACATCGCCGTGGAGTGGGAGAGCA
ACGGCCAGCCCGAGAACAACTACAAGACCACCCCCCCTGTGCTGGACAGCGATGGCAGCTTCT
TCCTGTACAGCAAGCTGACCGTGGACAAGAGCAGATGGCAGCAGGGCAACGTGTTCAGCTGCT
CCGTGATGCACGAGGCCCTGCACAATCACTACACCCAGAAGAGCCTGAGCCTGTCCCCTGGCA
AG SEQ ID 75 - S307118G03 chimeric light chain
DIQMTQTASSLSASLGDRVTISCSASQGISNYLNWYQQKPDGTVKLLIYYTSSLHSGVPSRFSGSGSG
TDYSLTISNLEPEDIATYYCQQYSKLPWTFGGGTKLELKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSS
PVTKSFNRGEC SEQ ID 76 - S307118G03 chimeric light chain (DNA sequence)
GATATCCAGATGACACAGACTGCATCCTCCCTGTCTGCCTCTCTGGGAGACAGAGTCACCATCA
GTTGCAGTGCAAGTCAGGGCATTAGCAATTATTTAAACTGGTATCAGCAGAAACCAGATGGAACT
GTTAAACTCCTGATCTATTACACATCAAGTTTACACTCAGGAGTCCCATCAAGGTTCAGTGGCAG
TGGGTCTGGGACAGATTATTCTCTCACCATCAGCAACCTGGAACCTGAAGATATTGCCACTTACT
ATTGTCAGCAGTATAGTAAGCTTCCGTGGACGTTCGGTGGAGGCACCAAGCTGGAGCTGAAACG -continued

SEQUENCE LISTING

TACGGTGGCCGCCCCCAGCGTGTTCATCTTCCCCCCCAGCGATGAGCAGCTGAAGAGCGGCAC
CGCCAGCGTGGTGTGTCTGCTGAACAACTTCTACCCCCGGGAGGCCAAGGTGCAGTGGAAGGT
GGACAATGCCCTGCAGAGCGGCAACAGCCAGGAGAGCGTGACCGAGCAGGACAGCAAGGACT
CCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCG
AGTGC

SEQ ID 77 - S307118G03 humanised H0 variable heavy
QVQLVQSGAEVKKPGSSVKVSCKASGGTFSDYYMKWVRQAPGQGLEWMGEIYPNNGGITYNQKFK
GRVTITADKSTSTAYMELSSLRSEDTAVYYCARGYEFVYWGQGTLVTVSS SEQ ID 78 - S307118G03 humanised HO variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCGGCACCTTCAGCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAGGGGCTACGAGTTCGTGTATTG
GGGCCAGGGCACACTAGTGACCGTGTCCAGC SEQ ID 79 - S307118G03 humanised H1 variable heavy
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCARGYEFVYWGQGTLVTVSS SEQ ID 80 - S307118G03 humanised H1 variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAGGGGCTACGAGTTCGTGTATTG
GGGCCAGGGCACACTAGTGACCGTGTCCAGC SEQ ID 81 - S307118G03 humanised H2 variable heavy
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCANGYEFVYWGQGTLVTVSS SEQ ID 82 - S307118G03 humanised H2 variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAACGGCTACGAGTTCGTGTATTG
GGGCCAGGGCACACTAGTGACCGTGTCCAGC SEQ ID 83 - S307118G03 humanised H3 variable heavy
QVQLVQSGAEVKKPGSSVKVSCKASGYTFTDYYMKWVRQAPGQGLEWIGEIYPNNGGITYNQKFKG
RATLTVDKSTSTAYMELSSLRSEDTAVYYCANGYEFVYWGQGTLVTVSS SEQ ID 84 - S307118G03 humanised H3 variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATAGGCGAGATCTACCCCAACAACGGGGGCATCACCTACAACCAGAA
GTTCAAGGGCAGGGCGACCCTCACCGTCGACAAAAGCACCAGCACCGCCTACATGGAACTGAG
CAGCCTGAGGAGCGAGGACACCGCCGTGTACTACTGCGCCAACGGCTACGAGTTCGTGTATTG
GGGCCAGGGCACACTAGTGACCGTGTCCAGC SEQ ID 85 - S307118G03 humanised H4 variable heavy
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCADGYEFVYWGQGTLVTVSS SEQ ID 86 - S307118G03 humanised H4 variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCGACGGCTACGAGTTCGTGTATTG
GGGCCAGGGCACACTAGTGACCGTGTCCAGC SEQ ID 87 - S307118G03 humanised H5 variable heavy
QVQLVQSGAEVKKPGSSVKVSCKASGYTFTDYYMKWVRQAPGQGLEWIGEIYPNNGGITYNQKFKG
RATLTVDKSTSTAYMELSSLRSEDTAVYYCANGYEFDYWGQGTLVTVSS SEQ ID 88 - S307118G03 humanised H5 variable heavy (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATAGGCGAGATCTACCCCAACAACGGGGGCATCACCTACAACCAGAA -continued

SEQUENCE LISTING

GTTCAAGGGCAGGGCGACCCTCACCGTCGACAAAAGCACCAGCACCGCCTACATGGAACTGAG
CAGCCTGAGGAGCGAGGACACCGCCGTGTACTACTGCGCCAACGGCTACGAGTTCGACTATTG
GGGCCAGGGCACACTAGTGACCGTGTCCAGC

SEQ ID 89 - S307118G03 humanised L0 variable light
DIQMTQSPSSLSASVGDRVTITCSASQGISNYLNWYQQKPGKAPKLLIYYTSSLHSGVPSRFSGSGS
GTDFTLTISSLQPEDFATYYCQQYSKLPWTFGQGTKLEIKR SEQ ID 90 - S307118G03 humanised L0 variable light (DNA sequence)
GACATCCAGATGACCCAGAGCCCCTCAAGCCTGAGCGCCAGCGTGGGCGACAGGGTGACTATC
ACCTGCAGCGCCTCCCAGGGCATCAGCAACTACCTGAACTGGTACCAGCAGAAGCCCGGCAAG
GCCCCTAAGCTGCTGATCTACTACACCAGCAGCCTGCACAGCGGCGTGCCCAGCAGGTTCTCC
GGCAGCGGCAGCGGAACCGACTTCACCCTGACCATTAGCAGCCTCCAGCCCGAGGACTTCGCC
ACCTACTACTGCCAGCAGTACAGCAAGCTGCCCTGGACCTTCGGCCAGGGCACCAAACTGGAG
ATCAAGCGT SEQ ID 91 - S307118G03 humanised L1 variable light
DIQMTQSPSSLSASVGDRVTITCSASQGISNYLNWYQQKPGKAPKLLIYYTSSLHSGVPSRFSGSGS
GTDYTLTISSLQPEDFATYYCQQYSKLPWTFGQGTKLEIKR SEQ ID 92 - S307118G03 humanised L1 variable light (DNA sequence)
GACATCCAGATGACCCAGAGCCCCTCAAGCCTGAGCGCCAGCGTGGGCGACAGGGTGACTATC
ACCTGCAGCGCCTCCCAGGGCATCAGCAACTACCTGAACTGGTACCAGCAGAAGCCCGGCAAG
GCCCCTAAGCTGCTGATCTACTACACCAGCAGCCTGCACAGCGGCGTGCCCAGCAGGTTCTCC
GGCAGCGGCAGCGGAACCGACTACACCCTGACCATTAGCAGCCTCCAGCCCGAGGACTTCGCC
ACCTACTACTGCCAGCAGTACAGCAAGCTGCCCTGGACCTTCGGCCAGGGCACCAAACTGGAG
ATCAAGCGT

SEQ ID 93 - S307118G03 CDRH1
DYYMK

SEQ ID 94 - S307118G03 CDRH2
EIYPNNGGITYNQKFKG

SEQ ID 95 - S307118G03 CDRH3
GYEFVY

SEQ ID 96 - S307118G03 CDRL1
SASQGISNYLN

SEQ ID 97 - S307118G03 CDRL2
YTSSLHS

SEQ ID 98 - S307118G03 CDRL3
QQYSKLPWT

SEQ ID 99 - S307118G03 humanised H5 CDRH3
GYEFDY

SEQ ID 100 - S307118G03 humanised H0 heavy chain
QVQLVQSGAEVKKPGSSVKVSCKASGGTFSDYYMKWVRQAPGQGLEWMGEIYPNNGGITYNQKFK
GRVTITADKSTSTAYMELSSLRSEDTAVYYCARGYEFVYWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID 101 - S307118G03 humanised H0 heavy chain (polynucleotide)
CAGGTGCAGCTGGTGCAGAGCGGCGCCGAAGTGAAGAAGCCCGGCTCCAGCGTGAAGGTGAG
CTGCAAGGCTAGCGGCGGCACCTTCAGCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAGGGGCTACGAGTTCGTGTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA

SEQUENCE LISTING

GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG

SEQ ID 102 - S307118G03 humanised H1 heavy chain
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCARGYEFVYWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID 103 - S307118G03 humanised H1 heavy chain (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAGGGGCTACGAGTTCGTGTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG SEQ ID 104 - S307118G03 humanised H2 heavy chain
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCANGYEFVYWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID 105 - S307118G03 humanised H2 heavy chain (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCAACGGCTACGAGTTCGTGTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG SEQ ID 106 - S307118G03 humanised H3 heavy chain
QVQLVQSGAEVKKPGSSVKVSCKASGYTFTDYYMKWVRQAPGQGLEWIGEIYPNNGGITYNQKFKG
RATLTVDKSTSTAYMELSSLRSEDTAVYYCANGYEFVYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTI -continued

SEQUENCE LISTING

SKAKGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID 107 - S307118G03 humanised H3 heavy chain (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATAGGCGAGATCTACCCCAACAACGGGGGCATCACCTACAACCAGAA
GTTCAAGGGCAGGGCGACCCTCACCGTCGACAAAAGCACCAGCACCGCCTACATGGAACTGAG
CAGCCTGAGGAGCGAGGACACCGCCGTGTACTACTGCGCCAACGGCTACGAGTTCGTGTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG SEQ ID 108 - S307118G03 humanised H4 heavy chain
QVQLVQSGAEVKKPGSSVKVSCKASGYTFTDYYMKWVRQAPGQGLEWMGEIYPNNGGITYNQKFK
GRVTITADKSTSTAYMELSSLRSEDTAVYYCADGYEFVYWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID 109 - S307118G03 humanised H4 heavy chain (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATGGGCGAGATCTACCCCAACAACGGGGGCATCACCTACAACCAGAA
GTTCAAGGGCAGGGTGACCATCACCGCCGACAAAAGCACCAGCACCGCCTACATGGAACTGAG
CAGCCTGAGGAGCGAGGACACCGCCGTGTACTACTGCGCCGACGGCTACGAGTTCGTGTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG SEQ ID 110 - S307118G03 humanised H5 heavy chain
QVQLVQSGAEVKKPGSSVKVSCKASGYTFTDYYMKWVRQAPGQGLEWIGEIYPNNGGITYNQKFKG
RATLTVDKSTSTAYMELSSLRSEDTAVYYCANGYEFDYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID 111 - S307118G03 humanised H5 heavy chain (DNA sequence)
CAGGTGCAGCTGGTGCAGAGCGGCGCCGAAGTGAAGAAGCCCGGCTCCAGCGTGAAGGTGAG
CTGCAAGGCTAGCGGCTACACCTTCACCGACTACTACATGAAGTGGGTGAGGCAGGCCCCCGG
CCAGGGACTGGAGTGGATAGGCGAGATCTACCCCAACAACGGGGGCATCACCTACAACCAGAA
GTTCAAGGGCAGGGCGACCCTCACCGTCGACAAAAGCACCAGCACCGCCTACATGGAACTGAG
CAGCCTGAGGAGCGAGGACACCGCCGTGTACTACTGCGCCAACGGCTACGAGTTCGACTATTG
GGGCCAGGGCACACTAGTGACCGTGTCCAGCGCCAGCACCAAGGGCCCCAGCGTGTTCCCCCT
GGCCCCCAGCAGCAAGAGCACCAGCGGCGGCACAGCCGCCCTGGGCTGCCTGGTGAAGGACT -continued

SEQUENCE LISTING

ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG

SEQ ID 112 - S307118G03 humanised L0 light chain
DIQMTQSPSSLSASVGDRVTITCSASQGISNYLNWYQQKPGKAPKLLIYYTSSLHSGVPSRFSGSGS
GTDFTLTISSLQPEDFATYYCQQYSKLPWTFGQGTKLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC SEQ ID 113 - S307118G03 humanised L0 light chain (DNA sequence)
GACATCCAGATGACCCAGAGCCCCTCAAGCCTGAGCGCCAGCGTGGGCGACAGGGTGACTATC
ACCTGCAGCGCCTCCCAGGGCATCAGCAACTACCTGAACTGGTACCAGCAGAAGCCCGGCAAG
GCCCCTAAGCTGCTGATCTACTACACCAGCAGCCTGCACAGCGGCGTGCCCAGCAGGTTCTCC
GGCAGCGGCAGCGGAACCGACTTCACCCTGACCATTAGCAGCCTCCAGCCCGAGGACTTCGCC
ACCTACTACTGCCAGCAGTACAGCAAGCTGCCCTGGACCTTCGGCCAGGGCACCAAACTGGAG
ATCAAGCGTACGGTGGCCGCCCCCAGCGTGTTCATCTTCCCCCCCAGCGATGAGCAGCTGAAG
AGCGGCACCGCCAGCGTGGTGTGTCTGCTGAACAACTTCTACCCCCGGGAGGCCAAGGTGCAG
TGGAAGGTGGACAATGCCCTGCAGAGCGGCAACAGCCAGGAGAGCGTGACCGAGCAGGACAG
CAAGGACTCCACCTACAGCCTGAGCAGCACCCTGACCCTGAGCAAGGCCGACTACGAGAAGCA
CAAGGTGTACGCCTGTGAGGTGACCCACCAGGGCCTGTCCAGCCCCGTGACCAAGAGCTTCAA
CCGGGGCGAGTGC SEQ ID 114 - S307118G03 humanised L1 light chain
DIQMTQSPSSLSASVGDRVTITCSASQGISNYLNWYQQKPGKAPKLLIYYTSSLHSGVPSRFSGSGS
GTDYTLTISSLQPEDFATYYCQQYSKLPWTFGQGTKLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC SEQ ID 115 - S307118G03 humanised L1 light chain (DNA sequence)
GACATCCAGATGACCCAGAGCCCCTCAAGCCTGAGCGCCAGCGTGGGCGACAGGGTGACTATC
ACCTGCAGCGCCTCCCAGGGCATCAGCAACTACCTGAACTGGTACCAGCAGAAGCCCGGCAAG
GCCCCTAAGCTGCTGATCTACTACACCAGCAGCCTGCACAGCGGCGTGCCCAGCAGGTTCTCC
GGCAGCGGCAGCGGAACCGACTACACCCTGACCATTAGCAGCCTCCAGCCCGAGGACTTCGCC
ACCTACTACTGCCAGCAGTACAGCAAGCTGCCCTGGACCTTCGGCCAGGGCACCAAACTGGAG
ATCAAGCGTACGGTGGCCGCCCCCAGCGTGTTCATCTTCCCCCCCAGCGATGAGCAGCTGAAG
AGCGGCACCGCCAGCGTGGTGTGTCTGCTGAACAACTTCTACCCCCGGGAGGCCAAGGTGCAG
TGGAAGGTGGACAATGCCCTGCAGAGCGGCAACAGCCAGGAGAGCGTGACCGAGCAGGACAG
CAAGGACTCCACCTACAGCCTGAGCAGCACCCTGACCCTGAGCAAGGCCGACTACGAGAAGCA
CAAGGTGTACGCCTGTGAGGTGACCCACCAGGGCCTGTCCAGCCCCGTGACCAAGAGCTTCAA
CCGGGGCGAGTGC SEQ ID 116 - S332121F02 murine variable heavy chain
EVQLQQSGPVLVKPGASVKMSCEASGYTFTDYYMNWVKQSHGKTLEWIGVINPYNGGTDYNQKFK
GKATLTVDKSSSTAYMELNSLTSEDSAVYYCARSVYDYPFDYWGQGTLVTVSS SEQ ID 117 S332121F02 murine variable heavy chain (DNA sequence)
GAGGTGCAGCTGCAGCAGAGCGGCCCCGTGCTGGTGAAGCCTGGAGCCAGCGTGAAAATGAG
CTGCGAAGCCAGCGGCTACACCTTCACCGACTACTACATGAACTGGGTGAAGCAGAGCCACGG
CAAGACCCTGGAGTGGATCGGCGTGATCAACCCCTACAACGGGGGCACCGACTACAACCAGAA
GTTCAAGGGCAAGGCCACTCTGACCGTGGACAAGAGCTCCAGCACCGCCTACATGGAACTGAA
CAGCCTCACCTCTGAGGACAGCGCCGTCTATTACTGCGCCAGGAGCGTGTACGACTACCCCTTC
GACTACTGGGGCCAGGGCACACTAGTGACCGTGTCCAGC SEQ ID 118 - S332121F02 chimeric heavy chain
EVQLQQSGPVLVKPGASVKMSCEASGYTFTDYYMNWVKQSHGKTLEWIGVINPYNGGTDYNQKFK
GKATLTVDKSSSTAYMELNSLTSEDSAVYYCARSVYDYPFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK -continued

SEQUENCE LISTING

SEQ ID 119 - S332121F02 chimeric heavy chain (DNA sequence)
GAGGTGCAGCTGCAGCAGAGCGGCCCCGTGCTGGTGAAGCCTGGAGCCAGCGTGAAAATGAG
CTGCGAAGCCAGCGGCTACACCTTCACCGACTACTACATGAACTGGGTGAAGCAGAGCCACGG
CAAGACCCTGGAGTGGATCGGCGTGATCAACCCCTACAACGGGGGCACCGACTACAACCAGAA
GTTCAAGGGCAAGGCCACTCTGACCGTGGACAAGAGCTCCAGCACCGCCTACATGGAACTGAA
CAGCCTCACCTCTGAGGACAGCGCCGTCTATTACTGCGCCAGGAGCGTGTACGACTACCCCTTC
GACTACTGGGGCCAGGGCACACTAGTGACCGTGTCCAGCGCCAGCACCAAGGGCCCCAGCGT
GTTCCCCCTGGCCCCCAGCAGCAAGAGCACCAGCGGCGGCACAGCCGCCCTGGGCTGCCTGG
TGAAGGACTACTTCCCCGAACCGGTGACCGTGTCCTGGAACAGCGGAGCCCTGACCAGCGGCG
TGCACACCTTCCCCGCCGTGCTGCAGAGCAGCGGCCTGTACAGCCTGAGCAGCGTGGTGACCG
TGCCCAGCAGCAGCCTGGGCACCCAGACCTACATCTGTAACGTGAACCACAAGCCCAGCAACAC
CAAGGTGGACAAGAAGGTGGAGCCCAAGAGCTGTGACAAGACCCACACCTGCCCCCCCTGCCC
TGCCCCCGAGCTGCTGGGAGGCCCCAGCGTGTTCCTGTTCCCCCCCAAGCCTAAGGACACCCT
GATGATCAGCAGAACCCCCGAGGTGACCTGTGTGGTGGTGGATGTGAGCCACGAGGACCCTGA
GGTGAAGTTCAACTGGTACGTGGACGGCGTGGAGGTGCACAATGCCAAGACCAAGCCCAGGGA
GGAGCAGTACAACAGCACCTACCGGGTGGTGTCCGTGCTGACCGTGCTGCACCAGGATTGGCT
GAACGGCAAGGAGTACAAGTGTAAGGTGTCCAACAAGGCCCTGCCTGCCCCTATCGAGAAAACC
ATCAGCAAGGCCAAGGGCCAGCCCAGAGAGCCCCAGGTGTACACCCTGCCCCCTAGCAGAGAT
GAGCTGACCAAGAACCAGGTGTCCCTGACCTGCCTGGTGAAGGGCTTCTACCCCAGCGACATC
GCCGTGGAGTGGGAGAGCAACGGCCAGCCCGAGAACAACTACAAGACCACCCCCCCTGTGCTG
GACAGCGATGGCAGCTTCTTCCTGTACAGCAAGCTGACCGTGGACAAGAGCAGATGGCAGCAG
GGCAACGTGTTCAGCTGCTCCGTGATGCACGAGGCCCTGCACAATCACTACACCCAGAAGAGCC
TGAGCCTGTCCCCTGGCAAG SEQ ID 120 - S332121F02 murine variable light chain
DIVLTQSPASLAVSLGQRATISCRASESVSIHGTHLMHWYQQKPGQPPKLLIYAASNLESGVPARFSG
SGSETDFTLNIHPVEEEDAATYFCQQSIEDPRTFGGGTKLEIK SEQ ID 121 - S332121F02 murine variable light chain (DNA sequence)
GACATCGTCCTGACCCAGAGCCCCGCCAGCCTGGCCGTGAGCCTGGGCCAGAGGGCCACAATC
AGCTGCAGGGCCTCTGAGTCCGTGAGCATCCACGGCACCCACCTGATGCACTGGTATCAGCAG
AAGCCCGGCCAGCCTCCCAAGCTGCTGATCTACGCCGCCAGCAACCTGGAGAGCGGCGTGCCC
GCTAGGTTCAGCGGAAGCGGCAGCGAGACCGACTTCACCCTGAACATCCACCCCGTGGAGGAG
GAAGACGCCGCCACCTACTTCTGCCAGCAGAGCATCGAGGACCCCAGGACCTTCGGCGGGGGC
ACCAAGCTCGAGATTAAGCGT SEQ ID 122 - S332121F02 chimeric light chain
MGWSCIILFLVATATGVHSDIVLTQSPASLAVSLGQRATISCRASESVSIHGTHLMHWYQQKPGQPPK
LLIYAASNLESGVPARFSGSGSETDFTLNIHPVEEEDAATYFCQQSIEDPRTFGGGTKLEIKRTVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID 123 - S332121F02 chimeric light chain (DNA sequence)
ATGGGCTGGTCCTGCATCATCCTGTTTCTGGTGGCCACCGCCACCGGCGTGCACAGCGACATC
GTCCTGACCCAGAGCCCCGCCAGCCTGGCCGTGAGCCTGGGCCAGAGGGCCACAATCAGCTG
CAGGGCCTCTGAGTCCGTGAGCATCCACGGCACCCACCTGATGCACTGGTATCAGCAGAAGCC
CGGCCAGCCTCCCAAGCTGCTGATCTACGCCGCCAGCAACCTGGAGAGCGGCGTGCCCGCTAG
GTTCAGCGGAAGCGGCAGCGAGACCGACTTCACCCTGAACATCCACCCCGTGGAGGAGGAAGA
CGCCGCCACCTACTTCTGCCAGCAGAGCATCGAGGACCCCAGGACCTTCGGCGGGGGCACCAA
GCTCGAGATTAAGCGTACGGTGGCCGCCCCCAGCGTGTTCATCTTCCCCCCCAGCGATGAGCA
GCTGAAGAGCGGCACCGCCAGCGTGGTGTGTCTGCTGAACAACTTCTACCCCCGGGAGGCCAA
GGTGCAGTGGAAGGTGGACAATGCCCTGCAGAGCGGCAACAGCCAGGAGAGCGTGACCGAGC
AGGACAGCAAGGACTCCACCTACAGCCTGAGCAGCACCCTGACCCTGAGCAAGGCCGACTACG
AGAAGCACAAGGTGTACGCCTGTGAGGTGACCCACCAGGGCCTGTCCAGCCCCGTGACCAAGA
GCTTCAACCGGGGCGAGTGC SEQ ID 124 - S322110D07 murine variable heavy chain
EVQLQQSGPELVKPGTSVKIPCKTSGYIFTDYSIDWVKQSHGKSLEWIGDIDPNYGDPIYNHKFKGKA
TLTVDRSSSTAYMELRSLTSEDTAVYFCARRATGTDWFAFWGQGTLVTVSS SEQ ID 125 - S322110D07 murine variable heavy chain (DNA sequence)
GAGGTGCAGCTGCAGCAGAGCGGCCCCGAGCTGGTGAAACCCGGCACCAGCGTGAAGATCCC
CTGCAAGACCTCTGGCTACATCTTCACCGACTACAGCATCGACTGGGTGAAGCAGAGCCACGGC
AAGTCTCTGGAGTGGATTGGGGACATCGACCCCAACTACGGCGACCCCATCTACAACCACAAGT
TCAAGGGCAAGGCCACCCTGACCGTGGACAGGAGCAGCAGCACCGCCTACATGGAACTCAGGA
GCCTGACCAGCGAGGACACCGCCGTGTATTTTTGCGCCAGGAGGGCCACCGGCACTGATTGGT
TCGCCTTCTGGGGCCAGGGCACACTAGTGACCGTGTCCAGC SEQ ID 126 - S322110D07 chimeric heavy chain
EVQLQQSGPELVKPGTSVKIPCKTSGYIFTDYSIDWVKQSHGKSLEWIGDIDPNYGDPIYNHKFKGKA
TLTVDRSSSTAYMELRSLTSEDTAVYFCARRATGTDWFAFWGQGTLVTVSSASTKGPSVFPLAPSSK
STSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK -continued

| SEQUENCE LISTING |
|---|

SEQ ID 127 - S322110D07 chimeric heavy chain (DNA sequence)
GAGGTGCAGCTGCAGCAGAGCGGCCCCGAGCTGGTGAAACCCGGCACCAGCGTGAAGATCCC
CTGCAAGACCTCTGGCTACATCTTCACCGACTACAGCATCGACTGGGTGAAGCAGAGCCACGGC
AAGTCTCTGGAGTGGATTGGGGACATCGACCCCAACTACGGCGACCCCATCTACAACCACAAGT
TCAAGGGCAAGGCCACCCTGACCGTGGACAGGAGCAGCAGCACCGCCTACATGGAACTCAGGA
GCCTGACCAGCGAGGACACCGCCGTGTATTTTTGCGCCAGGAGGGCCACCGGCACTGATTGGT
TCGCCTTCTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTG
GTGAAGGACTACTTCCCCGAACCGGTGACCGTGTCCTGGAACAGCGGAGCCCTGACCAGCGGC
GTGCACACCTTCCCCGCCGTGCTGCAGAGCAGCGGCCTGTACAGCCTGAGCAGCGTGGTGACC
GTGCCCAGCAGCAGCCTGGGCACCCAGACCTACATCTGTAACGTGAACCACAAGCCCAGCAAC
ACCAAGGTGGACAAGAAGGTGGAGCCCAAGAGCTGTGACAAGACCCACACCTGCCCCCCCTGC
CCTGCCCCCGAGCTGCTGGGAGGCCCCAGCGTGTTCCTGTTCCCCCCCAAGCCTAAGGACACC
CTGATGATCAGCAGAACCCCCGAGGTGACCTGTGTGGTGGTGGATGTGAGCCACGAGGACCCT
GAGGTGAAGTTCAACTGGTACGTGGACGGCGTGGAGGTGCACAATGCCAAGACCAAGCCCAGG
GAGGAGCAGTACAACAGCACCTACCGGGTGGTGTCCGTGCTGACCGTGCTGCACCAGGATTGG
CTGAACGGCAAGGAGTACAAGTGTAAGGTGTCCAACAAGGCCCTGCCTGCCCCTATCGAGAAAA
CCATCAGCAAGGCCAAGGGCCAGCCCAGAGAGCCCCAGGTGTACACCCTGCCCCCTAGCAGAG
ATGAGCTGACCAAGAACCAGGTGTCCCTGACCTGCCTGGTGAAGGGCTTCTACCCCAGCGACAT
CGCCGTGGAGTGGGAGAGCAACGGCCAGCCCGAGAACAACTACAAGACCACCCCCCCTGTGCT
GGACAGCGATGGCAGCTTCTTCCTGTACAGCAAGCTGACCGTGGACAAGAGCAGATGGCAGCA
GGGCAACGTGTTCAGCTGCTCCGTGATGCACGAGGCCCTGCACAATCACTACACCCAGAAGAG
CCTGAGCCTGTCCCCTGGCAAG SEQ ID 128 - S322110D07 murine variable light chain
DIQMTQSPASLSVSVGETVTITCRASENIYNNLAWYQQKQGKSPQLLVYAATILADGVPSRFSGSGSG
TQYSLKINSLQSGDFGTYYCQHFWGTPLTFGAGTKLELKR SEQ ID 129 - S322110D07 murine variable light chain (DNA sequence)
GACATCCAGATGACCCAGAGCCCCGCTAGCCTCAGCGTGTCCGTCGGCGAGACCGTGACCATC
ACCTGCAGGGCCAGCGAGAACATCTACAACAACCTGGCCTGGTATCAGCAGAAGCAGGGCAAA
AGCCCCCAGCTGCTGGTGTACGCCGCCACCATTCTGGCCGACGGCGTGCCCAGCAGGTTCTCT
GGAAGCGGCAGCGGCACCCAGTACAGCCTGAAGATCAACAGCCTGCAGAGCGGGGACTTCGG
CACCTACTACTGCCAGCACTTCTGGGGCACTCCCCTGACCTTCGGAGCCGGCACCAAGCTGGA
GCTGAAGCGT SEQ ID 130 - S322110D07 chimeric light chain
DIQMTQSPASLSVSVGETVTITCRASENIYNNLAWYQQKQGKSPQLLVYAATILADGVPSRFSGSGSG
TQYSLKINSLQSGDFGTYYCQHFWGTPLTFGAGTKLELKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC SEQ ID 131 - S322110D07 chimeric light chain (DNA sequence)
GACATCCAGATGACCCAGAGCCCCGCTAGCCTCAGCGTGTCCGTCGGCGAGACCGTGACCATC
ACCTGCAGGGCCAGCGAGAACATCTACAACAACCTGGCCTGGTATCAGCAGAAGCAGGGCAAA
AGCCCCCAGCTGCTGGTGTACGCCGCCACCATTCTGGCCGACGGCGTGCCCAGCAGGTTCTCT
GGAAGCGGCAGCGGCACCCAGTACAGCCTGAAGATCAACAGCCTGCAGAGCGGGGACTTCGG
CACCTACTACTGCCAGCACTTCTGGGGCACTCCCCTGACCTTCGGAGCCGGCACCAAGCTGGA
GCTGAAGCGTACGGTGGCCGCCCCCAGCGTGTTCATCTTCCCCCCCAGCGATGAGCAGCTGAA
GAGCGGCACCGCCAGCGTGGTGTGTCTGCTGAACAACTTCTACCCCCGGGAGGCCAAGGTGCA
GTGGAAGGTGGACAATGCCCTGCAGAGCGGCAACAGCCAGGAGAGCGTGACCGAGCAGGACA
GCAAGGACTCCACCTACAGCCTGAGCAGCACCCTGACCCTGAGCAAGGCCGACTACGAGAAGC
ACAAGGTGTACGCCTGTGAGGTGACCCACCAGGGCCTGTCCAGCCCCGTGACCAAGAGCTTCA
ACCGGGGCGAGTGC SEQ ID 132 - S332126E04 murine variable heavy chain
QVQLQQPGAELVKPGASVKLSCKASGYTFTNYWMHWVKQRPGQGLEWIGIIHPNSGSTNYNEKFKS
KATLTVDKSSSTAYMQLSSLTSEDSAVYYCARGIYDYPFAYWGQGTLVTVSS SEQ ID 133 - S332126E04 murine variable heavy chain (DNA sequence)
CAGGTGCAGCTCCAGCAGCCCGGAGCCGAACTGGTGAAGCCCGGAGCCAGCGTCAAACTGTCC
TGCAAGGCCAGCGGCTACACCTTCACCAACTACTGGATGCACTGGGTGAAGCAGAGGCCCGGC
CAGGGCCTGGAGTGGATCGGCATCATCCACCCCAACAGCGGGAGCACCAACTACAACGAGAAG
TTCAAGAGCAAGGCCACCCTGACCGTGGACAAGAGCAGCAGCACTGCCTACATGCAGCTGAGC
AGCCTGACCAGCGAGGACAGCGCTGTGTACTACTGCGCCAGGGGCATCTACGACTACCCCTTC
GCCTATTGGGGCCAGGGCACACTAGTGACCGTGTCCAGC SEQ ID 134 - S332126E04 Chimeric heavy chain
QVQLQQPGAELVKPGASVKLSCKASGYTFTNYWMHWVKQRPGQGLEWIGIIHPNSGSTNYNEKFKS
KATLTVDKSSSTAYMQLSSLTSEDSAVYYCARGIYDYPFAYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK -continued

SEQUENCE LISTING

SEQ ID 135 - S332126E04 Chimeric heavy chain (DNA sequence)
CAGGTGCAGCTCCAGCAGCCCGGAGCCGAACTGGTGAAGCCCGGAGCCAGCGTCAAACTGTCC
TGCAAGGCCAGCGGCTACACCTTCACCAACTACTGGATGCACTGGGTGAAGCAGAGGCCCGGC
CAGGGCCTGGAGTGGATCGGCATCATCCACCCCAACAGCGGGAGCACCAACTACAACGAGAAG
TTCAAGAGCAAGGCCACCCTGACCGTGGACAAGAGCAGCAGCACTGCCTACATGCAGCTGAGC
AGCCTGACCAGCGAGGACAGCGCTGTGTACTACTGCGCCAGGGGCATCTACGACTACCCCTTC
GCCTATTGGGGCCAGGGCACACTAGTGACCGTGTCCAGCGCCAGCACCAAGGGCCCCAGCGTG
TTCCCCCTGGCCCCCAGCAGCAAGAGCACCAGCGGCGGCACAGCCGCCCTGGGCTGCCTGGT
GAAGGACTACTTCCCCGAACCGGTGACCGTGTCCTGGAACAGCGGAGCCCTGACCAGCGGCGT
GCACACCTTCCCCGCCGTGCTGCAGAGCAGCGGCCTGTACAGCCTGAGCAGCGTGGTGACCGT
GCCCAGCAGCAGCCTGGGCACCCAGACCTACATCTGTAACGTGAACCACAAGCCCAGCAACAC
CAAGGTGGACAAGAAGGTGGAGCCCAAGAGCTGTGACAAGACCCACACCTGCCCCCCCTGCCC
TGCCCCCGAGCTGCTGGGAGGCCCCAGCGTGTTCCTGTTCCCCCCCAAGCCTAAGGACACCCT
GATGATCAGCAGAACCCCCGAGGTGACCTGTGTGGTGGTGGATGTGAGCCACGAGGACCCTGA
GGTGAAGTTCAACTGGTACGTGGACGGCGTGGAGGTGCACAATGCCAAGACCAAGCCCAGGGA
GGAGCAGTACAACAGCACCTACCGGGTGGTGTCCGTGCTGACCGTGCTGCACCAGGATTGGCT
GAACGGCAAGGAGTACAAGTGTAAGGTGTCCAACAAGGCCCTGCCTGCCCCTATCGAGAAAACC
ATCAGCAAGGCCAAGGGCCAGCCCAGAGAGCCCCAGGTGTACACCCTGCCCCCTAGCAGAGAT
GAGCTGACCAAGAACCAGGTGTCCCTGACCTGCCTGGTGAAGGGCTTCTACCCCAGCGACATC
GCCGTGGAGTGGGAGAGCAACGGCCAGCCCGAGAACAACTACAAGACCACCCCCCCTGTGCTG
GACAGCGATGGCAGCTTCTTCCTGTACAGCAAGCTGACCGTGGACAAGAGCAGATGGCAGCAG
GGCAACGTGTTCAGCTGCTCCGTGATGCACGAGGCCCTGCACAATCACTACACCCAGAAGAGCC
TGAGCCTGTCCCCTGGCAAG SEQ ID 136 - S332126E04 murine variable light chain
DIVLTQSPASLAVSLGQRATISCRASESVSIHGTHLMHWYQQKPGQPPKLLIYAASNLESGVPARFSG
SGSETDFTLNIHPVEEEDAATYFCQQSIEDPYTFGGGTKLEIKR SEQ ID 137 - S332126E04 murine variable light chain (DNA sequence)
GACATCGTGCTGACCCAGTCTCCCGCTAGCCTGGCCGTGTCTCTGGGCCAGAGGGCCACAATC
AGCTGCAGGGCCAGCGAGAGCGTCAGCATTCACGGCACCCACCTGATGCACTGGTACCAGCAG
AAGCCCGGCCAGCCTCCCAAGCTCCTGATCTACGCCGCCAGCAACCTGGAAAGCGGAGTGCCC
GCCAGGTTCAGCGGCAGCGGCTCCGAGACCGACTTCACCCTGAACATCCACCCCGTGGAGGAG
GAGGACGCCGCCACCTACTTCTGCCAGCAGAGCATCGAGGACCCCTACACCTTCGGCGGCGGC
ACCAAGCTGGAGATCAAGCGT SEQ ID 138 - S332126E04 Chimeric light chain
DIVLTQSPASLAVSLGQRATISCRASESVSIHGTHLMHWYQQKPGQPPKLLIYAASNLESGVPARFSG
SGSETDFTLNIHPVEEEDAATYFCQQSIEDPYTFGGGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC SEQ ID 139 - S332126E04 Chimeric light chain (DNA sequence)
GACATCGTGCTGACCCAGTCTCCCGCTAGCCTGGCCGTGTCTCTGGGCCAGAGGGCCACAATC
AGCTGCAGGGCCAGCGAGAGCGTCAGCATTCACGGCACCCACCTGATGCACTGGTACCAGCAG
AAGCCCGGCCAGCCTCCCAAGCTCCTGATCTACGCCGCCAGCAACCTGGAAAGCGGAGTGCCC
GCCAGGTTCAGCGGCAGCGGCTCCGAGACCGACTTCACCCTGAACATCCACCCCGTGGAGGAG
GAGGACGCCGCCACCTACTTCTGCCAGCAGAGCATCGAGGACCCCTACACCTTCGGCGGCGGC
ACCAAGCTGGAGATCAAGCGTACGGTGGCCGCCCCCAGCGTGTTCATCTTCCCCCCCAGCGAT
GAGCAGCTGAAGAGCGGCACCGCCAGCGTGGTGTGTCTGCTGAACAACTTCTACCCCCGGGAG
GCCAAGGTGCAGTGGAAGGTGGACAATGCCCTGCAGAGCGGCAACAGCCAGGAGAGCGTGAC
CGAGCAGGACAGCAAGGACTCCACCTACAGCCTGAGCAGCACCCTGACCCTGAGCAAGGCCGA
CTACGAGAAGCACAAGGTGTACGCCTGTGAGGTGACCCACCAGGGCCTGTCCAGCCCCGTGAC
CAAGAGCTTCAACCGGGGCGAGTGC SEQ ID 140 - S336105A07 murine variable heavy chain
EVKLLQSGGGLVQPGGSLKLSCAASGIDFSRYWMSWVRRAPGKGLEWIGEINPDRSTINYAPSLKDK
FIISRDNAKNTLYLQMSKVRSEDTALYYCAVFYYDYEGAMDYWGQGTSVTVSS SEQ ID 141 - S336105A07 murine variable heavy chain (DNA sequence)
GAGGTGAAGCTTCTCCAGTCTGGAGGTGGCCTGGTGCAGCCTGGAGGATCCCTGAAACTCTCCT
GTGCAGCCTCAGGAATCGATTTTAGTAGATACTGGATGAGTTGGGTTCGGCGGGCTCCAGGGAA
AGGACTAGAATGGATTGGAGAAATTAATCCAGATAGGAGTACAATCAACTATGCACCATCTCTAA
AGGATAAATTCATCATCTCCAGAGACAACGCCAAAAATACGCTGTACCTGCAAATGAGCAAAGTG
AGATCTGAGGACACAGCCCTTTATTACTGTGCAGTTTTCTACTATGATTACGAGGGTGCTATGGA
CTACTGGGGTCAAGGAACCTCAGTCACCGTCTCCTCA SEQ ID 142 - S336105A07 Chimeric heavy chain
EVKLLQSGGGLVQPGGSLKLSCAASGIDFSRYWMSWVRRAPGKGLEWIGEINPDRSTINYAPSLKDK
FIISRDNAKNTLYLQMSKVRSEDTALYYCAVFYYDYEGAMDYWGQGTSVTVSSAKTTAPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK -continued

SEQUENCE LISTING

SEQ ID 143 - S336105A07 Chimeric heavy chain (DNA sequence)
GAGGTGAAGCTTCTCCAGTCTGGAGGTGGCCTGGTGCAGCCTGGAGGATCCCTGAAACTCTCCT
GTGCAGCCTCAGGAATCGATTTTAGTAGATACTGGATGAGTTGGGTTCGGCGGGCTCCAGGGAA
AGGACTAGAATGGATTGGAGAAATTAATCCAGATAGGAGTACAATCAACTATGCACCATCTCTAA
AGGATAAATTCATCATCTCCAGAGACAACGCCAAAAATACGCTGTACCTGCAAATGAGCAAAGTG
AGATCTGAGGACACAGCCCTTTATTACTGTGCAGTTTTCTACTATGATTACGAGGGTGCTATGGA
CTACTGGGGTCAAGGAACCTCAGTCACCGTCTCCTCAGCCAAAACAACAGCCCCCAGCGTGTTC
CCCCTGGCCCCCAGCAGCAAGAGCACCAGCGGCGGCACAGCCGCCCTGGGCTGCCTGGTGAA
GGACTACTTCCCCGAACCGGTGACCGTGTCCTGGAACAGCGGAGCCCTGACCAGCGGCGTGCA
CACCTTCCCCGCCGTGCTGCAGAGCAGCGGCCTGTACAGCCTGAGCAGCGTGGTGACCGTGCC
CAGCAGCAGCCTGGGCACCCAGACCTACATCTGTAACGTGAACCACAAGCCCAGCAACACCAAG
GTGGACAAGAAGGTGGAGCCCAAGAGCTGTGACAAGACCCACACCTGCCCCCCCTGCCCTGCC
CCCGAGCTGCTGGGAGGCCCCAGCGTGTTCCTGTTCCCCCCCAAGCCTAAGGACACCCTGATG
ATCAGCAGAACCCCCGAGGTGACCTGTGTGGTGGTGGATGTGAGCCACGAGGACCCTGAGGTG
AAGTTCAACTGGTACGTGGACGGCGTGGAGGTGCACAATGCCAAGACCAAGCCCAGGGAGGAG
CAGTACAACAGCACCTACCGGGTGGTGTCCGTGCTGACCGTGCTGCACCAGGATTGGCTGAAC
GGCAAGGAGTACAAGTGTAAGGTGTCCAACAAGGCCCTGCCTGCCCCTATCGAGAAAACCATCA
GCAAGGCCAAGGGCCAGCCCAGAGAGCCCCAGGTGTACACCCTGCCCCCTAGCAGAGATGAGC
TGACCAAGAACCAGGTGTCCCTGACCTGCCTGGTGAAGGGCTTCTACCCCAGCGACATCGCCGT
GGAGTGGGAGAGCAACGGCCAGCCCGAGAACAACTACAAGACCACCCCCCCTGTGCTGGACAG
CGATGGCAGCTTCTTCCTGTACAGCAAGCTGACCGTGGACAAGAGCAGATGGCAGCAGGGCAA
CGTGTTCAGCTGCTCCGTGATGCACGAGGCCCTGCACAATCACTACACCCAGAAGAGCCTGAGC
CTGTCCCCTGGCAAG SEQ ID 144 - S336105A07 murine varaible light chain
DIVMTQSQKFMSTSVGDRVSVTCKASQNVDTNVAWYQQKPGQSPKALIYSASYRFSGVPDRFTGSG
SGTDFTLTISNVQSEDLAEYFCQQYNSFPFTFGSGTKLEIKR SEQ ID 145 - S336105A07 murine variable light chain (DNA sequence)
GACATTGTGATGACCCAGTCTCAAAAATTCATGTCCACATCAGTAGGAGACAGGGTCAGCGTCAC
CTGCAAGGCCAGTCAGAATGTGGATACTAATGTAGCCTGGTATCAACAAAAACCAGGGCAATCTC
CTAAAGCACTGATTTACTCGGCATCCTACCGGTTCAGTGGAGTCCCTGATCGCTTCACAGGCAGT
GGATCTGGGACAGATTTCACTCTCACCATCAGCAATGTGCAGTCTGAAGACTTGGCAGAGTATTT
CTGTCAGCAATATAACAGCTTTCCATTCACGTTCGGCTCGGGGACAAAGTTGGAAATAAAACGT SEQ ID 146 - S336105A07 chimeric light chain
DIVMTQSQKFMSTSVGDRVSVTCKASQNVDTNVAWYQQKPGQSPKALIYSASYRFSGVPDRFTGSG
SGTDFTLTISNVQSEDLAEYFCQQYNSFPFTFGSGTKLEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC SEQ ID 147 - S336105A07 chimeric light chain (DNA sequence)
GACATTGTGATGACCCAGTCTCAAAAATTCATGTCCACATCAGTAGGAGACAGGGTCAGCGTCAC
CTGCAAGGCCAGTCAGAATGTGGATACTAATGTAGCCTGGTATCAACAAAAACCAGGGCAATCTC
CTAAAGCACTGATTTACTCGGCATCCTACCGGTTCAGTGGAGTCCCTGATCGCTTCACAGGCAGT
GGATCTGGGACAGATTTCACTCTCACCATCAGCAATGTGCAGTCTGAAGACTTGGCAGAGTATTT
CTGTCAGCAATATAACAGCTTTCCATTCACGTTCGGCTCGGGGACAAAGTTGGAAATAAAACGTA
CGGTGGCCGCCCCCAGCGTGTTCATCTTCCCCCCCAGCGATGAGCAGCTGAAGAGCGGCACCG
CCAGCGTGGTGTGTCTGCTGAACAACTTCTACCCCCGGGAGGCCAAGGTGCAGTGGAAGGTGG
ACAATGCCCTGCAGAGCGGCAACAGCCAGGAGAGCGTGACCGAGCAGGACAGCAAGGACTCCA
CCTACAGCCTGAGCAGCACCCTGACCCTGAGCAAGGCCGACTACGAGAAGCACAAGGTGTACG
CCTGTGAGGTGACCCACCAGGGCCTGTCCAGCCCCGTGACCAAGAGCTTCAACCGGGGCGAGT
GC SEQ ID 148 - S335115G01 murine variable heavy chain
PVQLQQPGTELVRPGTSVKLSCKASGYTFTSYWMHWVKQRPGQGLEWIGVIDPSDSYTNYNQKFK
GKATLTVDTSSSTAYMQLSSLTSEDSAVYYCARQVFDYPMDYWGQGTSVTVSS SEQID 149 - S335115G01 murine variable heavy chain (DNA sequence)
CCGGTCCAACTGCAGCAGCCTGGGACTGAGCTGGTGAGGCCTGGGACTTCAGTGAAGTTGTCC
TGCAAGGCTTCTGGCTACACCTTCACCAGCTACTGGATGCACTGGGTAAAGCAGAGGCCTGGAC
AAGGCCTTGAGTGGATCGGAGTGATTGATCCTTCTGATAGTTATACTAACTACAATCAAAAGTTCA
AGGGCAAGGCCACATTGACTGTAGACACATCCTCCAGCACAGCCTACATGCAGCTCAGCAGCCT
GACATCTGAGGACTCTGCGGTCTATTACTGTGCAAGACAGGTGTTTGACTATCCTATGGACTACT
GGGGTCAAGGAACCTCAGTCACCGTCTCCTCA SEQ ID 150 - S335115G01 Chimeric heavy chain
PVQLQQPGTELVRPGTSVKLSCKASGYTFTSHWMHWVKQRPGQGLEWIGVIDPSDSYTNYNQKFK
GKATLTVDTSSSTAYMQLSSLTSEDSAVYYCARQVFDYPMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK -continued

SEQUENCE LISTING

SEQ ID 151 - S335115G01 Chimeric heavy chain (DNA sequence)
CCGGTCCAACTGCAGCAGCCTGGGACTGAGCTGGTGAGGCCTGGGACTTCAGTGAAGTTGTCC
TGCAAGGCTTCTGGCTACACCTTCACCAGCCACTGGATGCACTGGGTAAAGCAGAGGCCTGGAC
AAGGCCTTGAGTGGATCGGAGTGATTGATCCTTCTGATAGTTATACTAACTACAATCAAAAGTTCA
AGGGCAAGGCCACATTGACTGTAGACACATCCTCCAGCACAGCCTACATGCAGCTCAGCAGCCT
GACATCTGAGGACTCTGCGGTCTATTACTGTGCAAGACAGGTGTTTGACTATCCTATGGACTACT
GGGGTCAAGGAACACTAGTGACCGTGTCCAGCGCCAGCACCAAGGGCCCCAGCGTGTTCCCCC
TGGCCCCCAGCAGCAAGAGCACCAGCGGCGGCACAGCCGCCCTGGGCTGCCTGGTGAAGGAC
TACTTCCCCGAACCGGTGACCGTGTCCTGGAACAGCGGAGCCCTGACCAGCGGCGTGCACACC
TTCCCCGCCGTGCTGCAGAGCAGCGGCCTGTACAGCCTGAGCAGCGTGGTGACCGTGCCCAGC
AGCAGCCTGGGCACCCAGACCTACATCTGTAACGTGAACCACAAGCCCAGCAACACCAAGGTG
GACAAGAAGGTGGAGCCCAAGAGCTGTGACAAGACCCACACCTGCCCCCCCTGCCCTGCCCCC
GAGCTGCTGGGAGGCCCCAGCGTGTTCCTGTTCCCCCCCAAGCCTAAGGACACCCTGATGATC
AGCAGAACCCCCGAGGTGACCTGTGTGGTGGTGGATGTGAGCCACGAGGACCCTGAGGTGAAG
TTCAACTGGTACGTGGACGGCGTGGAGGTGCACAATGCCAAGACCAAGCCCAGGGAGGAGCAG
TACAACAGCACCTACCGGGTGGTGTCCGTGCTGACCGTGCTGCACCAGGATTGGCTGAACGGC
AAGGAGTACAAGTGTAAGGTGTCCAACAAGGCCCTGCCTGCCCCTATCGAGAAAACCATCAGCA
AGGCCAAGGGCCAGCCCAGAGAGCCCCAGGTGTACACCCTGCCCCCTAGCAGAGATGAGCTGA
CCAAGAACCAGGTGTCCCTGACCTGCCTGGTGAAGGGCTTCTACCCCAGCGACATCGCCGTGG
AGTGGGAGAGCAACGGCCAGCCCGAGAACAACTACAAGACCACCCCCCCTGTGCTGGACAGCG
ATGGCAGCTTCTTCCTGTACAGCAAGCTGACCGTGGACAAGAGCAGATGGCAGCAGGGCAACG
TGTTCAGCTGCTCCGTGATGCACGAGGCCCTGCACAATCACTACACCCAGAAGAGCCTGAGCCT
GTCCCCTGGCAAG SEQ ID 152 - S335115G01 murine variable light chain
DIVLTQSPASLAVSLGQRATISCRASESVSIHGTHLMHWYQQKPGQPPKLLIYAASNLESGVPARFSG
SGSETDFTLNIHPVEEEDAATYFCQQSIEDPWTFGGGTKLEIKR SEQ ID 153 - S335115G01 murine variable light chain (DNA sequence)
GACATTGTGCTGACCCAATCTCCAGCTTCTTTGGCTGTGTCTCTAGGGCAGAGGGCCACCATCT
CCTGCAGAGCCAGTGAAAGTGTCAGTATTCATGGTACTCATTTAATGCACTGGTACCAACAGAAA
CCAGGACAGCCACCCAAACTCCTCATCTATGCTGCATCCAACCTAGAATCTGGAGTCCCTGCCA
GGTTCAGTGGCAGTGGGTCTGAGACAGACTTCACCCTCAACATCCATCCTGTGGAGGAGGAGGA
TGCTGCAACCTATTTCTGTCAGCAAAGTATTGAGGATCCGTGGACGTTCGGTGGAGGCACCAAG
CTGGAAATCAAACGT SEQ ID 154 - S335115G01 Chimeric light chain
DIVLTQSPASLAVSLGQRATISCRASESVSIHGTHLMHWYQQKPGQPPKLLIYAASNLESGVPARFSG
SGSETDFTLNIHPVEEEDAATYFCQQSIEDPWTFGGGTKLEINRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC SEQ ID 155 - S335115G01 Chimeric light chain (DNA sequence)
GACATTGTGCTGACCCAATCTCCAGCTTCTTTGGCTGTGTCTCTAGGGCAGAGGGCCACCATCT
CCTGCAGAGCCAGTGAAAGTGTCAGTATTCATGGTACTCATTTAATGCACTGGTACCAACAGAAA
CCAGGACAGCCACCCAAACTCCTCATCTATGCTGCATCCAACCTAGAATCTGGAGTCCCTGCCA
GGTTCAGTGGCAGTGGGTCTGAGACAGACTTCACCCTCAACATCCATCCTGTGGAGGAGGAGGA
TGCTGCAACCTATTTCTGTCAGCAAAGTATTGAGGATCCGTGGACGTTCGGTGGAGGCACCAAG
CTGGAAATCAATCGTACGGTGGCCGCCCCCAGCGTGTTCATCTTCCCCCCCAGCGATGAGCAGC
TGAAGAGCGGCACCGCCAGCGTGGTGTGTCTGCTGAACAACTTCTACCCCCGGGAGGCCAAGG
TGCAGTGGAAGGTGGACAATGCCCTGCAGAGCGGCAACAGCCAGGAGAGCGTGACCGAGCAG
GACAGCAAGGACTCCACCTACAGCCTGAGCAGCACCCTGACCCTGAGCAAGGCCGACTACGAG
AAGCACAAGGTGTACGCCTGTGAGGTGACCCACCAGGGCCTGTCCAGCCCCGTGACCAAGAGC
TTCAACCGGGGCGAGTGC SEQ ID 156 - S335122F05 murine variable heavy chain
QVQLQQSGAELVRPGASVTLSCKASGYTFTDYEMHWVKQTPVHGLEWIGAIDPETGGTAYNQKFKG
KAILTADKSSSTAYMELRSLTSEDSAVYYCTRSIYDYYFDYWGQGTTLTVSS SEQ ID 157 - S335122F05 murine variable heavy chain (DNA sequence)
CAGGTTCAACTGCAGCAGTCTGGGGCTGAGCTGGTGAGGCCTGGGGCTTCAGTGACGCTGTCC
TGCAAGGCTTCGGGCTACACATTTACTGACTATGAAATGCACTGGGTGAAGCAGACACCTGTGC
ATGGCCTGGAATGGATTGGAGCTATTGATCCTGAAACTGGTGGTACTGCCTACAATCAGAAGTTC
AAGGGCAAGGCCATACTGACTGCAGACAAATCCTCCAGCACAGCCTACATGGAGCTCCGCAGCC
TGACATCTGAGGACTCTGCCGTCTATTACTGTACAAGATCGATTTATGATTACTACTTTGACTACT
GGGGCCAAGGCACCACTCTCACAGTCTCCTCA SEQ ID 158 - S335122F05 Chimeric heavy chain
QVQLQQSGAELVRPGASVTLSCKASGYTFTDYEMHWVKQTPVHGLEWIGAIDPETGGTAYNQKFKG
KAILTADKSSSTAYMELRSLTSEDSAVYYCTRSIYDYYFDYWGQGTTLTVSSAKTTPPSVFPLAPSSK
STSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK -continued

SEQUENCE LISTING

SEQ ID 159 - S335122F05 Chimeric heavy chain (DNA sequence)
CAGGTTCAACTGCAGCAGTCTGGGGCTGAGCTGGTGAGGCCTGGGGCTTCAGTGACGCTGTCC
TGCAAGGCTTCGGGCTACACATTTACTGACTATGAAATGCACTGGGTGAAGCAGACACCTGTGC
ATGGCCTGGAATGGATTGGAGCTATTGATCCTGAAACTGGTGGTACTGCCTACAATCAGAAGTTC
AAGGGCAAGGCCATACTGACTGCAGACAAATCCTCCAGCACAGCCTACATGGAGCTCCGCAGCC
TGACATCTGAGGACTCTGCCGTCTATTACTGTACAAGATCGATTTATGATTACTACTTTGACTACT
GGGGCCAAGGCACCACTCTCACAGTCTCCTCAGCCAAAACGACACCCCCCAGCGTGTTCCCCCT
GGCCCCCAGCAGCAAGAGCACCAGCGGCGGCACAGCCGCCCTGGGCTGCCTGGTGAAGGACT
ACTTCCCCGAACCGGTGACCGTGTCCTGGAACAGCGGAGCCCTGACCAGCGGCGTGCACACCT
TCCCCGCCGTGCTGCAGAGCAGCGGCCTGTACAGCCTGAGCAGCGTGGTGACCGTGCCCAGCA
GCAGCCTGGGCACCCAGACCTACATCTGTAACGTGAACCACAAGCCCAGCAACACCAAGGTGG
ACAAGAAGGTGGAGCCCAAGAGCTGTGACAAGACCCACACCTGCCCCCCCTGCCCTGCCCCCG
AGCTGCTGGGAGGCCCCAGCGTGTTCCTGTTCCCCCCCAAGCCTAAGGACACCCTGATGATCA
GCAGAACCCCCGAGGTGACCTGTGTGGTGGTGGATGTGAGCCACGAGGACCCTGAGGTGAAGT
TCAACTGGTACGTGGACGGCGTGGAGGTGCACAATGCCAAGACCAAGCCCAGGGAGGAGCAGT
ACAACAGCACCTACCGGGTGGTGTCCGTGCTGACCGTGCTGCACCAGGATTGGCTGAACGGCA
AGGAGTACAAGTGTAAGGTGTCCAACAAGGCCCTGCCTGCCCCTATCGAGAAAACCATCAGCAA
GGCCAAGGGCCAGCCCAGAGAGCCCCAGGTGTACACCCTGCCCCCTAGCAGAGATGAGCTGAC
CAAGAACCAGGTGTCCCTGACCTGCCTGGTGAAGGGCTTCTACCCCAGCGACATCGCCGTGGA
GTGGGAGAGCAACGGCCAGCCCGAGAACAACTACAAGACCACCCCCCCTGTGCTGGACAGCGA
TGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTG
TCCCCTGGCAAG SEQ ID 160 - S335122F05 murine variable light chain
DIVLTQSPASLAVSLGQRATISCRASESVSIHGTHLMHWYQQKPGQPPKLLIYAASNLESGVPARFSG
GGSETDFTLNIHPVEEEDGATYFCQQSIEYPRTFGGGTKLEINR SEQ ID 161 - S335122F05 murine variable light chain (DNA sequence)
GACATTGTGCTGACCCAATCTCCAGCTTCTTTGGCTGTGTCTCTAGGGCAGAGGGCCACCATCT
CCTGCAGAGCCAGTGAAAGTGTCAGTATTCATGGTACTCATTTAATGCACTGGTACCAACAGAAA
CCAGGACAGCCACCCAAACTCCTCATCTATGCTGCATCCAACCTAGAATCTGGAGTCCCTGCCA
GGTTCAGTGGCGGTGGGTCTGAGACAGACTTCACCCTCAACATCCATCCTGTGGAGGAGGAGG
ATGGTGCAACCTATTTCTGTCAGCAAAGTATTGAGTATCCTCGGACGTTCGGTGGAGGCACCAA
GCTGGAAATCAATCGT SEQ ID 162 - S335122F05 Chimeric light chain
DIVLTQSPASLAVSLGQRATISCRASESVSIHGTHLMHWYQQKPGQPPKLLIYAASNLESGVPARFSG
GGSETDFTLNIHPVEEEDGATYFCQQSIEYPRTFGGGTKLEINRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC SEQ ID 163 - S335122F05 Chimeric light chain (DNA sequence)
GACATTGTGCTGACCCAATCTCCAGCTTCTTTGGCTGTGTCTCTAGGGCAGAGGGCCACCATCT
CCTGCAGAGCCAGTGAAAGTGTCAGTATTCATGGTACTCATTTAATGCACTGGTACCAACAGAAA
CCAGGACAGCCACCCAAACTCCTCATCTATGCTGCATCCAACCTAGAATCTGGAGTCCCTGCCA
GGTTCAGTGGCGGTGGGTCTGAGACAGACTTCACCCTCAACATCCATCCTGTGGAGGAGGAGG
ATGGTGCAACCTATTTCTGTCAGCAAAGTATTGAGTATCCTCGGACGTTCGGTGGAGGCACCAA
GCTGGAAATCAATCGTACGGTGGCCGCCCCCAGCGTGTTCATCTTCCCCCCCAGCGATGAGCA
GCTGAAGAGCGGCACCGCCAGCGTGGTGTGTCTGCTGAACAACTTCTACCCCCGGGAGGCCAA
GGTGCAGTGGAAGGTGGACAATGCCCTGCAGAGCGGCAACAGCCAGGAGAGCGTGACCGAGC
AGGACAGCAAGGACTCCACCTACAGCCTGAGCAGCACCCTGACCCTGAGCAAGGCCGACTACG
AGAAGCACAAGGTGTACGCCTGTGAGGTGACCCACCAGGGCCTGTCCAGCCCCGTGACCAAGA
GCTTCAACCGGGGCGAGTGC

SEQ.I.D.NO: 164 - S332121F02 CDRH1
DYYNM

SEQ.I.D.NO: 165 - S332121F02 CDRH2
VINPYNGGTDYNQKFG

SEQ.I.D.NO: 166 - S332121F02 CDRH3
SVYDYPFDY

SEQ.I.D.NO: 167 - S332121F02 CDRL1
RASESVSIHGTHLMH

SEQ.I.D.NO: 168 - S332121F02 CDRL2
AASNLES

SEQ.I.D.NO: 169 - S332121F02 CDRL3
QQSIEDPRT

SEQ.I.D.NO: 170 - S322110D07 CDRH1
DYSID

-continued

| SEQUENCE LISTING |
| --- |

SEQ.I.D.NO: 171 - S322110D07 CDRH2
DIDPNYGDPIYNHKFKG

SEQ.I.D.NO: 172 - S322110D07 CDRH3
RATGTDWFAF

SEQ.I.D.NO: 173 - S322110D07CDRL1
RASENIYNNLA

SEQ.I.D.NO: 174 - S322110D07 CDRL2
AATILAD

SEQ.I.D.NO: 175 - S322110D07 CDRL3
QHFWGTPLT

SEQ.I.D.NO: 176 - S332126E04CDRH1
NYWMH

SEQ.I.D.NO: 177 - S332126E04 CDRH2
IIHPNSGSTNYNEKFKS

SEQ.I.D.NO: 178 - S332126E04 CDRH3
GIYDYPFAY

SEQ.I.D.NO: 179 - S332126E04 CDRL1
RASESVSIHGTHLMH

SEQ.I.D.NO: 180 - S332126E04 CDRL2
AASNLES

SEQ.I.D.NO: 181 - S332126E04 CDRL3
QQSIEDPYT

SEQ.I.D.NO: 182 - S336105A07 CDRH1
RYWMS

SEQ.I.D.NO: 183 - S336105A07 CDRH2
EINPDRSTINYAPSLKD

SEQ.I.D.NO: 184 - S336105A07 CDRH3
FYYDYEGAMDY

SEQ.I.D.NO: 185 - S336105A07 CDRL1
KASQNVDTNVA

SEQ.I.D.NO: 186 - S336105A07 CDRL2
SASYRFS

SEQ.I.D.NO: 187 - S336105A07 CDRL3
QQYNSFPFT

SEQ.I.D.NO: 188 - S335115G01 CDRH1
SYWMH

SEQ.I.D.NO: 189 - S335115G01 CDRH2
VIDPSDSYTNYNQKFKG

SEQ.I.D.NO: 190 - S335115G01 CDRH3
QVFDYPMDY

SEQ.I.D.NO: 191 - S335115G01 CDRL1
RASESVSIHGTHLMH

SEQ.I.D.NO: 192 - S335115G01 CDRL2
AASNLES

SEQ.I.D.NO: 193 - S335115G01 CDRL3
QQSIEDPWT

SEQ.I.D.NO: 194 - S335122F05 CDRH1
DYEMH

SEQ.I.D.NO: 195 - S335122F05 CDRH2
AIDPETGGTAYNQKFKG

SEQ.I.D.NO: 196 - S335122F05 CDRH3
SIYDYYFDY

-continued

| SEQUENCE LISTING |
|---|
| SEQ.I.D.NO: 197 - S335122F05 CDRL1<br>RASESVSIHGTHLMH |
| SEQ.I.D.NO: 198 - S335122F05 CDRL2<br>AASNLES |
| SEQ.I.D.NO: 199 - S335122F05 CDRL3<br>QQSIEYPRT |

The invention claimed is:

1. An immunoconjugate comprising an antibody and a cytotoxic agent, wherein said antibody comprises a heavy chain variable region set forth in SEQ. ID. NO:23 and a light chain variable region set forth in SEQ. ID. NO:31, and wherein said cytotoxic agent is selected from: monomethyl auristatin E (MMAE) and monomethyl auristatin F (MMAF).

2. The immunoconjugate of claim 1, wherein the antibody is an IgG1 isotype.

3. The immunoconjugate of claim 1, wherein the antibody binds human BCMA with a $K_D$ of greater than 0 and less than 150 pM at 25° C.

4. The immunoconjugate of claim 1, wherein the cytotoxic agent is covalently bound to said antibody.

5. The immunoconjugate of claim 1, wherein the cytotoxic agent is bound to said antibody via a linker.

6. The immunoconjugate of claim 5, wherein said linker is a cleavable linker.

7. The immunoconjugate of claim 5, wherein said linker is a non-cleavable linker.

8. The immunoconjugate of claim 5, wherein the linker is selected from 6-maleimidocaproyl(MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate(SPP), N-succinimidyl 4-(N-maleimidomethyl)cyclohexane-1 carboxylate (SMCC), and N-Succinimidyl (4-iodo-acetyl)aminobenzoate (SIAB).

9. The immunoconjugate of claim 1, wherein said immunoconjugate is engulfed by a tumor cell when contacted with a tumor cell.

10. The immunoconjugate of claim 1, wherein said antibody is afucosylated.

11. A pharmaceutical composition comprising the immunoconjugate of claim 1 and a pharmaceutically acceptable carrier.

12. A method of treating a human patient afflicted with a B cell lymphoma comprising administering to said human a therapeutically affective amount of the immunoconjugate of claim 1.

13. The method of claim 12, wherein the B cell lymphoma is selected from: Multiple Myeloma (MM) and Chronic Lymphocytic Leukemia (CLL).

14. An immunoconjugate comprising an antibody and a cytoxic agent wherein said antibody comprises the heavy chain amino acid sequence set forth in SEQ ID NO:55 and the light chain amino acid sequence set forth in SEQ ID NO:63 and the cytotoxic agent is monomethyl auristatin E (MMAE), wherein said MMAE is linked to said antibody via a valine-citrulline (val-cit) linker.

15. An immunoconjugate comprising an antibody and a cytoxic agent, wherein said antibody comprises the heavy chain amino acid sequence set forth in SEQ ID NO:55 and the light chain amino acid sequence set forth in SEQ ID NO:63, and the cytotoxic agent is monomethyl auristatin F (MMAF), wherein said MMAF is linked to said antibody via a 6-maleimidocaproyl(mc) linker.

* * * * *